US010738090B2

(12) United States Patent
Yung et al.

(10) Patent No.: US 10,738,090 B2
(45) Date of Patent: Aug. 11, 2020

(54) ENGINEERED MICROCOMPARTMENT PROTEIN AND RELATED METHODS AND SYSTEMS OF ENGINEERING BACTERIAL SYSTEMS FOR NON-NATIVE PROTEIN EXPRESSION AND PURIFICATION

(71) Applicants: LAWRENCE LIVERMORE NATIONAL SECURITY, LLC, Livermore, CA (US); THE REGENTS OF THE UNIVERSITY OF CALIFORNIA, Oakland, CA (US)

(72) Inventors: Mimi Cho Yung, Milpitas, CA (US); Timothy S. Carpenter, Livermore, CA (US); Tek Hyung Lee, Pleasanton, CA (US); David Savage, Berkeley, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/219,781

(22) Filed: Dec. 13, 2018

(65) Prior Publication Data

US 2019/0276501 A1 Sep. 12, 2019

Related U.S. Application Data

(60) Provisional application No. 62/598,984, filed on Dec. 14, 2017.

(51) Int. Cl.
*C12N 9/96* (2006.01)
*C07K 14/195* (2006.01)
*C07K 14/435* (2006.01)

(52) U.S. Cl.
CPC ...... *C07K 14/195* (2013.01); *C07K 14/43563* (2013.01); *C07K 14/43572* (2013.01); *C07K 2319/50* (2013.01)

(58) Field of Classification Search
CPC .................. C07K 14/195; C12N 9/96
See application file for complete search history.

(56) References Cited

U.S. PATENT DOCUMENTS

| | | |
|---|---|---|
| 10,155,951 B2 | 12/2018 | Yung et al. |
| 2016/0362697 A1 | 12/2016 | Yung et al. |

FOREIGN PATENT DOCUMENTS

| | | | |
|---|---|---|---|
| WO | WO 2015/054639 | * | 4/2015 |

OTHER PUBLICATIONS

Altschul, et al., "Gapped BLAST and PSI-BLAST: a new generation of protein database search Programs" Nucleic Acids Res., 1997. 25(17): 3389-3402. 14 pages.
Arp, D.J. et al., "Molecular and Cellular Fundamentals of Aerobic Cometabolism of Trichloroethvlene", Biodegradation 12, nn. 81-103, (2001).
Axen, et al., "A Taxonomy of Bacterial Microcompartment Loci Constructed by a Novel Scoring Method", PLOS Computational Biology, 10(10), 1-20, e1003898, Oct. 2014.
Batoni, et al., "Antimicrobial peptides and their interaction with biofilms of medically relevant bacteria", Biochim Biophys Acta, 2016. 1858(5): p. 1044-1060.
Beeby, et al., "Growth and localization of polyhydroxybutyrate granules in Ralsotnia eutropha", J Bacteriol., 194, 1092-1099, 2012.
Beller, et al., "Identification of c-type cytochromes involved in anaerobic, bacterial U(IV) oxidation", Biodegradation, 20:45-53, 2009.
Bermudez-Humaran, L.G., et al., "Lactococci and lactobacilli as mucosal delivery vectors for therapeutic proteins and DNA vaccines", Microbial Cell Factories, 2011. 10. 10 pages.
Berneche, S. et al. "Energetics of ion conduction through the K+ channel", Letters to Nature, Nov. 2001, vol. 414, pp. 73-77.
Boman, et al., "Mechanisms of action on *Escherichia coli* of cecropin P1 and PR-39, two antibacterial peptides from pig intestine", Infect Immun, 1993. 61(7): p. 2978-84.
Bourguet, et al., "Characterization of a novel endolytic protein, AmpD BCZK2532 as a Bacillus anthracis antimicrobial protein", Appl Environ Microbiol, Mar. 30, 2010. LLNL-JRNL-426611. 36 pages.
Canada, K.A. et al., "Directed Evolution of Toluene Ortho-Monooxygenase for Enhanced 1-Naphthol Synthesis and Chlorinated Ethene Degradation", *Journal of Bacteriology*, vol. 184, No. 2, pp. 344-349, (2002).
Carpenter, et al., "A multidomain outer membrane protein from Pasteurella multocida: modelling and simulation studies of PmOmpA", Biochim Biophys Acta. Nov. 2007; 1768(11):2831-40.
Carpenter, et al., "A Role for Loop-F in Modulating GABA Binding Affinity in the GABAA-Receptor", J Mol Biol, 2012, 422(2):310-23.
Carpenter, et al., "Identification of a Possible Secondary Picrotoxin-Binding Site on the GABAA Receptor", Chem Res Toxicol, 2013, 26(10:p. 1444-54.
Carpenter, et al., "Prediction of blood-brain barrier permeability from molecular dynamics simulations", Biophys J, 2014. 83a.

(Continued)

*Primary Examiner* — Karen Cochrane Carlson
(74) *Attorney, Agent, or Firm* — Steinfl Bruno LLP

(57) ABSTRACT

Engineered microcompartment proteins, and related engineered microcompartment, vectors, cells compositions, methods and systems configured to provide within a cell one or more proteins non-native to the cell are described, wherein the one or more proteins non-native to the cell are contained in at least one engineered microcompartment within the cell.

31 Claims, 49 Drawing Sheets
Specification includes a Sequence Listing.

(56) References Cited

OTHER PUBLICATIONS

Carpenter, et al., "Self-Assembly of a Simple Membrane Protein: Coarse Grain Molecular Dynamics Simulations of the Influenza M2 Channel", Biophys J, 2008. 95(8): p. 3790-801.
Cassidy-Amstutz, C., et al., "Identification of a minimal peptide tag for in vivo and in vitro loading of encapsulin", Biochemistry, 2016. 55(24): p. 3461-3468. 8 pages.
Chiu, W.A. et al., "Human Health Effects of Trichloroethylene: Key Findings and Scientific Issues", *Environmental Health Perspectives*, vol. 121, No. 3, pp. 303-311, (2013).
Cho, et al., "Purification of a polyhydroxybutyrate synthase from its native organism, Ralstonia eutropha: implications in the initiation and elongation of polymer formation in vivo", Biochemistry 51, 2276-2288, 2012. 30 pages/.
Choudhary, S. et al. "Engineered Protein Nano-Compartments for Targeted Enzyme Localization" PLoS ONE, Mar. 2012, vol. 7, No. 3, 11 pages.
Chung, B. et al. "Crystal Structure of MraY, an Essential Membrane Enzyme for Bacterial Cell Wall Synthesis" Science, Aug. 30, 2013, 1012-1016, Author Manuscript, 9 pages.
Cordova, et al., "The Nrf2-Keap1 pathway is an early responsive gene network in arsenic exposed lymphoblastoid cells", 2014, vol. 9, Issue 2, e88069, PloS One. 11 pages.
Cotruvo Jr., J.A. et al., "Metallation and Mismetallation of Iron and Manganese Proteins In Vitro and In Vivo: The Class I Ribonucleotide Reductases as a Case Study", *Metallomics*4(10), pp. 1020-1036, (2012), 32 pages.
Darkoh, C., et al., "Toxin Synthesis by Clostridium difficile is Regulated through Quorum Signaling", Mbio, 2015. 6(2). e02569-14. 10 pages.
Davis, et al., "Design, construction and characterization of a set of insulated bacterial promoters", Nucleic Acids Res, 2011. 39(3): p. 1131-41.
De Lorenzo, V., "Systems Biology Approaches to Bioremediation", *Current Opinion in Biotechnology*, 19, pp. 579-589,(2008).
Doherty, et al., "Overproduction of the toxic protein, bovine pancreatic DNaseI, in *Escherichia coli* using a tightly controlled T7-promoter-based vector", Gene, 1993. 136(1): p. 337-340.
Dong, et al., "Gratuitous overexpression of genes in *Escherichia coli* leads to growth inhibition and ribosome destruction", Journal of bacteriology, 1995. 177(6): p. 1497-1504.
Durand, S., et al., "Activation of RegB endoribonuclease by S1 ribosomal protein requires an 11 nt conserved sequence", Nucleic Acids Res, 2006. 34(22): p. 6549-60.
Eddy, S.R., Where did the BLOSUM62 alignment score matrix come from? Nature Biotechnology, 2004. 22(8): p. 1035-1036.
Eisenberg, S. et al., "PhiX174 Cistron A Protein is a Multifunctional Enzyme in DNA Replication", *Proc. Natl. Acad. Sci. USA*, vol. 74, No. 8, pp. 3198-3202, (1977).
Fan, C.G., et al., "Short N-terminal sequences package proteins into bacterial Microcompartments". Proceedings of the National Academy of Sciences of the United States of America, 2010. 107(16): p. 7509-7514.
Fujitani, S., et al., "Pneumonia Due to Pseudomonas aeruginosa Part I: Epidemiology, Clinical Diagnosis, and Source", Chest, 2011 139(4), 909-919.
Gao, et al., "Characterization of de novo synthesized GPCRs supported in nanoliproprotein discs", (2012) PloS One 7(9):e44911. 8 pages.
Gao, et al., "Characterizing diffusion dynamics of a membrane protein associated with nanolipoproteins using fluorescence correlation spectroscopy", Protein Science, 20, 437-47. (2011).
Gaspar, D. et al. "From antimicrobial to anticancer peptides. A review", Frontiers in Microbiology, Oct. 2013, vol. 4, Article 294, 16 pages.
Giacalone, M.J. et al., "Toxic Protein Expression in *Escherichia coli* using a Rhamnose-Based Tightly Regulated and Tunable Promoter System", *Biotechniques*, vol. 40, No. 3, pp. 355-363, (2006).
Gupta, et al., "Genetically programmable pathogen sense and destroy", ACS Synth Biol, 2013. 2(12): p. 715-23.
Harmon, Kozina, Maar, Carpenter, Branda, Negrete, and Carson, "Identification of critical amino acids within the nucleoprotein of Tacaribe virus important for anti-interferon activity", J Biol Chem, 2013, 288(12):p. 8702-11.
Harrison, J.J., et al., "Microtiter susceptibility testing of microbes growing on peg lids: a miniaturized biofilm model for high-throughput screening", Nat Protoc, 2010. 5(7): p. 1236-54.
Hazen, T. C. et al., "Complexity of Groundwater Contaminants at DOE Sites", *REP LBNL-4 I I 7E*, Berkeley, CA 94720, (2008), 58 pages.
He, et al., "Controlling the Diameter, Monodispersity and Solubility of ApoA1 Nanolipoprotein Particles using Telodendrime Chemistry", (2013), Protein Science 22, 1078-1086.
Hoskin, D. et al. "Studies on Anticancer Activities of Antimicrobial Peptides", Biochim. Biophys. Acta., Feb. 2008, 1778 (2), 357-375. Author Manuscript, 32 pages.
Hwang, I.Y., et al., "Reprogramming Microbes to Be Pathogen-Seeking Killers", ACS Synth Biol, 2014. 3(4): p. 228-237.
Johnson, et al., "Hidden Markov model speed heuristic and iterative HMM search procedure", BMC Bioinformatics, 2010. 11(431) 8 pages.
Keasling, J.D. "Synthetic Biology and the Development of Tools for Metabolic Engineering", *Metabolic Engineering*14, pp. 189-195, (2012).
Kerfeld, et al., "Bacterial microcompartments", Nature Reviews, 1-14. 2018.
Khalid, et al., "OmpA: Gating and dynamics via molecular dynamics simulations", Biochim Biophys Acta, 2008. 1778(9): p. 1871-80.
Khnouf, et al., "Cell-Free Expression of Soluble and Membrane Proteins in an Array Device for Drug Screening", Analytical Chemistry, 82(16),7021-7026, Aug. 15, 2010.
Kim, et al., "A rapid flow cytometry assay for the relative quantification of protein encapsulation into bacterial microcompartments", Biotechnol. J., 2014, 9, 348-354, DOI 10.1002/biot. 201300391.
Kim, et al., "Nanosensor dosimetry of mouse blood proteins after exposure to ionizing radiation", (2013) Nature/Scientific Reports, 19:2234. 8 pages.
Klingelhoefer, et al., "Peptide Nanopores and Lipid Bilayers: Interactions by Coarse-Grained Molecular Dynamics Simulations",Biophys J, 2009. 96(9): p. 3519-28.
Korendovych, et al., "Anion and carboxylic acid binding to monotopic and ditopic amidopryidine macrocycles", J. Org. Chem., 73, 4771-4782, 2008.
Korendovych, et al., "Anion binding to monotopic and ditopic macrocyclic amides", Org. Lett. 8, 15, 3171-3174, 2006.
Krizsan, A., et al., "Short Proline-Rich Antimicrobial Peptides Inhibit Either the Bacterial 70S Ribosome or the Assembly of its Large 50S Subunit". Chembiochem, 2015. 16(16): p. 2304-2308. 5 pages.
Krom, R.J., et al., "Engineered Phagemids for Nonlytic, Targeted Antibacterial Therapies", Nano Lett, 2015. 15(7): p. 4808-13.
Krumme, M.L. et al., "Degradation of Trichloroethylene by Pseudomonas Cepacia G4 and the Constitutive Mutant Strain G4 5223 PRI in Aquifer Microcosms", *Applied and Environmental Microbiology*, vol. 59, No. 8, pp. 2746-2749, (1993).
La Vallie, et al., "Enzymatic and chemical cleavage of fusion proteins", Curr Protoc Mol Biol, 1994, Chapter 16, Unit16.4B. 14 pages.
Lau, Y.H., et al., "Prokaryotic nanocompartments form synthetic organelles in a Eukaryote". Nature Communications, 9:1311. bioRxiv, 2018. 7 pages.
Lawrence, et al., (2014) ACS Synth Biol., vol. 3 (7), pp. 454-465. 24 pages.
Lee, M.J., et al., "Employing bacterial microcompartment technology to engineer a shell-free enzyme-aggregate for enhanced 1,2-propanediol production in *Escherichia coli*". Metabolic Engineering, 2016. 36: p. 48-56. 9 pages.
Li, et al., "Apidaecin-type peptides: biodiversity,structure-function relationships and mode of action", Peptides, 2006. 27(9): p. 2350-9.

(56) References Cited

OTHER PUBLICATIONS

Ly, S. et al. "Quantifying Interactions of a Membrane Protein Embedded in a Lipid Nanodisc using Fluorescence Correlation Spectroscopy", Biophysical Journal, vol. 106, L05-L08, Jan. 2014.
Ly, S. et al. "Quantifying Membrane Protein Interactions in Solution using Fluorescence Correlation Spectroscopy" Biophysical Journal, Aug. 15, 2013, 11 pages. LLNL-JRNL-642412.
Mamat, U., et al., "Detoxifying *Escherichia coli* for endotoxin-free production of recombinant proteins", Microbial Cell Factories, 2015. 14: p. 57. 15 pages.
Marr, et al., "Antibacterial peptides for therapeutic use: obstacles and realistic outlook", Current Opinion in Pharmacology, 2006. 6(5): p. 468-472.
McGinness, et al., "Engineering controllable protein degradation", Mol Cell, 2006. 22(5): p. 701-7. 7 pages.
Menzella, H.G., "Comparison of two codon optimization strategies to enhance recombinant protein production in *Escherichia coli*", Microbial cell factories, 2011. 10(1): p. 1. 8 pages.
Merritt, et al., "Growing and analyzing static biofilms", Curr Protoc Microbiol, 2005. Chapter 1: p. Unit 1B 1. Author manuscript. 29 pages.
Moon, H., et al., "Developing genetically engineered encapsulin protein cage nanoparticles as a targeted delivery nanoplatform", Biomacromolecules, 2014. 15(10): p. 3794-3801.
Morono, Y. et al., "Addition of Aromatic Substrates Restores Trichloroethylene Degradation Activity in Pseudomonas Putida FI", *Applied and Environmental Microbiology*, vol. 70, No. 5, pp. 2830-2835, (2004).
Newman, "Purification and Characterization of Toluene 2-Monooxygenas from Burkholderia cepacian G4", Biochemistry 1995, 34, 14066-14076.
Nguyen, et al. "The expanding scope of antimicrobial peptide structures and their modes of action" *Trends in Biotechnology*, Sep. 2011, vol. 29, No. 9, pp. 464-472.
Nichols, R.J., et al., "Encapsulins: molecular biology of the shell", Crit Rev Biochem Mol Biol, 2017, 52, 1-12.
Non-Final Office Action for U.S. Appl. No. 15/178,454, filed Jun. 9, 2016 on behalf of Lawrence Livermore National Security, LLC. dated Jan. 22, 2018. 14 pages.
Notice of Allowance for U.S. Appl. No. 15/178,454, filed Jun. 9, 2016 on behalf of Lawrence Livermore National Security, LLC. dated Aug. 14, 2018. 9 pages.
Parachin, et al., "Expression systems for heterologous production of antimicrobial peptides", Peptides, 2012. 38(2), 446-56.
Parsons, J. et al. "Synthesis of Empty Bacterial Microcompartments, Directed Organelle Protein Incorporation, and Evidence of Filament-Associated Organelle Movement", Molecular Cell, Apr. 2010, vol. 38, pp. 305-315.
Pearson, et al., "Searching protein sequence libraries: comparison of the sensitivity and selectivity of the Smith-Waterman and FASTA algorithms", Genomics, 1991. 11(3): 635-650. pp. 16.
Pieper, "Aerobic degradation of polychlorinated biphenyls", Appl. Microbiol. Biotechnol., 2005, 67:170-191, DOI 10.1007/s00253-004-1810-4.
Purnick, et al., "The second wave of synthetic biology: from modules to systems", Nat Rev Mol Cell Biol, 2009. 10(6): p. 410-22.
Quin, M.B. et al., "Designer Microbes for Biosynthesis", *Curr Opin Biotechnol.*, pp. 55-61, (2014), 14 pages.
Reddy, et al., (2004) "Antimicrobial peptides: premises and promises". International Journal of Antimicrobial Agents, vol. 24, pp. 536-547. (Year: 2004).
Rhodius, et al., "Design of orthogonal genetic switches based on a crosstalk map of sigmas, anti-sigmas, and promoters", Mol Syst Biol, 2013. 9: p. 702. 13 pages.
Riley, R. G. et al., "Chemical Contaminants on DOE lands and Selection of Contaminant Mixtures for Subsurface Science Research", *REP DOE/ER-0547t*, Washington, D.C.,(1992), 80 pages.

Rouse, et al., "Simulations of the BM2 proton channel transmembrane domain from influenza virus B", Biochemistry, 2009, 48(42): p. 9949-51.
Rui, L.Y. et al., "Metabolic Pathway Engineering to Enhance Aerobic Degradation of Chlorinated Ethenes and to Reduce their Toxicity by Cloning a Novel Glutathione S-Transferase. An Evolved Toluene O-Monooxygenase, and Gamma-Glutamylcysteine Synthetase", *Environmental Microbiology*, 6(5), pp. 491-500, (2004).
Rutherford, et al., "Bacterial quorum sensing: its role in virulence and possibilities for its control", Cold Spring Harb Perspect Med, 2012. 2(11). 26 pages.
Saeidi, N., et al., "Engineering microbes to sense and eradicate Pseudomonas aeruginosa, a human pathogen", Mol Syst Biol, 2011.7: p. 521. 11 pages.
Salis, et al., "Automated design of synthetic ribosome binding sites to precisley control protein expression", Nat Biotechnol, 2009. 27(10): p. 946-50.
Sargent, F., et al., "A synthetic system for expression of components of a bacterial Microcompartment", Microbiology-Sgm, 2013. 159: p. 2427-2436.
Schechter, et al., "On the active site of proteases. 3. Mapping the active site of papain; specific peptide inhibitors of papain", Biochem Biophys Res Commun., 1968 32(5): p. 898-902.
Schechter, et al., "On the size of the active site in proteases. I. Papain", Biochem Biophys Res Commun., 1967. 27(2): p. 157-162.
Schmelcher, et al., "Bacteriophage endolysins as novel antimicrobials", Future microbiology, 2012, 7(10), 1147-1171.
Scott, et al., "Biological properties of structurally related alpha-helical cationic antimicrobial peptides", Infect Immun, 1999, 67(4). 2005-2009.
Shaner, et al., "A guide to choosing fluorescent proteins", Nat Methods, 2005. 2(12): p. 905-9.
Sinha, et al., "The PduM Protein is a structural component of the microcompartments involved in coenzyme B-12-Dependent 1,2-Propanediol Degradation by *Salmonella enterica*", Journal of Bacteriology, 2012, 194(8), 1912-1918.
Smith, et al., "Identification of common molecular subsequences", J Mol Biol, 1981. 147(1): 195-197. p. 3.
Sun, AK. et al., "Trichloroethylene Degradation and Mineralization by Pseudomonads and Methylosinus Trichosporium OB3b", *Appl Microbial Biotechnol.*, 45, pp. 248-256, (1996).
Sutter, M., et al., "Structural basis of enzyme encapsulation into a bacterial nanocompartment". Nature Structural & Molecular Biology, 2008. 15(9): p. 939-947.
Van De Loosdrecht, A.A, et al., "A tetrazolium-based colorimetric MTT assay to quantitate human monocyte mediated cytotoxicity against leukemic cells from cell lines and patients with acute myeloid leukemia", J Immunol Methods, 1994. 174(1-2): p. 311-20.
Van Hylckama Vlieg, J.E. et al., "Formation and Detoxification of Reactive Intermediates in the Metabolism of Chlorinated Ethenes", *Journal of Biotechnology*85, pp. 81-102, (2001).
Volzing, et al., Antimicrobial peptides targeting Gram-negative pathogens, produced and delivered by lactic acid bacteria. ACS Synth Biol, 2013. 2(11): p. 643-50.
Wang, et al., "APD3: the antimicrobial peptide database as a tool for research and education", Nucleic Acids Res, 2016, 44(D1), D1087-D1093.
Whitchurch, C.B., et al., "Extracellular DNA required for bacterial biofilm Formation", Science, 2002. 295(5559): p. 1487.
Wolfe, M.S., "Intramembrane-cleaving proteases", Journal of Biological Chemistry, 2009, 284(21), 13969-13973.
Wong, et al., "Aliginate Lyase: Review of Major Sources and Enzyme Characteristics, Structure-Function Analysis, Biological Roles, and Applications", Annu Rev Microbiol, 2000, 54:289-340.
Wood, T.K., "Molecular Approaches in Bioremediation", *Current Opinion in Biotechnology*, 19, pp. 572-578, (2008).
Worsdofer, et al., "Directed evolution of a protein container", Science, 2011, 331(6017), 589-592.
Wyrobek, et al., "Low dose radiation response curves, networks and pathways in human lympblastoid cells from 1 to 10 cGy of active gamma radiation", Mutation Research 722 (2011), 119-130.

(56) References Cited

OTHER PUBLICATIONS

Yeager, C.M. et al., "Cytotoxicity Associated with Trichloroethylene Oxidation in Burkholderia Cepaci G4", *Applied and Environmental Microbiology*, vol. 67, No. 5, pp. 2107-2115, (2001).

Yeates, et al., "Bacterial microcompartment organelles: protein shell structure and evolution", Annu Rev Biophys, 2010, 39, 185-205.

Yeates, T. et al. "Protein-based organelles in bacteria: carboxysomes and related microcompartments" Nature Reviews: Microbiology, Sep. 2008, vol. 6, pp. 681-691.

Young, C. et al. "Recombinant protein expression and purification: A comprehensive review of affinity tags and microbial applications" Biotechnology Journal, 2012, vol. 7, pp. 620-634.

Yung, et al., "Biomineralization of uranium by PhoY phosphatase activity aids cell survival in Caulobacter crescentus", Appl. Environ. Microbiol., Mar. 26, 2014. LLNL-JRNL-652320. 36 pages.

Yung, et al., "Re-directing bacterial microcompartment systems to enhance recombinant expression of lysis protein E from bacteriophage ϕX174 in *Escherichia coli*", Microb Cell Fact, 2017. 16(1) 17 pages.

Yung, et al., "Shotgun proteomic analysis unveils survival and detoxification strategies by Caulobacter crescentus during exposure to uranium, chromium, and cadmium", J. Proteame Res., ASAP. (http://pubs.acs.org/doi/full/10.1021/pr400880s), 2014. 15 pages.

Yung, et al., 2015 SEED Poster Draft Engineering Bacterial MicroCompartments (BMCSs) to Shield Toxicity during Protein Expression and Purification.

Zhang, et al., "Antimicrobial peptide therapeutics for cystic fibrosis", Antimicrob Agents Chemother, 2005, 49(7),2921-7.

Zhang, et al., "Extracellular accumulation of recombinant proteins fused to the carrier protein YebF in *Escherichia coli*", Nat Biotechnol, 2006. 24(1): p. 100-4.

Zhao, et al., "The GABAA Receptor Target of Tetramethylenedisulfotetramine", PNAS, 2014. vol. 111, No. 23, 8607-8612.

Zylstra, G.J. et al., "Trichloroethylene Degradation by *Escherichia coli* Containing the Cloned Pseudomonas Putida FI Toluene Dioxygenase Genes", *Applied and Environmental Microbiology*, vol. 55, No. 12, pp. 3162-3166, (1989).

Newman L. M. et al., "Trichloroethylene oxidation by purified toluene 2-monooxygenase: products, kinetics, and turnover-dependent inactivation." *J. Bacteriol.* vol. 179, No. 1, 90-96 (Jan. 1997).

* cited by examiner

FIG. 2

```
T.mar    2  EFLKRSFAPLTEKQWQEIDNRAREIFKTQLYGRKFVDVEGPYGWEYAAHPLGEVEVLS--  59
            +FL + PL E++W ++    ++ + L GR+ +D+ GP G      P  E + +S M.xan    3  DFLGHAENPLREEEWARLNETVIQVARRSLVGRRILDIYGPLGAGVQTVPYDEFQGVSPG  62

T.mar   60  --------DENEVVKWGLR--KSLPLIELRATFTLDLWELDNLERGKPNVDLSSLEETVRK  110
                    E  +V    R   K++P+I    F L   +++       +D+S+

M.xan   63  AVDIVGEQETAMVFTDARKFKTIPII--YKDFLLHWRDIEAARTHNMPLDVSAAAGAAAL  120

T.mar  111  VAEFEDEVIFRGCEKSGVKGLLSFEER-KIECG--STPKDLLEAIVRALSIFSKDGIEGP  167
            A+  EDE+IF G  + G +GL++    R  +  G   ++P    +AIV A    ++ G  GP M.xan  121  CAQQEDELIFYGDARLGYEGLMTANGRLTVPLGDWTSPGGGFQAIVEATRKLNEQGHFGP  180

T.mar  168  YTLVINTDRW--INFLKEEAGHYPLEKRVEECLRGGKIITTPRIEDALVVSERGGDFKLI  225
            Y +V++   +  ++ + E+ G   +E   +     G       R E  +VVS    +  L M.xan  181  YAVVLSPRLYSQLHRIYEKTGVLEIETIRQLASDGVYQSNRLRGESGVVVSTGRENMDLA  240

T.mar  226  LGQDLSIGYEDREKDAVRLFITETFTFQVVNPEALILLK        264
            +  D+   Y   +        + E     ++ +P+A+  L+

M.xan  241  VSMDMVAAYLGASRMNHPFRVLEALLLRIKHPDAICTLE        279
```

FIG. 3

```
MDNLKRELAPL TEEAWAEIDEE ARETAKRHLAG RRVVDVEGPLG WGYSAVPLGRL EEIEGPAEGVQ
AGVRQVLPLPE LRVPFTLSRRD LDAVERGAKDL DLSPVAEAARK LARAEDRLIFN GYAEAGIEGLL
NASGnLKLPLS ADPGDIPDAIA EALTKLREAGV EGPYALVLSPD LYTALFRVYDG tGYPEIEHIKE
LVDGGVIWAPA LDGgAVLVSTR GGDFDLTLGQD LSIGYLSHDAD NVELFLTESFT
```

Single underline = P-domain

*Italic* = E-loop

Double underline = A-domain

FIG. 4A

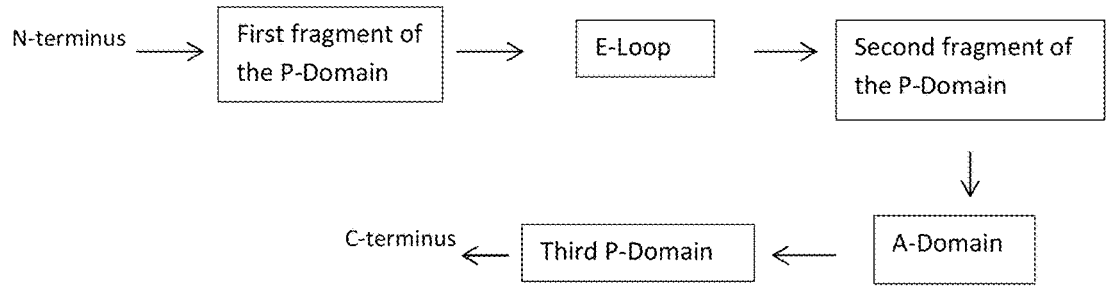

FIG. 4B

MEFLKRSFAP LTEKQWQEID NRAREIFKTQ LYGRKFVDVE GPYGWE*YAAH* 50

*PLGEVEVLSD ENEVVKWGLR KSLP*LIELRA TFTLDLWELD NLERGKPNVD 100

LSSLEETVRK VAEFEDEVIF RGCEKSGVKG LLSFEERKIE CGSTPKDLLE 150

AIVRALSIFS KDGIEGPYTL VINTDRWINF LKEEAGHYPL EKRVEECLRG 200

GKIITTPRIE DALVVSERGG DFKLILGQDL SIGYEDREKD AVRLFITETF 250

TFQVVNPEAL ILLKFSGGS

Single underline = P domain
*Italic* = E loop
double underline = A domain

```
                    90        100       110       120       130       140       150       160
              ....*....|....*....|....*....|....*....|....*....|....*....|....*....|....*....|
CONSENSUS      65 --V-QA-GVRQVLPLPELRVPFTLSRRDLDAVERGAKDLDLSPVAEAARKLARAEDRLIFNGYAEAGIEGllnasgnlkl 140
3DKY_E         65 ---V-KW-GLRKSLPLIELRATFTLDLWELDNLERGKPNVDLSSLEETVRKVAEFEDEVIFRGCEKSGVKGllsfee-rki 139
GI 122304915   73 ATV-FT-DVRKFKTIPIIYKDFLLHWRDIEAARIHNMPLDVSAAAGAAALCAQQEDELIFYGDPKLGHEGlmtatdrltv 150
GI 123527077   69 AVV-TV-RKRAVQPLIELCVPFTLKRAELEAIARGASDADLDPVIEAARAIAIAEDRAVFHGFAAGGITGigeasaehal 146
GI 123044215   66 --V-QA-RVRQVQPVIELRVGFTLDRAELADADRGADDLDLAPLEEAVRRIAVTENSVVFHGYQEAGLVGitqasshpql 141
GI 123046337   68 ---I-RA-QQRQVNFLVELRFPFTLSRAEVDDVARGSLDSDWQPVKDAAKAVAFAEDQSIFQGFDEAGIRGlgpssdnpvl 143
GI 81373191    65 ---V-QA-RQRVVAFLVELRVPFTLSREELDNVERGAKDTDLDAVKEAARRIAFAEDRAIFEGYPAAGITGiraaqsnapi 140
GI 81833634    65 ---A-SV-GVRMNTEVIELKIPFSFPESEVEAILREANAFDISSIEKAAKKVCVAENELVFYGLKKEGIEGlipsiphkpi 140
GI 74556699   156 ---I-QS-KSASLYEVPLINSQVKFYLGQKSDSRR--------TAVLAGKSFAKMENYLLLKNHP------lsplkiqlki 217
GI 81347829    72 SLS-EP-ARRVHLTIPLLYKDFILYWRDIEQAKQLGSPIDFSAAANAAQQCALLEDDLIFNGSTEFDVPGimnvkgkiah 149
GI 81344013    75 EPV-RT-GERKHVPVPTLYKDFVISWRDLEHWRQFNLPVDTTGVAAAASSLAVAEDKLILFGNQEMGIEGfltakgtlre 152
GI 123497228   67 DET-HV-HVPSVRALPVLHRTFRLGARAVEALERRGEPLTLTEAAEAARRIARAEDRLLFEGHAGAGVRGllehpglvev 144
GI 501179632   65 ---I-RA-VRRNVLFLVELRVPFTLARDAIDDVERGAGDSDWQPLKDAAKKIAFAEDRAVFDGYAAAGILGlregtsnpkl 140
GI 502293893   65 ---I-RS-LLREAQFLVELRVPFTLTRQAIDDVERGSEDSDWQPLKDAARMLAFAEDRAVFEGYAAAGIGGigkgssnaav 140
GI 501012501   65 --V-CT-GMYQVKFLVEARISFKLDRWEMDNLIRGAKDIKLDALEEAAEKMAIFEENMLYNGYKPGDIEGlieasshkls 140
GI 506340687   66 ---I-TY-GLHQVKFLVEVKVPFTLDIAEIDNAARGGKDIDLAALDEAAEKLARFEEEALYHGFAPAGIKGlsevssqtrl 141
GI 502591318   65 --V-DM-KLRQVQFLAEVRVPFTLDVTELDSVARGATNPDLDDVARAAERMVEAEDSAIFHGWAQAGIKGivdstpheal 140
GI 501194893   68 --V-SA-GVRLVRFLVEFRAPIRLELAELDAVGRGAQEPNIEDVVRAAEHAARFEDGAIFNGLAAAGIEGilevaphkpv 143
GI 490598858   65 ---I-SVIRGRTYRHIPLINEDFSLLWRDLEFSEQMGLPVDLSSASRAATQCALREDKLIFYGNDELGYKGlltedgivkf 141
GI 752720587   67 --V-KA-GLHQVKFLVELPEDFTLLDRWELDNIERGAQDIDLEPLEDAARKIALFEENAIYHGHNDGQIPGlktvltqdli 142
GI 501771872   65 ---A-SI-FQRQVLFLVEVEIPFRLHLEELEAFVRGAEDVNIDNLLESANELARIENKAIFFGMDSAGISGlvnssqq--- 137
GI 501163578   65 ---L-GW-GIRQVLPIVEIRNPFVLKQWELDNIERGLKTPDLEGLETAAKQLASFENKLILKGIEKANIIGlqtlakqnsv 140
GI 501434203   72 GVV-KV-KERKILPLPIIYKDFKIHWRDVESSKKFNIPIDFSVAAAAASQVAIAEDRLIFHGDIETGFPGllnvegknsi 149
GI 501367709   65 --V-EA-LQRHVVKVLERAPFTLKRSDIDDVERGAADPDWQPVKDAAVALASAEDRTVFYGSDSAGIQGiapasdnerl 140
GI 505232787   72 GIA-KI-RSRKFLPIPQIYKDFKIHWRDIETSRKLNIPLDVSVVALATREVALAEDRFIFHGDSEIGYPGllnvegrsii 149
GI 501923113   66 --V-KT-SGRKSVELPQIYQDFTLLWRDLENNISNKLPLDLSIVSQAAQTLANKEDNLIFNGNDFLELKGilnaegaqkl 141
GI 502776253   66 --V-VY-GVNTVLFLVEARINFSLDIWELDNIDRGARDIALDDLAEAARKMADFEENAVYNGFKDSGIVGlnqvaaknri 141
GI 502633921   66 ---V-PF-GVRQFQFMIETRVSFEISIWDLDDISRGAVDVDLSSLEDAARKMAEFEERAIYHGLDEGCIEGivksagytae 141
GI 496662878   65 -IGRI-VGRTQLELPLFYEDFTLLSRDMEYAAQTGYPLDLSVAIAAAKKASRREDDLILNGSKALGTDGlltvkgsski 141
GI 500836508   63 -------V-FSNKTLPLFYIHKTFNISKRDIASYEREGVTLDLKNLITAVRECATIEDRLIFEGINS---HGlvsapqtism 133
GI 501047338   65 ---A-HV-HVFRVRFLPVIHRTFALGARALEADAACGEPLVLSEASEAARQIARAEDRIVFEGLPRAGVSGlqhegavel 140
4PT2_P         73 AMV-FT-DARKFKTIPIIYKDFLLHWRDIEAARTHNMPLDVSAAAGAAALCAQQEDELIFYGDARLGYEGlmtangrltv 150
GI 501055150   63 ------I-SASVSLPLSLIRTEFSLGKRDLAAYERDHLILDTAPVACAAMDAAAKEDRIIFNGL--AGTPGllnaegagsl 134
GI 501691096   66 --------RSGFAEVDLIQTSFSLSKRDLAAYERDGMLPNTSAVAVAAIEAARQEDAVIFTGTD--QVKGlmntggsqsv 135
GI 494995233   72 EMT-QF-SRRVSMTIPILYKDFMLYWRDVAQARTLGMPLDMSAAANAAAGGALMEDDLIFNGAAEFDLPGlmnvkgrlth 149
GI 501364857   65 --V-IA-HLRASKPLVRLRVPFTLSRNEIDDVERGSQDSDWDPVKAAAKQLAFVEDRTIFEGYGAASIEGirsssnppl 140
GI 502892820   65 --V-QA-HLRDSRPLVRLRVPFTLSRKAIDSVERGAQDADWDPVKDAARSLAYAEDRAIFEGYPDASIPGirttaagsdl 140
GI 527109103   65 --V-IA-HARQSQFVIELRVPFTVSRQAIDDVERGAKDSDWQPVKDAAKQIAFAEDRAIFEGYPAASITGvrasqsnpel 140
GI 501346422   65 --V-AA-RARTSTFVIEWRVPFTLSRDAVDDVERGSADSDWQPVKDAARTCAFAEDMAIIDGYGAAGITGlrdqsshdpl 140
GI 501373147   65 --V-IA-KLSEVKALVQLTVPFTLSRDAIDAVERGANDSDWQAAKDAAKELAYAEDRAIFDGYKAAGIVGiregssntsl 140
GI 501587999   65 --V-LA-RQREVKFLVELRVPFELSRAAIDDVERGADDSDWQPAKDAAKTIAFAEDRAIFDGYADAAITGvrqqtsnpim 140
GI 500074236   65 --V-ES-HRREVNPLLELRVPFTLTRAAIDDVARGSNDSDWQPLKDAARKIALAEDRLVFLGHGDAGIRGilpetsnpiv 140
GI 501827525   65 --V-QT-ALREVKFLVELRVPFKLTRQAIDDVERGAEDSDWSPVKDAARKIAFAEDRSVFDGYAAAGIQGiregssnpil 140
GI 521295581   66 --V-RA-RLREVLPVMELRAAFSIDRGELDAIDRGADDIDLSALEEAARRVATTENSVVFHGYAEAGIIGiteasshpvl 141
```

FIG. 6 (continued)

```
                        170       180       190       200       210       220       230       240
                   ....*....|....*....|....*....|....*....|....*....|....*....|....*....|....*....|
CONSENSUS      141 pls---a--dpgdipdaiaeealtklreagvegpyalvlspdlytalfrvydgtgypeiehik-el-v-d-ggviwapal-d 211
3DKT_E         140 ecg---s--tpkdlleaivralsifskdgiegpytlvintdrwinflkeeag-hyplekrve-ec-lrg-gkiittpri-e 210
GI 122304915   151 plgdwa--tpgagyvaiveatrklnehghygpyavvlsprlysllhrifektgvleietir-ql-a-s-dgvfqsnrl-r 223
GI 123527077   147 dlp---a--dladfpgvlvralavlrdrgvdgpyalvlgrtvyqqlmetttpggypvlqhvr-rl-f-e-gpliwapgv-d 217
GI 123044215   142 tle---a--gtdtyprtvakavallrragiagpyalalepdsytavietaehggyllithlq-hi-l-d-gpvvqapgv-t 212
GI 123046337   144 slp---e--dpllipdavasalsalrlagvegpysvvldadaytavsetrde-ghpvfhhlr-dl-v-a-gdiiwapai-s 213
GI 81373191    141 tvp---d--darlvpeaitqaltalrlagvdgpysvllsaelytevsetsdh-gypirthie-rl-ipd-geiiwapai-d 211
GI 81833634    141 k-----a--kgdeilpavaegikelvnseiegpyalliqpqyfgklfgvagnsgypltlkla-el-lqg-nniivapal-k 210
GI 74556699    218 tgsdwn--vagnilldvlrayenltregfgkdvyilmsslnysktfrvvdrsgtyeiemik-ei-----gnvvptdiv-s 288
GI 81347829    150 irsdwm--ksgnaftdvvearnkllqlghtgpyalvlspelyalihrvhegthvleiehir-el-m-t-agiyqtpvi-k 222
GI 81344013    153 elsdwe--kvgnafqdvvkgisrlvekgfytnyylivnpkryfllnrihdntgllelegik-kv-v---kevyqtpii-p 224
GI 123497228   145 pagdwa--dpgragdallaaltalddagrhgpyaaavsparfyqlfrpfagtaltpyqqll-pa-f-e-ggivkapgl-r 217
GI 501179632   141 alp---s--sasdypaaiaaalnqlrlagvngpyavvlgagvytalsgg-ddegypvfrhie-sl-i-d-gkivwapai-e 210
GI 502293893   141 plp---a--tlddypeavaralndlklagcngpyvlvlggdvyraasggnee-gypifhhle-ri-v-d-ggviwapai-a 210
GI 501012501   141 qfg---n--ngeeimenlaqgmillkeayvdqpvtlvvgidawkrinremq--ghplinriq-el-t-g-skviyspvv-e 209
GI 506340687   142 qvs---s--npediaekvskaltalrktsvegpyalvvgpelwvalsghvr--gyplsqyle-tm-l-g-gqvivspfi-e 210
GI 502591318   141 av----a--svsdfpravlsaadtlrkagvtgpyalvlgpkayddlfaatqd-gypvakqvq-rlvv-d-gplvranal-a 210
GI 501194893   144 vip---a---peawpravaearevlraagvdgpyalalgpkaydelaaaaed-gyplrkhiegql-i-d-gpivwapal-e 213
GI 490598858   142 pis---nwsegenpfkdisiglakfiengivgrkalvvspnlfvqlrriqpgtgtteydrin-kl-l-d-gnifstpvl-k 214
GI 752720587   143 plg---n--tgseimesitrgiitlrkayisqnmtlivgeeawrkinkems--geplierih-el-t-g-skvvispiv-d 211
GI 501771872   138 tld---t--patglissvaeginnlvkagvngpytlllgpelyhslytrndr-gyplekris-di-i-g-gdilftpdl-e 207
GI 501163578   141 essk--s--slkdfvkslfevkkrfmeqgiegpytlvinkelwqdlftm---nlsypldlvvk-ei-i-d-akvkpmhev-d 210
GI 501434203   150 sisdwn--qtgeafkdilnaivklnengfynnfalvlnpqdyamlnrlygnsgileidqik-kl-f-d-vgvfttpvi-p 222
GI 501367709   141 slp---g--dvrefpnavakaktelrlagvagpynlllpaelytevtettdh-gypvhehvs-ri-l-gegsiiwapal-d 211
GI 505232787   150 knk---nfdeeggifktalacvetlvekgfsknlayilnpkdytkafriygnsgvleithik-el-f-d-vgvftshav-d 222
GI 501923113   142 qis---dwgqgenpytdivkainmirekgivgrfvlclsqslyfdlqriqqgtgmteaqris-sm-i---gnlynvpvi-k 213
GI 502776253   140 nmt---l--dkdnlvdaiseaqgrmrkegiasganlvwnpalwqflahvvp--ggtlgdtvr-rq-i-k-gdiiysetv-d 210
GI 502633921   142 lsv---s--kskdmimgiakgvrtmg-asvegpfalvggdklfaaidgfsep--ypmrknla-el-v-d--kviyapal-e 208
GI 496662878   142 kksdws--qgensfaditagvaqlaktgylgryalvvspdlfldlqrlqpntglleidrik-kl-i-g-dnvymtsvmgp 215
GI 500836508   134 els---dwknvgqaasdvieavtkldeagfhgpyllalspdrynllfrryesgnqteyehls-mi-i-k-g-iykapvl-k 205
GI 501047338   141 pagdws--dparvaddllgalakldeagrhgpyalavspgrfyqllrpypgtaltphqqlq-pa-f-a-ggivkapai-q 213
4PT2_P         151 plg---dwtspgggfqaiveatrklneqghfgpyavvlsprlysqlhriyektgvleietir-ql-a-s-dgvyqsnrl-r 223
GI 501055150   135 tlskwd--kvgaaadqiidavtkldeagfhgpyslalapaqynllllrrypqgdgteldhvs-si-v-g-dgvikapvl-k 207
GI 501691096   136 kla---swekigaaaddlikavtaldlagfhgpyalalsparynllfrrypqgsttelehlq-qm-i-t-dgifkapvl-k 208
GI 494995233   150 lksdwm--esgnafadiveaarnkllkmghsgpyalvvspelyslllhrvhkgtnvleiehvr-nl-v-t-dgvfqspti-k 222
GI 501364857   141 tlp---e--dpreipdvitqalselrlagvdgpysvllaadvytkvsetteh-gypirehln-rl-v-d-gdiiwapai-d 210
GI 502892820   141 klp---d--dprdipdvvsqalsdlrlagvdgpysvllsadvytrvsetsdh-gypvrehln-rl-v-d-gdiiwapai-d 210
GI 527109103   141 klp---i--dakdypeaisqaitslrlagvngpyslllnadaftainetsdh-gypirehlr-rv-l-d-geiiwapai-d 210
GI 501346422   141 plp---a--dardypvavsqavtrlrlagvdgpyrlllgadafteaaetsdh-gypvkthls-rl-v-d-deilwapav-k 210
GI 501373147   141 alp---a--dvadypnaiggalqqlrlagvdgpysvllgadaytalgeasdq-gypviehik-ri-v-n-geiiwapal-e 210
GI 501587999   141 tlp---a--dvrdypdaiahalsqlrlagvdgpyvlfgaeaytalaetsdh-gfpvlehvk-rl-v-e-dqifwapai-a 210
GI 500074236   141 alp---a--nvadypeavasavselrlagvngpyalilgttaftaanggaed-gypvlkhle-rl-v-d-vpvvwsqal-e 210
GI 501827525   141 plp---s--nvrgypdaiakavsqlrlagvngpyalvlgteaytaasggsdd-gypvfhhie-rv-v-d-ggiiwapai-e 210
GI 521295581   142 elg---a--dtdsyprtvakavallrragiggpyglaidpdgytaileatehggyllinhlk-qi-l-d-gpvvrapgv-r 212
```

FIG. 6 (continued)

```
                         250       260       270       280
                    ....*....|....*....|....*....|....*....|....
     CONSENSUS  212 -gg-avlvstrGGDFDLTLGQDLSIGYLSHDADNVELFLTESFT 253
     3DKT_E     211 -d--alvvserGGDFKLILGQDLSIGYEDREKDAVRLFITETFT 251
     GI 122304915 224 -gdsgvvvstgRENMDLTVAMDMVTAYLGASRMNHPFRVLEALI 266
     GI 123527077 218 -g--amlisqrGGDFELTVGRDFSIGYHDHDAQSVHLYLQESMT 258
     GI 123044215 213 -g--avvlslrGGDFVLESGQDLSIGYASHTADTVDLYLEESFT 253
     GI 123046337 214 -g--gyvlstrGGDNQLTLGTDLSIGYDSHTATDVTLYLEETFT 254
     GI 81373191  212 -g--afvlttrGGDYELTLGQDVSIGYLSHDADTVRLYFQQTMQ 252
     GI 81833634  211 -sg-allvslrGGDYELYSGMDIGVGYSEKKSTNHELFFFETLT 252
     GI 74556699  289 -ndeiyviskqG--FDILVFSDLNVEYLSKEKDYEVYLITEQIA 329
     GI 81347829  223 -gkrgvvidtgRQNIDLAVAVDVQTAFLDTENMNYLFRVYESVV 265
     GI 81344013  225 -edivllvsasPANFDLAIALDVNVAFVETSNMNHTFRVMEMVV 267
     GI 123497228 218 -dg-avvvvrsASGPQAVVGQELTAAYDGREGIFHLVSLAESVT 259
     GI 501179632 211 -g--gfvlstrGGDFELDIGQDFSIGYSSHSADSVELYLQESFT 251
     GI 502293893 211 -g--gfvlttrGGDFELDIGQDISIGYLSHSATTVELYLQESFT 251
     GI 501012501 210 -g--alllpydHEDLELTIGRDFSIGYEYHDAKTVQLFITESLT 250
     GI 506340687 211 -e--ayllstrGGDLEMTLGGDIAIGYASHDTEKVALFFLESFT 251
     GI 502591318 211 -g--alvmsmrGGDYELTVGQDLSIGYAFHDRSKVELFVAESFT 251
     GI 501194893 214 -g--gvllstrGGDFELTVGEDLSIGYDGHDRQVVELFLTESFT 254
     GI 490598858 215 -ddkavlvcsePQNIDLVIGQDMITSYLETKNLNHYFRIMETIL 257
     GI 752720587 212 -g--aylvpydHDDLELTIGLDFSIGYEHHDEHHVQLFITESFT 252
     GI 501771872 208 -gy-glllskrGGDFELIVGQDIAIGFSGQFGDELEFFLLESFT 249
     GI 501163578 211 -es--fvvsnrGGDFKLILGQDISLGYESKFDEQLKFFFTESLT 251
     GI 501434203 223 -qftavvvstgIENLDLFISQDMITSYLNYDNMDHYFRVFEILA 265
     GI 501367709 212 d---allvsarGGDYELHLGQDAAIGYTSHTAETVELYLRETLT 252
     GI 505232787 223 egk-tiavatgVENMDIFLVQDMISAFIDYENMDYYFRVFEILA 265
     GI 501923113 214 -gkkaalicaePQYMDLAVGIDMSTAYLEQKDLNHSFRIMETII 256
     GI 502776253 211 -g--allvadrEGDVELTTGQDFAIGYHSHDASKVNLFLTESFT 251
     GI 502633921 209 -g--allvslaGGHLQLTLGQDMSLGYEAHDSTTVRLFFTETFA 249
     GI 496662878 216 -gk-avlvcaePEYLDLAIGLDLSVGYLELADFNHTFRIMETAA 257
     GI 500836508 206 -ns-gvlmsdsEAYASIILGQDLSIGFIGPAEERFEFSISESLA 247
     GI 501047338 214 -dg-avivmrtPSGPRILVGQELAAAYDGREGIFHQISLVESVT 255
     4PT2_P       224 -gesgvvvstgRENMDLAVSMDMVAAYLGASRMNHPFRVLEALL 266
     GI 501055150 208 -kg-gvlvasgSQYASVALGQDLAVGYNGPVGDLLEFQIYESLA 249
     GI 501691096 209 -dg-gvliatgQQYAAIVLGQDMTIGFTGPSKESLDFTISESLA 250
     GI 494995233 223 -grsgvlvatgRHNLDLAIAEDFDSAFLGDEQMNSLFRVYECVV 265
     GI 501364857 211 -g--afvlttrGGDFDLQLGTDVAIGYTSHDADTVQLYLQETLT 251
     GI 502892820 211 -g--afvlttrGGDFDLRLGTDVEIGYLSHTADTVDLYLQETFT 251
     GI 527109103 211 -g--afllstrGGDYELHLGQDLSIGYLSHDANSVELYFQESMT 251
     GI 501346422 211 -g--gvllstrGGDFELCLGQDLSIGYADHDATSVHLYFQQAFT 251
     GI 501373147 211 -g--gsvlsmrGGDYELHLGQDVSIGYQSHTDSTVRLYLRETLT 251
     GI 501587999 211 -g--afvlttrGGDFELTLGQDVSIGYLSHTAETVQLYLQESFT 251
     GI 500074236 211 -g--gavvttrGGDFDLWLGQDISIGYLSHDAASVTLYLQESLT 251
     GI 501827525 211 -g--gfvlttrGGDFELDIGQDISIGYLSHSSTVVELYLQETFT 251
     GI 521295581 213 -g--avvlsqrGGDFILESGQDLSVGYSSHTAEEVELYLEQSFS 253
```

BOLD UPPERCASE = P-domain

*Italics = E-loop* bold lowercase = A-domain

FIG. 6 (continued)

mGNNRPVYIPQPRPPHPRI<u><u>ENLYFQGGTS</u></u>pdflghaenplreeewarlnetviqvarrsivgrrildiygplgagvqtvpyd
efqgvspgavdivgeqetamvftdarkfktipiiykdfllhwrdieaarthnmpldvsaaagaaalcaqqedelifygdarl
gyeglmtangrltvplgdwtspgggfqaiveatrklneqghfgpyavvlsprlysqlhriyektgvleietirqlasdgvyq
snrlrgesqvvvstgrenmdlavsmdmvaaylgasrmnhpfrvlealllrikhpdaictiegagaterr highlight in bold = Apidaecin Ia peptide

<u>double underline</u> = TEV protease cleavage site

<u>single underline</u> = Linker regions

FIG. 8 pMCY124 = Ap-Encap(K138)

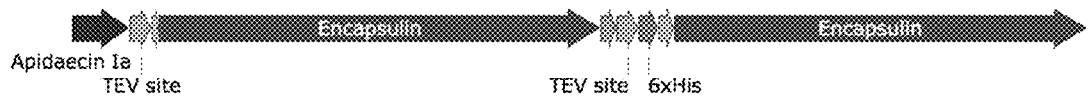

MGNNRPVYIPQPRPPHPRIENLYFQGGTSEFLKRSFAPLTEKQWQEIDNRAREI
FKTQLYGRKFVDVEGPYGWEYAAHPLGEVEVLSDENEVVKWGLRKSLPLIELRA
TFTLDLWELDNLERGKPNVDLSSLEETVRKVAEFEDEVIFRGCEKSGVKGLLSF
EERKGGGGGENLYFQG*HHHHHH*GGGGGIECGSTPKDLLEAIVRALSIFSKDGIE
GPYTLVINTDRWINFLKEEAGHYPLEKRVEECLRGGKIITTPRIEDALVVSERG
GDFKLILGQDLSIGYEDREKDAVRLFITETFTFQVVNPEALILLKFSGGS bold = Apidaecin Ia peptide
<u>double underline</u> = TEV protease cleavage site
<u>single underline</u> = Linker regions
*italics* = His6-tag
Normal font = Encapsulin

FIG. 15A pMCY125 = Ap-Encap(K71,K138)

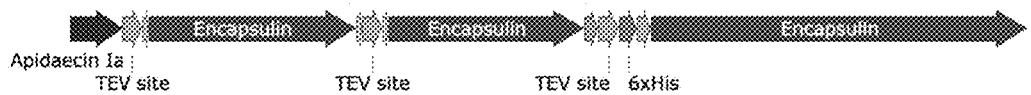

MGNNRPVYIPQPRPPHPRI<u>ENLYFQ</u>GGTSEFLKRSFAPLTEKQWQEIDNRAREIFKTQ
LYGRKFVDVEGPYGWEYAAHPLGEVEVLSDENEVVKWGLRKGG<u>ENLYFQ</u>GGGSLPLIE
LRATFTLDLWELDNLERGKPNVDLSSLEETVRKVAEFEDEVIFRGCEKSGVKGLLSFE
ERKGGGGG<u>ENLYFQG</u>*HHHHHH*GGGGGIECGSTPKDLLEAIVRALSIFSKDGIEGPYTL
VINTDRWINFLKEEAGHYPLEKRVEECLRGGKIITTPRIEDALVVSERGGDFKLILGQ
DLSIGYEDREKDAVRLFITETFTFQVVNPEALILLKFSGGS atg**GGGAACAACCGTCCCGTCTACATCCCACAGCCGCGCCCTCCACATCCCCG
TATT**<u>GAAAACTTGTATTTTCAAGGTGGTACCTCC</u>gagtttctgaaacgcagct
cgccccgctgaccgagaagcagtggcaggagatcgacaatcgcgccgcgag
atcttcaagacacagctgtacggtcgcaagttcgtggacgtggaaggcccgta
cggctgggaatatgccgcacaccctctggtgaggtggaggtgctgagcgacg
agaacgaagtggttaagtggggtctgcgcaag<u>GGTGGTGAAAACCTGTATTTC
CAAGGTGGTGG</u>Tagcctgccgttaatcgaactgcgcgcaaccttcaccctgga
cctgtgggagctggacaacctggagcgcggcaagccgaacgtggacctgagta
gcctggaggaaaccgtgcgtaaggtggccgagtttgaggacgaagtgattttc
cgcggctgcgagaagagcggcgttaagggtctgctgagcttcgaagagcgcaa
g<u>GGTGGGGGAGGCGGTGAAAACTTGTATTTTCAAGGT</u>*CATCATCACCACCATC
ATGGTGGAGGGGCGG*Catcgagtgcggcagcaccccgaaagatctgctggag
gccatcgttcgcgccctgagcatcttcagtaaggacggcatcgagggcccgta
caccctggtgattaacaccgaccgttggatcaacttcctgaaagaagaggcgg
gtcactacccgctggaaaaacgcgtggaagagtgtctgcgcggcggcaagatc
atcaccacacctcgcatcgaagacgccttagtggttagcgagcgcggcggcga
ctttaagctgatcctgggccaggacctgagcatcggctatgaggaccgtgaaa
aggacgccgtgcgtctgttcatcacagaaaccttcaccttccaggtggtgaac
ccggaagccctgatcctgctgaagttcagcggtGGATCCTAA bold = Apidaecin Ia peptide
<u>double underline</u> = TEV protease cleavage site
<u>single underline</u> = Linker regions
*italics* = His6-tag
Normal font = Encapsulin

FIG. 15B pMCY133 = Ap-Encap(D60,K138)

MGNNRPVYIPQPRPPHPRI<u>ENLYFQ</u>GGTSEFLKRSFAPLTEKQWQEIDNRAREI
FKTQLYGRKFVDVEGPYGWEYAAHPLGEVEVLSDGG<u>ENLYFQ</u>GGGENEVVKWGL
RKSLPLIELRATFTLDLWELDNLERGKPNVDLSSLEETVRKVAEFEDEVIFRGC
EKSGVKGLLSFEERKGGGG<u>ENLYFQG</u>*HHHHHH*GGGGIECGSTPKDLLEAIVR
ALSIFSKDGIEGPYTLVINTDRWINFLKEEAGHYPLEKRVEECLRGGKIITTPR
IEDALVVSERGGDFKLILGQDLSIGYEDREKDAVRLFITETFTFQVVNPEALIL
LKFSGGS

```
bold = Apidaecin Ia peptide
double underline = TEV protease
cleavage site
single underline = Linker regions
italics = His6-tag
Normal font = Encapsulin
```

FIG. 15C

| Construct | Sequence | SEQ ID NO |
|---|---|---|
| EncK138^His | MSEFLKRSFAPLTEKQWQEIDNRAREIFKTQLYGRKFVDVEGPYGWEYAAHPLGEVEVLSDENEVVKWGLRKSLPLIELRATFTLDLWELDNLERGKPNVDLSSLEETVRKVAEFEDEVIFRGCEKSGVKGLLSFEERKGGGG*HHHHHH*GGGGGIECGSTPKDLLEAIVRALSIFSKDGIEGPYTLVINTDRWINFLKEEAGHYPLEKRVEECLRGGKIITTPRIEDALVVSERGGDFKLILGQDLSIGYEDREKDAVRLFITETFTFQVVNPEALILLKFSGGS | 48 |
| HB-EncK138^T EV-His | MKWKSFIKKLTKAAKKVVTTAKKPLIVENLYFQGGGGG*T*SEFLKRSFAPLTEKQWQEIDNRAREIFKTQLYGRKFVDVEGPYGWEYAAHPLGEVEVLSDENEVVKWGLRKSLPLIELRATFTLDLWELDNLERGKPNVDLSSLEETVRKVAEFEDEVIFRGCEKSGVKGLLSFEERKGGGGGENLYFQG*HHHHHH*GGGGGIECGSTPKDLLEAIVRALSIFSKDGIEGPYTLVINTDRWINFLKEEAGHYPLEKRVEECLRGGKIITTPRIEDALVVSERGGDFKLILGQDLSIGYEDREKDAVRLFITETFTFQVVNPEALILLKFSGGS | 49 |
| HB-EncK71^TEV K138^TEV-His | MKWKSFIKKLTKAAKKVVTTAKKPLIVENLYFQGGGGGG*T*SEFLKRSFAPLTEKQWQEIDNRAREIFKTQLYGRKFVDVEGPYGWEYAAHPLGEVEVLSDENEVVKWGLRKGGENLYFQGGGSLPLIELRATFTLDLWELDNLERGKPNVDLSSLEETVRKVAEFEDEVIFRGCEKSGVKGLLSFEERKGGGGGENLYFQG*HHHHHH*GGGGGIECGSTPKDLLEAIVRALSIFSKDGIEGPYTLVINTDRWINFLKEEAGHYPLEKRVEECLRGGKIITTPRIEDALVVSERGGDFKLILGQDLSIGYEDREKDAVRLFITETFTFQVVNPEALILLKFSGGS | 50 |
| HB-EncD60^T EVK138^TEV-His | MKWKSFIKKLTKAAKKVVTTAKKPLIVENLYFQGGGGGG*T*SEFLKRSFAPLTEKQWQEIDNRAREIFKTQLYGRKFVDVEGPYGWEYAAHPLGEVEVLSDGENLYFQGGGENEVVKWGLRKSLPLIELRATFTLDLWELDNLERGKPNVDLSSLEETVRKVAEFEDEVIFRGCEKSGVKGLLSFEERKGGGGGENLYFQG*HHHHHH*GGGGGIECGSTPKDLLEAIVRALSIFSKDGIEGPYTLVINTDRWINFLKEEAGHYPLEKRVEECLRGGKIITTPRIEDALVVSERGGDFKLILGQDLSIGYEDREKDAVRLFITETFTFQVVNPEALILLKFSGGS | 51 |
| HB-EncV57^TEV K138^TEV-His | MKWKSFIKKLTKAAKKVVTTAKKPLIVENLYFQGGGGG*T*SEFLKRSFAPLTEKQWQEIDNRAREIFKTQLYGRKFVDVEGPYGWEYAAHPLGEVEVGGENLYFQGGGLSDENEVVKWGLRKSLPLIELRATFTLDLWELDNLERGKPNVDLSSLEETVRKVAEFEDEVIFRGCEKSGVKGLLSFEERKGGGGGENLYFQG*HHHHHH*GGGGGIECGSTPKDLLEAIVRALSIFSKDGIEGPYTLVINTDRWINFLKEEAGHYPLEKRVEECLRGGKIITTPRIEDALVVSERGGDFKLILGQDLSIGYEDREKDAVRLFITETFTFQVVNPEALILLKFSGGS | 52 |
| HB-EncK71^TEV | MKWKSFIKKLTKAAKKVVTTAKKPLIVENLYFQGGGGG*T*SEFLKRSFAPLTEKQWQEIDNRAREIFKTQLYGRKFVDVEGPYGWEYAAHPLGEVEVLSDENEVVKWGLRKGGENLYFQGGGSLPLIELRATFTLDLWELDNLERGKPNVDLSSLEETVRKVAEFEDEVIFRGCEKSGVKGLLSFEERKGGGGKIITTPRIEDALVVSERGGDFKLILGQDLSIGYEDREKDAVRLFITETFTFQVVNPEALILLKFSGGS | 53 |
| EncK138^His-HB | MEFLKRSFAPLTEKQWQEIDNRAREIFKTQLYGRKFVDVEGPYGWEYAAHPLGEVEVLSDENEVVKWGLRKSLPLIELRATFTLDLWELDNLERGKPNVDLSSLEETVRKVAEFEDEVIFRGCEKSGVKGLLSFEERKGGGGGENLYFQG*HHHHHH*GGGGIECGSTPKDLLEAIVRALSIFSKDGIEGPYTLVINTDRWINFLKEEAGHYPLEKRVEECLRGGKIITTPRIEDALVVSERGGDFKLILGQDLSIGYEDREKDAVRLFITETFTFQVVNPEALILLKFSGGSENLYFQGKWKSFIKKLTKAAKKVVTTAKKPLIV | 54 |
| HB-Trx | MKWKSFIKKLTKAAKKVVTTAKKPLIVENLYFQGG*T*MSDKIIHLTDDSFDTDVLKADGAILVDFWAEWCGPCKMIAPILDEIADEYQGKLTVAKLNIDQNPGTAPKYGIRGIPTLLLFKNGEVAATKVGALSKGQLKEFLDANLAGSGSG*T**HHHHHH* | 55 |
| HB-SUMO | MKWKSFIKKLTKAAKKVVTTAKKPLIVENLYFQG*GT*MSDSEVNQEAKPEVKPETHINLKVSDGSSEIFFKIKKTTPLRRLMEAFAKRQGKEMDSLRFLYDGIRIQADDQTPEDLDMEDNDIIEAHREQIGGGSL*EHHHHHH* | 56 |
| HB-GST | MKWKSFIKKLTKAAKKVVTTAKKPLIVENLYFQGG*T*MSPILGYWKIKGLVQPTRLLLEYLEEKYEEHLYERDEGDKWRNKKFELGLEFPNLPYYIDGDVKLTQSMAIIRYIADKHNMLGGCPKERAEISMLEGAVLDIRYGVSRIAYSKDFETLKVDFLSKLPEMLKMFEDRLCHKTYLNGDHVTHPDFMLYDALDVVLYMDPMCLDAFPKLVCFKKRIEAIPQIDKYLKSSKYIAWPLQGWQATFGGGDHPPKGSL*EHHHHHH* | 57 |
| HB-MBP | MKWKSFIKKLTKAAKKVVTTAKKPLIVENLYFQGG*T*MKIEEGKLVIWINGDKGYNGLAEVGKKFEKDTGIKVTVEHPDKLEEKFPQVAATGDGPDIIFWAHDRFGGYAQSGLLAEITPDKAFQDKLYPFTWDAVRYNGKLIAYPIAVEALSLIYNKDLLPNPPKTWEEIPALDKELKAKGKSALMFNLQEPYFTWPLIAADGGYAFKYENGKYDIKDVGVDNAGAKAGLTFLVDLIKNKHMNADTDYSIAEAAFNKGETAMTINGPWAWSNIDTSKVNYGVTVLPTFKGQPSKPFVGVLSAGINAASPNKELAKEFLENYLLTDEGLEAVNKDKPLGAVALKSYEEELVKDPRIAATMENAQKGEIMPNIPQMSAFWYAVRTAVINAASGRQTVDEALKDAQTGSL*EHHHHHH* | 58 |

FIG. 22B

ENGINEERED MICROCOMPARTMENT PROTEIN AND RELATED METHODS AND SYSTEMS OF ENGINEERING BACTERIAL SYSTEMS FOR NON-NATIVE PROTEIN EXPRESSION AND PURIFICATION

CROSS REFERENCE TO RELATED APPLICATIONS

The present application claims priority to U.S. provisional application No. 62/598,984, entitled "Engineered Microcompartment Protein and Related Methods and Systems of Engineering Bacterial Systems for Non-native Protein Expression and Purification" filed on Dec. 14, 2017, which is incorporated by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

FIELD

The present disclosure relates to protein production in cell systems and in particular to engineering microcompartment proteins and related bacterial systems for non-native protein expression and purification and related cells, compositions, methods and systems.

BACKGROUND

Production of non-native proteins has been the subject of research in several fields, including commercial and academic fields in connection with applications involving production in a cell of a protein non-native to that cell.

Despite the presence of various approaches, expression, production and/or purification in a cell of proteins non-native to said cell for various uses is still challenging.

SUMMARY

Provided herein, are engineered microcompartment proteins and related engineered microcompartments, vectors, cells, compositions, methods and systems that can be used in several embodiments for non-native protein expression, production and/or purification.

According to a first aspect, an engineered microcompartment protein is described. The engineered microcompartment protein comprises an encapsulin protein having sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{18}$-$X_{20}$-$X_{21}$- $X_{22}$-$X_{23}$-$X_{24}$-$X_{25}$-$X_{26}$-$X_{27}$-$X_{28}$-$X_{29}$-$X_{30}$ $X_{31}$-$X_{32}$-$X_{33}$ $X_{34}$-$X_{35}$-$X_{36}$-$X_{37}$-$X_{38}$-$X_{39}$-$X_{40}$-$X_{41}$-$X_{42}$-$X_{43}$-$X_{44}$-$X_{45}$-$X_{46}$-$X_{47}$-$X_{48}$-$X_{49}$-$X_{50}$-$X_{51}$-$X_{52}$-$X_{53}$-$X_{54}$-$X_{55}$-$X_{56}$-$X_{57}$-$X_{58}$-$X_{59}$-$X_{60}$-$X_{61}$-$X_{62}$-$X_{63}$-$X_{64}$-$X_{65}$-$X_{66}$-$X_{67}$-$X_{68}$-$X_{69}$-$X_{70}$-$X_{71}$-$X_{72}$-$X_{73}$-$X_{74}$-$X_{75}$-$X_{76}$-$X_{77}$-$X_{78}$-$X_{79}$-$X_{80}$-$X_{81}$-$X_{82}$-$X_{83}$-$X_{84}$ $X_{85}$-$X_{86}$-$X_{88}$-$X_{89}$-$X_{90}$-$X_{91}$-$X_{92}$-$X_{93}$-$X_{94}$-$X_{95}$-$X_{96}$-$X_{97}$-$X_{98}$-$X_{99}$-$X_{100}$-$X_{101}$-$X_{102}$-$X_{103}$-$X_{104}$-$X_{105}$-$X_{106}$-$X_{107}$-$X_{108}$-$X_{109}$-$X_{110}$-$X_{111}$-$X_{112}$-$X_{113}$-$X_{114}$-$X_{115}$-$X_{116}$-$X_{117}$-$X_{118}$-$X_{119}$-$X_{120}$-$X_{121}$-$X_{122}$-$X_{123}$-$X_{124}$-$X_{125}$-$X_{126}$-$X_{127}$-$X_{128}$-$X_{129}$-$X_{130}$-$X_{131}$-$X_{132}$-$X_{133}$-$X_{134}$-$X_{135}$-$X_{136}$-$X_{137}$-$X_{138}$-$X_{139}$-$X_{140}$-$X_{141}$-$X_{142}$-$X_{143}$-$X_{144}$-$X_{145}$-$X_{146}$-$X_{147}$-$X_{148}$-$X_{149}$-$X_{150}$-$X_{151}$-$X_{152}$-$X_{153}$-$X_{154}$-$X_{155}$-$X_{156}$-$X_{157}$-$X_{158}$-$X_{159}$-$X_{160}$-$X_{161}$-$X_{162}$-$X_{163}$-$X_{164}$-$X_{165}$-$X_{166}$-$X_{167}$-$X_{168}$-$X_{169}$-$X_{170}$-$X_{171}$-$X_{172}$-$X_{173}$-$X_{174}$-$X_{175}$-$X_{176}$-$X_{177}$-$X_{178}$-$X_{179}$-$X_{180}$-$X_{181}$-$X_{182}$-$X_{183}$-$X_{184}$-$X_{185}$-$X_{186}$-$X_{187}$-$X_{188}$-$X_{189}$-$X_{190}$-$X_{191}$-$X_{192}$-$X_{193}$-$X_{194}$-$X_{195}$-$X_{196}$-$X_{197}$-$X_{198}$-$X_{199}$-$X_{200}$-$X_{201}$-$X_{202}$-$X_{203}$-$X_{204}$-$X_{205}$-$X_{206}$-$X_{207}$-$X_{208}$-$X_{209}$-$X_{210}$-$X_{211}$-$X_{212}$-$X_{213}$-$X_{214}$-$X_{215}$-$X_{216}$-$X_{217}$-$X_{218}$-$X_{219}$-$X_{220}$-$X_{221}$-$X_{222}$-$X_{223}$-$X_{224}$-$X_{225}$-$X_{226}$-$X_{227}$-$X_{228}$-$X_{229}$-$X_{230}$-$X_{231}$-$X_{232}$-$X_{233}$-$X_{234}$-$X_{235}$-$X_{236}$-$X_{237}$-$X_{238}$-$X_{239}$-$X_{240}$-$X_{241}$-$X_{242}$-$X_{243}$-$X_{244}$-$X_{245}$-$X_{246}$-$X_{247}$-$X_{248}$-$X_{249}$ $X_{250}$-$X_{251}$-$X_{252}$-$X_{253}$ (SEQ ID NO: 1)

in which $X_1$ is M, $X_2$ is D, $X_3$ is N, $X_4$ is L, $X_5$ is K, $X_6$ is R, $X_7$ is E, $X_8$ is L, $X_9$ is A, $X_{10}$ is P, $X_{11}$ is L, $X_{12}$ is T, $X_{13}$ is E, $X_{14}$ is E, $X_{15}$ is A, $X_{16}$ is W, $X_{17}$ is A, $X_{18}$ is E, $X_{19}$ is I, $X_{20}$ is D, $X_{21}$ is E, $X_{22}$ is E, $X_{23}$ is A, $X_{24}$ is R, $X_{25}$ is E, $X_{26}$ is T, $X_{27}$ is A, $X_{28}$ is K, $X_{29}$ is R, $X_{30}$ is H, $X_{31}$ is L, $X_{32}$ is A, $X_{33}$ is G, $X_{34}$ is R, $X_{35}$ is R, $X_{36}$ is V, $X_{37}$ is V, $X_{38}$ is D, $X_{39}$ is V, $X_{40}$ is E, $X_{41}$ is G, $X_{42}$ is P, $X_{43}$ is L, $X_{44}$ is G, $X_{45}$ is W, $X_{46}$ is G, $X_{47}$ is Y, $X_{48}$ is S, $X_{49}$ is A, $X_{50}$ is V, $X_{51}$ is P, $X_{52}$ is L, $X_{53}$ is G, $X_{54}$ is R, $X_{55}$ is L, $X_{56}$ is E, $X_{57}$ is E, $X_{58}$ is I, $X_{59}$ is E, $X_{60}$ is G, $X_{61}$ is P, $X_{62}$ is A, $X_{63}$ is E, $X_{64}$ is G, $X_{65}$ is V, $X_{66}$ is Q, $X_{67}$ is A, $X_{68}$ is G, $X_{69}$ is V, $X_{70}$ is R, $X_{71}$ is Q, $X_{72}$ is V, $X_{73}$ is L, $X_{74}$ is P, $X_{75}$ is L, $X_{76}$ is P, $X_{77}$ is E, $X_{78}$ is L, $X_{79}$ is R, $X_{80}$ is V, $X_{81}$ is P, $X_{82}$ is F, $X_{83}$ is T, $X_{84}$ is L, $X_{85}$ is S, $X_{86}$ is R, $X_{87}$ is R, $X_{88}$ is D, $X_{89}$ is L, $X_{90}$ is D, $X_{91}$ is A, $X_{92}$ is V, $X_{93}$ is E, $X_{94}$ is R, $X_{95}$ is G, $X_{96}$ is A, $X_{97}$ is K, $X_{98}$ is D, $X_{99}$ is L, $X_{100}$ is D, $X_{101}$ is L, $X_{102}$ is 5, $X_{103}$ is P, $X_{104}$ is V, $X_{105}$ is VA, $X_{106}$ is E, $X_{107}$ is A, $X_{108}$ is A, $X_{109}$ is R, $X_{110}$ is L, $X_{111}$ is L, $X_{112}$ is A, $X_{113}$ is R, $X_{114}$ is A, $X_{115}$ is E, $X_{116}$ is D, $X_{117}$ is R, $X_{118}$ is L, $X_{119}$ is I, $X_{120}$ is F, $X_{121}$ is N, $X_{122}$ is G, $X_{123}$ is Y, $X_{124}$ is A, $X_{125}$ is E, $X_{126}$ is A, $X_{127}$ is G, $X_{128}$ is I, $X_{129}$ is E, $X_{130}$ is G, $X_{131}$ is L, $X_{132}$ is L, $X_{133}$ is N, $X_{134}$ is A, $X_{135}$ is 5, $X_{136}$ is G, $X_{137}$ is N, $X_{138}$ is L, $X_{139}$ is K, $X_{140}$ is L, $X_{141}$ is P, $X_{142}$ is L, $X_{143}$ is 5, $X_{144}$ is A, $X_{145}$ is D, $X_{146}$ is P, $X_{147}$ is G, $X_{148}$ is D, $X_{149}$ is I, $X_{150}$ is P, $X_{151}$ is D, $X_{152}$ is A, $X_{153}$ is I, $X_{154}$ is A, $X_{155}$ is E, $X_{156}$ is A, $X_{157}$ is L, $X_{158}$ is T, $X_{159}$ is K, $X_{160}$ is L, $X_{161}$ is R, $X_{162}$ is E, $X_{163}$ is A, $X_{164}$ is G, $X_{165}$ is V, $X_{166}$ is E, $X_{167}$ is G, $X_{168}$ is P, $X_{169}$ is Y, $X_{170}$ is A, $X_{171}$ is L, $X_{172}$ is V, $X_{173}$ is L, $X_{174}$ is S, $X_{175}$ is P, $X_{176}$ is D, $X_{177}$ is L, $X_{178}$ is Y, $X_{179}$ is T, $X_{180}$ is A, $X_{181}$ is L, $X_{182}$ is F, $X_{183}$ is R, $X_{184}$ is V, $X_{185}$ is Y, $X_{186}$ is D, $X_{187}$ is G, $X_{188}$ is T, $X_{189}$- is G, $X_{190}$ is Y, $X_{191}$ is P, $X_{192}$ is E, $X_{193}$ is I, $X_{194}$ is E, $X_{195}$ is H, $X_{196}$ is I, $X_{197}$ is K, $X_{198}$ is E, $X_{199}$ is L, $X_{200}$ is V, $X_{201}$ is D, $X_{202}$ is G, $X_{203}$ is G, $X_{204}$ is V, $X_{205}$ is I, $X_{206}$ is W, $X_{207}$ is A, $X_{208}$ is P, $X_{209}$ is A, $X_{210}$ is L, $X_{211}$ is D, $X_{212}$ is G, $X_{213}$ is G, $X_{214}$ is A, $X_{215}$ is V, $X_{216}$ is L, $X_{217}$ is V, $X_{218}$ is S, $X_{219}$ is T, $X_{220}$ is R, $X_{221}$ is G, $X_{222}$ is G, $X_{223}$ is D, $X_{224}$ is F, $X_{225}$ is D, $X_{226}$ is L, $X_{227}$ is T, $X_{228}$ is L, $X_{229}$ is G, $X_{230}$ is Q, $X_{231}$ is D, $X_{232}$ is L, $X_{233}$ is S, $X_{234}$ is I, $X_{235}$ is G, $X_{236}$ is Y, $X_{237}$ is L, $X_{238}$ is S, $X_{239}$ is H, $X_{240}$ is D, $X_{241}$ is A, $X_{242}$ is D, $X_{243}$ is N, $X_{244}$ is V, $X_{245}$ is E, $X_{246}$ is L, $X_{247}$ is F, $X_{248}$ is L, $X_{249}$ is T, $X_{250}$ is E, $X_{251}$ is S, $X_{252}$ is F, $X_{253}$ is T (SEQ ID NO: 1)

or a sequence with at least 22% sequence identity or at least 40% sequence similarity to SEQ ID NO:1.

In the engineered microcompartment protein, the encapsulin protein comprises a P-Domain (Peripheral Domain), an E-Loop (Elongated Loop) and an A-Domain (Axial Domain).

In the engineered microcompartment protein, the P-Domain of the encapsulin protein comprises a first fragment of the P-domain having an N-terminus and a C-terminus and comprising residues configured to form, in a folded encapsulin protein, a secondary structure comprising in a direction N-terminus to C-terminus a 4 to 26 residues alpha helix α1, linked to a 0 to 22 residues first non-structured region (such as a loop region), linked to a 4 to 11 residues alpha helix α2, linked to a 3 to 9 residues beta strand β1, linked to a 3 to 13 residues second non-structured region.

a second fragment of the P-Domain having an N-terminus and a C-terminus and comprising residues configured to form, in a folded encapsulin protein, a secondary structure comprising a direction N-terminus to C-terminus a 9 to 15 residues beta strand β4, linked to a 6 to 15 residues alpha helix α3, linked to a 0 to 10 residues first non-structured region, a 18 to 29 residues alpha helix α4, and a 9 to 21 residues second non-structured region; and a third fragment of the P-domain having an N-terminus and a C-terminus and comprising residues configured to form, in a folded microcompartment protein, a secondary structure comprising in a direction N-terminus to C-terminus a 4 to 10 residues beta strand β9, linked to a 3 to 16 residues first non-structured region, linked to a 7 to 13 residues beta strand β10, linked to a 1 to 15 residues second non-structured region, linked to a 10 to 19 residues beta strand β11.

In the engineered microcompartment protein, the E-Loop of the encapsulin protein has an N-terminus and a C-terminus and comprises residues configured to form in a folded encapsulin protein, a secondary structure comprising in a direction N-terminus to C-terminus a 8 to 16 residues beta strand β2, linked to a 2 to 24 residues first non-structured region, linked to a 7 to 15 residues beta strand β3, linked to a 0 to 6 residues second non-structured region.

In the engineered microcompartment protein, the A-Domain of the encapsulin protein has an N-terminus and a C-terminus and comprises residues configured to form in a folded encapsulin protein, a secondary structure comprising in a direction N-terminus to C-terminus a 0 to 8 residues beta strand β5 linked to a 1 to 15 residues first non-structured region, linked to a 16 to 23 residues alpha helix α5, linked to a 3 to 11 residues second non-structured region, linked to a 3 to 11 residues beta strand β6, linked to a 9 to 16 residues alpha helix α6, linked to a 1 to 24 third non-structured region, linked to a 0 to 16 residues alpha helix α7, linked to a 0 to 8 residues fourth non-structured region, linked to a 1 to 10 residues beta strand β7, linked to a 1 to 12 residues fifth non-structured region, linked to a 3 to 10 residues beta strand β8, linked to a 2 to 12 residues sixth non-structured region.

In the engineered microcompartment protein, the P-domain, A-domain and E-loop are arranged together in a configuration comprising, in a direction N-terminus to C-terminus, the first fragment of the P-domain linked to the E-loop linked to the second fragment of the P-domain linked to the A-domain linked to the third fragment of the P-domain.

In the engineered microcompartment protein, a target protein having an N-terminus, a C-terminus is inserted at the N-terminus of the first segment of the P-domain of the encapsulin protein alone or together with a linker and/or a tag at least one first protease cleavage site is inserted between the C-terminus of the target protein and the N-terminus of the first segment of the P-Domain of the encapsulin protein alone or together with a linker and/or a tag; and at least one second protease cleavage site is inserted at the C-terminus of the E-loop of the encapsulin protein or within 1-17 amino acids adjacent to the C-terminus of the E-loop of the encapsulin protein and/or within 2-14 amino acids adjacent to the N-terminus of the A-domain of the encapsulin protein, alone or together with a linker and/or a tag, to enable digestion of the encapsulin and release of the target protein.

In some embodiments wherein the engineered microcompartment proteins are designed to be non cage forming proteins, the at least one second protease cleavage site is inserted at the C-terminus of the E-loop of the encapsulin protein or within 1-8 amino acids adjacent to the C-terminus of the E-loop of the encapsulin protein (within β3 of the E-loop).

In some embodiments wherein the engineered microcompartment proteins are designed for cage forming proteins, the at least one second protease cleavage site can be inserted within 9-17 amino acids from the C-terminus of the E-loop of the encapsulin protein (within the loop region between β2 and β3 of the E-loop), and/or inserted within 2-14 amino acids adjacent to the N-terminus of the A-domain (in the flexible region between the N-terminus of the A-domain and α5, including β5).

In some embodiments, the target protein is a protein non-native to one or more bacterial cell (herein also indicated as non-native protein) and capable of causing cell damage (herein also indicated as non-native toxic protein). In some embodiments the at least one first protease and the at least one second protease cleavage site can be same or different.

According to a second aspect, an engineered microcompartment is described, the engineered microcompartment comprising a same or different at least one engineered microcompartment protein herein described. In particular, in some embodiments, the engineered microcompartment proteins of the engineered microcompartment have a same target protein, at least one first protease cleavage site and/or at least one second protease cleavage site.

According to a third aspect, a method is described to produce in a bacterial cell a protein non-native to the bacterial cell. The method comprises introducing into the bacterial cell at least one first polynucleotide encoding at least one engineered microcompartment protein herein described in which the target protein is the protein non-native to the bacterial cell. In the method, the at least one first polynucleotide is operatively linked to one or more first regulatory elements leading to the expression of the at least one engineered microcompartment protein in the bacterial cell. In the method the introducing is performed to obtain expression in the bacterial cell of the at least one engineered microcompartment protein to obtain the protein non-native to the bacterial within at least one engineered microcompartment formed by the at least one engineered microcompartment protein.

In some embodiments, the protein non-native to the bacterial cell is a toxic non-native protein capable of reacting with a native membrane substrate of the bacterial cell with a reaction resulting in a damage of the bacterial cell, and the engineered microcompartment protein is provided in the bacterial cell to shield the bacterial cell from toxicity during intracellular production of the toxic non-native protein in the bacterial cell.

According to a fourth aspect, a system is described to produce, in bacterial cell, a protein non-native to the bacterial cell. The system comprises at least one first polynucleotide encoding at least one engineered microcompartment protein herein described wherein the target protein is the protein non-native to the bacterial cell, the at least one engineered microcompartment protein operatively linked to one or more first regulatory elements configured to enable the expression of the at least one engineered microcompartment protein in one or more bacterial cell, the at least one engineered microcompartment protein capable of assembling with one or more same and/or different engineered microcompartment proteins to form at least one microcompartment within the one or more bacterial cell.

The system additionally comprises at least one of:

the one or more bacterial cells capable of expressing the at least one first polynucleotide to provide an expressed engineered microcompartment protein herein described;

at least one second polynucleotide encoding for at least one protease, the at least one second polynucleotide operably linked to one or more second regulatory elements leading to the expression of the at least one protease capable of targeting the at least one first protease cleavage site and/or the at least one second protease cleavage site of the engineered microcompartment protein to release the non-native protein from the engineered microcompartment protein in the bacterial cell to obtain the non-native protein; and at least one protease capable of targeting the at least one first protease cleavage site and/or the at least one second protease cleavage site of the engineered microcompartment protein to release the protein non-native to the bacterial cell from the engineered microcompartment protein in the bacterial cell.

In the system, the at least one first polynucleotide, the at least one second polynucleotide the at least one protease and the one or more bacterial cells are combined or simultaneously or sequentially used in the methods to produce in a bacterial cell a protein non-native to the bacterial cell herein described.

In some embodiments, the at least one non-native protein in the engineered microcompartment protein is a non-native toxic protein capable of causing cell damage, and the engineered microcompartment protein is provided in the cell to shield cell from toxicity during intracellular production of a toxic non-native protein.

According to a fifth aspect, a method is described to produce a non-native protein in a bacterial cell comprising at least one engineered microcompartment protein herein described in which the target protein is a protein non-native to the cell. The method comprises introducing into the bacterial cell at least one second polynucleotide encoding the at least one protease capable of cleaving the at least one first protease cleavage site and/or the at least one second protease cleavage site within the engineered microcompartment protein. In the method, the at least one second polynucleotide is operably linked to one or more second regulatory elements configured to enable expression in the bacterial cell of the at least one protease. In the method, the introducing is performed to obtain the non-native protein from the engineered microcompartment protein upon cleaving of the at least one first protease cleavage site and/or the at least one second protease cleavage site by the at least one protease expressed in the bacterial cell.

According to a sixth aspect a system to produce a non-native protein from a bacterial cell comprising at least one engineered microcompartment protein herein described in which the target protein is a protein non-native to the cell, the system comprises one or more bacterial cells comprising at least one engineered microcompartment protein herein described assembled with one or more same and/or different microcompartment proteins to form at least one engineered microcompartment within the cell.

The system also comprises at least one second polynucleotide encoding for at least one protease, the at least one second polynucleotide operably linked to one or more second regulatory elements leading to the expression of the at least one protease capable of targeting the at least one first protease cleavage site and/or the at least one second protease cleavage site of the engineered microcompartment protein to release the non-native protein from the engineered microcompartment protein in the bacterial cell to obtain the non-native protein; and at least one protease capable of targeting the at least one first protease cleavage site and/or the at least one second protease cleavage site of the engineered microcompartment protein to release the non-native protein from the engineered microcompartment protein in the one or more bacterial cells.

In the system, the one or more bacterial cells, the at least one second polynucleotide, and the at least one protease are used either simultaneously or sequentially in the methods to provide one or more non-native proteins in from one or more bacterial cell comprising an engineered microcompartment protein herein described.

In some embodiments, the at least one non-native protein in the engineered microcompartment protein is a non-native toxic protein capable of reacting with a native membrane substrate with a reaction resulting in a cell damage, and the engineered microcompartment protein is provided in the cell to shield cell from toxicity during intracellular production of a toxic non-native protein.

According to a seventh aspect, a vector is described comprising at least one polynucleotide encoding for an engineered microcompartment protein herein described alone or in combination with regulatory elements in accordance with the disclosure.

According to an eight aspect, a bacterial cell is described obtained by any one of the methods and/or with any one of the systems of the present disclosure.

According to a ninth aspect, a composition is described. The composition comprises the engineered microcompartment protein, the engineered microcompartment and/or the bacterial cell herein described.

Engineered microcompartment proteins and related engineered microcompartments, vectors, cells compositions methods and systems herein described can be used in some embodiments in connection with expression, production and/or purification in a bacterial cell of one or more proteins toxic to the bacterial cell or precursor thereof.

Engineered microcompartment proteins and related engineered microcompartments, vectors, cells compositions methods and systems herein described can be used in some embodiments to shield bacteria from toxicity during expression, production and/or purification of non-native toxic protein.

Engineered microcompartment proteins and related engineered microcompartments, vectors, cells compositions methods and systems herein described can be used in some embodiments in connection with expression, production and/or purification in a bacterial cell of one or more proteins degradable in the bacterial thereof.

Engineered microcompartment proteins and related engineered microcompartments, vectors, cells compositions methods and systems herein described can be applied in several fields, including basic biology research, applied biology, bioengineering, bio-energy, medical research, medical diagnostics, therapeutics, bio-fuels, and in additional fields where expression, production and/or purification in a bacterial cell of proteins which are degradable and/or cytotoxic to the bacterial cell and/or their precursors can be used.

The details of one or more embodiments of the disclosure are set forth in the accompanying drawings, incorporated herein by reference in its entirety and the description below.

Other features, objects, and advantages will be apparent from the following description, and the claims.

BRIEF DESCRIPTION OF DRAWINGS

The accompanying drawings, which are incorporated into and constitute a part of this specification, illustrate one or more embodiments of the present disclosure and, together with detailed description and the examples, serve to explain the principles and implementations of the disclosure.

Figure 2:
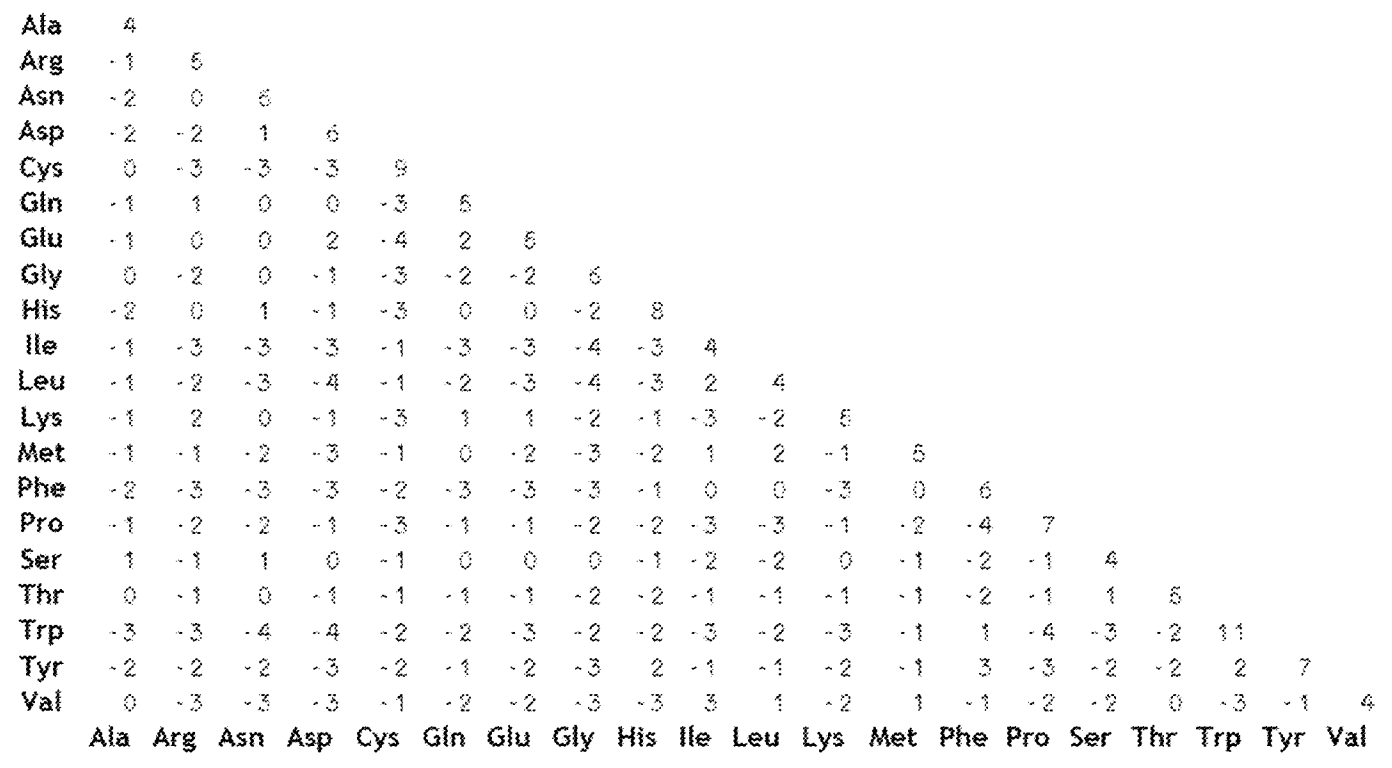

FIG. 2 illustrates a BLOSUM62 matrix used for sequence alignment of proteins

FIG. 3 shows a pairwise alignment of an encapsulin from *T. maritima* (*T. mar*, SEQ ID NO: 45) and an encapsulin from *M. xanthus* (*M. xan*, SEQ ID NO: 46).

FIG. 4A shows the consensus sequence of exemplary encapsulins (SEQ ID NO: 132). FIG. 4B illustrates the segmentation of secondary structures of the encapsulins with regard to the consensus sequence.

FIG. 5 shows an exemplary encapsulin sequence from *T. maritima* (SEQ ID: 133).

FIG. 6 shows sequence alignment of 44 exemplary members from the PF04454 protein family and in particular, GI 122304915 (SEQ ID NO: 86), GI 123527077 (SEQ ID NO: 87), GI 123044215 (SEQ ID NO: 88), GI 123046337 (SEQ ID NO: 89), GI 81373191 (SEQ ID NO: 90), GI 81833634 (SEQ ID NO: 95), GI 74556699 (SEQ ID NO: 96), GI 81347829 (SEQ ID NO: 97), GI 81344013 (SEQ ID NO: 98), GI 123497228 (SEQ ID NO: 99), GI 501179632 (SEQ ID NO: 100), GI 502293893 (SEQ ID NO: 101), GI 501012501 (SEQ ID NO: 102), GI 506340687 (SEQ ID NO: 103), GI 502591318 (SEQ ID NO: 104), GI 501194893 (SEQ ID NO: 105), GI 490598858 (SEQ ID NO: 106), GI 752720587 (SEQ ID NO: 107), GI 501771872 (SEQ ID NO: 108), GI 501163578 (SEQ ID NO: 109), GI 501434203 (SEQ ID NO: 110), GI 501367709 (SEQ ID NO: 111), GI 505232787 (SEQ ID NO: 112), GI 501923113 (SEQ ID NO: 113), GI 502776253 (SEQ ID NO: 114), GI 502633921 (SEQ ID NO: 115), GI 496662878 (SEQ ID NO: 116), GI 500836508 (SEQ ID NO: 117), GI 501047338 (SEQ ID NO: 118), 4PT2_P (SEQ ID NO: 119), GI 501055150 (SEQ ID NO: 120), GI 501691096 (SEQ ID NO: 121), GI 494995233 (SEQ ID NO: 122), GI 501364857 (SEQ ID NO: 123), GI 502892820 (SEQ ID NO: 124), GI 527109103 (SEQ ID NO: 125), GI 501346422 (SEQ ID NO: 126), GI 501373147 (SEQ ID NO: 127), GI 501587999 (SEQ ID NO: 128), GI 500074236 (SEQ ID NO: 129), GI 501827525 (SEQ ID NO: 130), GI 521295581 (SEQ ID NO: 131) as well as 3DKT_E (SEQ ID NO: 145) and CONSENSUS (SEQ ID NO: 144).

FIG. 7 shows a schematic illustration of insertion sites for target proteins, protease cleavage sites and/or tags in embodiments herein described. In particular, FIG. 7B, FIG. 7C (SEQ ID NO: 93) and FIG. 7D (SEQ ID NO: 94) shows insertion sites of a protease cleavage sites in engineered microcompartment herein described.

FIG. 8 shows in one embodiment an exemplary engineered microcompartment protein comprising Apidaecin Ia peptide fused to the N-terminus of an encapsulin protein from *M. xanthus* through a TEV protease cleavage site and a linker region (SEQ ID: 134).

FIGS. 15A-C illustrate the design and sequences of the exemplary protease-sensitive AMP-encapsulin fusions (SEQ ID NO: 135-138).

FIG. 22B shows a table reporting the amino acid sequences of HB-Enc constructs (SEQ ID NO: 48-54) and fusions of HB peptide to other common carrier proteins (SEQ ID NO: 55-58). Plain text, indicates Enc or carrier protein sequence, Italics, linker; Bold, TEV recognition site; Bold underlined, HBCM2; Italics underlined, His-tag.

FIG. 31 Panel B shows inhibition assays for various concentrations of chemically synthesized M-HBCM2-TEV peptide. The peptide has an MIC <5 µg/mL, consistent with native HBCM2 peptide.

FIG. 34 Panel A shows an image of a gel illustrating expression of the HB-Trx, HB-SUMO, HB-GST, and HB-MBP constructs in FIGS. 22A-B in BL21(DE3) *E. coli* from a T7 IPTG inducible promoter. Samples were resolved on an any-kDa SDS-PAGE gel and stained with Commassie blue. T denotes the total cell lysate, while S denotes the soluble fraction. FIG. 34 Panel B shows an image of a gel illustrating protease sensitivity of the constructs in cell lysate. BL21(DE3) *E. coli* expressing the constructs were either 1) lysed in the presence of BPER-II and lysozyme; 2) lysed in the absence of BPER-II by French pressure lysis; or 3) lysed in the absence of BPER-II by French pressure lysis and then incubated at 4° C. overnight. Samples were resolved on an any-kDa SDS-PAGE gel and stained with Commassie blue. For both Panels A and B, black arrows denote size of full-length fusions.

DETAILED DESCRIPTION

Figure 1A:
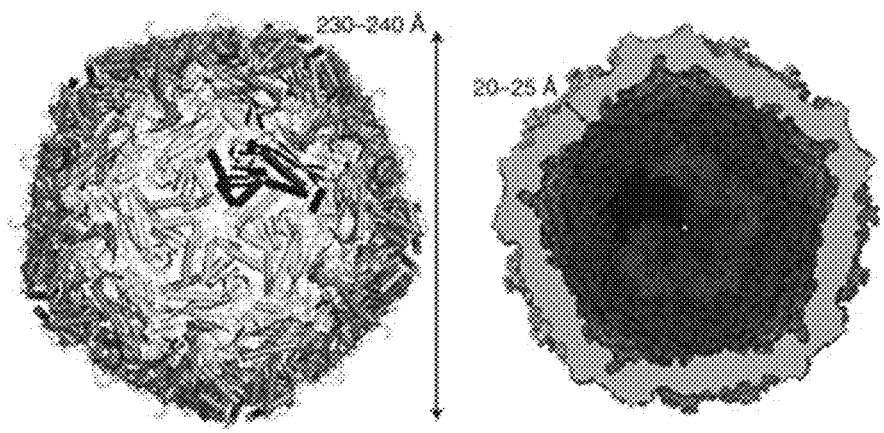
FIG. 1A illustrates a crystal structure of an exemplary encapsulin cage with 60 monomer units (one unit highlighted in red). The left panel shows a view from the outside on the five-fold symmetry axis. One pentamer is highlighted in cyan, with one monomer in red. The right panel shows a view to the inside of the shell, which is cut open in the middle and shown in a surface representation.

Provided herein are engineered microcompartment proteins and related engineered microcompartments, bacterial cells, compositions, methods and systems that can be used in several embodiments for expression, production and/or purification in a bacterial cell of proteins non-native to the bacterial cell.

The term 'microcompartment' or 'bacterial microcompartment' as used herein indicated organelles within a bacterial cell in which a protein shell encloses enzymes and other proteins. Microcompartments are typically about 40-200 nanometers in diameter and are entirely made of proteins in which the shell functions like a membrane, as it is selectively permeable. Exemplary microcompartments are described in application Ser. No. 15/178,454 filed on Jun. 6, 2016 and published on Dec. 15, 2016 with publication number US206/0362697 incorporated herein by reference in its entirety.

In embodiments herein described, the microcompartments are encapsulin microcompartments and the related microcompartment proteins are encapsulins or encapsulin like The term "encapsulin" or "encapsulin-like" as used herein indicates proteins that are capable of self-assembling in a bacterial cell to form a microcompartment in which interior molecules (e.g., DNA, RNA, protein) can be encaged. In some instances encapsulin proteins can be native to the bacterial cells where they are expressed.

Accordingly, the wording "encapsulin-like microcompartments" or "cage" or "BMC" as used herein refers to organelles produced, and in particular possibly natively produced, by bacteria or viruses to organize and sequester biological molecules, such as DNA, RNA, or protein in a bacterial cell within the confines of a protein shell. Accordingly encapsulin microcompartment can be native or non-native to the cells where produced as would be understood by a skilled person. The encapsulin microcompartments typically have pseudo-icosahedral structures that can be 10 to 400 nm in diameter with a thickness of 20-30 Å [1]. Encapsulin-like protein protomers assemble into pentameric and/or hexameric shapes that further assemble to form the icosahedral microcompartment where the pentagons form the vertices and the hexagons form the flat facets of the compartment. All compartments have a total 20T triangular faces that are formed from 12 pentagons and 10(T−1) hexagons. T is defined as the triangulation number, which can be any non-negative integer that fits $T=h^2+k^2+hk$, where h and k are also non-negative integers (e.g., T can be 1, 3, 4, 7, etc.). Compartments with different numbers of protomers and T values can result in different sized and shaped compartments.

Encapsulin microcompartments typically comprise a microcompartment protein or shell protein forming the shell of the microcompartment and one or more interior proteins identifiable by a skilled person. An encapsulin shell protein typically has three common conserved domains: a peripheral domain (P-domain), an axial domain (A-domain), and an elongated loop (E-loop). Common examples of encapsulin shell proteins include encapsulins Enc A from *Thermotoga maritima* and *Myxococcus xanthus*, and Pfv from *P. furiosus*. [1].

Common examples of encapsulins interior proteins comprise EncB, EncC, and EncD from *M. xanthus* wherein EncB and EncC are ferritin-like proteins that are thought to bind and sequester iron, while EncD has unknown function. Together they are thought to sequester iron under oxidative stress conditions [McHugh, 2014]. Other interior exemplary encapsulins comprise the dye-decoloring peroxidase DyP protein from *T. maritima* as an internal protein.

Encapsulin-like microcompartments can be of bacterial or viral origin. Exemplary encapsulin-like proteins of bacterial origin include encapsulin or virus-like compartments from *Thermotoga maritima* (T=1, 24 nm diameter), *Pyrococcus furiosus* (T=3, 31 nm diameter), and *Myxococcus xanthus* (T=3, 31 nm diameter). Exemplary encapsulin-like proteins of viral origin include HK97 phage capsid (T=7, 66 nm diameter).

Figure 1B:
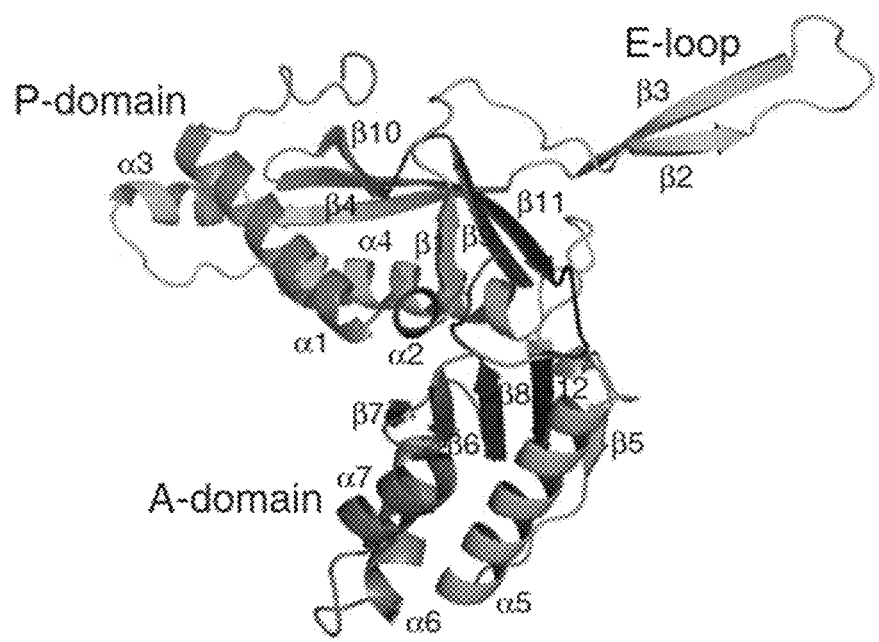
FIG. 1B shows the *T. maritima* encapsulin monomer showing the A- and P-domains and the protruding E-loop. The monomer is colored in a rainbow scheme from the N terminus (blue) to the C terminus (red), the domains are named according to the homologous gp5 major capsid protein of the HK97 virus (PDB 1OHG). This figure is adapted from Sutter, M., et al., *Structural basis of enzyme encapsulation into a bacterial nanocompartment*. Nature Structural & Molecular Biology, 2008. 15(9): p. 939-947.

A representative example of encapsulin proteins is provided by *Thermotoga maritima* encapsulin. In *T. maritima* encapsulin microcompartment, sixty monomers of *T. maritima* encapsulin assemble into a spherical superstructure with icosahedral T=1 symmetry, a diameter of 230-240 Å and a thickness of 20-25 Å. [2] as shown in FIG. 1A. The peripheral domain (P-domain), axial domain (A-domain), and elongated loop (E-loop) of Enc A of *T. maritima* are schematically shown in FIG. 1B.

Microcompartments from bacteria can be isolated and detected by methods and systems exemplified herein (see Example 28) and by additional methods and systems identifiable by a skilled person upon review of the present disclosure.

In embodiments herein described, microcompartment proteins comprised within engineered microcompartment proteins of the disclosure are encapsulin proteins having sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$- $X_{22}$-$X_{23}$-$X_{24}$-$X_{25}$-$X_{26}$-$X_{27}$-$X_{28}$-$X_{29}$-$X_{30}$ $X_{31}$-$X_{32}$-$X_{33}$ $X_{34}$-$X_{35}$-$X_{36}$-$X_{37}$-$X_{38}$-$X_{39}$-$X_{40}$-$X_{41}$-$X_{42}$-$X_{43}$-$X_{44}$-$X_{45}$-$X_{46}$-$X_{47}$-$X_{48}$-$X_{49}$-$X_{50}$-$X_{51}$-$X_{52}$-$X_{53}$-$X_{54}$-$X_{55}$-$X_{56}$-$X_{57}$-$X_{58}$-$X_{59}$-$X_{60}$-$X_{61}$-$X_{62}$-$X_{63}$-$X_{64}$-$X_{65}$-$X_{66}$-$X_{67}$-$X_{68}$-$X_{69}$-$X_{70}$-$X_{71}$-$X_{72}$-$X_{73}$-$X_{74}$-$X_{75}$-$X_{76}$-$X_{77}$-$X_{78}$-$X_{79}$-$X_{80}$-$X_{81}$-$X_{82}$-$X_{83}$-$X_{84}$-$X_{85}$-$X_{86}$-$X_{87}$-$X_{88}$-$X_{89}$-$X_{90}$-$X_{91}$-$X_{92}$-$X_{93}$-$X_{94}$-$X_{95}$-$X_{96}$-$X_{97}$-$X_{98}$-$X_{99}$-$X_{100}$-$X_{101}$-$X_{102}$-$X_{103}$-$X_{104}$-$X_{105}$-$X_{106}$-$X_{107}$-$X_{108}$-$X_{109}$-$X_{110}$-$X_{111}$-$X_{112}$-$X_{113}$-$X_{114}$-$X_{115}$-$X_{116}$-$X_{117}$-$X_{118}$-$X_{119}$-$X_{120}$-$X_{121}$-$X_{122}$-$X_{123}$-$X_{124}$-$X_{125}$-$X_{126}$-$X_{127}$-$X_{128}$-$X_{129}$-$X_{130}$-$X_{131}$-$X_{132}$-$X_{133}$-$X_{134}$-$X_{135}$-$X_{136}$-$X_{137}$-$X_{138}$-$X_{139}$-$X_{140}$-$X_{141}$-$X_{142}$-$X_{143}$-$X_{144}$-$X_{145}$-$X_{146}$-$X_{147}$-$X_{148}$-$X_{149}$-$X_{150}$-$X_{151}$-$X_{152}$-$X_{153}$-$X_{154}$-$X_{155}$-$X_{156}$-$X_{157}$-$X_{158}$-$X_{159}$-$X_{160}$-$X_{161}$-$X_{162}$-$X_{163}$-$X_{164}$-$X_{165}$-$X_{166}$-$X_{167}$-$X_{168}$-$X_{169}$-$X_{170}$-$X_{171}$-$X_{172}$-$X_{173}$-$X_{174}$-$X_{175}$-$X_{176}$-$X_{177}$-$X_{178}$-$X_{179}$-$X_{180}$-$X_{181}$-$X_{182}$-$X_{183}$-$X_{184}$-$X_{185}$-$X_{186}$-$X_{187}$-$X_{188}$-$X_{189}$-$X_{190}$-$X_{191}$-$X_{192}$-$X_{193}$-$X_{194}$-$X_{195}$-$X_{196}$-$X_{197}$-$X_{198}$-$X_{199}$-$X_{200}$-$X_{201}$-$X_{202}$-$X_{203}$-$X_{204}$-$X_{205}$-$X_{206}$-$X_{207}$-$X_{208}$-$X_{209}$-$X_{210}$-$X_{211}$-$X_{212}$-$X_{213}$-$X_{214}$-$X_{215}$-$X_{216}$-$X_{217}$-$X_{218}$-$X_{219}$-$X_{220}$-$X_{221}$-$X_{222}$-$X_{223}$-$X_{224}$-$X_{225}$-$X_{226}$-$X_{227}$-$X_{228}$-$X_{229}$-$X_{230}$-$X_{231}$-$X_{232}$-$X_{233}$-$X_{234}$-$X_{235}$-$X_{236}$-$X_{237}$-$X_{238}$-$X_{239}$-$X_{240}$-$X_{241}$-$X_{242}$-$X_{243}$-$X_{244}$-$X_{245}$-$X_{246}$-$X_{247}$-$X_{248}$-$X_{249}$ $X_{250}$-$X_{251}$-$X_{252}$-$X_{253}$ (SEQ ID NO: 1).

in which $X_1$ is M, $X_2$ is D, $X_3$ is N, $X_4$ is L, $X_5$ is K, $X_6$ is R, $X_7$ is E, $X_8$ is L, $X_9$ is A, $X_{10}$ is P, $X_{11}$ is L, $X_{12}$ is T, $X_{13}$ is E, $X_{14}$ is E, $X_{15}$ is A, $X_{16}$ is W, $X_{17}$ is A, $X_{18}$ is E, $X_{19}$ is I, $X_{20}$ is D, $X_{21}$ is E, $X_{22}$ is E, $X_{23}$ is A, $X_{24}$ is R, $X_{25}$ is E, $X_{26}$ is T, $X_{27}$ is A, $X_{28}$ is K, $X_{29}$ is R, $X_{30}$ is H, $X_{31}$ is L, $X_{32}$ is A, $X_{33}$ is G, $X_{34}$ is R, $X_{35}$ is R, $X_{36}$ is V, $X_{37}$ is V, $X_{38}$ is D, $X_{39}$ is V, $X_{40}$ is E, $X_{41}$ is G, $X_{42}$ is P, $X_{43}$ is L, $X_{44}$ is G, $X_{45}$ is W, $X_{46}$ is G, $X_{47}$ is Y, $X_{48}$ is 5, $X_{49}$ is A, $X_{50}$ is V, $X_{51}$ is P, $X_{52}$ is L, $X_{53}$ is G, $X_{54}$ is R, $X_{55}$ is L, $X_{56}$ is E, $X_{57}$ is E, $X_{58}$ is I, $X_{59}$ is E, $X_{60}$ is G, $X_{61}$ is P, $X_{62}$ is A, $X_{63}$ is E, $X_{64}$ is G, $X_{65}$ is V, $X_{66}$ is Q, $X_{67}$ is A, $X_{68}$ is G, $X_{69}$ is V, $X_{70}$ is R, $X_{71}$ is Q, $X_{72}$ is V, $X_{73}$ is L, $X_{74}$ is P, $X_{75}$ is L, $X_{76}$ is P, $X_{77}$ is E, $X_{78}$ is L, $X_{79}$ is R, $X_{80}$ is V, $X_{81}$ is P, $X_{82}$ is F, $X_{83}$ is T, $X_{84}$ is L, $X_{85}$ is S, $X_{86}$ is R, $X_{87}$ is R, $X_{88}$ is D, $X_{89}$ is L, $X_{90}$ is D, $X_{91}$ is A, $X_{92}$ is V, $X_{93}$ is E, $X_{94}$ is R, $X_{95}$ is G, $X_{96}$ is A, $X_{97}$ is K, $X_{98}$ is D, $X_{99}$ is L, $X_{100}$ is D, $X_{101}$ is L, $X_{102}$ is S, $X_{103}$ is P, $X_{104}$ is V, $X_{105}$ is VA, $X_{106}$ is E, $X_{107}$ is A, $X_{108}$ is A, $X_{109}$ is R, $X_{110}$ is L, $X_{111}$ is L, $X_{112}$ is A, $X_{113}$ is R, $X_{114}$ is A, $X_{115}$ is E, $X_{116}$ is D, $X_{117}$ is R, $X_{118}$ is L, $X_{119}$ is I, $X_{120}$ is F, $X_{121}$ is N, $X_{122}$ is G, $X_{123}$ is Y, $X_{124}$ is A, $X_{125}$ is E, $X_{126}$ is A, $X_{127}$ is G, $X_{128}$ is I, $X_{129}$ is E, $X_{130}$ is G, $X_{131}$ is L, $X_{132}$ is L, $X_{133}$ is N, $X_{134}$ is A, $X_{135}$ is S, $X_{136}$ is G, $X_{137}$ is N, $X_{138}$ is L, $X_{139}$ is K, $X_{140}$ is L, $X_{141}$ is P, $X_{142}$ is L, $X_{143}$ is S, $X_{144}$ is A, $X_{145}$ is D, $X_{146}$ is P, $X_{147}$ is G, $X_{148}$ is D, $X_{149}$ is I, $X_{150}$ is P, $X_{151}$ is D, $X_{152}$ is A, $X_{153}$ is I, $X_{154}$ is A, $X_{155}$ is E, $X_{156}$ is A, $X_{157}$ is L, $X_{158}$ is T, $X_{159}$ is K, $X_{160}$ is L, $X_{161}$ is R, $X_{162}$ is E, $X_{163}$ is A, $X_{164}$ is G, $X_{165}$ is V, $X_{166}$ is E, $X_{167}$ is G, $X_{168}$ is P, $X_{169}$ is Y, $X_{170}$ is A, $X_{171}$ is L, $X_{172}$ is V, $X_{173}$ is L, $X_{174}$ is S, $X_{175}$ is P, $X_{176}$ is D, $X_{177}$ is L, $X_{178}$ is Y, $X_{179}$ is T, $X_{180}$ is A, $X_{181}$ is L, $X_{182}$ is F, $X_{183}$ is R, $X_{184}$ is V, $X_{185}$ is Y, $X_{186}$ is D, $X_{187}$ is G, $X_{188}$ is T, $X_{189}$ is G, $X_{190}$ is Y, $X_{191}$ is P, $X_{192}$ is E, $X_{193}$ is I, $X_{194}$ is E, $X_{195}$ is H, $X_{196}$ is I, $X_{197}$ is K, $X_{198}$ is E, $X_{199}$ is L, $X_{200}$ is V, $X_{201}$ is D, $X_{202}$ is G, $X_{203}$ is G, $X_{204}$ is V, $X_{205}$ is I, $X_{206}$ is W, $X_{207}$ is A, $X_{208}$ is P, $X_{209}$ is A, $X_{210}$ is L, $X_{211}$ is D, $X_{212}$ is G, $X_{213}$ is G, $X_{214}$ is A, $X_{215}$ is V, $X_{216}$ is L, $X_{217}$ is V, $X_{218}$ is 5, $X_{219}$ is T, $X_{220}$ is R, $X_{221}$ is G, $X_{222}$ is G, $X_{223}$ is D, $X_{224}$ is F, $X_2$25 is D, $X_{226}$ is L, $X_{227}$ is T, $X_{228}$ is L, $X_{229}$ is G, $X_{230}$ is Q, $X_{231}$ is D, $X_{232}$ is L, $X_{233}$ is 5, $X_{234}$ is I, $X_{235}$ is G, $X_{236}$ is Y, $X_{237}$ is L, $X_{238}$ is 5, $X_{239}$ is H, $X_{240}$ is D, $X_{241}$ is A, $X_{242}$ is D, $X_2$43 is N, $X_{244}$ is V, $X_{245}$ is E, $X_{246}$ is L, $X_{247}$ is F, $X_{248}$ is L, $X_{249}$ is T, $X_{250}$ is E, $X_{251}$ is 5, $X_{252}$ is F, $X_{253}$ is T (SEQ ID NO: 1) or a sequence with at least 22% sequence identity or at least 40% sequence similarity to SEQ ID NO:1.

In preferred embodiments, the engineered microcompartment protein of the disclosure, the encapsulin protein has SEQ ID NO: 1 or a sequence with at least 30% sequence identity, a 40% sequence identity, at least a 50% sequence identity, or more preferably at least a 60% sequence identity or greater with SEQ ID NO: 1 or at least 40% sequence similarity, preferably at least 50% sequence similarity, at least 60% sequence similarity or a greater similarity to SEQ ID NO:1.

The term "sequence identity" indicates the amount of characters that are identical between two different sequences following alignment of the sequences. The percent identity is calculated from the number of exact character matches divided by the total number of aligned characters, including gaps, multiplied by 100%.

The term "sequence similarity" indicates the amount of characters that are similar between two different sequences following alignment of the sequences. Different from the "identity", which refers to an exact match between two nucleotides or amino acids, similarity refers to a resemblance between two residues that is greater than one would expect at random and provides a predictable structure. Amino acids are considered similar if they have a positive value in a substitution matrix, such as BLOSUM-62 (FIG. 2). BLOSUM-62 is a probability matrix based on observed substitutions found in a broad sampling highly aligned sequences [3] and is used in the BLAST alignment tool. Percent similarity is calculated from the number of similar amino acid matches (based on the substitution matrix) divided by the total number of aligned characters, including gaps, multiplied by 100%.

Sequence identity and sequence similarity can be detected by commonly used searching programs, like BLAST, PSI-BLAST [4], SSEARCH [5] [6], FASTA [7] and the HMMER3 [8] which can produce accurate statistical estimates of protein sequences that share sequence identity, similarity and also have similar structures.

The identity or similarity between sequences is typically measured by a process that comprises the steps of aligning two polypeptide or polynucleotide sequences to form aligned sequences, then detecting the number of matched characters, characters similar or identical between the two aligned sequences, and calculating the total number of matched characters divided by the total number of aligned characters in each polypeptide or polynucleotide sequence, including gaps. The similarity or identity result is expressed as a percentage.

An exemplary alignment is illustrated in FIG. 3 which shows a pairwise alignment of encapsulin from *T. maritima* compared to encapsulin from *M. xanthus*. In the representative example of FIG. 3 a total of 279 residues are aligned. 64 of the residues have an exact match between the two sequences which is denoted as the given letter symbol in the line between the two sequences. In this case, the percent identity is 64/279×100%=23% identity. 122 of the residues (including the 64 exact identities) have positive values based on the BLOSUM-62 similarity matrix, which are denoted with either a + symbol or the letter symbol in the line between the two sequences. In this case, the percent similarity is 122/279×100%=43%.

In embodiments herein described, an encapsulin protein which either has SEQ ID NO: 1 or a sequence of the disclosure with at least 22% sequence identity or at least 40% sequence similarity to SEQ ID NO:1, comprises a P-Domain divided into a first fragment, a second fragment and a third fragment, an E-Loop and an A-Domain, each having an N-terminus and a C-terminus.

The term the "amino terminus" or "N-terminus" indicate the amino acid residue of a linear polypeptide chain at one of the extremities of the linear polypeptide chain which, when not involved in a peptide bond, presents an amino group. The term the "carboxyl terminus" "C-terminus" indicate the amino acid residue of a linear polypeptide chain at one of the extremities of the linear polypeptide chain which, when not involved in a peptide bond, presents a carboxyl group. Unless otherwise indicated, counting of residues in a polypeptide is performed from the N-terminal end (NH2-group). An N terminus or a C-terminus of a polypeptide is typically comprised within a "tail" of the protein which indicates a segment or fragment at the related end of the protein.

The term "fragment' or "segment" as related to the protein indicates any continuous part of a protein sequence from single amino acid up to the full protein associated to an identifiable structure within the protein. An "identifiable structure" in the sense of the disclosure indicates a spatial arrangement of the primary structure or portions thereof which can be detected by techniques such as crystallography, hydrophobicity analysis or additional techniques known by a skilled person. In some instances, a protein segment or fragment can comprise one or more secondary structures of the protein.

The "secondary structure" of a protein refers to local sub-structures with a repeating geometry identifiable within crystal structure of the protein, circular dichroism or by additional techniques identifiable by a skilled person. In some instances, a secondary structure of a protein can be identified by the patterns of hydrogen bonds between backbone amino and carboxyl groups. Secondary structures can also be defined based on a regular, repeating, geometry, being constrained to approximate values of the dihedral angles w and φ of the amino acids in the secondary structure unit on the Ramachandran plot. Two main types of secondary structure are the alpha helix and the beta strand or beta sheets as will be identifiable by a skilled person. Both the alpha helix and the beta sheet represent a way of establishing non-covalent hydrogen bonds between constituents of the peptide backbone. Secondary structure formation can be promoted by formation of hydrogen bonds between backbone atoms. Amino acids that can minimize formation of a secondary structure by destabilizing the structure of the hydrogen bonding interactions are referred to as secondary structure breakers. Amino acids that can promote formation of a secondary structure by stabilizing formation of hydrogen bonding interactions are referred to as structure makers.

Several sequential secondary structures may form a "supersecondary unit" or "structural motif." A "supersecondary unit" or "structural motif" indicates a segment of the protein that forms an identifiable three-dimensional structure formed by adjacent secondary structure elements optionally linked by unstructured protein regions. In structural motifs the secondary structures are typically comprised with a same orientation one with respect to another. In particular some structural motifs (e.g. zinc fingers, a Greek key or helix-turn helix) are conserved in different proteins as will be understood by a skilled person.

The "tertiary structure" of a protein refers to the three-dimensional structure of a protein, stabilized by non-covalent interactions among non-adjacent segments of the protein and optionally by one or more additional compounds or ions interacting through covalent or non-covalent interactions with one or more segments of the proteins. Exemplary non-covalent interactions stabilizing the three dimensional structure of the proteins comprise non-specific hydrophobic interactions, burial of hydrophobic residues from water, specific tertiary interactions, such as salt bridges, hydrogen bonds, the tight packing of side chains, chelation and disulfide bonds and additional interactions identifiable by a skilled person. Exemplary covalent interactions among compounds or ions and segments of the protein comprise, N-linked glycosylation, cytochrome C heme attachment and additional interaction identifiable by a skilled person.

In embodiments herein described, the first fragment of the P-Domain of an encapsulin protein of SEQ ID NO: 1 or of a sequence with at least 22% sequence identity or at least 40% sequence similarity to SEQ ID NO:1, comprises residues configured to form, in a folded encapsulin protein, a secondary structure comprising in a N-terminus C-terminus direction, a 4 to 26 residues alpha helix α1, followed by a 0 to 22 residues first non-structured region (e.g. forming a loop), linked to a 4 to 11 residues alpha helix α2, linked to a 3 to 9 residues beta strand β1, linked to a 3 to 13 residues second non-structured region. In particular, in embodiments, where the encapsulin protein has SEQ ID NO: 1, the first fragment of the P-Domain can be formed by residues X2 to X46. A representative example of the structure of a first fragment of the P-domain according to these embodiments is provided by the first segment of the P-domain of the encapsulin shell protein EnCA illustrated in FIG. 1B. As shown, the first segment of the P-Domain in the representative EncA of FIG. 1B consists of a mixed α/β structure, contains the N terminus and is fragmented with regard to primary sequence (FIG. 1B, orange secondary structure bars). The first fragment or segment of the P-domains contains two alpha helices α1, α2 and one beta strand β1.

In embodiments herein described, the second fragment of the P-Domain of an encapsulin protein comprising residues of SEQ ID NO: 1 or of a sequence with at least 22% sequence identity or at least 40% sequence similarity to SEQ ID NO:1, comprises residues configured to form, in a folded encapsulin protein, a secondary structure comprising in a N-terminus to C-terminus direction a 9 to 15 residues beta strand β4, linked to a 6 to 15 residues alpha helix α3, linked to a 0 to 10 residues first non-structured region, linked to a 18 to 29 residues alpha helix α4, linked to a 9 to 21 residues second non-structured region. In particular, in embodiments, where the encapsulin protein has SEQ ID NO: 1, the second fragment of the P-Domain can be formed by residues X75 to X130. A representative example of the structure of a second fragment of the P-domain according to these embodiments is provided by the second segment of the P-domain of the encapsulin shell protein EnCA illustrated in FIG. 1B. As shown, the second segment of the P-Domain in the representative EncA of FIG. 1B consists of the second segment of the P-domain contains one beta strand β4 and two alpha helices α3 and α4.

In embodiments herein described, the third fragment of the P-Domain of an encapsulin protein comprising residues of SEQ ID NO: 1 or of a sequence with at least 22% sequence identity or at least 40% sequence similarity to SEQ ID NO:1, comprises residues configured to form, in a folded encapsulin protein, a secondary structure comprising in a N-terminus to C-terminus direction, a 4 to 10 residues beta strand β9, linked to by a 3 to 16 residues first non-structured region, linked to a 7 to 13 residues beta strand β10, linked to a 1 to 15 residues second non-structured region, linked to a 10 to 19 residues beta strand β11. In particular, embodiments, where the microcompartment protein has SEQ ID NO: 1, the third fragment of the P-Domain can be formed by residues X221 to X253. A representative example of the structure of a second fragment of the P-domain according to these embodiments is provided by the third segment of the P-domain of the encapsulin shell protein EncA illustrated in FIG. 1B. As shown, the third segment of the P-Domain in the representative EncA of FIG. 1B consists of the third segment of the P-domain contains three beta strands β9, β10, and β11. A conserved hydrophobic core is located between the helical and β-sheet regions.

In the engineered microcompartment protein, the E-Loop of the encapsulin protein of an encapsulin protein comprising residues of SEQ ID NO: 1 or of a sequence with at least 22% sequence identity or at least 40% sequence similarity to SEQ ID NO:1, comprises residues configured to form in a folded encapsulin protein, a secondary structure comprising in an N-terminus to C-terminus direction, a 8 to 16 residues beta strand β2, linked to a 2 to 24 residues first non-structured region, linked to a 7 to 15 residues beta strand β3, linked to a 0 to 6 residues second non-structured region. In particular, in embodiments, where the microcompartment protein has SEQ ID NO: 1, the E-Loop can be formed by residues X47 to X74. A representative example of the structure of an E-Loops according to these embodiments is provided by the E-Loop of the encapsulin shell protein EnCA is illustrated in FIG. 1B. In the illustration of FIG. 1B, the E-loop adopts a flexible loop conformation and is responsible for the formation of contacts between the two-fold symmetry-related subunits by providing a strand that completes a β-sheet formed by both subunits. The E-loop contains two β strands: β2 and β3.

In the engineered microcompartment protein, the A-Domain of an encapsulin protein comprising residues of SEQ ID NO: 1 or of a sequence with at least 22% sequence identity or at least 40% sequence similarity to SEQ ID NO:1, comprises residues configured to form, in a folded encapsulin protein, a secondary structure comprising in an N-terminus to C-terminus direction a 0 to 8 residues beta strand β5, linked to a 1 to 15 residues first non-structured region, linked to a 16 to 23 residues alpha helix α5, linked to a 3 to 11 residues second non-structured region, linked to a 3 to 11 residues beta strand β6, a 9 to 16 residues alpha helix α6, a 1 to 24 third non-structured region, linked to a 0 to 16 residues alpha helix α7, linked to a 0 to 8 residues fourth non-structured region, linked to a 1 to 10 residues beta strand β7, linked to a 1 to 12 residues fifth non-structured region, linked to a 3 to 10 residues beta strand β8, linked to a 2 to 12 residues sixth non-structured region In in particular, in embodiments, where the microcompartment protein has SEQ ID NO: 1, the A-Domain can be formed by residues X131 to X220. A representative example of the structure of an A-Domain according to these embodiments provided by the A-Domain of the encapsulin shell protein EnCA is illustrated in FIG. 1B. In the illustration of FIG. 1B, the A-domain forms a compact structure consisting of three helical segments and a five-stranded β-sheet. The A-domain also contains the C terminus of the encapsulin shell protein. This domain has few connections to the rest of the monomer and mediates the contacts of the five-fold symmetry interface. The A-domain contains four beta strands β5, β6, β7, β8 and three alpha helices α5, α6, α7.

In an encapsulin of an engineered microcompartment protein herein described, each P-domain, A-domain and E-loop of the engineered microcompartment proteins of the current disclosure has a N-terminus and a C-terminus, and the P-domain, A-domain and E-loop are arranged together in a configuration comprising in a direction N-terminus to C-terminus the first fragment of the P-domain linked to the E-loop linked to the second fragment of the P-domain linked to the A-domain linked to the third fragment of the P-domain. In particular, in encapsulin protein used for constructing engineered microcompartment proteins herein described the C-terminus of the first fragment of P-domain is covalently attached to the N-terminus of the E-loop, the C-terminus of the E-loop is covalently linked to the N-terminus of the second fragment of the P-domain, the C-terminus of the second fragment of the P-domain is covalently attached to the N-terminus of the A-domain, and the C-terminus of the A-domain is covalently attached to the N-terminus of the third fragment of the P-domain (see configuration of the representative EncA of FIG. 1B).

In some embodiments, the encapsulin protein has SEQ ID NO: 1 or a sequence with at least 22% sequence identity or at least 40% sequence similarity to SEQ ID NO:1 and residues X2 to X46, X75 to X130 and X221 to X253 form a P-domain, in which residues X2 to X46 form a first fragment of the P-domain, X75 to X130 form a second fragment of the P-domain and X221 to X253 form a third fragment of the P-domain.

In particular, in some embodiments, one insertion site can be located within the loop region of the E-loop between β2 and β3, comprising X57 to X65, another insertion site can be located within β3 of the E-loop, comprising X66 to X74, and/or another insertion site can be located in the flexible region between the N-terminus of the A-domain and α5, including β3, comprising X132 to X144, as will be understood by a skilled person.

In some embodiments, the encapsulin protein has SEQ ID NO: 1 or a sequence with at least 22% sequence identity or at least 40% sequence similarity to SEQ ID NO:1 and residues X47 to X74 form an E-loop.

In some embodiments, the encapsulin protein has SEQ ID NO: 1 or a sequence with at least 22% sequence identity or at least 40% sequence similarity to SEQ ID NO:1 and residues X131 to X220 form an A-domain, residues X221 to X253 form a third fragment of the P-domain Various embodiments of encapsulin proteins in the sense of the disclosure that can be used for constructing an engineered microcompartment herein described, have a consensus sequence of SEQ ID NO:2 reported below. The amino acids highlighted in bold in SEQ ID NO: 2 and in other sequences herein described (see e.g. *T. maritima* encapsulin sequence (FIG. 5) indicates either identical or highly conserved among the different encapsulins used for constructing an engineered microcompartment herein described, unless otherwise indicated. The wording "highly conserved" indicates identical/conserved amino acids passing a 3.0 bit conservation setting based on pfam alignment tool for all 44 sequences in pfam 04454 (see the website www.ncbi.nlm.nih.gov/Structure/cdd/cddsrv.cgi at the filing date of the present disclosure).

```
                                                           (SEQ ID NO: 2)
MDNLKRELAPL TEEAWAEIDEE ARETAKRHLAG RRVVDVEGPLG WGYSAVPLGRL    55

EEIEGPAEGVQ AGVRQVLPLPE LRVPFTLSRRD LDAVERGAKDL DLSPVAEAARK   110

LARAEDRLIFN GYAEAGIEGLL NASGnLKLPLS ADPGDIPDAIA EALTKLREAGV   165

EGPYALVLSPD LYTALFRVYDG tGYPEIEHIKE LVDGGVIWAPA LDGgAVLVSTR   220

GGDFDLTLGQD LSIGYLSHDAD NVELFLTESFT
```

FIG. 4 shows an additional representation of consensus sequences SEQ ID NO: 2 with complete indication of the related P-Domain, E-Loop and E Domain (FIG. 4A) as well as a schematic representation of the related configuration in the encapsulin sequence (FIG. 4B).

In particular, consensus sequence SEQ ID NO: 2 contains 253 amino acids forming a 3-D configuration having a P-domain, A-domain and an E-loop. In particular, in consensus sequence SEQ ID NO: 2, residues DNLKRELAPL TEEAWAEIDEE ARETAKRHLAG RRVVDVEGPLG WG (SEQ ID NO:3) provide the consensus for the first fragment of the P-domain containing two alpha helices α1, α2 and one beta strand β1, in which the amino acids highlighted in bold are either identical or highly conserved among the different encapsulins forming the consensus of the fragment. Residues YSAVPLGRL EEIEGPAEGVQ AGVRQVLP (SEQ ID NO: 4) provide the consensus for the E-loop containing two β strands: β2 and β3. Residues LPE LRVPFTLSRRD LDAVERGAKDL DLSPVAEAARK LARAEDRLIFN GYAEAGIEG (SEQ ID NO:5) provide the consensus for the second fragment of the P-domain containing one beta strand β4 and two alpha helices α3 and α4 in which the amino acids highlighted in bold are either identical or highly conserved among the different encapsulins forming the consensus of the fragment. Residues LL NASGnLKLPLS ADPGDIPDAIA EALTKLREAGV EGPYALVLSPD LYTALFRVYDG tGYPEIEHIKE LVDGGVIWAPA LDGgAVLVSTR (SEQ ID NO: 6) provide the consensus for the A-domain containing four beta strands β5, β6, β7, β8 and three alpha helices α5, α6, α7 and residues GGDFDLTL-GQD LSIGYLSHDAD NVELFLTESFT (SEQ ID NO:7) form the third fragment of the P-domain containing three beta strands β9, β10, and β11 in which the amino acids highlighted in bold are either identical or highly conserved among the different encapsulins forming the consensus of each respective fragment.

A skilled person will be able to identify encapsulin proteins in the sense of the disclosure from the consensus sequence SEQ ID NO: 2 following one or more sequence alignments upon reading of the present disclosure.

In some embodiments, encapsulin proteins used for constructing an engineered microcompartment herein described have at least a 30% sequence identity, at least a 40% sequence identity, at least a 50% sequence identity, or at least a 60% sequence identity or greater with the encapsulin protein of SEQ ID NO: 2.

In some embodiments, encapsulin proteins used for constructing an engineered microcompartment herein described have at least a 50% sequence similarity, at least a 60% sequence similarity or a greater similarity with the encapsulin shell protein of SEQ ID NO: 2.

In some embodiments, encapsulin proteins used for constructing an engineered microcompartment herein described, have a sequence of the E-Loop which following sequence alignment provide a consensus sequence YSAVPLGRL EEIEGPAEGVQ AGVRQVLP (SEQ ID NO:4) In some of those embodiments, the encapsulin proteins in the sense of the disclosure comprise an E-loop having a primary sequence of at least 22% sequence identity, 30% sequence identity, a 40% sequence identity, a 50% sequence identity, a 60% sequence identity or greater with respect to SEQ ID NO: 4. In some of these embodiments the E loop sequences of engineered microcompartment proteins herein described comprise a V57 residue and/or a D60 residue such as 3KDT (T. maritima)

YAAHPLGEVEVLSDENEVVKWGLRKSLP (SEQ ID NO: 59), GI 501012501

YTVVPEGRLKKIEDNPGNVCTGMYQVKP (SEQ ID NO: 60), GI 502591318

YAAVNTGELRPIDDTPEDVDMKLRQVQP (SEQ ID NO: 61), GI 501771872

YAAVNTGRRTALEDKAEGASIFQRQVLP (SEQ ID NO: 62), and GI 501367709 FSALGTGHVSRVAADTPGVEALQRHVVR (SEQ ID NO: 63).

In some embodiments, encapsulin proteins used for constructing an engineered microcompartment herein described, have a sequence of the A-domain which following sequence alignment provide a consensus sequence LL NASGnLKLPLS ADPGDIPDAIA EALTKLREAGV EGPYALVLSPD LYTALFRVYDG tGYPEIEHIKE LVDGGVIWAPA LDGgAVLVSTR (SEQ ID NO: 6). In some of those embodiments, the encapsulin proteins in the sense of the disclosure comprise A-domain having a primary sequence of at least 22% sequence identity, 30% sequence identity, a 40% sequence identity, a 50% sequence identity, a 60% sequence identity or greater with respect to SEQ ID NO: 6. In some of these embodiments the A-domain sequences of engineered microcompartment proteins herein described comprise 3DKT: LLSFEERKIECGSTPKDLLEAIVRALSIFSKDGIEGPYTLVINTDRWINFLKEEAGH YPLEKRVEECLRGGKIITTPRIEDALVVSER (SEQ ID NO: 64), GI 501179632: LREGTSNPKLALPSSASDYPAAIAAALNQLRLAGVNGPYAVVLGAGVYTALSGG DDEGYPVFRHIESLIDGKIVWAPAIEGGFVLSTR (SEQ ID NO: 65), GI 490598858: LLTEDGIVKFPISNWSEGENPFKDISIGLAKFIENGIVGRKALVVSPNLFVQLQRIQ PGTGTTEYDRINKLLDGNIFSTPVLKDDKAVLVCSE (SEQ ID NO: 66), GI 501923113: ILNAEGAQKLQISDWGQGENPYTDIVKAINMIREKGIVGRFVLCLSQSLYFDLQRI QQGTGMTEAQRISSMIGNLYNVPVIKGKKAALICAE (SEQ ID NO: 67), and GI 496662878: LLTVKGSSKIKKSDWSQGENSFADITAGVAQLAKT GYLGRYALVVSPDLFLDLQ RLQPNTGLLEIDRIKKLIGDNVYMTSVMGPGKAVLVCAE (SEQ ID NO: 68).

In some embodiments, encapsulin proteins used for constructing an engineered microcompartment herein described, have a sequence of the P-domain which following sequence alignment provides a consensus sequence MDNLKRELAPL TEEAWAEIDEE ARETAKRHLAG RRVVDVEGPLG WG (SEQ ID NO:3) for the first fragment, the consensus sequence LPE LRVPFTLSRRD LDAVERGAKDL DLSPVAEAARK LARAEDRLIFN GYAEAGIEG (SEQ ID NO:5) for the second fragment and the consensus sequence GGDFDLTLGQD LSIGYLSHDAD NVELFLTESFT (SEQ ID NO:7) for the third fragment. In some of those embodiments, the encapsulin proteins in the sense of the disclosure comprise P-domain having a primary sequence with at least 22% sequence identity, 30% sequence identity, a 40% sequence identity, a 50% sequence identity, a 60% sequence identity or greater with respect to SEQ ID NO: 3, 5- and 7.

An exemplary encapsulin shell protein from T. maritima has a SEQ ID NO: 47 shown in FIG. 5, comprising the P-domain, E-loop and A-domain.

Figure 6:
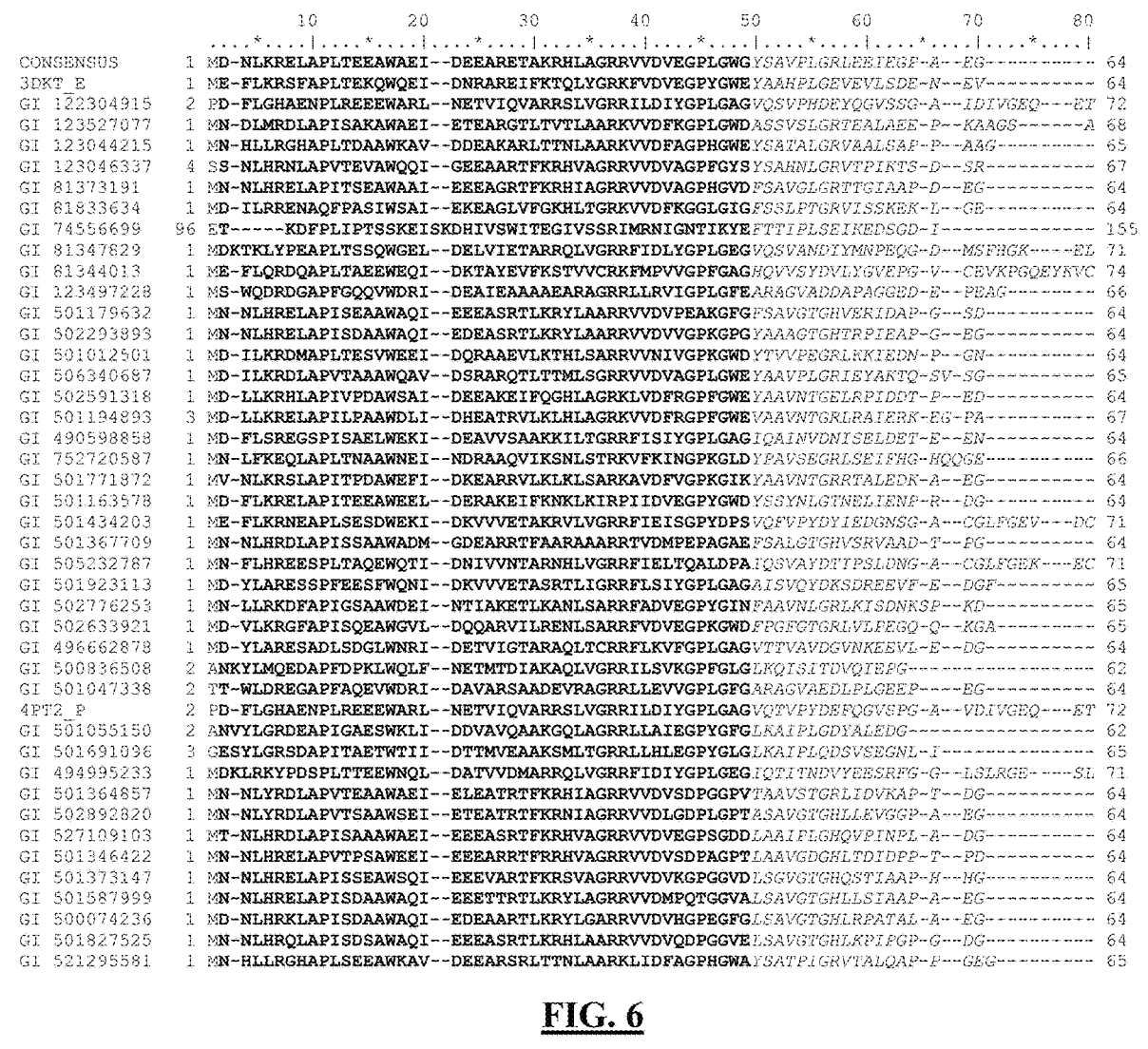

In some embodiments, the encapsulin proteins herein used for constructing the engineered microcompartment proteins comprise the encapsulin proteins from the protein family PF04454 (Linocin_M18, Encapsulating protein for peroxidase), COG1659, and the DUF2184 superfamily. Proteins in this family are found in eubacteria and archaea, and can form nanocompartments within the bacterium which contain ferritin-like proteins or peroxidases, enzymes involved in oxidative-stress response. Detailed information about this protein family can be found in the pfam web site as will be understood by a person skilled in the art (see the website pfam.xfam.org/family/PF04454 at the filing date of the present disclosure). A sequence alignment of 44 exemplary members from the PF04454 family are shown in FIG. 6.

In some embodiments, the encapsulin proteins herein used for constructing the engineered microcompartment proteins comprise the members of Phage_capsid pfam05065 (see the website pfam.xfam.org/family/PF05065 at the filing date of the present disclosure) and HK97 family of viral capsid proteins (TIGR01554) that have at least 22% identity or at least 40% similarity to SEQ ID NO:1.

In some embodiments, encapsulins herein described comprise homologous proteins of the encapsulin protein or SEQ ID NO: 1 or SEQ ID NO: 47 with at least 22% sequence identity or 40% sequence similarity, in which one or more residues forming the P-domain, E-loop and A-domain are replaced with a functionally equivalent residue.

A functionally equivalent residue of an amino acid used herein typically refers to other amino acid residues having physiochemical and stereochemical characteristics substantially similar to the original amino acid. The physiochemical characteristics include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

In embodiments according to the instant disclosure, a microcompartment protein is engineered to introduce in the encapsulin protein a target protein and at least one protease cleavage site configured to allow release of the target protein from the engineered microcompartment protein upon cleavage of the at least one protease cleavage site in the engineered microcompartment protein.

In particular in embodiments herein described:

a target protein having an N-terminus, a C-terminus and a sequence up to 80 amino acids in length is inserted at the N-terminus of the first segment of the P-domain of the encapsulin protein alone or together with a linker and/or a tag;

at least one first protease cleavage site is inserted between the C-terminus of the target protein and the N-terminus of the first segment of the P-Domain of the encapsulin protein alone or together with a linker and/or a tag; and at least one second protease cleavage site is inserted, alone or together with a linker and/or a tag, within 9 to 17 amino acids and/or 0-8 amino acids adjacent to the C-terminus of the E-loop of the encapsulin protein and/or within 2-14 amino acids adjacent to the N-terminus of the A-domain of the encapsulin protein to enable digestion of the encapsulin and release of the target protein.

As used herein, in relation to proteins, the term "insertion" of a first protein or fragment thereof in a second protein or fragment thereof refers to the introduction of the first protein or fragment thereof in between two adjacent amino acids of the first protein or fragment thereof. As a result, an inserted first protein is located in between the two adjacent amino acids of the second protein.

In particular, an insertion of a first protein in a second protein is performed by forming a first covalent bond between the N-terminal amino acid of the first protein with a first amino acid of the two adjacent amino acids the second protein, and a second covalent bond between the C-terminal amino acid of the first protein with a second amino acid of the two adjacent amino acids of the second protein. As would be understood by a skilled person, a covalent bond between two amino acids in a protein is typically a peptide bond, which is a covalent bond between a carboxyl group and an amino group of two molecules or portions thereof, which results in releasing a molecule of water.

Accordingly, an insertion of a second protein in a first protein when performed at a protein level typically results in breaking the peptide bond between the two adjacent amino acids of the first protein and forming two new peptide bonds: one between one of the two adjacent amino acids of the first protein and the N-terminal amino acid of the second protein and the other peptide bond formed between the other one of the two adjacent amino acid of the first protein and the C-terminal amino acid of the second protein.

Figure 7A:
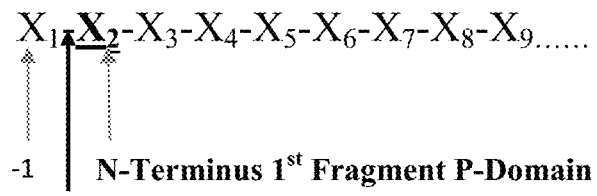
FIG. 7A shows insertion sites of a target protein in engineered microcompartment herein described (SEQ ID NO: 91).

In embodiments of the disclosure, insertion at the N-terminus of the first segment of the P-Domain is performed at the position between the N-terminus of the first segment of the P-Domain and the adjacent residue upstream in the encapsulin protein. For example, in embodiments where the encapsulin protein has SEQ ID NO: 1, the non-native protein can be introduced at an insertion position −1 relative to the N-terminus of the first segment of the P-Domain of the encapsulin protein. As a consequence, in embodiments where the encapsulin protein has SEQ ID NO: 1 the target protein or an insertion region comprising the target protein optionally together with a tag and/or a linker can be inserted between the adjacent residues X1 and X2 of the microcompartment protein. A schematic illustration of such insertion is illustrated in FIG. 7A. In some embodiments, the insertion region comprising the target protein alone or together with at least one tag and/or one linker comprises up to 80 amino acid residues.

Figure 7B:
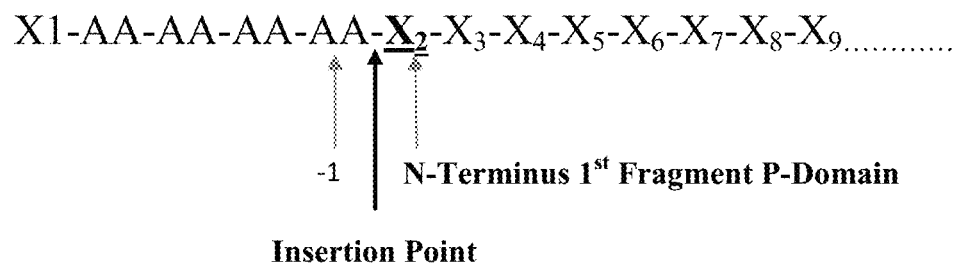
FIG. 7B shows insertion sites of a target protein in engineered microcompartment herein described (SEQ ID NO: 92).

In embodiments of the disclosure, insertion of the at least one first protease cleavage site between the C-terminus of the target protein and the N-terminus of the first segment of the P-Domain of the encapsulin protein is performed at the position between the N-terminus of the first segment of the P-Domain and the adjacent residue upstream in the target protein. For example, in embodiments where the encapsulin protein has SEQ ID NO: 1, the target protein can be introduced at an insertion position −1 to position relative to the N-terminus of the first segment of the P-Domain of the encapsulin protein. As a consequence in embodiments where the encapsulin protein has SEQ ID NO: 1 the at least one first protease or an insertion region comprising the at least one first protease optionally together with a tag and/or a linker can be inserted between the residues X2 of the microcompartment protein and the residue immediately upstream residue X2. A schematic illustration of such insertion is illustrated in FIG. 7B in which the residues of the inserted target proteins are indicated as AA. In some embodiments, the insertion region comprising the at least one first protease alone or together with at least one tag and/or one linker, comprises up to 22 amino acid residues.

In embodiments of the disclosure, insertion of the at least one second protease cleavage site within 9-17 and/or 0-8 amino acids adjacent to the C-terminus of the E-loop of the encapsulin protein and/or within 2-14 amino acids adjacent to the N-terminus of the A-domain of the encapsulin protein, can be performed at any one of the 9 to 17 amino acids and/or 0 to 8 adjacent residues upstream of the C-terminus of the E-Loop and/or 2-14 amino acids downstream of the N-terminus of the A-Domain.

As a consequence in embodiments where the encapsulin protein has SEQ ID NO: 1 the at least one second protease or an insertion region comprising the at least one second protease optionally together with a tag and/or a linker, can be inserted between any one of residues X57 and X74 of the microcompartment protein and/or between any one of residues X132 to X144 of the microcompartment protein. In particular, in SEQ ID NO: 1 residues X57 to X65 define the loop region of the E-loop domain (the first unstructured region of the E-Loop between beta-strands β2 and β3 of the E-Loop of the protein and residues X66 to X74 define beta strand β3 of the E-loop, and residues X132 to X144 define within the beta-strand β5 and the subsequent second unstructured region of the A Domain of the protein as will be understood by a skilled person.

Figure 7C:
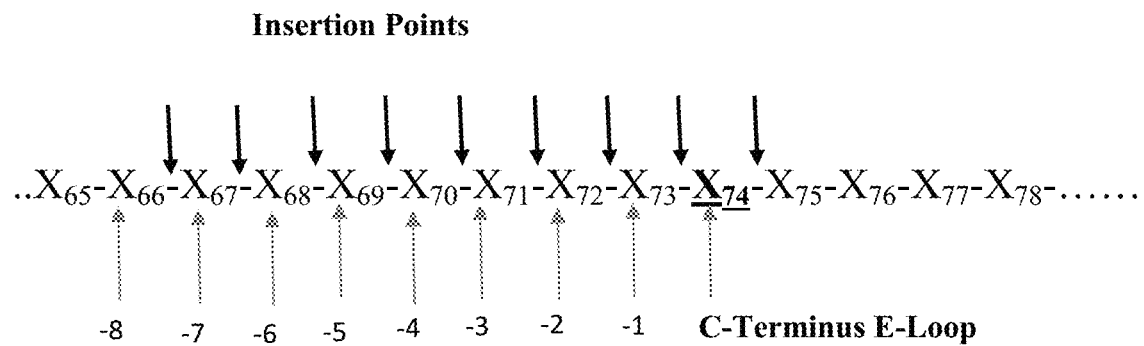
Figure 7D:
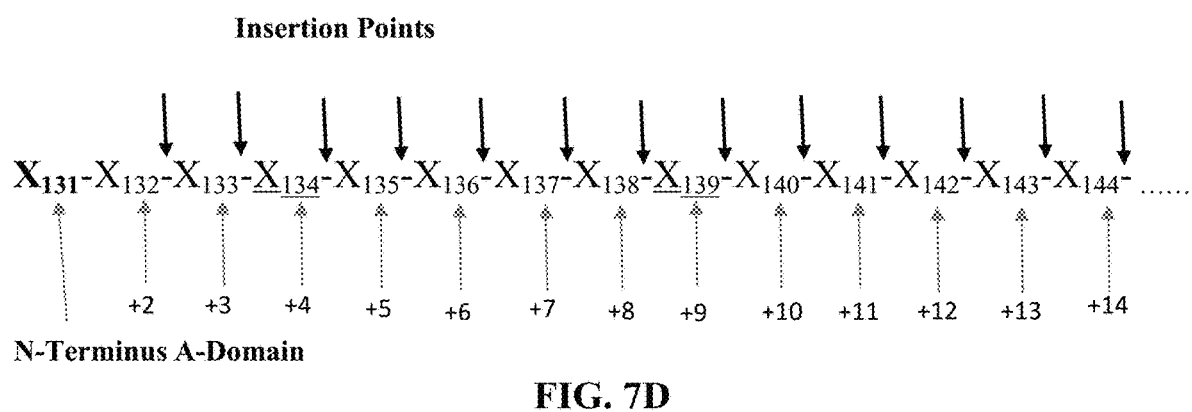

A schematic illustration of such insertion is illustrated in FIG. 7C and FIG. 7D. In some embodiments, the insertion regions comprising the at least one second protease alone or together with at least one tag and/or one linker, can independently comprise up to 22 amino acid residues.

Exemplary sequences showing possible insertion points for the at least one second protease with bolded and bolded italics fonts are YSAVPLGRL EEIEGPAEGVQ AGVRQVLP (SEQ ID NO: 4), and LL NASGnLKLPLS ADPGDIPDAIA EALTKLREAGV EGPYALVLSPD LYTALFRVYDG tGYPEIEHIKE LVDGGVIWAPA LDGgAVLVSTR (SEQ ID NO: 6).

Preferred insertion points for the at least one second protease cleavage site in SEQ ID NO: 1 are $X_{57}$ (corresponding to V57 in constructs exemplified in the example section of the present disclosure); $X_{60}$ (corresponding to D60 in constructs exemplified in the example section of the present disclosure); $X_{71}$ (corresponding to K71 in constructs exemplified in the example section of the present disclosure); and X$_{139}$ (corresponding to K138 in constructs exemplified in the example section of the present disclosure) which can be provided alone or in any combination selected in view of the resulting engineered microcompartment protein as will be understood by a skilled person upon reading of the present disclosure.

Exemplary sequences of engineered microcompartment proteins enclosing the above insertion points for the at least one second protease cleavage site are reported below wherein the related residues are reported in bold fonts.

```
                                            (SEQ ID NO: 4)
YSAVPLGRL EEIEGPAEGVQ AGVRQVLP (SEQ ID NO: 6)
LL NASGnLKLPLS ADPGDIPDAIA EALTKLREAGV EGPYALVLSPD

LYTALFRVYDG tGYPEIEHIKE LVDGGVIWAPA LDGgAVLVSTR
```

In embodiments herein described the engineered microcompartment proteins can be cage forming or non-cage forming depending on the positioning of the at least one second protease cleavage site.

The wording "cage forming" as used herein indicates an engineered microcompartment protein configured to form upon translation within cytoplasm of a cell or in a cell free environment, an encapsulin like microcompartment as described herein. Conversely, the wording non-cage forming as used herein indicates an engineered microcompartment protein configured not to form upon translation within a cytoplasm of a cell or in a cell free environment, an encapsulin like microcompartment as described herein In particular in some embodiments, an engineered microcompartment protein can be designed to include the at least one second protease cleavage site can be within the loop region of the E-loop domain (the first unstructured region of the E-Loop, between beta-strands β2 and β3 of the protein) to provide a cage forming engineered microcompartment protein. Examples are insertions at any of positions X57 and X65 in SEQ ID NO 1, and any of the position 11 (E) to 19 (V) (EIEGPAEGV—SEQ ID NO: 139) in SEQ ID NO; 4. Representative examples are provided by insertions at residues V57 and D60 in T. maritima encapsulin (see Examples 17 to 24). In particular, in order to obtain cage forming microcompartment proteins one insertion can be performed at any one of the residues (see e.g. the insertion of a GG-ENLYFQG-GG SEQ ID NO: 140 or residue of a same or smaller dimension after 1 residue in the region of the Enc from T. maritima which already has 9 amino acids).

In some embodiments, an engineered microcompartment protein can be designed to include the at least one second protease cleavage site on the β5 beta strand prior to α5 of the A-Domain to provide a cage forming engineered microcompartment protein. Examples are insertions at any of positions X132 and X144 in SEQ ID NO 1, and any of the position 2 (L) to 14 (A) of sequence LNASGnLKLPLSA (SEQ ID NO: 141) in SEQ ID NO: 6.

In some embodiments, an engineered microcompartment protein can be designed to include the at least one second protease cleavage site in the loop region of the E-loop (in the first unstructured region of the E-loop between β2 and β3) and in the A domain and the resulting engineered microcompartment proteins are also expected to be cage forming.

In some embodiments, an engineered microcompartment protein can be designed to include at least one second protease cleavage site in the E-loop domain within the beta-strand β3 to provide a non-cage forming engineered microcompartment protein. In particular, a disruption of cage-formation occurs if there is an insertion within β3 of the E-loop (e.g. X71 in SEQ ID NO; 1 and K71 construct in the examples) while cage formation would not be disrupted if there is an insertion after X139 in SEQ ID NO; 1 (see K138 constructs in the examples). In some of these embodiments, the addition of this site can improve the kinetics of peptide release. An example is an insertion at any of positions X66 and X74 in SEQ ID NO 1, and any of the position 20 (Q) to 28 (P) (Q AGVRQVLP SEQ ID NO: 142) in SEQ ID NO; 4. A representative example is provided by insertion following residue K71 in T. maritima encapsulin. (see Examples 17 to 24).

Non-cage forming insertion point for the at least one second protease are expected to be dominant with respect to the cage formation of engineered microcompartment proteins of the present disclosure.

Accordingly, engineered microcompartment proteins comprising the at least one protease cleavage site in the β3 strand of the E Loop are expected to be non cage forming when in combination with additional second protease cleavage sites in the A Domain are and/or other regions of the E-Loop also expected to be non cage forming. In particular, any insertion within β3 strand of the E-loop domain is expected to be non-cage forming. As a consequence engineered microcompartment proteins comprising the at least one protease cleavage site in the β3 strand of the E Loop and in the loop region of the E-loop (in the first unstructured region of the E-loop between β2 and β3) are also expected to be non cage forming.

In some embodiments the at least one first protease cleavage site and the at least one second protease cleavage site comprise a same protease cleavage sites. In some embodiments the at least one first protease cleavage site and the at least one second protease cleavage site comprise different protease cleavage sites.

The wording "protease cleavage site in the sense of the disclosure indicates target sites for proteolytic cleavage by enzymes such peptidases, proteases or proteolytic cleavage enzymes which break peptide bond between amino acids in proteins. The general nomenclature of cleavage site positions of the substrate were formulated by Schechter and Berger, 1967 [9] and Schechter and Berger, 1968 [10] Accordingly, the cleavage site is designated between P1-P1', incrementing the numbering in the N-terminal direction of the cleaved peptide bond (P2, P3, P4, etc.). On the carboxyl side of the cleavage site the numbering is incremented in the same way (P1', P2', P3' etc.).

Protease cleavage sites that can be inserted in engineered microcompartment proteins of the disclosure comprise regions up to 25 residues. In particular, protease cleavage sites are inserted in a configuration which makes them surface accessible. In some embodiments protease cleavage site are included in an unstructured segment or within an alpha helical or beta sheet secondary structured segment. Exemplary protease cleavage sites that can be inserted in engineered microcompartment proteins herein described comprise TEV protease cleavage sites with sequence ENLYFQG, (SEQ ID NO:69) which is unstructured and others identifiable by a skilled person upon reading of the present disclosure (see also Table 2 and Example 3).

In some embodiments of the engineered microcompartment protein herein described, the at least one cleavage site is comprised within an inserted region of up to 25 residues further comprising linkers and/or tags as will be understood by a skilled person upon reading of the present disclosure.

In embodiments herein described target proteins that can be inserted comprise any protein having 1 to 80 residues possibly comprised within an inserted region of up to 80 residues further comprising linkers and/or tags as will be understood by a skilled person upon reading of the present disclosure.

The term "protein" as used herein indicates a polypeptide with secondary, tertiary, and possibly quaternary structure. The protein's secondary, tertiary, and quaternary structure can occur on a variety of length scales (tenths of A to nm) and time scales (ns to s), so that in various instances the secondary, tertiary and possibly quaternary structures are dynamic and not perfectly rigid.

The term "polypeptide" as used herein indicates a polymer composed of two or more amino acid monomers and/or analogs thereof wherein the portion formed by the alpha carbon, the amine group and the carboxyl group of the amino acids in the polymer forms the backbone of the polymer. As used herein the term "amino acid", "amino acid monomer", or "amino acid residue" refers to any of the naturally occurring amino acids, any non-naturally occurring amino acids, and any artificial amino acids, including both D and L optical isomers of all amino acid subsets. In particular, amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid.

The term "polypeptide" includes amino acid polymers of any length including full length proteins, as well as analogs and fragments thereof. The polypeptide provides the primary structure of a protein wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds. Polypeptides in the sense of the present disclosure are usually composed of a linear chain of amino acid residues covalently linked by peptide bond.

In particular, in some embodiments of the present disclosure, the target protein of the engineered microcompartment protein of the disclosure can be a protein which is non-native to the bacterial cell where the engineered microcompartment protein is configured to be expressed based on the experimental design.

The wording "native" as used herein with reference to a compound and a cell, identifies a compound, molecule or structure naturally provided and in particular produced in the cell. Therefore, a native protein or a native substrate when described in connection with a cell, refers to a protein and/or substrate that is itself naturally provided and in particular, produced in the referenced cell. Conversely, the term "non-native" as used herein with reference to a protein and/or a substrate in connection with a cell, refers to a protein and/or substrate that is itself not naturally produced in the referenced cell.

In embodiments wherein the target protein is a non-native protein, the non-native protein herein described include toxic non-native proteins and non-toxic non-native proteins which in some cases can be degraded within a target bacterial cell where expression production and/or purification of the non-native protein is desired. Accordingly, engineered microcompartment proteins compositions, in some embodiments are configured to allow compartmentalization of certain toxic or non-toxic proteins in cells where said proteins are non-native, thus shielding the cell from toxicity from said toxic non-native proteins or shielding the non-native proteins from the cell environment.

Exemplary non-toxic non-native proteins that can be introduced as target protein in the engineered microcompartment proteins of the disclosure include proteins that can be proteolyzed by protease within the host cell and in in particular, proteins which are particularly sensitive to native proteases present in the host cells. In such cases, the engineered microcompartment proteins can protein the non-native proteins from proteolysis in the host. Exemplary non-native non-toxic proteins include proteins susceptible to Lon protease, OmpT and ClpXP in *E. coli*. Non-toxic non-native proteins also include proteins that are difficult to fold, including those that require disulfide bonds for proper folding and function. The engineered microcompartment proteins can provide an enclosed structure to prevent aggregation and facilitate proper folding.

The term "toxic non-native protein", as used throughout, refers to a protein or peptide that is itself not naturally produced by a reference cell and is toxic to the host cell when provided or produced in said cell.

In particular, toxic non-native proteins in the sense of the disclosure in connection with cells where they are expressed produced and/or purified indicates proteins or peptides that are not native to said cell and can react with a native cellular target substrate to provide cell damage by triggering a series of linked biological or chemical reactions within the cell resulting in damage to said cell.

The wording "native cellular target substrate" or "native cellular substrate" as used herein indicates a compound molecule or structure that is naturally occurring in a cell and is a part of reactions taking place in the cell to keep the cell alive. Exemplary native cellular target substrates in the sense of the disclosure comprise native cellular lipids, proteins, nucleic acids and/or related cellular structures, such as cell membrane or cell chromatin.

Exemplary reactions between a native cellular target substrate and a non-native protein, particularly a toxic non-native protein, which exemplary reactions trigger a series of linked biological or chemical reactions in the cell resulting in a damage to the cell, comprise binding and/or bond cleavage resulting in disruption and/or inactivation of the cellular target substrate. For example, targeting of membrane lipids damages the cell membrane which, on its turn, impacts the state of cell electrolytes, e.g. calcium, which when constantly increased, induces apoptosis.

The word "damage" as used herein refers to a physical harm caused to a cell in such a way as to impair its normal function. In particular, cell damage can occur as a result of disruption the normal homeostasis of an affected cell. Among other causes, cell damage can be due to physical, chemical, or, biological, factors resulting from targeting of cell components such as DNA and the cell membrane. Cell damage can be reversible or irreversible. Depending on the extent of injury, the cellular response may be adaptive and where possible, homeostasis is restored. Cell death occurs when the severity of the injury exceeds the cell's ability to repair itself and can occur by necrosis or apoptosis.

Toxicity in the sense of the disclosure in particular occurs when a non-native protein interferes with the normal proliferation and homeostasis of the microorganism and the visible result is slower growth rate, low final cell density, and death ([11]-[12]) Toxicity of a non-native protein can therefore be detected with reference cell growth before production of a non-native toxic protein (basal growth) and after detection of possible toxicity of vectors or other expression system for production of the non-native protein within a cell which can be performed with approaches discussed for example in reference (2) or otherwise identifiable by a skilled person upon reading of the present disclosure. After control of basal growth and of toxicity of the expression system, the culture can be grown until the expression of the non-native protein. Following expression of the non-native protein, if the non-native protein is toxic, cell growth will be impaired or arrested depending on the level of toxicity. In some cases, the level of toxicity of a non-native protein can be dependent on a threshold of host tolerance. In such situations, toxicity of a non-native protein can be dependent on the level of expression of the non-native protein in comparison with the threshold of host tolerance which should be reached and exceeded for the protein to have toxicity as will be understood by a skilled person.

Examples of proteins or peptides that are toxic and therefore harmful to a cell include antimicrobial peptides, as well as proteases and lysins, which are harmful to bacterial cells through direct targeting of cytoplasmic, membrane, DNA or protein synthesis.

In particular, toxic non-native protein that can be included in engineered microcompartment proteins of the instant disclosure, are toxic proteins or peptides that are non-native to the cell where they are produced and that have a native cellular target substrate which is a native membrane substrate.

The wording "membrane" as used herein indicates a biological membrane that separates the interior of a cell from the outside environment and can have different structure and configurations in different type of cells as will be understood by a skilled person. In particular, the wording "membrane" as used herein is intended to encompass: i) a cell plasma membrane (also identified as inner membrane in Gram negative bacteria) typically formed by a phospholipid bilayer with embedded proteins, ii) the outer membrane of Gram-negative bacteria formed by a phospholipid bilayer with embedded proteins different in composition from the inner membrane (e.g. rich in lipopolysaccharide), as well as iii) the cell wall, a structural layer that surrounds some types of cells, situated outside the cell membrane and is mainly composed of peptidoglycan (amino acids and sugars). In particular, cell wall can be made of peptidoglycan (also called murein), which is made from polysaccharide chains cross-linked by unusual peptides containing D-amino acids.

The wording "native membrane substrate" as used herein indicates a compound that is naturally located in the membrane of a cell in the sense of the disclosure and in particular in the membrane of the cell where the toxic non-native protein is expressed or to be expressed. Native membrane substrates comprise proteins, peptidoglycans, and lipids located in the plasma membrane, inner membrane, outer membrane or cell wall of a cell in the sense of the disclosure.

An exemplary native membrane substrate that can be targeted by toxic proteins herein described are peptidoglycan and lipopolysaccharide (LPS) biosynthesis proteins, which are enzymes such as MraY, LpxK, KdtA, LpxL, LpxM, MraG, FtsW catalyzing biosynthesis of peptidoglycans of the cell wall and LPS in the outer membrane. In particular MraY (phospho-MurNAc-pentapeptide translocase) is an integral membrane enzyme that catalyzes an essential step of bacterial cell wall biosynthesis: the transfer of the peptidoglycan precursor phospho-MurNAc-pentapeptide to the lipid carrier undecaprenyl phosphate [13]) Non-native toxic proteins such as LysE react with peptidoglycan with resulting damage to the cell wall and to the cell. LpxK is a gene encoding tetraacyldisaccharide 4'-kinase, an enzyme that phosphorylates the 4'-position of a tetraacyldisaccharide 1-phosphate precursor (DS-1-P) of lipopolysaccharide lipid A. This enzyme belongs to the family of transferases, specifically those transferring phosphorus-containing groups (phosphotransferases) with an alcohol group as acceptor. KdtA is a gene encoding 3-deoxy-D-manno-octulosonic acid transferase, which is involved in lipopolysaccharide (LPS) biosynthesis. This enzymes catalyzes the transfer of two 3-deoxy-D-manno-octulosonate (Kdo) residues from CMP-Kdo to lipid IV(A), the tetraacyldisaccharide-1,4'-bisphosphate precursor of lipid A. LpxM is a gene encoding Lipid A biosynthesis myristoyltransferase, an enzyme that catalyzes the transfer of myristate from myristoyl-acyl carrier protein (ACP) to Kdo(2)-(lauroyl)-lipid IV(A) to form Kdo(2)-lipid A. In vitro, the protein can acylate Kdo(2)-lipid IV(A), but the acylation of (Kdo)2-(lauroyl)-lipid IV(A) is about 100 times faster. In vitro, the protein can use lauroyl-ACP but displays a slight kinetic preference for myristoyl-ACP. LpxL is a gene encoding Lipid A biosynthesis lauroyltransferase, an enzyme that catalyzes the transfer of laurate from lauroyl-acyl carrier protein (ACP) to Kdo(2)-lipid IV(A) to form Kdo(2)-(lauroyl)-lipid IV(A). This enzyme has 10-fold selectivity for lauroyl-ACP over myristoyl-ACP. In vitro, this enzyme can also catalyze a slow second acylation reaction leading to the formation of Kdo(2)-(dilauroyl)-lipid IV(A). FtsW is a gene encoding lipid II flippase FtsW protein, a cell division protein that transports lipid-linked peptidoglycan precursors from the inner to the outer leaflet of the cytoplasmic membrane. This protein is required for localization of FtsI and may also play a role in the stabilization of the FtsZ ring during cell division.

Additional, native membrane substrates that can be targeted by native toxic proteins herein described are peptidoglycans comprising a pentapeptide motif A(D/N)LXX (SEQ ID NO:8), where X can be any amino acid with the central position in the pentapeptide motif (also designated as position i) being usually a leucine, position i−2 being usually an alanine and the two subsequent positions (i+1 and i+2) configured so that the side chains of positions i−2 and i point into the hydrophobic interior of the protein while the side chains of positions i−1, i+1 and i+2 are exposed on the surface of the proteins. Those peptidoglycans can be targeted for example by non-native lysin proteins with a peptidase domain which can be identified for example using a BLAST search on NCBI. For instance, Ply500 has a pfam02557: VanY: D-alanyl-D-alanine carboxypeptidase motif which would react with a pentapeptide motif in a peptidoglycan. Additional lysins can be identified by a skilled person upon reading of the present disclosure.

Further native membrane substrates that can be targeted by native toxic proteins are peptidoglycans comprising a sugar motif, such as GlcNAc-X-GlcNAc with X being any amino acid and other sugar motifs identifiable by a skilled person. These native membrane substrates can be targeted by non-native lysins proteins having an amidase domain, which can also be identified for example using a BLAST search, and additional lysins identifiable by a skilled person.

Additional native membrane substrates that can be targeted by native toxic proteins herein described are phospholipids in the inner membrane. In those embodiments, one or more non-native toxic proteins can bind to lipid and inhibit proper structure of the lipid bilayer membrane, causing holes to form in the membrane. Examples of toxic proteins targeting phospholipids are AMPs having alpha helical or beta-sheet that disrupt inner membrane such as cecropin, magainin, melittin, and protegrin I.

Further native membrane substrates that can be targeted by native toxic proteins are lipids in the outer membrane (e.g., Lipid II and LPS). Examples of toxic proteins targeting lipids of the outer membrane comprise cationic antimicrobial peptides such as cecropin P1, defensins, and nisins.

Additional native membrane substrates that can be targeted by native toxic proteins herein described are outer membrane proteins such as integral outer membrane proteins folding into antiparallel beta-barrels. (e.g. proteins belonging to the OmpA membrane domain, the OmpX protein, phospholipase A, general porins (OmpF, PhoE), substrate-specific porins (LamB, ScrY) and the TonB-dependent iron siderophore transporters FhuA and FepA). Examples of toxic proteins targeting lipids of the outer membrane proteins are cationic antimicrobial peptides. An example is inhibition of OmpF porin by HP(2-20) peptide. Additional cationic antimicrobial peptides expected to be found in ([14] [15]).

In embodiments herein described, the non-native proteins are expressed in constructs where one or more non-native proteins is fused to at least one encapsulin protein herein described to form protein to provide an engineered microcompartment protein, in which the non-native protein can be later released by cleaving from the engineered microcompartment protein. Some non-native proteins have an extended, non-helical structures (e.g., LL-37, Apidaecin Ia) while others have an alpha helical structure (e.g., HBCM2— which is a hybrid of cecropin and melittin, which are both alpha helical).

In some embodiments, "toxic non-native protein" that can be used as target protein in engineered microcompartment protein and in related cells compositions methods and systems of the instant disclosure comprise antimicrobial peptides targeting cell membrane, proteases targeting proteins in a native cell membrane as defined herein, and lysins as will be understood by a skilled person.

The term "Antimicrobial peptides" or "AMPs", indicates peptides generally less than 200 amino acids and typically between 12 and 50 amino acids, having two or more positively charged residues provided by arginine, lysine or, in acidic environments, histidine, and a large proportion (generally >50%) of hydrophobic residues and having an antimicrobial activity as would be understood by a skilled person. The secondary structures of AMPs typically follow 4 themes, including i) α-helical, ii) β-stranded due to the presence of 2 or more disulfide bonds, iii) β-hairpin or loop due to the presence of a single disulfide bond and/or cyclization of the peptide chain, and iv) extended as would be understood by a skilled person. The final cellular configuration of AMPs typically contains hydrophilic amino acid residues aligned along one side and hydrophobic amino acid residues aligned along the opposite side of a helical molecule. AMPs can cause cell damage by reacting with membrane components to induce membrane permeabilization or with a range of cytoplasmic targets. In some instances, amino acid composition, amphipathicity, cationic charge and size of AMPs allow them to attach to and insert into membrane bilayers to form pores by 'barrel-stave', 'carpet' or 'toroidal-pore' mechanisms. In some instances, AMPs can bind target intracellular molecules which are crucial to cell viability thus resulting in cell damage through inhibition of cell wall synthesis, alteration of the cytoplasmic membrane, activation of autolysin, inhibition of DNA, RNA, and protein synthesis, and/or inhibition of enzymes identifiable by a skilled person. In general, the antimicrobial activity of these peptides is determined by measuring the minimal inhibitory concentration (MIC), which is the lowest concentration of drug that inhibits bacterial growth. Antimicrobial peptides have been demonstrated to kill Gram negative and Gram-positive bacteria, enveloped viruses, fungi and even transformed or cancerous cells. In some embodiments, the AMPs herein used for the constructing engineered microcompartment proteins have an extended or alpha helical structure.

In some embodiments, AMPs that can be produced or provided in a cell according to methods and systems of the disclosure and related cell and compositions comprise cationic AMPs that target phospholipids in the inner membrane, such as cecropin, magainin, melittin, and protegrin I, or derivatives thereof.

In some embodiments, AMPs that can be produced or provided in a cell according to methods and systems of the disclosure and related cell and compositions comprise cationic AMPs that target native outer membrane proteins, such as HP(2-20) peptide capable of targeting and inhibiting OmpF porin as well as SMAP-29 and CAP-18 both capable of targeting and inhibiting outer membrane protein I (OprI).

In particular, the term "cecropins" indicate AMPs of about 31-37 amino acid residues having alpha helical conformation and being capable of targeting native membrane substrates of both Gram-positive and Gram-negative bacteria. Cecropins isolated from insects other than *Hyalophora cecropia* (Cecropia moth) are also known as bactericidin, lepidopterin, sarcotoxin, and additional names identifiable by a skilled person. Exemplary cecropin comprise Cecropin A (KWKLFKKIEKVGQNIRDGIIKAGPAVAVVGQATQ-IAK SEQ ID NO: 20) having a secondary structure with two α helices, and being capable of forming a ion channels at low peptide to lipid ratios and pores at high peptide to lipid ratios as will be understood by a skilled person. Exemplary cecropins also comprise: Cecropin B (KWKVFKKIEK-MGRNIRNGIVKAGPAIAVLGEAKAL SEQ ID NO: 21) having two α helices in the secondary structure, CECD from *Aedes aegypti* (Yellowfever mosquito), Papiliocin (A lepidopteran) from *Papilio xuthus* an Asian swallowtail butterfly, and Cecropin P1, an antibacterial peptide from *Ascaris suum*, a parasitic nematode that resides in the pig intestine. Cecropin derivatives comprise peptides modified cecropins (e.g. cecropin A, and cecropin B). In some embodiments, derivatives of cecropins have anticancer properties and are called anticancer peptides (ACPs) ([16] In particular hybrid ACPs based on Cecropin A have been studied for anticancer properties ([17])

The term "magainins" indicate a class of antimicrobial peptides found in the African clawed frog *Xenopus laevis* identifiable by a skilled person The term "melittin" indicates the principal active component of apitoxin (bee venom), a powerful stimulator of phospholipase A2 as will be understood by a skilled person. Melittin is a peptide consisting of 26 amino acids with the sequence GIGAVLKVLTTGLPALISWIKRKRQQ (SEQ ID NO:22).

The term "protegrins" indicates small peptides containing 16-18 amino acid residues. The amino acid composition of protegrins contains six positively charged arginine residues and four cysteine residues. Their secondary structure is classified as cysteine-rich β-sheet antimicrobial peptides, AMPs that display limited sequence similarity to certain defensins and tachyplesins. In solution, the peptides fold to form an anti-parallel β-strand with the structure stabilized by two cysteine bridges formed among the four cysteine residues. Protegrins bind to lipopolysaccharide, a property that may help them to insert into the membranes of gram-negative bacteria and permeabilize them. The term "defensins" as used herein identifies small cysteine-rich cationic proteins found in vertebrates, invertebrates and plants. Defensins have 18-45 amino acids including six to eight conserved cysteine residues. Most defensins function by binding to the microbial cell membrane, and, once embedded, forming pore-like membrane defects that allow efflux of essential ions and nutrients.

The term "nisins" as used herein identifies a polycyclic peptide produced by the bacterium *Lactococcus lactis* having 34 amino acid residues, including the uncommon amino acids lanthionine (Lan), methyllanthionine (MeLan), didehydroalanine (Dha), and didehydroaminobutyric acid (Dhb). These unusual amino acids are provided by posttranslational modification of the precursor peptide. In these reactions, a ribosomally synthesized 57-mer is converted to the final peptide. The unusual amino acids originate from serine and threonine, and the enzyme-catalyzed addition of cysteine residues to the didehydro amino acids result in the multiple (five) thioether bridges.

In some embodiments, AMPs that can be produced or provided in a cell according to methods and systems of the disclosure and related cell and compositions comprise HBCM2, HBCM3 and Apidaecin Ia.

The term "HBCM2" and "HBCM3" refers to hybrid (HB) of silk moth cercropin (C) and bee melittin (M) antimicrobial peptides. These are residue optimized peptides that have high efficacy against *Pseudomonas aeruginosa* [18, 19]. They originate from cercropin from silk moth and melittin from bees, which are both alpha helical in secondary structure and therefore, HBCM2 and HBCM3 are also thought to be alpha helical in structure.

The term "Apidaecin Ia" (AP) refers to a series of small, proline-rich, 18- to 20-residue peptides produced by insects. They are the largest group of Pro-rich antimicrobial peptides known to date. Structurally, apidaecins consist of two regions, the conserved region, responsible for the general antibacterial capacity, and the variable region, responsible for the antibacterial spectrum. The small, gene-encoded and unmodified apidaecins are predominantly active against many Gram-negative bacteria by special antibacterial mechanisms. The mechanism of action by which apidaecins kill bacteria involves an initial non-specific binding of the peptides to an outer membrane (OM) component. This binding is followed by invasion of the periplasmic space, and by a specific and essentially irreversible combination with a receptor/docking molecule that may be a component of a permease-type transporter system on inner membrane (IM). In the final step, the peptide is translocated into the interior of the cell where it meets its ultimate target. Evidence that apidaecins are non-toxic for human and animal cells is a prerequisite for using them as novel antibiotic drugs.

The term "protease" (also called a peptidase or proteinase or proteolytic enzyme) indicates any enzyme that performs proteolysis, (begins protein catabolism) by hydrolysis of the peptide bonds that link amino acids together in a polypeptide chain. Proteases can be classified into seven broad groups based on the amino acid at the (protease's) active site used to perform a nucleophilic attack on the substrate: Serine proteases—using a serine alcohol; Cysteine proteases—using a cysteine thiol; Threonine proteases—using a threonine secondary alcohol; Aspartic proteases—using an aspartate carboxylic acid; Glutamic proteases—using a glutamate carboxylic acid; Metalloproteases—using a metal, usually zinc; Asparagine peptide lyases—using an asparagine to perform an elimination reaction (not requiring water), as would be understood by a skilled person. In particular, Aspartic, glutamic and metallo-proteases activate a water molecule which performs a nucleophilic attack on the peptide bond to hydrolyse it. Serine, threonine and cysteine proteases use a nucleophilic residue in attack (usually in a catalytic triad). That residue performs a nucleophilic attack to covalently link the protease to the substrate protein, releasing the first half of the product. This covalent acyl-enzyme intermediate is then hydrolyzed by activated water to complete catalysis by releasing the second half of the product and regenerating the free enzyme. Proteases are involved in digesting long protein chains into shorter fragments by splitting the peptide bonds that link amino acid residues. Some detach the terminal amino acids from the protein chain (exopeptidases, such as aminopeptidases, carboxypeptidase A); others attack internal peptide bonds of a protein (endopeptidases, such as trypsin, chymotrypsin, pepsin, papain, and elastase). Some proteases can be promiscuous and react with wide range of protein substrates. This is the case for example of digestive enzymes such as trypsin which have to be able to cleave the array of proteins ingested into smaller peptide fragments. Promiscuous proteases typically bind to a single amino acid on the substrate and so only have specificity for that residue. For example, trypsin is specific for the sequences . . . K\ . . . or . . . R\ . . . ('\'=cleavage site). Some proteases are specific and only cleave substrates with a certain sequence or amino acid structure. Proteases, being themselves proteins, can be cleaved by other protease molecules, sometimes of the same variety. This acts as a method of regulation of protease activity. Some proteases are less active after autolysis (e.g. TEV protease) whilst others are more active (e.g. trypsinogen). Specific proteases targeting native membrane substrates are expected to be usable in methods and systems described herein.

In some embodiments herein described, the proteases inserted as target protein in engineered microcompartment proteins herein described are generally non-specific in their recognition site, meaning their recognition sequence are recognized by a large number of protein substrates. A lack specificity of a protease can be due to a short recognition sequence and/or promiscuity of the protease. Proteases can also be used for cleaving toxic non-native proteins from the engineered microcompartment proteins. Such proteases used for cleaving toxic non-native proteins would be highly specific for a unique recognition sequence that is not commonly found in protein substrates. For instance, TEV protease has a relatively long recognition sequence (ENLYFQ\S (orG)) (SEQ ID NO: 70) that is not commonly found in other proteins. Therefore, it can be used to specifically digest the engineered encapsulin microcompartment and/or release the toxic protein from the encapsulin microcompartment to obtain the toxic protein of interest without resulting in non-specific side products and damage to host cells which in some instance can cause death to the cell. In the case of cellular expression, these specific proteases can digest the encapsulin microcompartments with limited digestion of other cellular proteins that may result in cellular toxicity.

In particular, specific proteases that target membrane substrates can be compartmentalized with methods herein described. Exemplary specific proteases comprise intramembrane proteases that cleave the transmembrane domain of proteins, such as YaeL from *E. coli* and SpoIVFB from *Bacillus subtilis*, additional proteases described in ([20]). In particular, intramembrane proteases such as YaeL (also called RseP) in *Escherichia coli* play a role in coordinating cell growth and cell division through intramembrane proteolysis of RseA. SpoIVFB is an intramembrane metalloprotease, in *Bacillus subtilis* that cleaves factors required for sporulation (processing of pro-sigma-K to active SigK). Additional proteases such as endopeptidases that target peptidoglycan. The term "endopeptidases" identifies proteolytic peptidases that break peptide bonds of nonterminal amino acids (i.e. within the molecule), in contrast to exopeptidases, which break peptide bonds from end-pieces of terminal amino acids. The relevant peptidase domain can be found by BLAST search on NCBI as will be understood by a skilled person. Additional proteases that target membrane substrates can be identified by a skilled person upon reading of this disclosure.

The term "lysins", also known as endolysins or murein hydrolases, indicates hydrolytic enzymes produced by bacteriophages in order to cleave the host's cell wall during the final stage of the lytic cycle or natively by bacteria themselves in order to remodel their own cell wall. Usually lysins are monomeric proteins with a 25 to 40 kDa range in size. A notable exception is the streptococcal PlyC endolysin, which is 114 kDa and composed of two different gene products, PlyCA and PlyCB, with a ratio of eight PlyCB subunits for each PlyCA in its active conformation as will be understood by a skilled person. Lysins comprise an at least one domain catalyzing the hydrolysis of peptidoglycan and a domain binding to the cell wall substrate. In lysins, the catalytic domain is responsible for the cleavage of peptidoglycan bonds, and can be one of the following five types of lysin catalytic domain: Endo-β-N-acetylglucosaminidase, N-acetylmuramidase (lysozyme-like), Endopeptidase, N-acetylmuramoyl-L-alanine amidase, γ-D-glutaminyl-L-lysine endopeptidase identifiable by a skilled person. In lysins, the cell-binding domain (CBD) binds to a specific substrate found in the host bacterium's cell wall, usually a carbohydrate. In contrast to the catalytic domain, the cell-binding domain is variable, which allows a great specificity and decreases bacterial resistance. Binding affinity to the cell wall substrate tends to be high, possibly so as to sequester onto cell wall fragments any free enzyme, which could compete with phage progeny from infecting adjacent host bacteria. In lysins usually, two or more different catalytic domains are linked to a single cell-binding domain. This is typical in many staphylococcal lysins as well as the streptococcal PlyC holoenzyme, which contains two catalytic domains. Catalytic domains are highly conserved in phage lysins of the same class. In monomeric lysins, the catalytic domain is typically at the N-terminal end of the protein and the cell binding domain is located at the C-terminal end of the protein and the two domains are separated by a short linker region. Target cellular substrate of lysins are peptidoglycans, which consists of cross-linked amino acids and sugars which form alternating amino sugars: N-acetylglucosamine (NAG) and N-acetylmuramic acid (NAM). Endo-β-N-acetylglucosaminidase lysins cleave NAGs while N-acetylmuramidase lysins (lysozyme-like lysins) cleave NAMs. Endopeptidase lysins cleave any of the peptide bonds between amino acids, whereas N-acetylmuramoyl-l-alanine amidase lysins (or simply amidase lysins) hydrolyze the amide bond between the sugar and the amino acid moieties. Finally, the recently discovered γ-d-glutaminyl-1-lysine endopeptidase lysins cleave the gamma bond between D-glutamine and L-lysine residues. Lysins typically target one of the five bonds in peptidoglycan (murein), the main component of bacterial cell walls, which allows the release of progeny virions from the lysed cell in the case of phage lysins and the remodeling of cell wall in the case of native bacterial lysins. These enzymes are being used as antibacterial agents due to their high effectiveness and specificity in comparison with antibiotics, which are susceptible to bacterial resistance.

In some embodiments, lysins that can be produced or provided in a cell according to methods and systems of the disclosure and related cell and compositions comprise lysozyme-like lysins, such as Cpl-1 and Cpl-7 that target *S. pneumoniae* peptidoglycan, amidase lysins, such as PlyPSA that targets *L. monocytogenes* peptidoglycan and endopeptidases that target the pentapeptide motif of peptidoglycan, such as Ply500 that targets *L. monocytogenes* peptidoglycan and additional lysins described in reference ([21]).

In particular, the term "lysozyme like lysins" indicates lysins with a catalytic N-acetylmuramidase (lysozyme-like) domain, the term "amidase lysins" identifies with an amidase domain such as amidase 3 domain as shown in the website ncbi.nlm.nih.gov/Structure/cdd/cddsrv.cgi-?uid=119407 at the date of filing of the instant disclosure.

In some embodiments herein described, toxic non-native proteins are non-native proteins or peptides that act within the membrane either by direct interaction/disruption of the membrane or through inhibition of membrane biosynthesis proteins. Examples of such toxic non-native proteins include LysE protein from phiX174 bacteriophage and antimicrobial peptides [22]. LysE protein binds to and inhibits the peptidoglycan biosynthesis protein MraY located in the bacterial membrane, thus resulting in cell lysis, and antimicrobial peptides targeting the bacterial cell membrane, and/or targeting other cellular target substrate other than DNA [23].

In some embodiments herein described, target proteins introduced in engineered microcompartment protein are non-native AMPs lacking disulfide bonds, such as cecropin, melittin, and apidaecin AMPs.

In some embodiments described, the toxic non-native proteins introduced as target proteins of engineered microcompartment protein are pro-rich antimicrobial peptides. Examples of toxic non-native proteins that can be used in engineered microcompartment proteins, engineered microcompartment, related vectors, cells compositions methods and systems of the disclosure include apidaecin and antimicrobial peptides which target membrane substrates, and are harmful to bacterial cells (see Example 1).

In embodiments according to the instant disclosure a microcompartment protein is engineered to introduce at least one non-native protein having a sequence up to 80 amino acids in length at the N-terminus of the first segment of the P-domain of the microcompartment protein, together with at least one protease cleavage site inserted between the C-terminus of the non-native protein and the N-terminus of the first segment of the P-Domain of the microcompartment protein.

FIG. 8 shows another exemplary engineered microcompartment protein (SEQ ID NO: 23) comprising Apidaecin Ia peptide fused to the N-terminus of an encapsulin protein from *M. xanthus* through a TEV protease cleavage site and a linker region.

In some embodiments, the target protein can be fused to the N-terminus of the encapsulin protein or encapsulin-like proteins. For example, the target protein can be inserted in an insertion region between the first and second position (the M in X1 and E in X2) of the encapsulin shell protein having the SEQ ID NO: 47 (see Example 12-15). In some of those embodiments, a linker can be comprised within the insertion region placed between the non-native protein and the N-terminus of the encapsulin protein. In some embodiments, the linker comprises a protease cleavage site in order to enable later cleavage of the target protein from encapsulin via a protease that specifically targets at the protease cleavage site. Exemplary recognition sequences and cleavage sites of proteases include the ones shown in Table 2 as well as others identifiable by a person skilled in the art.

Exemplary engineered microcompartments designed to include a peptide fused to the N-terminus of an engineered encapsulin protein through a protease cleavage site and a linker region are described in Example 17 of the present disclosure.

In some embodiments, the engineered protein is configured so that cleavage of the target protein from encapsulin via a protease that specifically targets at the protease cleavage site results in a target protein having N-terminal residues of the cleavage site attached to its C-terminus. In some of those embodiments the N-terminal residues of the cleavage site can be undesired as for example they can interfere with the activity of the cleaved target protein.

In those embodiments, the engineered microcompartment protein can be configured to include a proline residue between the N-terminus of the protease cleavage site and the C-terminus of the target protein. In those embodiments the N-terminal residues of the cleavage site attached to the target protein can be digested with carboxypeptidase that proteolyzes from the C-terminus of the target protein but does not have peptidase activity at proline residues (see Example 27).

Exemplary embodiments wherein insertion of a proline residue between the N-terminus of the protease cleavage site and the C-terminus of the target protein can be desired are provided by constructs including protease cleavage sites with the overall charge of their N-terminal residues interferes with the proper folding and/or activity of the target protein. Examples of these protease cleavage sites include: the enterokinase protease cleavage site (DDDDK SEQ ID NO: 71), the TEV protease cleavage site (ENLYFQ/G SEQ ID NO: 72), and the HRV-3C protease cleavage site (LEVLFQ/GP SEQ ID NO: 73) whose N-terminal residues have an overall negative charge, as well as the thrombin protease cleavage site (LVPR/GS SEQ ID NO: 74) whose N-terminal residues have an overall positive charge. These N-terminal residues may interfere with a target peptide depending on the configuration of the target peptide.

In those embodiments, a proline can be inserted between the N-terminal residue of the protease cleavage site (e.g., N-terminal D residue of the enterokinase protease cleavage site) and the C terminus of the target protein or a protease cleavage site with an overall net neutral charge can be selected in order to retain or improve the activity of the target peptide in its native state. Examples of such protease cleavage site include the recognition sequence for the Factor Xa IEGR (Table 2)

In general in embodiments, wherein a target peptide has a configuration which is known or expected to be incompatible with one or more protease cleavage sites (e.g. because of negatively or positively charged N terminal residues of the protease cleavage site or other incompatibilities), replacement of the protease cleavage site with an alternative protease cleavage which does not interfere with the target protein of interest can be performed. In the alternative placement of a proline in the construct between the N-terminus of the cleavage site and the C terminus of the target protein, can also be performed to allow digestion of the N-terminal residues of the cleavage site attached to the C-terminus of the target protein.

Protease cleavage sites can be tested to determine if following cleavage, the residual protease cleavage site on the C-terminus of the target protein interferes with the target protein activity by comparing the activity of the target protein with and without the residual protease cleavage site at its C-terminus. The target protein with and without the residual protease cleavage site at its C-terminus can be obtained by chemical synthesis methods (e.g., solid phase peptide synthesis) via commercial sources (e.g., Elim biopharmaceuticals). Activity of the target protein can be determined by an appropriate enzymatic or cell inhibition assay.

As an alternative, the target protein fused to a proline residue followed by the protease cleavage site followed by the engineered microcompartment protein can be translated in the cytoplasm of a cell and purified using methods identifiable by a skilled person. The purified material can be digested with the appropriate protease to obtain the target protein with the residual protease cleavage site on its C-terminus. The target protein with the residual protease cleavage site can be further digested with carboxypeptidase to obtain the target protein with a residual proline at its C-terminus. The activities of the target protein with the residual protease cleavage site versus the residual proline can be compared to each other as well as a chemically synthesized target protein with no residual amino acids at its C-terminus. This method will determine if any residual amino acids at the C-terminus of a target protein affects its activity.

In some embodiments, one or more protease sites can also be inserted within the encapsulin shell protein to enable full digestion of the encapsulin cage and thus full release of the non-native protein. The protease cleavage sites can be inserted within 1-8 amino acids adjacent to the C-terminus of the E-loop of the SEQ ID NO:1 at the β3 β-sheet region close to the P-domain. In some other embodiments, the protease cleavage sites can be inserted within 1-8 amino acids adjacent to the N-terminus of the A-domain at the surface-exposed region (see Examples 12-17).

In some embodiments, the engineered microcompartment protein can further include one or more tags inserted in the engineered microcompartment protein.

The term "tag" as used herein means protein tags comprising peptide sequences introduced onto a recombinant protein. Tags can be removable by chemical agents or by enzymatic means, such as proteolysis or splicing. Tags can be attached to proteins for various purposes: Affinity tags are appended to proteins so that they can be purified from their crude biological source using an affinity technique. These include chitin binding protein (CBP), and the poly(His) tag. The poly(His) tag is a widely-used protein tag; it binds to metal matrices. Chromatography tags can be used to alter chromatographic properties of the protein to afford different resolution across a particular separation technique. Often, these consist of polyanionic amino acids, such as FLAG-tag. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Protein tags can allow specific enzymatic modification (such as biotinylation by biotin ligase) or chemical modification (such as reaction with FlAsH-EDT2 for fluorescence imaging). Tags can be combined, in order to connect proteins to multiple other components. However, with the addition of each tag comes the risk that the native function of the protein may be abolished or compromised by interactions with the tag. Therefore, after purification, tags are sometimes removed by specific proteolysis (e.g. by TEV protease, Thrombin, Factor Xa or Enteropeptidase).

Exemplary tags comprise the following, among others known to persons skilled in the art: Peptide tags, such as: AviTag, a peptide allowing biotinylation by the enzyme BirA and so the protein can be isolated by streptavidin (GLNDIFEAQKIEWHE (SEQ ID NO:24)); Calmodulin-tag, a peptide that can be bound by the protein calmodulin (KRRWKKNFIAVSAANRFKKISSSGAL (SEQ ID NO:25)); polyglutamate tag, a peptide binding efficiently to anion-exchange resin such as Mono-Q (EEEEEE (SEQ ID NO:26)); E-tag, a peptide recognized by an antibody (GAPVPYPDPLEPR (SEQ ID NO:27)); FLAG-tag, a peptide recognized by an antibody (DYKDDDDK (SEQ ID NO:28)); HA-tag, a peptide from hemagglutinin recognized by an antibody (YPYDVPDYA (SEQ ID NO: 29)); His-tag, typically 5-10 histidines that can be bound by a nickel or cobalt chelate (HHHHHH (SEQ ID NO:30)); Myc-tag, a peptide derived from c-myc recognized by an antibody (EQKLISEEDL (SEQ ID NO:31)); NE-tag, a novel 18-amino-acid synthetic peptide (TKENPRSNQEESYDD-NES (SEQ ID NO:32)) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS (SEQ ID NO:33)); SBP-tag, a peptide which binds to streptavidin (MDEKTTGWRGGHVVEGLAGELEQLRARLEHH-PQGQREP (SEQ ID NO:34)); Softag 1, for mammalian expression (SLAELLNAGLGGS (SEQ ID NO:35)); Softag 3, for prokaryotic expression (TQDPSRVG (SEQ ID NO:36)); Strep-tag, a peptide which binds to streptavidin or the modified streptavidin called streptactin (Strep-tag II: WSHPQFEK (SEQ ID NO:37)); TC tag, a tetracysteine tag that is recognized by FlAsH and ReAsH biarsenical compounds (CCPGCC (SEQ ID NO:38)); V5 tag, a peptide recognized by an antibody (GKPIPNPLLGLDST (SEQ ID NO:39)); VSV-tag, a peptide recognized by an antibody (YTDIEMNRLGK (SEQ ID NO:40)); Xpress tag (DLYDD-DDK (SEQ ID NO:41)); Covalent peptide tags such as: Isopeptag, a peptide which binds covalently to pilin-C protein (TDKDMTITFTNKKDAE (SEQ ID NO:42 Spy-Tag, a peptide which binds covalently to SpyCatcher protein (AHIVMVDAYKPTK (SEQ ID NO:43)); SnoopTag, a peptide which binds covalently to SnoopCatcher protein (KL-GDIEFIKVNK (SEQ ID NO:44)).

In embodiments described herein, any of the tags of SEQ ID NO:24-44, and other tags known to those skilled in the art, can comprise one or more amino acid substitutions, insertions, or deletions that do not alter the function of the tag, and can further comprise one or more additional amino acids, up to a maximum tag length of 100 amino acids. In preferred embodiments, the tag comprises up to a maximum of 20 amino acids in length.

In some embodiments, the protein tag can be a polyhistidine tag. A polyhistidine-tag is an amino acid motif in proteins that typically consists of six histidine (His) residues typically, often at the N- or C-terminus of the protein. It is also known as hexahistidine-tag, 6xHis-tag, His6 tag and by the trademarked name His-tag (registered by EMD Biosciences). The total number of histidine residues can vary in the tag. N- or C-terminal his-tags can also be followed or preceded, respectively, by a suitable amino acid sequence that facilitates a removal of the polyhistidine-tag using endopeptidases. This extra sequence is not necessary if exopeptidases are used to remove N-terminal His-tags (e.g., Qiagen TAGZyme). Polyhistidine-tagging can be used to detect protein-protein interactions in the same way as a pull-down assay. Fluorescent hexahistidine CyDye tags are also available. These use Nickel covalent coordination to EDTA groups attached to fluorophores in order to create dyes that attach to the polyhistidine tag. This technique has been shown to be effective for following protein migration and trafficking. This technique can also be effective in order to measure distance via Fluorescent Resonance Energy Transfer.

In some embodiments, engineered microcompartment proteins comprise tags up to 8 amino acids in length inserted within the engineered microcompartment proteins as described herein. Exemplary tags include peptide tags such as AviTag, E-tag, FLAG-tag, $His_6$-tag, Strep-tag and as well as other known to persons skilled in the art.

In some embodiments, the tags can be inserted within the A-domain of the encapsulin protein. In particular, the tags can be inserted within 1-8 residues adjacent to the N-terminus of the A-domain of SEQ ID NO: 47 (see Example 12 and 18). In some embodiments, the tags can be inserted in the E-loop.

In some embodiments herein described, an insertion region comprising at least one first protease cleavage site and the insertion region comprising the at least one second protease cleavage site have independently lengths up to 22 amino acids including any linker, protease cleavage sites and tags.

The term "linker" as used herein indicates a short peptide sequences that occur between protein domains. Linkers are often composed of flexible residues like glycine and serine so that the adjacent protein domains are free to move relative to one another. In particular, in engineered microcompartment protein of the disclosure linkers are typically peptide of 2 to 5 residues in combination with a protease cleavage site, a target protein, and/or a tag as will be understood by a skilled person upon reading of the present disclosure. The linker between the protease cleavage site and the encapsulin protein can comprise at least one glycine residue. The linker can be as short as two amino acids in length.

Exemplary linkers include GGGGS (SEQ ID NO:75), GSGSG (SEQ ID NO:76), GGGG (SEQ ID NO:77), GGG (SEQ ID NO:78), GG (SEQ ID NO:79), GS(SEQ ID NO:80), GSGS(SEQ ID NO:81), GGGS(SEQ ID NO:82), GGS(SEQ ID NO:83), GTS (SEQ ID NO:84), GGGGT ($G_4T$) (SEQ ID NO: 85) and others identifiable by a person skilled in the art.

In some embodiments wherein a target protein is packaged within a cage-forming encapsulin construct, the presence of a linker between the protease cleavage site and the N-terminus of the engineered encapsulin is preferred. In some embodiments insertion of a linker of at least 5 residues in length containing at least 1 glycine residue between the protease cleavage site and the encapsulin protein can facilitate the release of the target protein following the protease digestion (Example 19).

In some embodiments, the engineered microcompartment proteins can be designed to be cage forming engineered microcompartment proteins or non cage forming engineered microcompartment proteins as described herein.

Preferred cage forming engineered microcompartment proteins typically comprise one protease cleavage site between the C-terminus of the peptide and N-terminus of the engineered encapsulin. Preferred cage forming engineered microcompartment proteins typically also comprise a linker between the first protease cleavage site and the N-terminus of the engineered encapsulin wherein the linker is preferably flexible (containing at least 1 glycine residue) and greater than 2 amino acids in length. A typical linker is a pentaglycine linker (GGGGG SEQ ID NO: 143). The linker length is selected not to exceed a length that would cause the (peptide)+(protease cleavage site)+(linker) to be >80 amino acids. Preferred cage forming engineered microcompartment proteins further comprise one protease cleavage site within the loop region of the E-loop domain. This region is the unstructured region between beta-strands P2 and P3. Examples are insertions following residues V57 and D60 in *T. maritima* encapsulin. An additional protease cleavage site can also be placed in the A-domain within the beta-strand β5 and the subsequent unstructured region. An example is insertion following residue K138 in *T. maritima* encapsulin. The addition of this site may improve the kinetics of peptide release.

Preferred cage forming microcompartment proteins can be advantageously used for example when production of a protease-sensitive peptide where the cage protects the peptide from proteolysis during expression; storage of a peptide to protect it from proteolysis within cells or in vitro as purified protein are desired.

Preferred cage forming microcompartment proteins are also expected to be advantageously used when improved secondary structure formation (e.g., disulfide bond formation) during peptide expression is desired.

Preferred non-cage forming engineered microcompartment proteins typically comprise one protease cleavage site between the C-terminus of the peptide and N-terminus of the engineered encapsulin. Preferred non-cage forming engineered microcompartment proteins typically also comprise a linker between the first protease cleavage site and the N-terminus of the engineered encapsulin. The linker is preferably flexible (containing at least 1 glycine residue) and can be as short as 2 amino acids in length. The linker is selected not to exceed a length that would cause the (peptide)+(protease cleavage site)+(linker) to be >80 amino acids. Preferred non-cage forming engineered microcompartment proteins typically further comprise one protease cleavage site in beta-strand β3 of the E-loop domain, within 9 amino acids of the N-terminus of the adjacent P-domain fragment. An example is an insertion following residue K71 in *T. maritima* encapsulin. An additional protease cleavage site followed by an affinity purification tag can also be placed in the A-domain within the beta-strand β5 and the subsequent unstructured region. An example is insertion following residue K138 in *T. maritima* encapsulin. Here, the affinity tag can be used for purification of the construct, which is accessible in a non-cage forming encapsulin mutant.

Preferred non-cage forming microcompartment proteins can be advantageously used for example when high yield production and release of a peptide—purification shall be done rapidly and in the presence of protease inhibitors to prevent any proteolysis. Non-cage forming microcompartment proteins are also expected to be advantageous when an improved secondary structure formation (e.g., disulfide bond formation) during peptide synthesis is desired.

A skilled person will be able to identify how to configure an engineered microcompartment protein of the disclosure based on the target protein and other features of the related production. For example, in some embodiments wherein the target protein is protease-sensitive, the insertion of the one or more protease sites within the encapsulin shell protein is preferably selected to provide a cage forming engineered microcompartment protein to maximize incorporation of expressed peptide into an encapsulin cage such that the cage-forming encapsulin construct can protect the target protein from proteolysis during expression or for the storage of the expressed target protein within cells or in vitro as purified protein. The cage-forming encapsulin construct is also expected to facilitate improved secondary structure formation, such as disulfide bond formation, during peptide expression.

In some of these embodiments, the protease cleavage site can be preferably provided within the unstructured loop region of the E-loop domain. In some exemplary embodiments exemplified in Example 18 the protease cleavage site can be inserted following residues V57 and D60 in *T. maritima* encapsulin. Insertion of a protease site following K138 in *T. maritima* (corresponding to the region within 2-24 amino acids of the N-terminus of the A-domain (the A-domain within the beta-strand β5 and the subsequent unstructured region) also maintains cage formation.

In embodiments, wherein the target protein is protease-sensitive, protease cleavage sites can be selected to provide a non-cage forming engineered microcompartment protein in embodiments wherein purification of the non-cage forming engineered microcompartment protein is performed under conditions to prevent proteolysis, such as in the presence of additives that prevent proteolysis such as B-PER II detergent or protease inhibitors. In addition, or in the alternative purification can be performed within the timeframe when degradation of less 50% of the protein is detected, typically within 16 hrs. or less. Methods to detect protein degradation comprise densitometry performed on Western blot or SDS-PAGE of the proteins in the lysate comprising the protein and additional techniques identifiable by a skilled person. In some of those embodiments, a protease cleavage site can be placed at the C terminus of E-Loop domain or within 1-8 amino acids adjacent to the C-terminus of the E-loop domain within beta-strand β3. An exemplary embodiment is an insertion following residue K71 in *T. maritima* encapsulin (see Example 18).

In some embodiments wherein fast release of the target protein is desired, the insertion of the one or more protease sites within the encapsulin shell protein is preferably selected to provide a non-cage forming engineered microcompartment protein comprising at least one protease cleavage site in the beta-strand β3 of the E-loop domain or in combination with at least one protease cleavage site in the unstructured region of the E-Loop and/or the A domain within the beta-strand β5 and the subsequent unstructured region. The second insertion can improve the kinetics of peptide release in some embodiments. An exemplary embodiment is provided by constructs comprising a protease cleavage site following residue K71 in *T. maritima* encapsulin (see Example 18).

In some of these embodiments wherein a high yield production and release of a target peptide is desired, a protease cleavage site can be selected within 0-8 amino acids residues adjacent to the C-terminus of the E-loop of the encapsulin protein within the beta-strand β3. In an exemplary embodiment the protease cleavage site is inserted following residue K71 in *T. maritima* encapsulin (Example 18). Such insertion site can effectively disrupt cage formation (see Example 19).

In several embodiments, the non-native protein to be produced or provided with methods of the disclosure comprise proteins or peptides that can be used as chemotherapeutic drugs in treating cancer to kill, inhibit growth or halt the replication and/or spread of cancerous cells in a patient. In some of those embodiments, the non-native protein or peptides are AMPs that can be used in cancer treatment.

In methods and systems herein described and related cell and compositions, one or more target proteins and in particular one or more proteins non-native to a bacterial cell are expressed in said cell within at least one engineered microcompartment protein to form at least one engineered microcompartment comprising the one or more toxic non-native proteins within the microcompartment.

The term "express" as used herein with reference to proteins or peptide indicates the way in which proteins or peptides are synthesized, modified and regulated in living organisms. Typically, protein expression includes DNA transcription, RNA processing, translation, and post-translational modification of a protein as will be understood by a skilled person. In particular, the term protein expression refers the process of generating a specific protein within a cell and includes the transcription of the recombinant DNA to messenger RNA (mRNA) and the translation of mRNA into polypeptide chains, which are ultimately folded into functional proteins and may be targeted to specific subcellular or extracellular locations Expression system for protein production comprise a combination of an expression vector, its cloned DNA, and the host cell for the vector that provide a context to allow a non-native gene function in a host cell, that is, produce proteins. Example expression systems are 1) BL21(DE3) host cells that express protein from an expression vector that contains a pT7 phage promoter; and 2) BL21 host cells that express protein from expression vectors that contain pT5 or pRha promoters. Additional expression systems and related host cells, vector and promoters are identifiable by a skilled person The term "cell" or "bacterial cell" as used herein indicates a bacterial cell with bacteria indicating several prokaryotic microbial species which include but are not limited to Gram-positive bacteria, Proteobacteria, Cyanobacteria, Spirochetes and related species, Planctomyces, *Bacteroides, Flavobacteria, Chlamydia*, Green sulfur bacteria, Green non-sulfur bacteria including anaerobic phototrophs, Radioresistant micrococci and related species, *Thermotoga* and *Thermosipho thermophiles*. More specifically, the wording "Gram positive bacteria" refers to cocci, nonsporulating rods and sporulating rods, such as, for example, *Actinomyces, Bacillus, Clostridium, Corynebacterium, Erysipelothrix, Lactobacillus, Listeria, Mycobacterium, Myxococcus, Nocardia, Staphylococcus, Streptococcus* and *Streptomyces*. The term "Proteobacteria" refers to purple photosynthetic and non-photosynthetic gram-negative bacteria, including cocci, nonenteric rods and enteric rods, such as, for example, *Neisseria, Spirillum, Pasteurella, Brucella, Yersinia, Francisella, Haemophilus, Bordetella, Escherichia, Salmonella, Shigella, Klebsiella, Proteus, Pseudomonas, Bacteroides, Acetobacter, Aerobacter, Agrobacterium, Azotobacter, Spirilla, Serratia, Vibrio, Rhizobium, Chlamydia, Rickettsia, Treponema* and *Fusobacterium*. Cyanobacteria, e.g., oxygenic phototrophs.

In embodiments herein described cytotoxic proteins are expressed inside engineered microcompartment proteins, the engineered microcompartment proteins can shield the cells from toxicity of the cytotoxic proteins, allowing the cells to grow and thus produce more cytotoxic proteins.

In some embodiments, methods of the present disclosure comprises introducing into the cell at least one polynucleotide encoding at least one engineered microcompartment protein herein described, the at least one polynucleotide operatively linked to one or more first regulatory elements leading to the expression of the at least one engineered microcompartment protein in the cell, the at least one engineered microcompartment protein capable of assembling with one or more same and/or different microcompartment proteins to form at least one empty microcompartment within the cell.

As used throughout, "regulatory elements" are regions of non-coding DNA which regulate the transcription of nearby genes. Examples of regulatory elements are promoters and enhancers. Enhancers are regions of DNA that can be bound with proteins (activators) to activate transcription of a gene or transcription. Promoters are regions of DNA that initiate transcription of a particular gene. In the embodiments described, types of promoters used are over-expression promoters, low-level promoters and tunable promoters. Tunable promoters are not constitutive and can be activated or inactivated as a result of culturing conditions and/or additional elements. In some embodiments, tunable promoters are activated in the presence of a compound introduced into the culture media. Examples of tunable promoters include pRha. In the embodiments described, selection of a promoter is determined by several factors including, but not limited to, the nature of the protein being expressed and the desired expression level of the expressed protein. In the embodiments described, low-level promoters are used when the toxic non-native protein is not efficiently localized to the interior of a microcompartment so as to reduce toxicity to a cell from accumulation of the toxic non-native protein in the cell. In the embodiments described, the use of tunable promoters is used to express a protein at a certain level and/or time during culturing of the cell. In the embodiments described, the type of promoter used is influenced by the interplay between the microcompartment proteins and the toxic non-native proteins.

Accordingly, selection of the appropriate regulatory elements and the at least one polynucleotide can be performed with procedures identifiable by a skilled person.

As used throughout, "operably linked" is defined as a functional linkage between two or more elements. In particular, the term "operably linked" or "operably connected" indicates an operating interconnection between two elements finalized to the expression and translation of a sequence. Functional linkages between elements in the sense of the present disclosure are identifiable by a skilled person. For example, an operable linkage between a polynucleotide of interest and a regulatory sequence (i.e., a promoter) comprises a functional link that allows for expression of the polynucleotide of interest. Another example of operable linkage is provided by a control sequence ligated to a coding sequence in such a way that expression of the coding sequence is achieved under conditions compatible with the control sequences. Operably linked elements are contiguous or non-contiguous and comprise polynucleotides in a same or different reading frame. Additionally, "operably linked" refers to proteins that are linked together wherein the linkage does not impact the function of the individual proteins.

In embodiments herein described, the engineered microcompartment protein comprises encapsulin or encapsulin-like proteins fused with a toxic non-native protein at the N-terminus of the encapsulin and inserted with one or more protease cleavage sites described herein. In some embodiments, one or more protein tags can be added through genetic modification of the engineered microcompartment proteins herein described in accordance with the present disclosure.

In some embodiments an engineered microcompartment protein can be introduced in a cell to form an engineered microcompartment according to a method to provide an engineered microcompartment protein in a bacterial cell herein described. The method comprises introducing into the cell at least one polynucleotide encoding at least one engineered microcompartment protein herein described. The at least one polynucleotide operatively linked to one or more first regulatory elements leading to the expression of the at least one engineered microcompartment protein in the cell, the at least one microcompartment protein capable of assembling with one or more same and/or different microcompartment proteins to form at least one microcompartment within the cell. The assembled engineered microcompartment proteins encompass an interior target protein.

As used throughout, "introducing into the cell" with respect to the polynucleotides refers to inserting a polynucleotide encoding a protein or peptide into a cell or population of cells. One of ordinary skill in the art can readily appreciate that a variety of methods can be used to achieve this such as transformation, transfection, viral transduction and/or injection. In the embodiments described, successful introduction of a polynucleotide into a cell can be assessed by selecting for cells that have taken up the polynucleotide. This is done, for example, by incorporating into the polynucleotide an antibiotic resistance marker against an antibiotic that a cell is typically sensitive to. In some embodiments described, ampicillin resistance genes and kanamycin resistance genes are used on polynucleotides to assess positive insertion of a polynucleotide into a bacterial cell sensitive to ampicillin and kanamycin. Following insertion of a polynucleotide carrying an ampicillin resistance gene, for instance, cells are grown in media containing ampicillin to select for cells that have successfully taken up the polynucleotide.

Introduction of a polynucleotide can be performed for example by chemical transformation or electroporation or other methods identifiable by a skilled person. In some exemplary embodiments performed in *E. coli*, chemical transformation can be performed by incubating CaCl$_2$)-treated *E. coli* cells with the plasmid(s) of interest and heat shocking the cells at 42° C. for an appropriate time period (<60 s) to encourage the cells to take up the plasmid(s). Cells are then diluted with rich medium and incubated at 37° C. to allow for heat shock recovery and expression of one or more antibiotic resistance genes. Cells are then plated on solid-agar medium supplemented with the appropriate antibiotic to select for cells that have taken up the polynucleotide. Similarly, in electroporation, *E. coli* cells are incubated with the polynucleotide of interest and electroporated at an appropriate voltage to increase cells uptake of the polynucleotide as will be understood by a skilled person. Subsequent steps are the same as for chemical transformation.

In some embodiments, introducing into the cell the at least one polynucleotide can be performed by introducing an expression vector comprising the at least one polynucleotide and the one or more first regulatory elements in a configuration leading to transcription of the engineered microcompartment protein carried on the expression vector.

As used throughout, an "expression vector" is a plasmid or virus designed for protein expression in cells. The expression vector is used to introduce a specific gene into a target cell and uses the cell's mechanism for protein synthesis to produce the protein encoded by the gene. In the embodiments described, genes delivered include toxic non-native proteins (such as Ap and HBCM-2) and microcompartment proteins (such as encapsulin of SEQ ID NO: 47). In the embodiments described, a plasmid is engineered to contain regulatory sequences that act as enhancer and/or promoter regions and lead to efficient transcription of the gene carried on the expression vector. Such plasmids also contain selection markers, such as antibiotic resistance markers, to select for cells that have successfully taken up the plasmid. The plasmids herein used for the expression of the engineered microcompartment can also comprise linker sequences, tags and protease cleavage sites. Examples of constructs are pMCY124, pMCY125, and pMCY133 (see Example 12-15).

In order to introduce the engineered microcompartment proteins to a cell, one or more genes encoding the appropriate engineered microcompartment proteins can be cloned and placed under the control of a promoter (constitutive or inducible) in a given plasmid or other vector of interest containing an antibiotic resistance marker. Genes for coding the non-native protein and encapsulin protein can be place in tandem behind a given promoter with appropriate ribosomal re-initiation sites to ensure all proteins are expressed. The plasmid containing one or more engineered microcompartment genes is then transformed into the host organism by either chemical transformation or electroporation. In the case of a constitutive promoter, microcompartment protein is expressed from the plasmid constantly during growth of the host organism. In the case of an inducible promoter, microcompartment protein is expressed from the plasmid by addition of inducer to growth medium (e.g. IPTG, rhamnose).

In some embodiments, the one or more first regulatory elements comprise an over-expression promoter, a low-level constitutive promoter or a tunable promoter. For example, in some embodiments, the one or more first regulatory elements can comprise a T7, pTet, pRha or pT5 promoter.

In some embodiments, the engineered microcompartment proteins can be designed and altered to support functional expression of the cytotoxic non-native proteins to be encapsulated inside one or more engineered microcompartment. For instance, the expression system can be engineered to over-express the encapsulin shell proteins and the non-native proteins to improve yields, thus allowing for higher expression of encapsulated non-native proteins.

In some embodiments, where the engineered microcompartment proteins are to be overexpressed, expression of one or more appropriate engineered microcompartment proteins can be placed under the control of a highly inducible promoter (e.g., T7, T5, rhamnose). The engineered microcompartment proteins can also be over-expressed from a high copy number plasmid containing an appropriate origin (e.g., pUC) in order to ensure multiple copies of the appropriate genes are expressed. The nucleotide sequence of the microcompartment protein genes can be optimized based on host organism codon usage in order to achieve overexpression as well as according to approaches such as the ones described in reference ([24]) and other approaches identifiable by a skilled person.

In some embodiments herein described, one or more genes for toxic non-native proteins are fused to one or more genes for encapsulin proteins under the control of an inducible promoter in a given plasmid or other vector of interest to form the at least one polynucleotide encoding an engineered microcompartment protein. The plasmid (or other vector) containing the polynucleotide for the engineered microcompartment protein can be transformed into a host cell by chemical transformation or electroporation and selected for using antibiotic resistance markers or other markers identifiable by a skilled person.

In some embodiments, at least one polynucleotide comprises one or more polynucleotides encoding for two or more microcompartment proteins.

In some embodiments, the at least one polynucleotide comprises one or more polynucleotides encoding for encapsulins (see Examples 12-16).

In some embodiments, the at least one polynucleotide comprises one or more polynucleotides encoding for one or more of non-native proteins. The non-native protein insertions comprise up to 80 amino acids in length (see Examples 15-17).

In some embodiment herein described, the genes encoding for toxic non-native proteins are operably linked to one another and/or to the genes encoding for encapsulin proteins through a linker. The linker between the non-native protein genes and between the non-native protein gene and the encapsulin gene is configured not to impact the expression of the polynucleotide and the proper folding of the formed engineered microcompartment proteins. The linker also comprises a protease cleavage site specific to a protease, thus allowing the release of the toxic non-native proteins from the encapsulin proteins by proteolysis.

In some embodiments, the at least one polynucleotide encoding the engineered microcompartment also comprises one or more protease cleavage sites inserted within the genes encoding encapsulins to ensure full digestion of the encapsulin cage and thus full release of the non-native proteins (Examples 12-17).

In some embodiments, two or more polynucleotides can be introduced in combination, simultaneously or sequentially. Whether to introduce two or more polynucleotides in combination, sequentially or simultaneously depends on the nature of the proteins being expressed from the polynucleotides and the desired results. In the embodiments described, polynucleotides are expressed sequentially, for instance, so as to effectively select for positive insertion of the polynucleotides. For instance, a first polynucleotide encoding for a microcompartment protein and containing an ampicillin resistance gene can be introduced into a group of cells that are sensitive to ampicillin and kanamycin. Following insertion of the first polynucleotide, the cells are cultured in the presence of ampicillin to select for those that have taken up the first polynucleotide. Next, these cells are introduced to a second polynucleotide encoding for a toxic non-native protein and containing a kanamycin resistance gene. Following insertion of the first polynucleotide, the cells are cultured in the presence of kanamycin to select for those that have taken up the second polynucleotide. The resulting cells are thus selected for successful incorporation of both polynucleotides. A similar strategy is taken when the second polynucleotide encodes for a protein that is extremely toxic to the cells and/or inefficiently localized to the interior of a microcompartment. In such an example, a first polynucleotide encoding for a microcompartment protein is introduced before the second polynucleotide encoding for the toxic protein so as to prevent the cell from toxicity following expression of the protein from the second polynucleotide.

In the embodiments described herein, polynucleotides introduced into a cell encode for a single protein or peptide or several proteins or peptides that function together.

As used throughout, "conditions" for culturing the cells refer to the various elements required to select and/or maintain cells as well as to the various elements required to obtain the desired amount of protein expression from the polynucleotides. Elements required for these purposes include culture media, antibiotics, chemical inducers to promote expression from a promoter (e.g., isopropyl-B-D-thiogalactopyranoside, rhamnose, arabinose), $CO_2$ concentrations, temperature, agitation (in rotations per minute, rpm) and additional factors required to ensure that the proteins are expressed; other elements would be readily appreciated by one of ordinary skill in the art. Additionally, elements include factors that are required for the expressed proteins to function as intended.

In embodiments herein described, the methods further comprises introducing into the cell at least one second polynucleotide encoding one or more proteases, each protease capable of cleaving at a protease cleavage site inserted within the engineered microcompartment protein, thus releasing the non-native protein from the engineered microcompartment protein. The at least one second polynucleotide is operably linked to one or more second regulatory elements leading to the expression of the at least one protease.

Exemplary proteases include Human Rhinovirus (HRV) 3C Protease, Enterokinase, Factor Xa, Tobacco etch virus protease (TEV protease), Thrombin and others known to a person skilled in the art.

In some embodiments, introducing into the cell the at least one second polynucleotide encoding for the proteases is performed by introducing an expression vector comprising the at least one polynucleotide of the at least one second polynucleotide and the one or more second regulatory elements in a configuration leading to transcription of the protease carried on the expression vector.

In some embodiments, the one or more second regulatory elements comprise a promoter, a low-level constitutive promoter or a tunable promoter. In some embodiments, the one or more second regulatory elements comprise an enhancer.

In some of those embodiments, the one or more second regulatory elements are different from the one or more first regulatory elements operably linked to the polynucleotide encoding the engineered microcompartment protein. In some embodiment, the second regulatory elements in the polynucleotide encoding the proteases comprise a pRha or pT7 promoter while the first regulatory elements in the polynucleotide encoding the engineered microcompartment proteins comprise pTet or pT5.

In particular, in embodiments herein described, introducing the second polynucleotide is performed in combination with the introducing of the first polynucleotide to obtain the toxic non-native protein within the cell.

In some embodiments, proteases can be added directly to the lysed cells or purified engineered microcompartment proteins to release the non-native protein from the microcompartment proteins. In some of these embodiments, the method further comprises purifying the at least one engineered microcompartment protein and adding to the purified engineered microcompartment protein at least one protease targeting the protease cleavage sites of the engineered microcompartment protein to release the non-native target protein from the engineered microcompartment protein to obtain the non-native target protein.

The target protein can be purified by size exclusion chromatography or by a centrifugal filter with an appropriate molecular weight cutoff in order to separate the target protein from the microcompartment protein based on size. Alternatively, ion exchange chromatography or reverse phase (e.g., C18) chromatography can be used when appropriate as will be understood by a skilled person.

Purification of the at least one engineered microcompartment protein can be performed rapidly (within 16 hrs. e.g. within 4 h or less) and/or in the presence of suitable additives and/or protease inhibitors to prevent any proteolysis of the engineered microcompartment proteins at this stage. In some other embodiments, the at least one protease can be added to lysed cells expressing the engineered microcompartment proteins herein described. In some embodiments, lysis of the cells can be performed rapidly within 4 h or other suitable time in view of the reaction mixture. Rapid purification of the microcompartment or rapid lysis of the cells are particularly preferred for non cage forming engineered microcompartment protein comprising a protease sensitive target protein as will be understood by a skilled person.

The term "protease-sensitive" as described herein indicates proteins that are targeted for proteolytic degradation by native proteases in the host cell or cell free reaction where the expression of the protein is performed.

In embodiments in which an engineered microcompartment protein comprises a proline between the N-terminus of the first at least one protease cleavage site and the C terminus of the target protein the method can further comprise, contacting the purified non native target protein with a carboxypeptidase to allow reaction of the carboxypeptidase with the carboxy terminal residues of the purified non-native target protein.

First, different protease cleavage sites between the C-terminus of the peptide and the N-terminus of the engineered encapsulin should be tested to determine if there is a residual protease cleavage site that does not interfere with peptide activity.

These additional contacting of the purified target protein can be performed to achieve activation of a non-active peptide to an active peptide or improvement of the activity of an active peptide.

In some embodiments, the present disclosure provides a method to express significant amounts of non-native, cytotoxic proteins in a host organism for isolation and production purposes. The method can be applied to proteins of interest that are difficult to produce due to their cytotoxicity to the host organism. In an exemplary method, cytotoxic, non-native proteins are engineered to be encapsulated in encapsulin cage in E. coli in order to prevent their cytotoxicity. As proof of this concept, in some examples herein described, the cytotoxic non-native proteins Ap from honey bee were fused to encapsulins to form engineered microcompartment proteins in the cytoplasm of E. coli, thus shielding the toxicity of Aps from the cells as described in Example 12-15 and 24. In some other examples, the cytotoxic non-native HBCM-2 peptides were fused to encapsulins to form engineered microcompartment proteins thus shielding the toxicity of the peptides from the cells (Example 16-17).

In some embodiments, the engineered microcompartment proteins formed by fusing cytotoxic target proteins, such as non-native HBCM-2 and AP, to encapsulins can achieve a robust expression while remaining less susceptible to proteolysis in comparison with fusion proteins of the same cytotoxic non-native peptides with other common carrier proteins (Example 24). In particular, the engineered microcompartment proteins formed by fusing cytotoxic non-native target proteins to encapsulins also confer limited toxicity to the host cells even at a high over-expression level (Example 23).

In some embodiments, the methods herein described can produce a large amount of active, cytotoxic non-native proteins in vivo or in vitro (following cleavage from the engineered microcompartment protein) having the same level of activity as the chemically synthesized proteins (see Example 22). In some embodiments, the present disclosure addresses issues associated with production of non-native, cytotoxic proteins in the host organism E. coli, and can be associated with in vitro purification systems (cell free expression, as described in the www webpage lifetechnologies.com) excretion tags excreting the cytotoxic proteins from E. coli (as described in the www webpage dna20.com), which are used to produce cytotoxic proteins.

In some embodiments, methods and systems of the disclosure herein described can be used express cytotoxic proteins directly in bacterial microcompartments to minimize toxicity, and/or reduce problems associated with proper folding and secretion associated with secretion tags. The methods, systems and related compositions and cells of the disclosure can result in several embodiments with reduced costs and higher production levels compared to those of prior methods.

In some embodiments, engineered microcompartment proteins, related engineered microcompartment and related vectors, cells, compositions, methods and systems can be used to introduce in a same engineered microcompartment a same or different target protein.

An exemplary illustration of steps of methods to provide one or more target proteins such as toxic or non-toxic non-native proteins herein described and in particular Ap are illustrated with reference to exemplary engineered microcompartment proteins expressed in E. coli cells through use of specific regulatory sequences as will be understood by a skilled person.

A first fusion gene encoding an engineered microcompartment protein is created, the fusion gene comprising a gene of the desired non-native protein fused to the N-terminus of a gene encoding an encapsulin protein. Protease cleavage site such as TEV or thrombin can also be placed between the non-native protein and the encapsulin protein to later cleave off the non-native protein. Protease cleavage sites are also placed within the encapsulin proteins to enable digestion of the encapsulin and thus release of the non-native protein.

The fusion gene is then placed under the control of an inducible promoter in a plasmid of interest, which is then transformed into an E. coli expression strain (e.g., C43 cells). The transformed E. coli cells then grow in an appropriate medium (LB medium) at an appropriate temperature.

A second gene encoding a protease can be created and co-expressed with the fusion gene encoding an engineered microcompartment protein.

The cells are induced for engineered microcompartment protein formation using the inducer for the plasmid containing the microcompartment proteins (e.g., IPTG for the pT5 promoter).

Alternatively, instead of co-expression of the fusion gene and the protease-encoding gene, proteases can be added directly to lysed cells expressing the engineered microcompartment protein or to purified engineered microcompartment protein.

In order to isolate the toxic protein of interest inside microcompartments, the cells are harvested after desired induction time and resuspended in an appropriate buffer. The cells are then lysed by an appropriate method including sonication, French press lysis, detergent lysis with lysozyme and other methods identifiable to a person skilled in the art. The cell debris can be removed by centrifugation at 12,000 g, 4° C. for 10 min and supernatant can be collected.

To collect the toxic protein of interest, appropriate detergent is added to the soluble fraction if necessary (e.g., Empigen BB) and incubated for sufficient time to solubilize desired protein. The soluble fraction is then loaded on an affinity chromatography column. The column is washed and the desired protein is eluted with the appropriate buffers. The fractions containing the desired protein can then be collected and stored as necessary.

Engineered microcompartment proteins, engineered microcompartments, and related vectors, cells, compositions, methods and systems of the present disclosure can be applied broadly to other cytotoxic proteins for expression and purification from bacterial cells by replacing the gene for Ap with the gene for a cytotoxic protein (toxic, non-native protein) of interest and by replacing the medium and regulatory sequences of E. coli with the ones of a desired bacteria as will be understood by a skilled person. Thus, the methods, systems, cell and compositions of the disclosure have wide applications in the biosciences, where this novel technology could be used for the efficient production of proteins that are normally difficult to produce.

In embodiments herein described, engineered microcompartment proteins, engineered microcompartments, and related vectors, cells, compositions, methods and systems of the present disclosure can be used to produce a toxic non-native protein, by expressing the toxic non-native protein within BMC in a bacterial cell and by isolating the toxic non-native protein from the bacterial cell.

In some embodiments, engineered microcompartment proteins, engineered microcompartments, and related vectors, cells, compositions, methods and systems of the present disclosure can be used to shield the toxicity of pathway intermediates and increase reaction efficiencies in nature. In those embodiments, a toxic non-native protein can be expressed within a BMC and additional molecule forming the pathway can be provided within the cell. In those embodiments, small molecule substrates and products of the enzymes can passively diffuse in and out of the BMCs via pores in the shell proteins, while pathway intermediates remain sequestered inside the BMCs. In such case, not only the toxic pathway intermediates can be shielded from the host organism, but the local concentration of enzymes and substrates also increases, leading to improved reaction efficiency.

In several embodiments, the present disclosure provides engineered microcompartment proteins, engineered microcompartments, and related vectors, cells, compositions, methods and systems of the present disclosure that provide a bioengineering application of microcompartments that has not been previously explored.

In some embodiments, a bacterial cell obtainable by any one of the methods of the disclosure is described, and in particular a cell comprising at least one toxic non-native protein within at least one engineered microcompartment within the cell.

In some embodiments, a bacterial cell herein described further comprises various toxic non-native proteins wherein the various non-toxic proteins function and/or aggregate independently of or in combination with one another.

In some embodiments, in a bacterial cell herein described the various non-toxic proteins reside within the at least one microcompartment within the cell either independently of or in combination with one another.

In some embodiments, in a bacterial cell herein described various non-toxic proteins reside within at least two or more microcompartments within a cell.

In some embodiments, in bacterial a cell herein described at least one of the microcompartments comprises at least one additional component.

In some embodiments, in a cell herein described the at least one additional component is presented to the at least one toxic-nonnative protein.

In some embodiments, a composition is described comprising one or more bacterial cells obtained from any one of the methods of the disclosure, and/or by any one of the systems of the disclosure and/or any one of the cells herein described together with a suitable vehicle.

In some embodiments, the engineered microcompartment proteins, and related target proteins, insertion regions, tags. Linkers, engineered microcompartments, bacterial cells herein described can be comprised in a composition together with a suitable vehicle. The term "vehicle" as used herein indicates any of various media acting usually as solvents, carriers, binders or diluents for the non-native toxic proteins and/or related cells that are comprised in the composition as an active ingredient. In particular, the composition including the non-native toxic proteins and/or related cells can be used in one of the methods or systems herein described.

As disclosed herein, the engineered microcompartment proteins, the target proteins, insertion regions, tags, linkers regulatory sequences, vectors and/or related cells herein described can be provided as a part of systems to produce one or more non-native toxic proteins, and in particular can be used in methods to produce or provide a non-native toxic protein herein described. The systems can be provided in the form of kits of parts. In a kit of parts, the non-native toxic proteins, regulatory sequences, vectors and/or related cells and other reagents to produce or provide a non-native toxic protein can be comprised in the kit independently. The non-native toxic proteins, regulatory sequences, vectors and/or related cells can be included in one or more compositions, and each component can be in a composition together with a suitable vehicle.

Exemplary components of a kit of parts and of constructs herein described comprise the nucleotide sequence of the linkers, protease cleavage sites, and histidine affinity tags that are codon optimized for maximum expression in E. coli such as the one described in the Examples section. Additional components can include labeled molecules and in particular, labeled polynucleotides, labeled antibodies, labels, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, flash drives, or by indication of a Uniform Resource Locator (URL), which contains a pdf copy of the instructions for carrying out the assay, for carrying out the assay, will usually be included in the kit. The kit can also contain, depending on the particular method used, other packaged reagents and materials (i.e. wash buffers and the like).

Further details concerning methods and system, cells and compositions of the present disclosure will become more apparent hereinafter from the following detailed disclosure of examples by way of illustration only with reference to an experimental section.

EXAMPLES

The engineered microcompartment proteins herein described and related engineered microcompartments, methods and systems for engineering bacterial cells, as well as bacterial cells herein described are further illustrated in the following examples, which are provided by way of illustration and are not intended to be limiting.

In particular, the following examples illustrate exemplary methods and systems for expressing non-native, cytotoxic proteins or pathways involving these proteins in engineered microcompartment proteins for synthetic biology applications. The following examples demonstrate that engineered microcompartment proteins are useful platforms to produce in a bacterial cell proteins that are toxic and/or degradable in the cell minimizing cytotoxicity and degradation while improve efficiency of non-native protein expression compared to other convention approach for protein expression. The development of this platform can be broadly used in various fields including biofuels, biopharmaceuticals, biodefense, bioremediation as well as many other applications in bioscience in general.

A person skilled in the art will appreciate the applicability and the necessary modifications to adapt the features described in detail in the present section, to additional non-native proteins and bacterial systems and related methods and systems according to embodiments of the present disclosure.

Example 1: Exemplary AMPs

Exemplary AMP used in some experiments herein described are listed in Table 1.

TABLE 1

Amino acid sequences of exemplary AMP

| AMP peptide | Amino acid sequence | SEQ ID NO |
|---|---|---|
| HBCM2 | KWKSFIKKLTKAAKKVVTTAKKPLIV | 9 |
| HBCM3 | KWKKFIKSLTKSAAKTVVKTAKKPLIV | 10 |
| Cecropin PR-39 | RRRPRPPYLPRPRPPPFFPPRLPPRIPPGFPPRFPPRFP | 11 |
| Apidaecin Ia | GNNRPVYIPQPRPPHPRI | 12 |

HBCM2 and HBCM3 are two AMPs that have activity against antibiotic-resistant *P. aeruginosa*. These two AMPs are optimized hybrid peptides of moth cecropin and bee melittin [18, 19]. These peptides also have been shown to have anti-inflammatory activity in cystic fibrosis mouse models [19]. Non-lytic AMPs cecropin PR-39 and apidaecin Ia, which are derived from pig and honeybee, respectively [25, 26] are also expressed. Collins and coworkers have shown that these two AMPs have high bactericidal activity but do not induce lysis of pathogens, avoiding release of endotoxins that may be toxic to the human host [27]. Thus, they may be better suited for therapeutic applications. All four of these AMPs (Table 1) lack cysteine residues and thus do not require disulfide bond formation for activity, making them more amenable to heterologous expression [28]. Other AMPs with activity toward *P. aeruginosa* based on the Antimicrobial Peptide Database can also be screened for expression [22].

Example 2: Encapsulation Strategies Using Encapsulins

Protein expression systems can be designed to express the AMPs encapsulated inside an encapsulin microcompartment system. In encapsulin systems (e.g., ferritin cages), a single, repeating encapsulin protein is responsible for encapsulating an interior protein, in a typical ratio of 60 encapsulins to 6 interior proteins [2, 29]. In contrast to other BMC systems, in which several different BMC shell proteins are required to encapsulate interior protein [30], encapsulin systems are less complex with a single encapsulating protein. They are therefore expected to have improved formation of compartments in a recombinant system, and thus higher loading of interior protein, compared to traditional BMC systems. These expression systems are initially designed under traditional inducible promoters (e.g., pTet, pT5) in order to test and optimize maximum production levels.

Figure 9A:
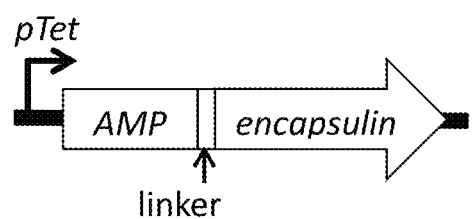
FIGS. 9A-B illustrate two exemplary systems for encapsulation of AMPs.
Figure 9B:
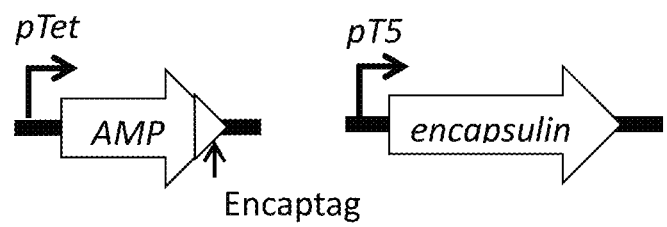

In order to target the AMPs to the interior of encapsulins, two potential strategies (FIG. 9A-B) are employed. In the first strategy (FIG. 9A), the encapsulin shell protein will be directly fused to the C-terminus of the given AMP in one single polypeptide chain. The first strategy design is based on initial studies that suggest that interior protein-encapsulin fusions allow all interior proteins to be encapsulated by the encapsulin shells, without sacrificing the integrity of the formed encapsulin compartments. This fusion system is, furthermore, predicted to have more AMP molecules loaded into the encapsulin compartments (60:60 encapsulin:interior protein), compared to the native system (60:6 encapsulin:interior protein) [2], which should encourage higher production of AMPs in the recombinant system. The linker region between the interior protein and encapsulin can be optimized for efficient loading of AMPs into the encapsulins. Here, computational modeling can be performed to guide linker optimization for efficient loading into the compartments.

In some scenarios, the mechanism of action for AMP toxicity is carried out in the *E. coli* host before encapsulation occurs. This is a possibility since 60 units of the fusion protein will need to be synthesized to assemble one full encapsulin compartment, but only 1 unit of the fusion protein can cause toxicity. Thus, as an alternative to the first strategy, in the second strategy (FIG. 9B) a known C-terminal encapsulin targeting tag (18 amino acids, Encaptag) [2] will be fused to the AMP peptide and the AMP-Encaptag will be co-expressed with the encapsulin shell protein from two different promoter systems, pTet and pT5. In this system, the encapsulin shell proteins will be expressed first so that when the AMP-Encaptag protein is subsequently expressed, there will be sufficient encapsulin shell protein available for immediate AMP encapsulation. Toxicity shielding of AMPs and production amounts in either strategy will be determined using growth assays and SDS-PAGE/Western blots for quantification. If toxicity is shielded, better growth and higher production of AMPs can be expected in cells expressing AMP-encapsulin compared to AMP alone. Expression optimization will be performed to determine the maximum amount of encapsulated AMP that can be produced with limited toxicity to the host *E. coli* cells.

Example 3: Identification of Proteolysis Conditions

Once an expression system for encapsulating AMPs is established, conditions to release the AMPs from the interior of the encapsulins by proteolysis can then be developed. Here, proteolytical cleavage of AMPs from the encapsulin shell/Encaptag as well as cleavage of specific sites in the encapsulin shell protein can be applied so that the entire structure can be degraded for release of AMPs.

Figure 11:
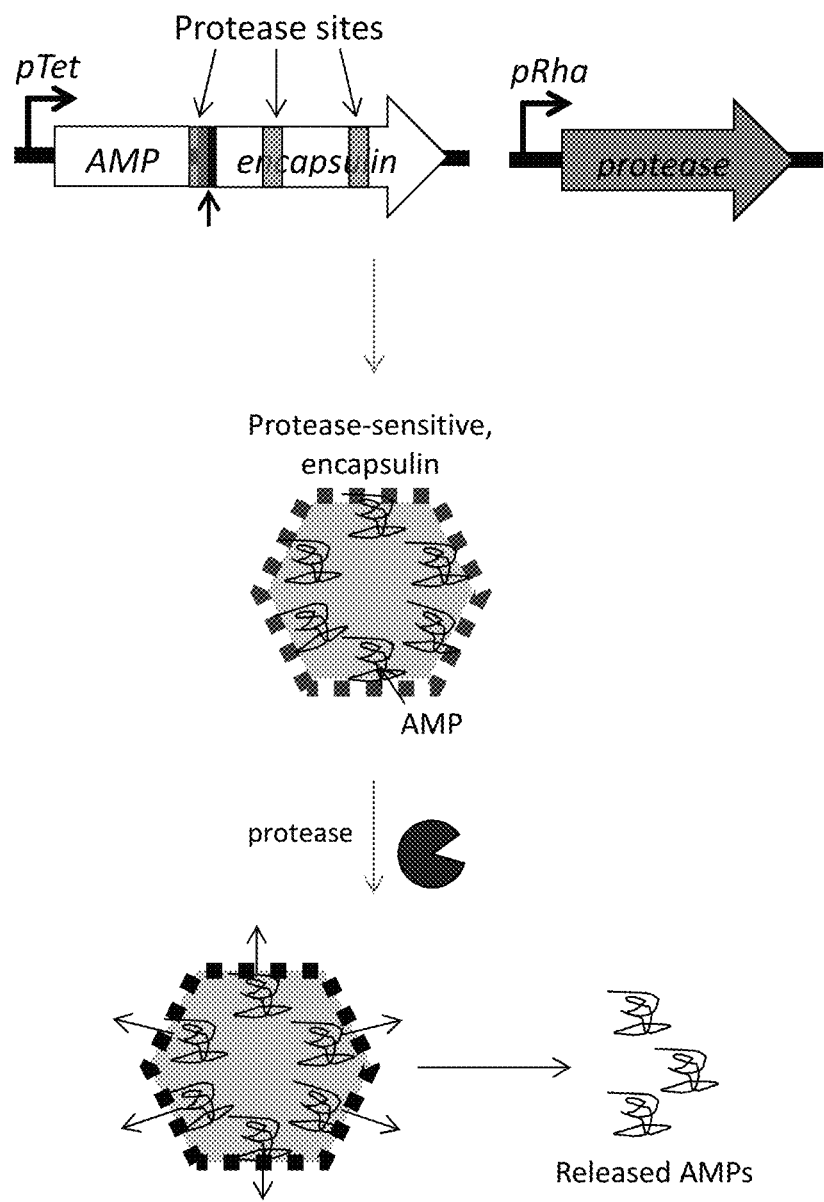
FIG. 11 illustrates the design of a protease-sensitive encapsulin.
Figure 12:
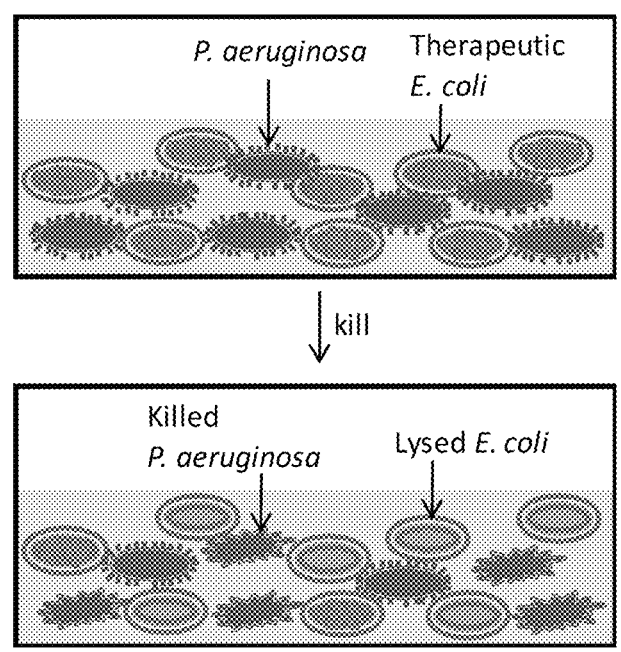
FIG. 12 illustrates an exemplary testing of therapeutic delivery system efficacy in bacterial liquid culture.
Figure 13:
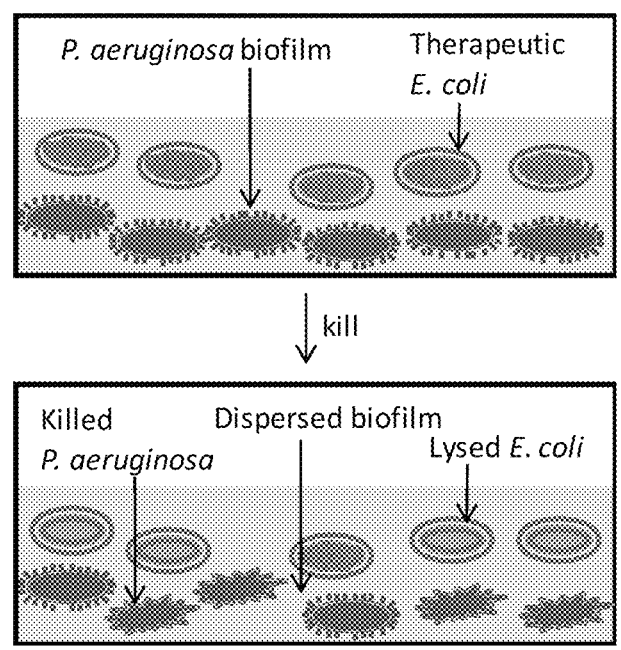
FIG. 13 illustrates an exemplary testing of therapeutic delivery system efficacy in biofilm.

FIG. 11 illustrates the design of a protease-sensitive encapsulin. Antimicrobial peptide (AMP) is fused to the N-terminus of the encapsulin protein. Specific protease recognition sites are inserted between the AMP and encapsulin protein as well as within the encapsulin protein itself. The fusion protein is expressed from a T7 inducible promoter and purified. The purified fusion is digested with a specific protease that targets the protease recognition sites and the AMPs are released and thus can be isolated for a desired function.

Known protease cleavage sites (i.e., thrombin, enterokinase) [31] will be inserted between the AMP protein and encapsulin shell/Encaptag as well as within the encapsulin shell protein itself. Computation modeling will be used to identify potential cleavage insertion sites that would cause the encapsulin compartments to fall apart upon protease cleavage but would otherwise not affect the integrity of and loading into the compartments. Expression of AMP-encapsulin systems with appropriate protease cleavage sites will be tested for toxicity shielding and production amounts using growth assays and SDS-PAGE/Western blots. Microcompartments from stable AMP-encapsulin systems will be subsequently isolated using established differential centrifugation methods [2, 32] and treated with an appropriate protease to determine if AMP can be efficiently released from the compartments. Efficient release will be assessed by separation of AMP from encapsulin via size-exclusion chromatography or Ni-NTA affinity chromatography, where the AMP will be tagged with a $His_6$ tag that will not be cleaved from the AMP during proteolysis. If release of AMP is efficient, the AMP and encapsulin can be expected to purify as separate fractions during chromatography, whereas if release is inefficient, co-purification of the components is expected.

Recognition sequences and cleavage sites of exemplary proteases are shown in Table 2. / forward slash (/) indicates where protease cleaves the protein sequence.

TABLE 2

/ forward slash (/) indicates where protease cleaves the protein sequence.
Table 2: Recognition sequences and cleavage sites of exemplary proteases

| Enzyme Name | Sequence and Cleavage | SEQ ID NO |
|---|---|---|
| Human Rhinovirus (HRV) 3C Protease | LEVLFQ/GP | 13 |
| Enterokinase | DDDDK/ | 14 |
| Factor Xa | IEGR/ | 15 |
| Tobacco etch virus protease (TEV protease) | ENLYFQ/G | 16 |
| Thrombin | LVPR/GS | 17 |

Example 4: Release of AMPs from *E. coli*

Once an appropriate protease-sensitive AMP-encapsulin system is identified, experiments can be performed to test whether AMP can be released from encapsulin within the *E. coli* host organism and subsequently from the cell itself by co-expression of the AMP-encapsulin system and the appropriate protease.

In these studies, the AMP-encapsulin system will be expressed first from a pTet (and pT5 if necessary) promoter. Once high levels of AMP-encapsulin are produced, protease expression will be induced from a different promoter (i.e., pT7 or pRha). A lysis protein, such as colicin E7 lysis protein [33] may also need to be co-expressed with the protease to achieve efficient lysis of the bacterial cell to release the AMPs. The kinetics of AMP release from cells into the spent medium over time upon proteolysis/lysis induction will be assessed via SDS-PAGE/Western blot.

In order to compare the lysis system to known systems [33, 34], control strains of *E. coli* that 1) secrete the AMP candidates via YebF secretion signals [35] and 2) produce AMPs without encapsulin, will be generated, which are released by lysis. The rate and total amounts of AMP released will be compared among the control strains and the protease-sensitive AMP-encapsulin strain in order to demonstrate improved AMP release in the latter system.

Example 5: Design of a Control System

The AMP-encapsulin and protease/lysis systems can be coupled to a specific pathogen, quorum-sensing system for *P. aeruginosa*. The quorum sensing system from *P. aeruginosa* was primarily chosen as a proof-of-principle because it is highly specific to *P. aeruginosa*, has been very well studied [36], and has already been adapted for synthetic biology applications [33, 34, 37]. *P. aeruginosa* has a unique N-acylhomoserine lactone (AHL) quorum sensing molecule, called 3-oxo-C12-homoserine lactone (3OC12HSL), that is specifically and directly sensed by the native transcription factor LasR. Binding of 3OC12HSL to LasR induces dimerization of LasR, which then is able to bind to and drive expression from pLasI promoters [36].

Figure 10:
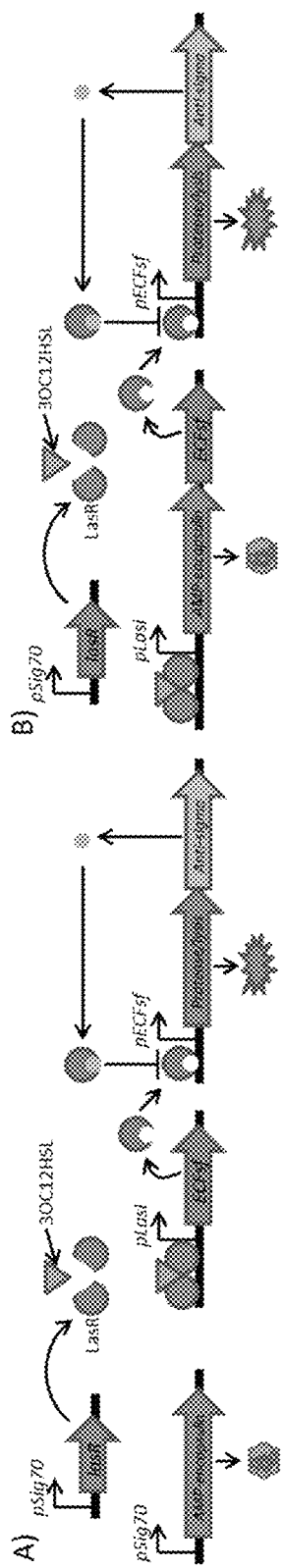
FIG. 10 illustrates a design of sense-control-release systems for *P. aeruginosa*. Panel A) Primary circuit strategy. LasR and AMP-encapsulin are produced from constitutive sigma70 promoters. 3OC12HSL-bound LasR drives expression of an ECF sigma factor (ECFsf), which in turn drives expression of the protease/lysis cassette as well as an anti-sigma factor. The anti-sigma factor inhibits the ECFsf and thus turns off expression of the protease/lysis cassette in a negative feedback loop. Panel B) Alternative circuit where 3OC12HSL-bound LasR drives expression of AMP-encapsulin and the ECFsf.

The LasR/pLasI system can be adapted to drive expression of the protease that specifically cleaves the encapsulins and if necessary, a lysis protein to lyse the *E. coli* Nissle 1917 host and ultimately release AMPs at high concentrations. Encapsulated AMPs can be expressed at high constitutive levels in order to ensure that they will be immediately released at high doses upon lysis. LasR can be expressed at medium constitutive levels to ensure that 3OC12HSL can be detected at any time (FIG. 10, panel A). Established, synthetic sigma70 promoters of different strengths can be used for constitutive expression [38] and these constructs will be inserted into the genome of the *E. coli* host to prevent variability in expression levels among cells.

In order to minimize premature proteolysis/lysis of the *E. coli* host, a negative feedback loop logic can be engineered into the protease/lysis cassette (FIG. 10, panel A). Here, the LasR transcription factor will drive expression of an ECF sigma factor (ECFsf) that is orthogonal to the other host *E. coli* sigma factors [39]. This sigma factor will then activate a unique ECFsf promoter to drive expression of the protease/lysis cassette as well as an anti-sigma factor. The anti-sigma factor will bind and inhibit the ECFsf to prevent further expression of the protease/lysis cassette. Thus, the protease/lysis cassette will only have sustained expression under high concentrations of 3OC12HSL, where the ECFsf is able to out-compete the anti-sigma factor. Alternatively, the anti-sigma factor can be constitutively expressed in order to create a threshold-gated switch, where a set concentration of ECFsf would need to accumulate to overcome the anti-sigma factor. Here, the expression levels of the anti-sigma factor would set the desired threshold. Constitutive expression of the anti-sigma factor also has the added benefit of reducing leaky expression from ECF promoters, which can also lead to premature lysis [39].

Example 6: Optimization and Testing of the System

Initial experiments can be conducted with fluorescent protein reporters (e.g., mVenus) [40] instead of the AMP-encapsulin and protease/lysis cassettes. With these reporters, the concentrations of 3OC12HSL needed to turn on different components of the circuit can be tested and these concentrations can be correlated to cell densities of *P. aeruginosa* [37]. Further optimization of this system can be performed to obtain the correct degree of expression at an appropriate 3OC12HSL concentration, which may involve altering any of the following: lifetimes of the components via ssrA degradation tags [41], translational production levels via changes in the ribosome binding site (RBS) [42], and copy number of the anti-sigma factor gene to enable sufficient inhibition of the ECFsf. Computational modeling of the rates of production and degradation of the system components will be performed to guide and improve design, according to current synthetic biology practices [43]. Then, the system can be tested using the actual AMP-encapsulin and protease/lysis gene cassettes. The amounts of AMP released into the medium over time can be measured using SDS-PAGE/Western blots as well as the degree of lysis using optical density at 600 nm and microscopy. These measurements can establish whether the system can efficiently deliver a high dose of AMPs. Experiments with *P. aeruginosa* and exogenously added AMPs can be conducted to determine if the amounts of AMPs released by the system are sufficient to kill the pathogen.

In some cases, the constitutive production of the AMP-encapsulins may be detrimental to the overall fitness of the host *E. coli* cell, either due to incomplete encapsulation or metabolic burden. In these cases, the system can be designed to only produce the AMP-encapsulin when 3OC12HSL is detected and subsequently lyse the cells after an appropriately spaced delay period at high 3OC12HSL levels (FIG. 10, panel B). The ECFsf downstream of the AMP-encapsulin can be expressed and the stability of the ECFsf (via ssrA tags) can be adjusted to only drive expression of the protease/lysis cassette at high 3OC12HSL levels, which may require further optimization.

Example 7: A Sense-Control-Release System for *Clostridium difficile*

A sense-control-release system for *Clostridium difficile* can also be developed based on recent studies identifying a putative, two-component, quorum-sensing system that can sense a unique *C. difficile* autoinducing peptide (AIP) and activate toxin production in the virulent form of *C. difficile* [44]. This system can replace the *P. aeruginosa* LasR sensing component in the sense-control-release system to specifically detect virulent *C. difficile* instead of *P. aeruginosa* and release a therapy in response. Because *C. difficile* is a gram-positive bacterium, the system need to be expressed in a gram-positive host, such as the probiotic gut organism, *Lactococcus lactis*, which has already been bioengineered for therapy applications [45, 46].

Example 8: Testing of Therapeutic Delivery System Efficacy in Bacterial Liquid Culture The efficacy of the encapsulated AMP delivery system in killing *P. aeruginosa* can be tested. Initial studies are performed in bacterial liquid culture of planktonic *P. aeruginosa* cells (FIG. 12). Different concentrations of the therapeutic *E. coli* can be mixed with different concentrations of *P. aeruginosa* and the degree of killing of the *P. aeruginosa* can be measured by Bactolight live/dead staining (Thermo), OD600, and/or colony forming unit (CFU) counting over time. The *E. coli* can be differentiated from the *P. aeruginosa* in microscopy experiments by expressing a fluorescent protein marker in the *E. coli*. From these experiments, the number of *E. coli* cells required to kill a certain population of *P. aeruginosa* can be determined. As controls, two *E. coli* strains can be constructed that express the following in response to 3OC12HSL detection: 1) secreted AMPs and 2) non-encapsulated AMPs followed by lysis. The ability of these control strains to kill *P. aeruginosa* can be compared to that of the encapsulated AMP delivery system, in order to demonstrate improved killing in the latter system.

Example 9: Testing of Therapeutic Delivery System Efficacy in Biofilm Model

The ability of the therapeutic *E. coli* to kill biofilms of *P. aeruginosa* can also be tested (FIG. 13). Biofilms of *P. aeruginosa* are commonly found in infections [47]. Biofilms can be grown on pegs of polystyrene attached to a lid of a microtiter plate according to standard practices [48]. Biofilms can then be treated with different concentrations of the therapeutic *E. coli* by immersing the biofilm pegs in *E. coli* culture dispensed in the wells of a microtiter plate. The degree of biofilm dispersal can be assayed over time using standard crystal violet staining followed by absorbance measurements at 595 nm [49] as well as live/dead staining and/or CFU counting. Control strains described for the liquid culture can also be tested to demonstrate improved killing in our AMP-encapsulin strain.

Example 10: Engineered Therapeutic Cells for Improved Killing in Biofilm Model AMPs have been shown to be more effective against bacterial biofilms compared to traditional small molecule antibiotics due their ability to act on non-growing cells as well as inhibit biofilm formation by preventing adhesion and the production of biofilm components (i.e., EPS) [50]. However, there is a possibility that the AMPs released by the E. coli are ineffective against the biofilm because they are not able to penetrate the EPS/DNA matrix to access the *P. aeruginosa* cells. In this case, a separate strain of *E. coli* can be engineered that will release DNaseI or alginate lyase (AL) via lysis in response to *P. aeruginosa* detection in order to break up the biofilm. Both DNaseI and AL have been shown to be effective in dispersing *P. aeruginosa* biofilms [51, 52]. The AMP-encapsulin gene cassette can be swapped for the genes for DNaseI or AL to create the new strains. The DNaseI/AL strain and the original AMP-encapsulin strain can be mixed together and tested to determine if the combination treatment is more effective in killing *P. aeruginosa* using the methods previously described.

In order for the therapeutic *E. coli* to find and stay localized at the biofilm long enough for efficient therapeutic release, the *E. coli* can be engineered to chemotax toward the 3OC12HSL, using the method developed by Chang and coworkers [34], where LasR was designed to drive expression of cheZ, which promotes smooth swimming toward a metabolite of interest in a AcheZ genetic background. Improved killing with the additional cheZ system can be demonstrated using the methods previously described.

Example 11: Testing of Therapeutic Delivery System Efficacy in Host Tissue Culture Model The ability of our therapeutic *E. coli* to kill *P. aeruginosa* can also be tested in a host tissue culture model (FIG. 143). A co-culture of *P. aeruginosa* with intestinal epithelial cells can be treated with different concentrations of the therapeutic *E. coli*. In addition to assessing killing of the *P. aeruginosa* by live/dead staining and/or CFU counting, the fitness of the intestinal epithelial cells can also be tested by standard MTT assays [53] to determine if lysis of the *E. coli* or *P. aeruginosa* is detrimental to the host cells. The correlation between number of lysed cells and lower fitness of host cells, if any, can be quantified. If lysis of the *E. coli* results in significant loss of host cell fitness, several gene deletions in the *E. coli* strain can be made, which force the cells to only produce lipid $IV_A$, instead of lipid A, the component of bacterial LPS that is responsible for endotoxic activity; lipid $IV_A$, a precursor to lipid A has been shown to lack endotoxic activity [54]. While these deletions have been demonstrated to effectively reduce the endotoxic effect of *E. coli* [54], these deletions may reduce the fitness of the *E. coli* cells, which will need to be assessed to determine they have any effect on the use of our therapeutic *E. coli*.

Example 12: Growth and Expression of Constructs 124, 125, and 133 in C43(DE3) *E. coli* Cells In this example, engineered microcompartment proteins are constructed and expressed in C43 (DE3) *E. coli* cells.

Figure 14:
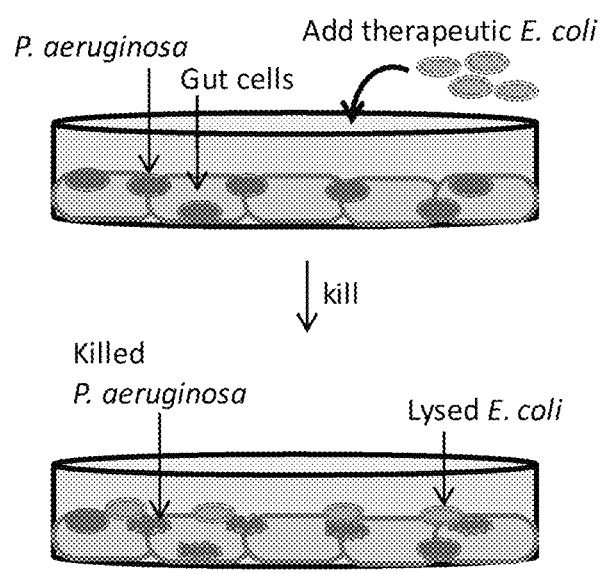
FIG. 14 illustrates an exemplary testing of therapeutic delivery system efficacy in in host tissue culture model

As shown in FIGS. 14A-C, the gene sequence for Apidaecin Ia peptide (Ap) was fused to the 3' end of gene sequences for various encapsulin (Encap) constructs. The gene fusions were placed under the control of a T7 promoter in the commercially available pET24a vector. These gene fusions include those that express the following proteins: 1) Ap fused to Encapsulin containing a TEV protease cleavage site and His-tag after position K138 (Ap-Encap(K138) from pMCY124) (FIG. 15A); 2) Ap fused to Encapsulin containing a TEV protease site after position K71 and the TEV protease site and His-tag after position K138 (Ap-Encap (K71,K138) from pMCY125) (FIG. 15B); and 3) Ap fused to Encapsulin containing a TEV protease site after position D60 and the TEV protease site and His-tag after position K138 (Ap-Encap(D60,K138) from pMCY133) (FIG. 15C).

In the constructs herein described, a linker comprised of a Tobacco Etch Virus (TEV) protease site (sequence: ENLYFQG) followed by a GTS (Gly-Thr-Ser) linker is placed between the Ap peptide and encapsulin monomer, in order to enable later cleavage of Ap from encapsulin via TEV protease.

In constructs pMCY125 and pMCY133, within the encapsulin monomer, two specific protease sites are also inserted to enable digestion of the encapsulin cage.

In pMCY125, the first site is inserted following amino acid residue K71 in the encapsulin monomer. This site is chosen because of its location between the surface-accessible E-loop and P-domain of the encapsulin structure. Cleavage at this location was predicted to disrupt the structure of the encapsulin cage. A TEV protease site surrounded by double Gly (Gly-Gly) linkers on both sides of the site is inserted following residue K71. The second site was inserted following amino acid residue K138. This site was shown to be surface-accessible and insertion of a $His_6$-tag at this location allowed for Ni-NTA affinity purification of the encapsulin cage [55]. A TEV protease site was inserted directly adjacent to the $His_6$-tag on the N-terminal side. Thus, the following sequence was inserted following residue K138: a pentaglycine linker (Glyn), a TEV protease site, a $His_6$-tag, and another pentaglycine linker. The $His_6$-tag was used for affinity purification of the Ap-EncapK71K138 construct. The codon-optimized nucleotide sequence for pMCY125 (SEQ ID NO: 18) is also shown in FIG. 15A.

Figure 16:
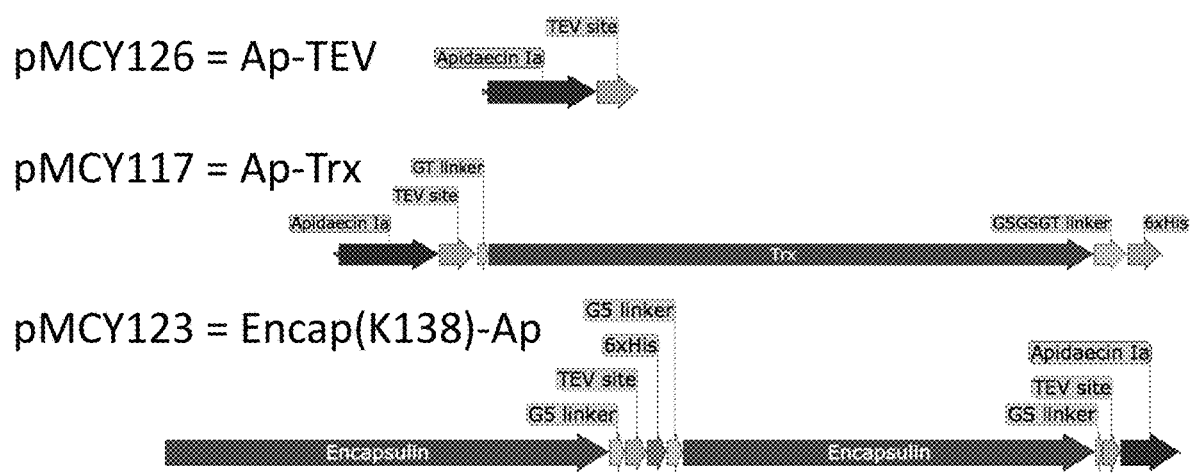
FIG. 16 illustrate exemplary Ap-containing constructs as controls.

As controls, gene fusions expressing the following proteins were also prepared: 1) Ap fused to a TEV protease cleavage site alone (Ap-TEV from pMCY126); 2) Ap fused to thioredoxin (Ap-Trx from pMCY117); and 3) Ap fused to the C-terminus of Encapsulin containing the TEV protease site and His-tag after position K138 (Encap(K138)-Ap from pMCY123—Here, Ap peptide would be outward facing in the Encapsin compartment, making it potentially toxic and susceptible to proteolysis.) All gene constructs are diagramed in FIG. 16. The peptide Apidaecin Ia has a sequence of SEQ ID NO: 19: GNNRPVYIPQPRPPHPRIENLYFQ All DNA plasmids containing the gene constructs were transformed into C43(DE3) *E. coli* cells (Lucigen) and expression of the corresponding protein constructs were tested. Cells were grown in 10 mL of Luria-Bertani (LB) medium in 50-mL flasks to mid-log phase (optical density at 600 nm (OD600) of 0.4). Isopropyl β-D-thiogalactoside (IPTG) was then added to the culture to a final concentration of 0.1 mM and culture was grown for another 4 h at 30° C. to induce protein expression. After induction, cells were harvested and resuspended in 400 uL of lysis buffer containing 60% BPER-II detergent (Thermo-Fisher) in buffer A (50 mM Tris pH8.0, 500 mM KCl, 12.5 mM $MgCl_2$) supplemented with 0.1 mg/mL lysozyme and 10 U/mL of DNaseI. Cells were lysed by incubating at 4° C. with occasional mixing for 15 min. Cells were then centrifuged at 12,000 g, 4° C. for 25 min and the supernatant was collected as the soluble fraction. Samples prior to centrifugation were saved as the "whole" samples, while the supernatant after centrifugation was saved as the "soluble" samples.

Figure 17:
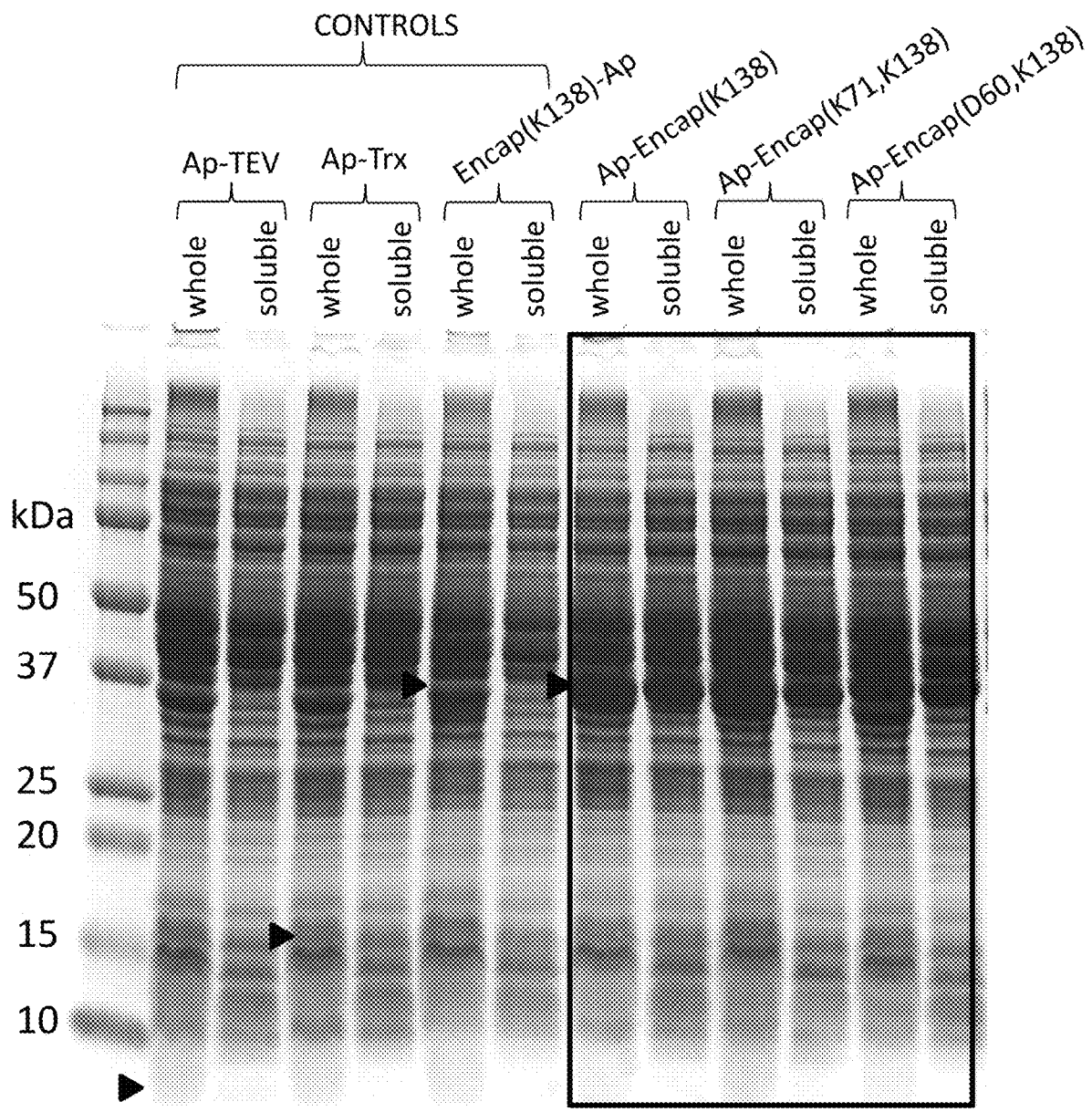
FIG. 17 shows in one embodiment expression of constructs pMCY124, pMCY125 and pMCY133 in comparison with control constructs.

All samples were resolved on an any-kDa SDS-PAGE gel (Bio-rad) and stained with Coomassie blue (FIG. 17). Arrows denote predicted location of the expressed protein. Samples expressing fusions with Ap on the N-terminus of Encapsulin are highlighted within the box. Only these fusions show high expression of soluble, induced protein (only soluble protein is available for purification). All control samples do not have detectable expression of the given protein construct.

Example 13: Purification of Constructs 124, 125, and 133

Purification of the protein constructs Ap-Encap(K138), Ap-Encap(K71,K138), and Ap-Encap(D60, K138) described in Example 12 is performed in this example.

Protein was purified using Ni-NTA affinity resin that binds to the His-tag on the Encapsulin constructs. Cells from 50 mL of culture were harvested and resuspended in phosphate buffer (50 mM sodium phosphate pH 8.0, 500 mM NaCl) supplemented with 10 mM imidazole and 10 U/mL of DNaseI. Cells were lysed via a French Pressure cell at 14,000 psi and then centrifuged at 12,000 g, 4° C. for 25 min. The supernatant (soluble) was isolated, added to 250 uL of Ni-NTA resin (Qiagen), and equilibrated with the resin at 4° C. for 45 min with rocking. The resin was then packed into a column and the flow through (FT) was collected. The resin was then washed with 5×1 mL fraction of 20 mM imidazole in phosphate buffer. Protein was eluted with 7×200 uL fractions of 250 mM imidazole in phosphate buffer (fractions E1-E7). Fractions E2-E7 were pooled for each sample, concentrated, dialyzed into 25 mM sodium phosphate pH 7.5, 100 mM NaCl, and stored for analysis.

Figure 18:
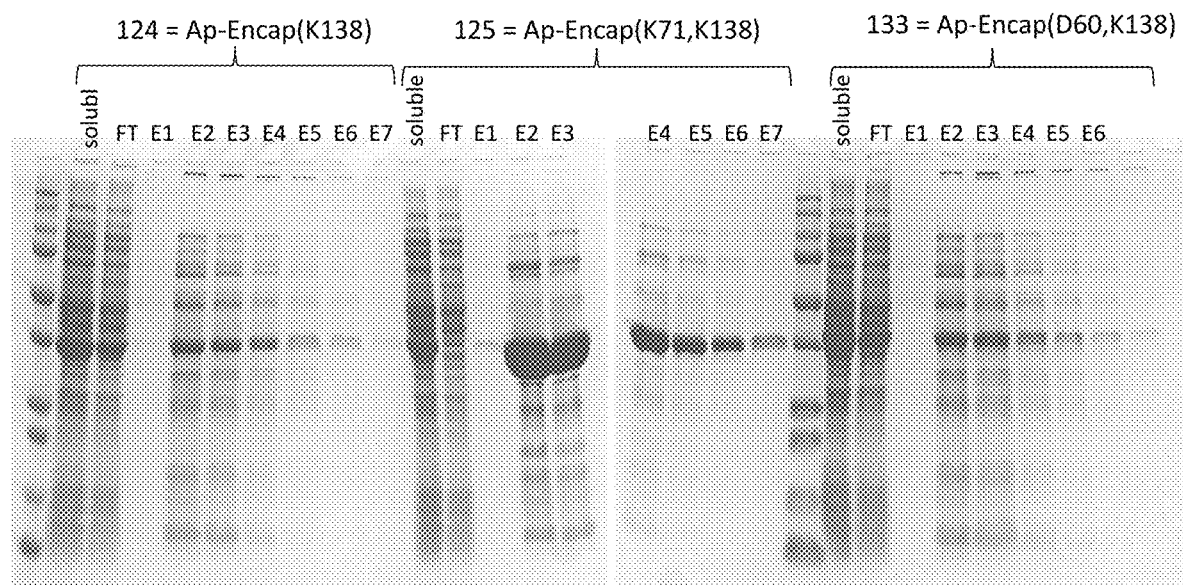
FIG. 18 shows in one embodiment purification of constructs pMCY124, pMCY125 and pMCY133.

For each purification, samples of the soluble fraction before purification, the flow through, and elution fractions E1-E7 were resolved on an any-kDa SDS-PAGE and stained with Coomassie blue (FIG. 18).

Based on the gel, only the Ap-Encap(K71,K138) protein bound to the Ni-NTA resin to high affinity and was thus subsequently purified to high purity (~99% pure). The other constructs did not bind well to the column and thus could not be purified to high purity. These results suggest that the Ap-Encap(K71,K138) protein may have an altered structure compared to the other two proteins, allowing for greater accessibility of the His-tag for purification.

Final yields from the purification are shown in Table 3.

TABLE 3

Yields from the purification for constructs 124, 125 and 133

| Construct | mg/ mL | total uL | total mg | L culture | mg/L culture | Theoret. Ap mg/L culture |
|---|---|---|---|---|---|---|
| 124 = Ap-Encap(K138) | 1.02 | 300 | 0.307 | 0.05 | 6.1 | 0.51 |
| 125 = Ap-Encap(K71, K138) | 5.40 | 280 | 1.51 | 0.05 | 30.3 | 2.5 |
| 133 = Ap-Encap(D60, K138) | 1.38 | 260 | 0.359 | 0.05 | 7.2 | 0.58 |

In Table 3, the columns from left to right show: construct name, concentration of the purified protein in mg/mL, total volume in uL, total amount in mg, total volume of culture that the protein originated from in L, yield of protein in mg of protein per L of original culture, and theoretical yield of the Ap peptide after protease cleavage assuming 100% proteolysis in mg of Ap peptide per L of original culture. The Ap-Encap(K71,K138) protein clearly has the highest yield, nearly 5 times higher than the other proteins.

Example 14: TEV Protease Cleavage of the Purified AP-Encapsulin Fusions

In this example, experiments were conducted to show TEV protease cleavage of the purified Ap-Encapsulin fusions.

60 ug of purified material was digested with 30 U of TEV protease enzyme in a 80 uL reaction with 1 mM DTT and 1×TEV protease buffer from Promega. Aliquots of digested material were removed after 1 h, 3 h, and 20 h of digestion at 30° C. A sample without TEV protease was also prepared as the 0 h sample.

Figure 19A:
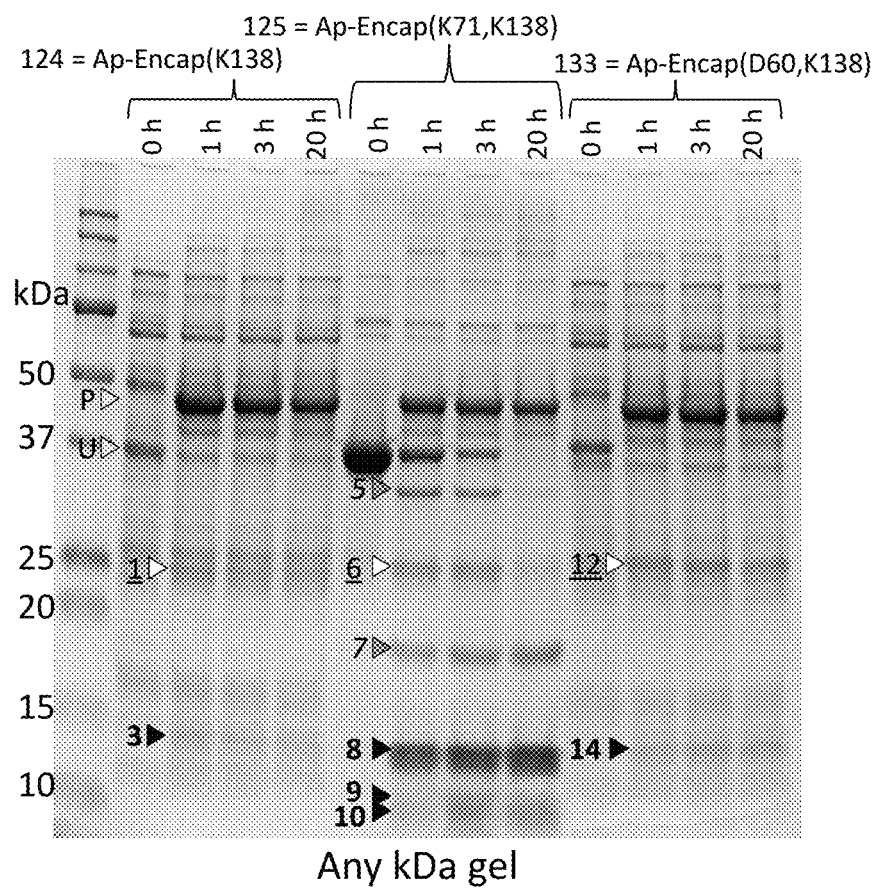
FIGS. 19A-C show in one embodiment TEV protease cleavage of the purified Ap-encapsulin fusions. All samples were analyzed by SDS-PAGE using both an any-kDa gel to analyze fragment >15 kDa (FIG. 19A) and a 16.5% Tris-Tricine gel to analyze fragments <15 kDa (FIG. 19B). Samples were also analyzed by Western blot using an anti-TEV site antibody (FIG. 19C). Arrows on the gels above show digested fragments.
Figure 19B:
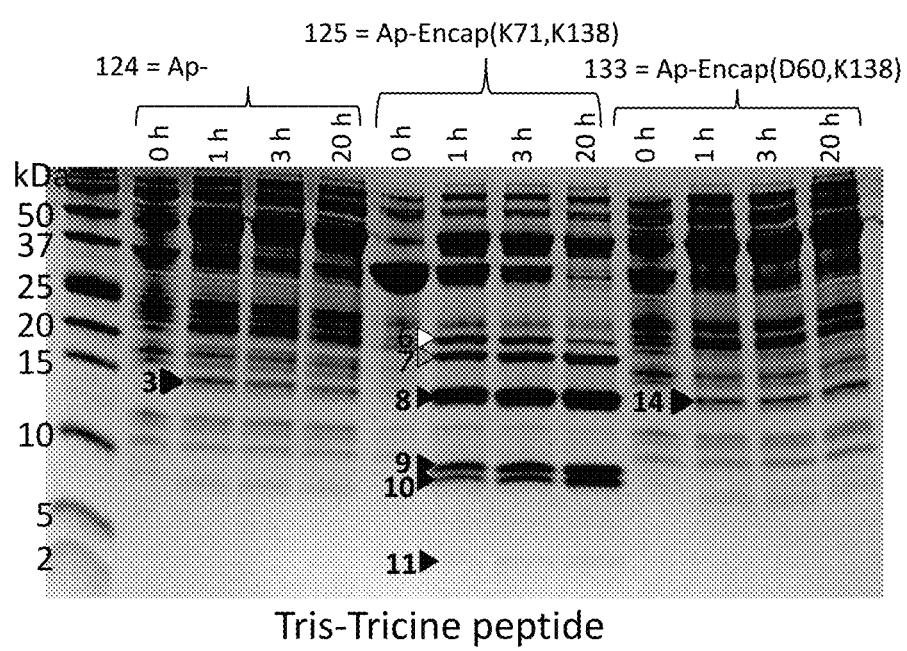
Figure 19C:
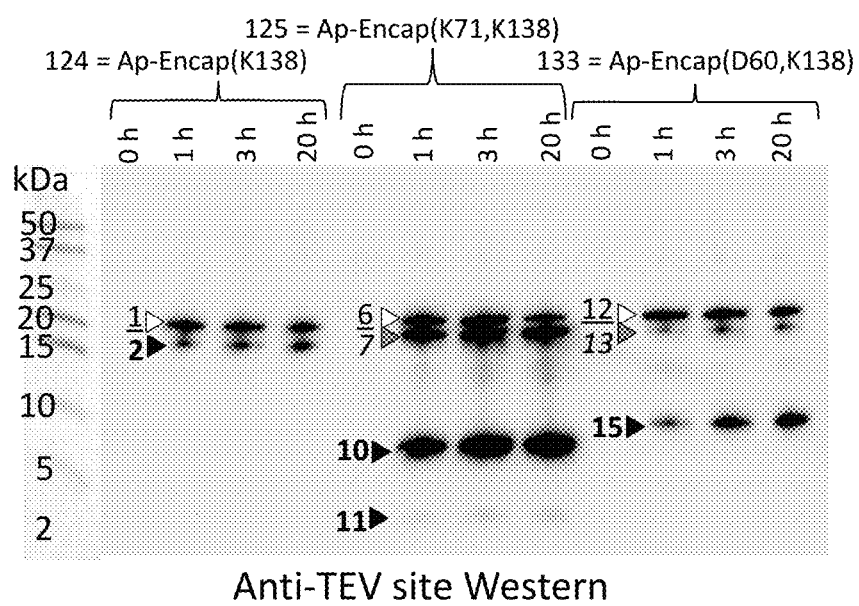

All samples were analyzed by SDS-PAGE using both an any-kDa gel to analyze fragment >15 kDa (FIG. 19A) and a 16.5% Tris-Tricine gel to analyze fragments <15 kDa (FIG. 19B). Samples were also analyzed by Western blot using an anti-TEV site antibody (FIG. 19C). Arrows on the gels above show digested fragments.

P (light gray arrow) denotes TEV protease. U (light gray arrow) denotes undigested material. Underlined numbers (white arrows) denote partially digested material containing Ap peptide. Italicized numbers (dark gray arrows) denote partially digested material NOT containing Ap peptide. Bold numbers (black arrows) denote fully digested material. Table 4 below shows the predicted protein fragments expected from digestion. The numbers are the expected fragment sizes in kDa. The numbers in parentheses correspond to the numbers shown on the gels and Western blot.

TABLE 4

Predicted protein fragments from digestion

| Degree of digestion | Construct | 124 | 125 | 133 |
|---|---|---|---|---|
| Undigested | Ap-Encap1-Encap2-Encap3 | 36.2 | 37.2 | 37.3 |
| partial digestion | Encap1-Encap2-Encap3 | | 34.2 (*5*) | 34.3 |
| | Ap-Encap1-Encap2-TEV | | 21.4 (6) | 21.5 (12) |
| | Encap2-Encap3 | | 24.7 | 26.1 |
| | Encap1-Encap2-TEV | 33.2 | 18.4 (*7*) | 18.5 (*13*) |
| | Ap-Encap1-TEV or Ap-Encap2-TEV | 20.4 (1) | 12.5 | 11.2 |
| full digestion | Encap3 | 15.8 (3) | 15.8 (8) | 15.8 (14) |
| | Encap2-TEV | 17.4 (2) | 8.9 (10) | 10.3 (15) |
| | Encap1-TEV | | 9.5 (9) | 8.2 |
| | Ap-TEV | 3.0 | 3.0 (11) | 3.0 |

The data of Table 4 show that construct 125 (Ap-Encap (K71, K138)) is digested by TEV protease to near completion, which is most clearly observed by the disappearance of undigested material (U) and band (6) denoted by the white arrow and the appearance of the Ap peptide band (11) after 20 h digestion. The other constructs do not have clear disappearance of undigested bands denoted by the white arrows based on Western blot, suggesting that they are not well digested by TEV protease. It is also noted that the amount of construct 125 is much higher than the other 2 constructs. Therefore, in the Western blot, the proportion of the band denoted by the white arrow relative to the original is much lower than the other constructs, suggesting nearly complete digestion.

Example 15: Expression of Tandem Ap Peptides Fused to Encapsulin in C43 (DE3) E. coli Cells This example shows expression of tandem Ap peptides fused to the Encapsulin construct with insertions after K71 and K138.

Figure 20A:
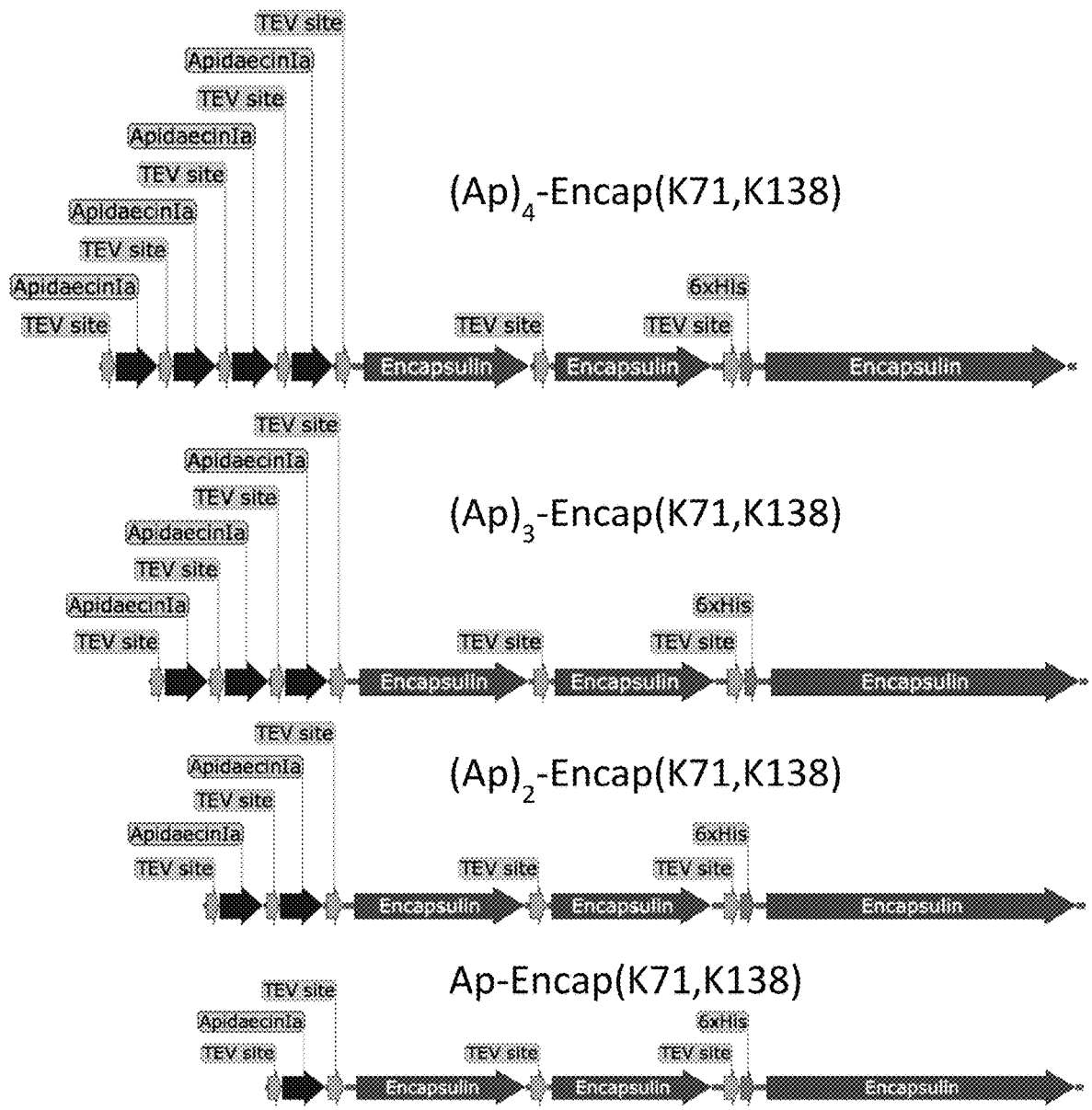
FIG. 20A illustrates gene cassettes expressing up to 4 Ap peptides fused to a single Encapsulin construct.

Gene cassettes expressing up to 4 Ap peptides fused to a single Encapsulin construct were made (FIG. 20A). TEV protease cleavage sites were placed between each Ap peptide as well as prior to the first Ap peptide and prior to the Encapsulin construct in order to ensure the same Ap peptide sequence is obtained upon full protease digestion. The sizes of the tandem Ap peptides that were fused to the Encapsulin construct are as follows: 1×Ap=32 amino acids; 2×Ap=57 amino acids; 3×Ap=82 amino acids; 4×Ap=107 amino acids. The gene cassettes were placed under the control of a T7 promoter in the commercially available pET24a. The DNA plasmids were transformed in C43(DE3) E. coli cells and expressed under the same conditions as described above. Cells were lysed and soluble fractions were also obtained in the same manner as described above.

Figure 20B:
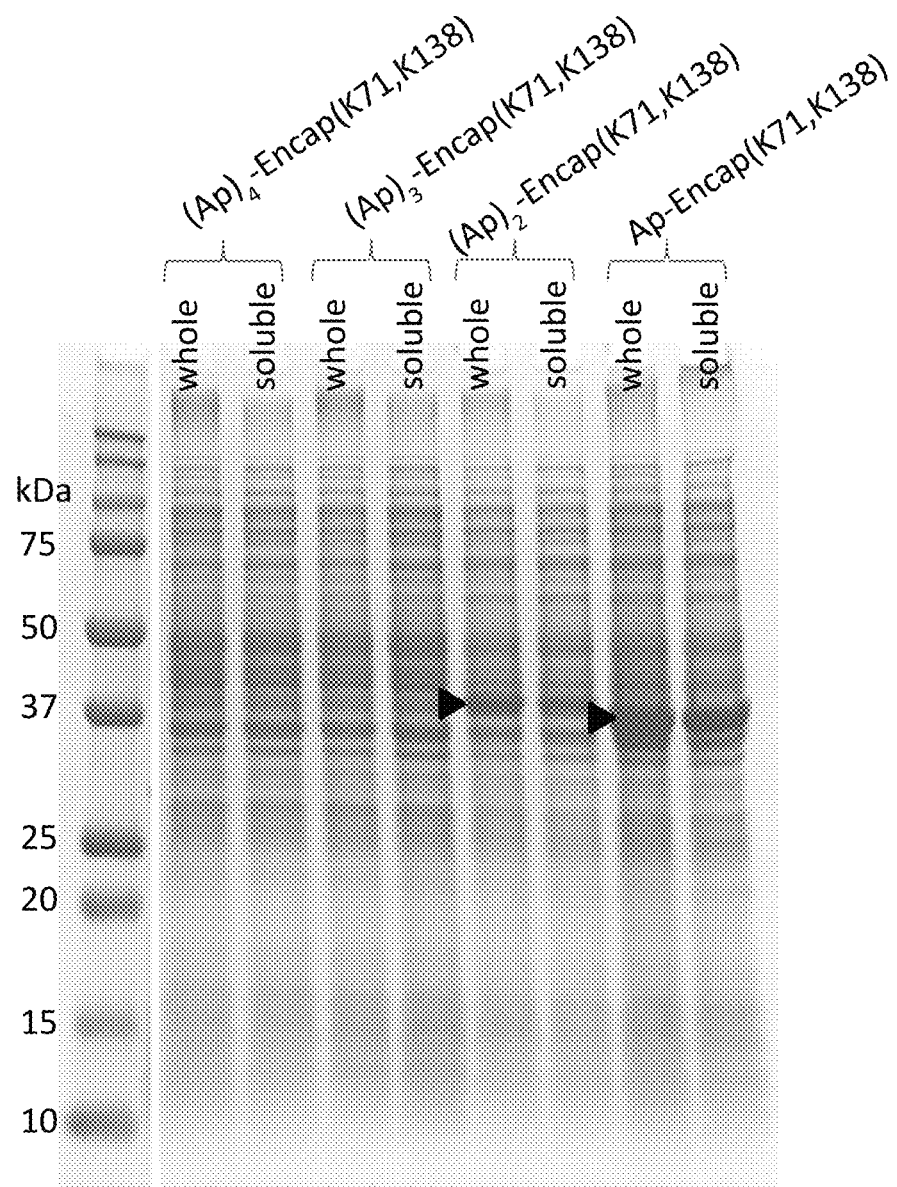
FIG. 20B shows the expression of the gene cassettes in FIG. 19A with the samples resolved on an any-kDa SDS-PAGE gel and stained with Coomassie blue. Red arrows denote predicted location of the expressed protein.

All "whole" and "soluble" samples were resolved on an any-kDa SDS-PAGE gel and stained with Coomassie blue (FIG. 20B). Arrows denote predicted location of the expressed protein. Only 1×Ap and 2×Ap peptide fused to Encapsulin could be expressed. The 3×Ap and 4×Ap peptide-Encapsulin fusions were not detectable by SDS-PAGE. These data suggest that up to 57-amino acid peptides could be fused to Encapsulin in order to achieve expression. An 82-amino acid peptide fused to Encapsulin could not be expressed, suggesting this fusion and fusions with larger peptide attachments can not properly form Encapsulin microcompartments in order to achieve expression.

Example 16: Expression of Tandem HBCM-2 (HB) Peptides Fused to Encapsulin in C43(DE3) E. coli Cells This example describes the expression of tandem HBCM-2 (HB) peptides fused to the Encapsulin construct with insertions after K71 and K138. The HBCM-2 peptide has a sequence of SEQ ID NO: 9 from Table 1.

Figure 21A:
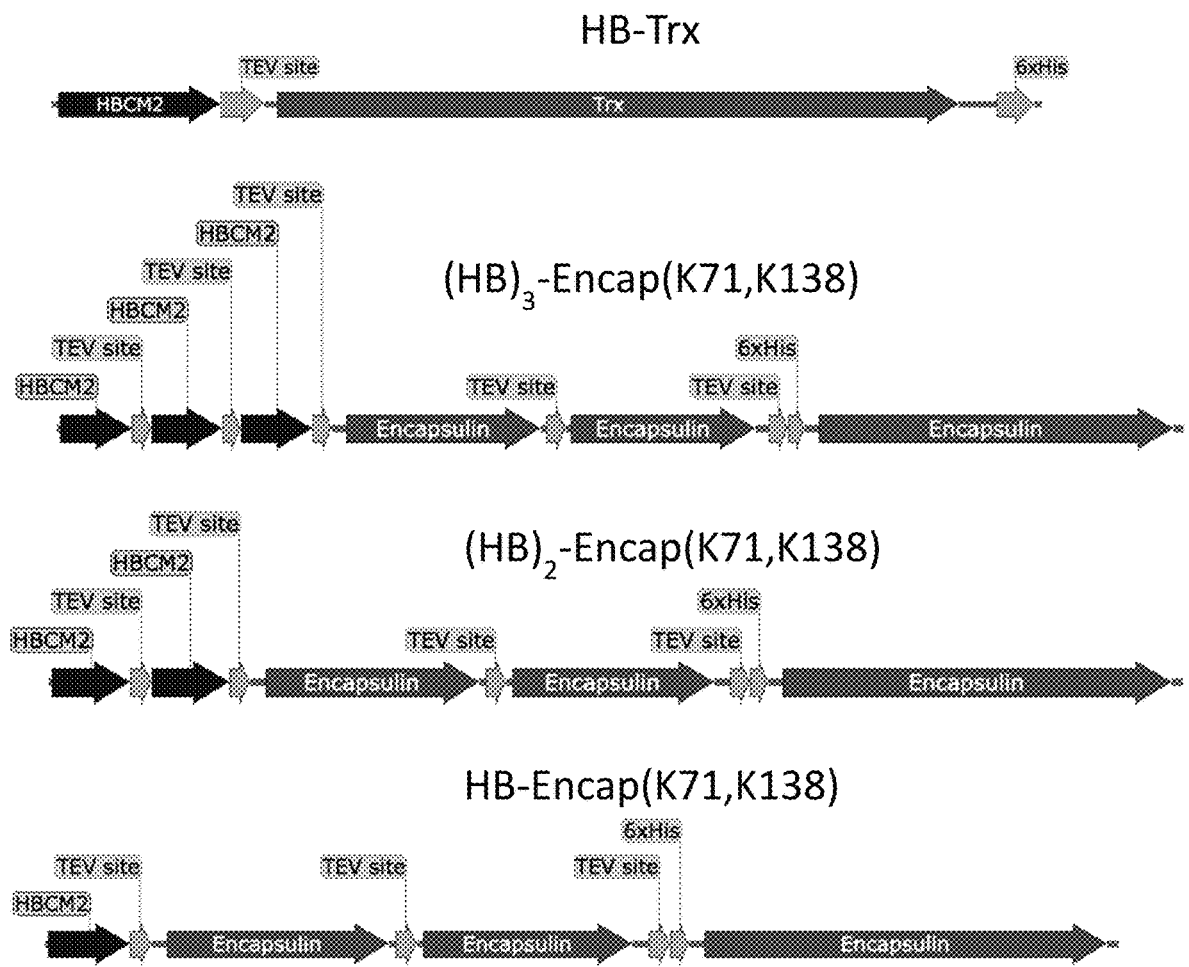
FIG. 21A illustrates gene cassettes expressing up to 3 HB peptides fused to a single Encapsulin construct as well as a control of HB fused to thioredoxin (Trx).

Gene cassettes expressing up to 3 HB peptides fused to a single Encapsulin construct were made as well as a control of HB fused to thioredoxin (Trx) (FIG. 21A). The sizes of the tandem HB peptides that were fused to the Encapsulin construct are as follows: 1×HB=33 amino acids; 2×HB=66 amino acids; 3×HB=99 amino acids. The gene cassettes were placed under the control of a T7 promoter in the commercially available pET24a. The DNA plasmids were transformed in C43(DE3) E. coli cells and expressed under the same conditions as described above. Cells were lysed and soluble fractions were also obtained in the same manner as described above.

Figure 21B:
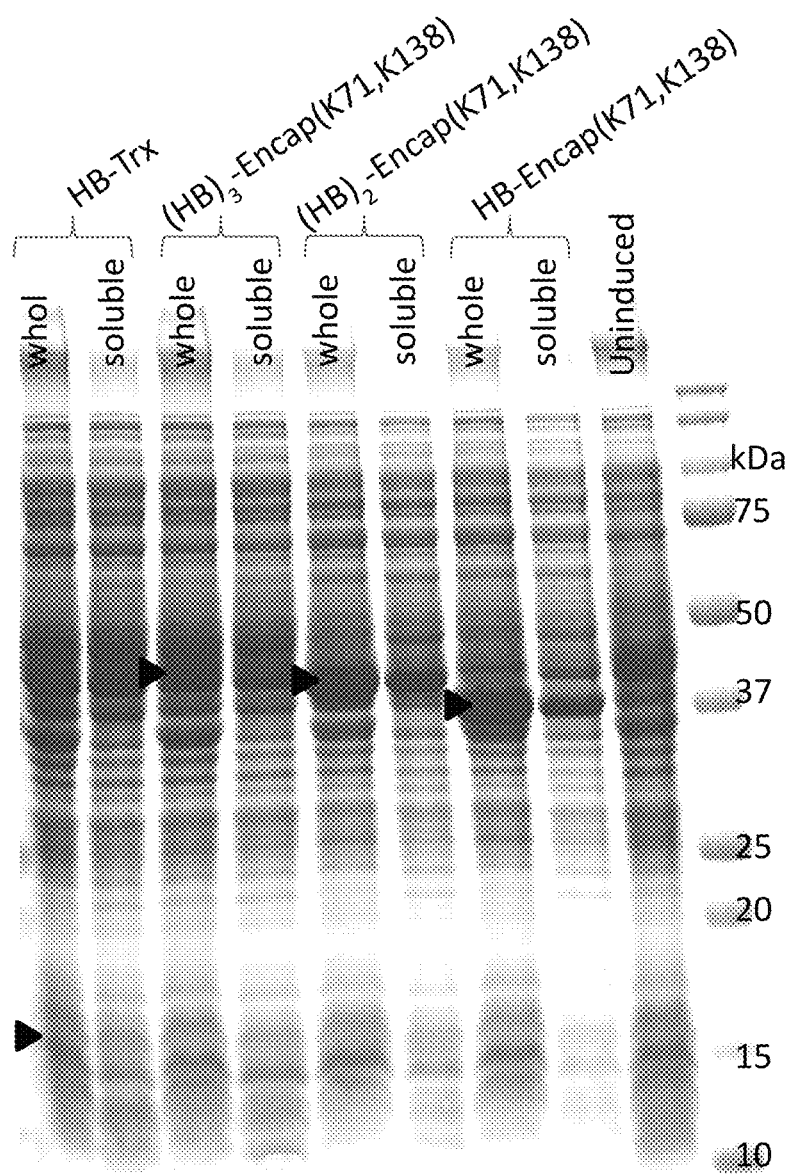
FIG. 21B shows the expression of the gene cassettes in FIG. 21A with the samples resolved on an any-kDa SDS-PAGE gel and stained with Coomassie blue. Red arrows denote predicted location of the expressed protein.

All "whole" and "soluble" samples were resolved on an any-kDa SDS-PAGE gel and stained with Coomassie blue (FIG. 21B). Arrows denote predicted location of the expressed protein. Only 1×HB and 2×HB peptide fused to Encapsulin could be expressed. The 3×HB peptide-Encapsulin and HB-Trx fusions were not detectable by SDS-PAGE. These data suggest that up to 66-amino acid peptides could be fused to Encapsulin in order to achieve expression. A 99-amino acid peptide fused to Encapsulin could not be expressed, suggesting this fusion and fusions with larger peptide attachments cannot properly form Encapsulin microcompartments in order to achieve expression.

These data confirm the observation at HB can only be expressed when fused to Encapsulin, but not to Trx, demonstrating that only Encapsulin has a toxicity/proteolysis shielding effect that allows HB to be expressed.

Example 17: Design of HB-Enc Constructs with TEV Protease Cleavage Site Insertions HB-Enc constructs with TEV protease cleavage site insertions were designed based on the following approach.

To express HBCM2 within the lumen of an encapsulin cage, the peptide was directly fused to the N-terminus of the Enc monomer, which is luminal-facing based on the X-ray crystal structure of the encapsulin cage [56]. This strategy was chosen to maximize incorporation of expressed peptide into the Enc cage. Targeting sequences that associate with the lumen of the Enc cage have been identified for loading interior protein [56, 57]. However, quantitative loading using targeting tags in this and other protein compartment systems is often incomplete in heterologous systems and remains a significant challenge [58] [57, 59-61] Direct fusion is expected to ensure each peptide is associated with Enc monomer to maximize loading into the Enc cage.

Figure 22A:
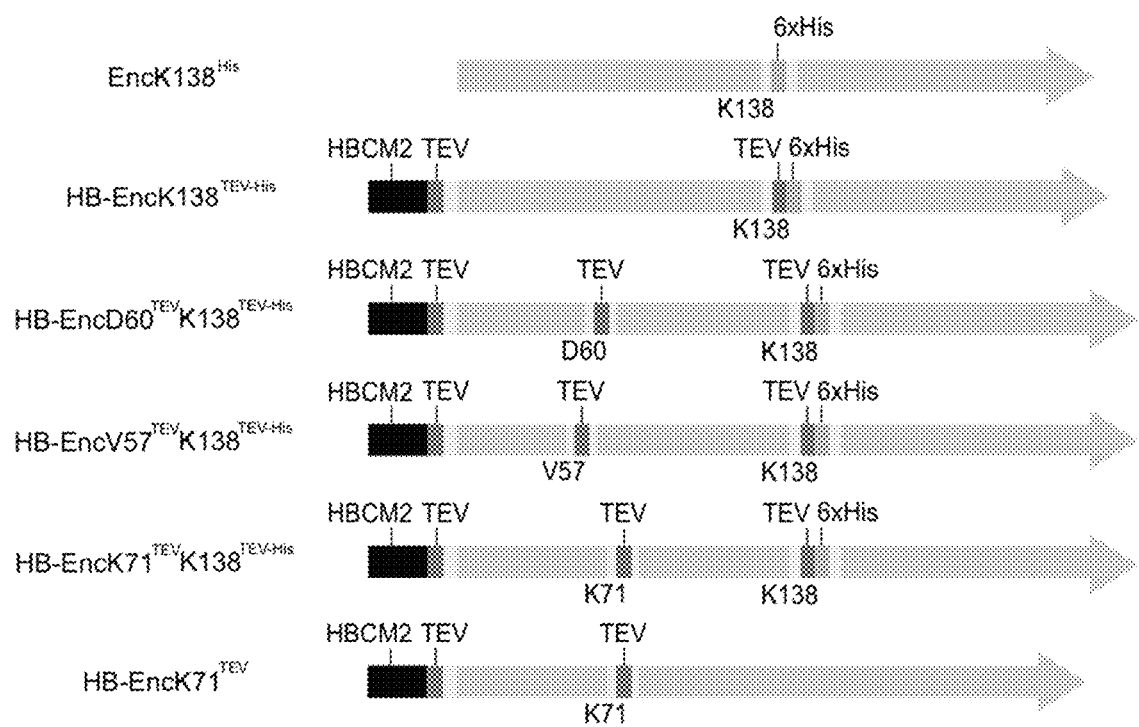
FIG. 22A shows a schematic illustration of gene constructs for HBCM2 fusions with engineered Enc. TEV denotes TEV protease recognition sites. 6×His denotes a hexa-histidine tag for purification. Linkers shown in light gray are described in FIG. 22B.

To isolate HBCM2 following purification of the Enc cage, TEV protease recognition sites were placed between the peptide and the Enc monomer as well as at several surface accessible locations to encourage cage disassembly (FIGS. 22A-B). Kang and coworkers [55] previously demonstrated that a $His_6$-tag could be placed after exterior residue K138 (EncK138$^{His}$) and was sufficiently surface exposed for purification via Ni-NTA chromatography. Thus, a construct, HB-EncK138$^{TEV\text{-}His}$, containing the following features was initially designed: 1) HBCM2, a TEV site, followed by a $G_4$T-linker fused to the N-terminus of Enc; and 2) a TEV site followed by a $His_6$-tag inserted after residue K138 with Gs-linkers flanking both ends of the insert.

Additional sites within the Enc monomer were also identified, which would be surface accessible and amenable to insertion with minimal disruption to the cage structure by examining the conservation of each residue and its flexibility (RMSF^2) based on a reported crystal structure PDB: 3DKT. Residues within the loop of the E-domain of Enc were found to be surface accessible with the highest degree of flexibility and relatively low conservation. Residues D60 and V57 were chosen for insertion because they are at the middle and start of the loop, respectively. Additionally, K71 was also chosen for insertion because its location at the end of the E-domain, immediately preceding the P-domain was thought to hold promise for cage disassembly; the residue is exposed to the exterior and has minimal conservation.

Thus, HB-Enc fusions were constructed with a TEV site flanked with $G_2$-linkers following residues D60, V57 or K71, in addition to the TEV-His insertion following residue K138. These constructs are referred to as HB-EncD60$^{TEV}$K138$^{TEV\text{-}His}$, HB EncV57$^{TEV}$K138$^{TEV\text{-}His}$, and HB-EncK71$^{TEV}$K138$^{TEV\text{-}His}$, respectively (FIG. 22A).

Example 18: Expression of HB Peptide Fused to Different Engineered Encapsulin (Enc) Constructs Compared to HB Peptide Fused to Other Common Carrier Proteins in C43(DE3) E. coli The constructs comprising HB peptide designed as indicated in Example 17 were tested in comparison with constructs where HB peptide is fused to other common carrier proteins. In particular, expression of N-terminal HB-fusions to the following other common carrier proteins with C-terminal His-tags was also tested: Small ubiquitin-like modifier (SUMO), thioredoxin (Trx), glutathione S-transferase (GST), and maltose-binding protein (MBP).

The amino acid sequences of the tested constructs are shown in FIG. 22B.

In particular, in order to perform the testing, all DNA plasmids were transformed and expressed in C43(DE3) cells as described in Example 12, except that cells were grown in 25 mL of LB medium in 150-mL flasks. IPTG induction was conducted overnight for 17 h at 18° C. to enhance soluble protein expression. Cells were harvested and lysed also as described in Example 12.

Figure 23A:
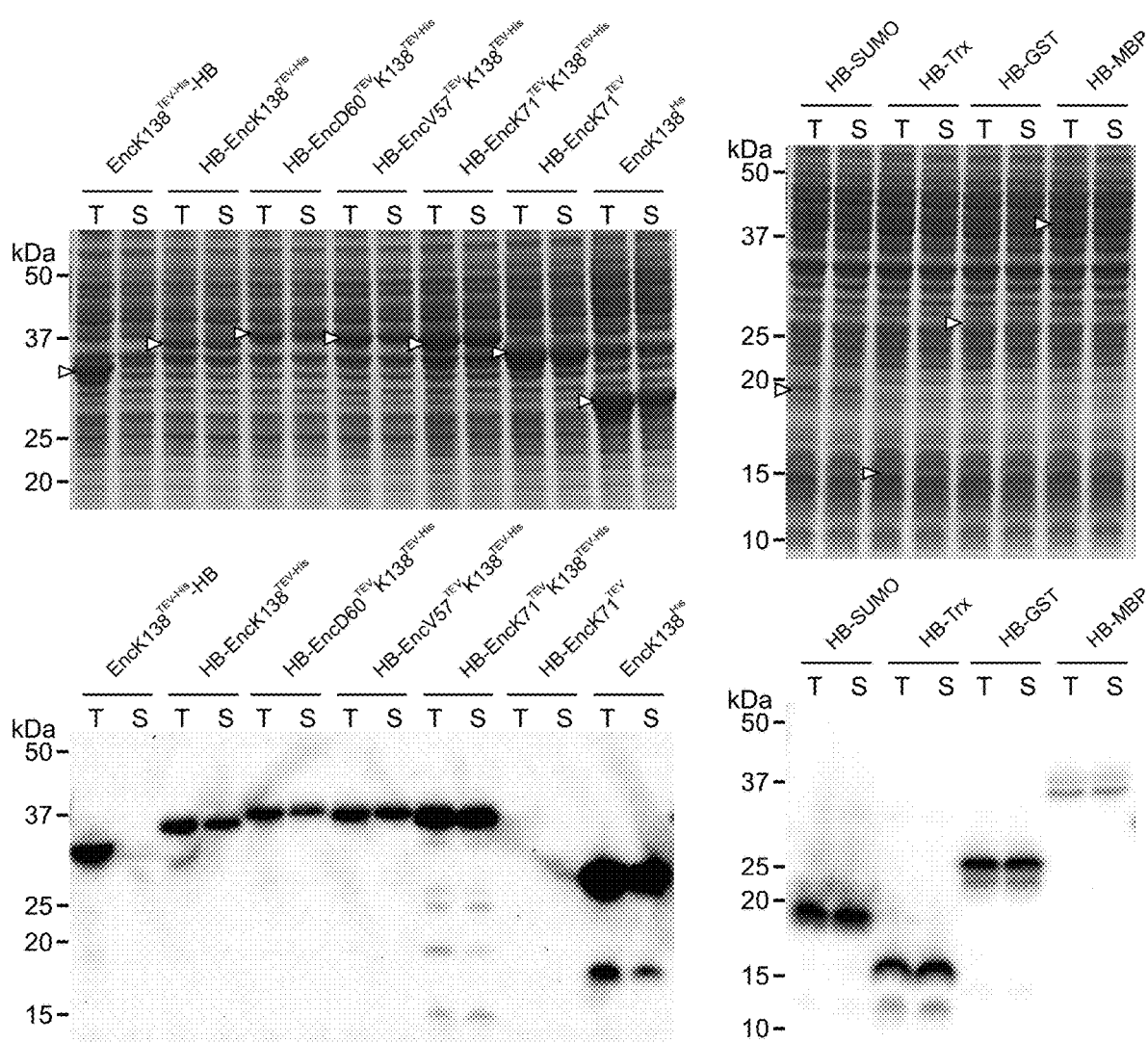
FIG. 23A shows images illustrating the results of experiments to detect the expression of the HB fusion constructs in FIGS. 22A-B in C43(DE3) *E. coli* from a T7 IPTG inducible promoter. Samples were resolved on an any-kDa SDS-PAGE gel and stained with Commassie blue (top) or blotted to a PVDF membrane and probed with mouse anti-His$_6$ primary antibody and rabbit anti-mouse HRP conjugated secondary antibody (bottom). T denotes the total cell lysate, while S denotes the soluble fraction. Arrows denote expected size of the expressed protein.

All N-terminal HB-Enc constructs showed over-expression of soluble HB-Enc protein by SDS-PAGE and anti-His-tag Western blot (FIG. 23A). In contrast, a C-terminal Enc-HB fusion was not expressed as soluble protein. The HB-EncK71$^{TEV}$K138$^{TEV\text{-}His}$ construct showed the most robust expression with the highest cell density ($OD_{600}$ of 5.8) (FIG. 23B), compared to the other double TEV site containing constructs ($OD_{600}$ of 3.7-4.0). Removal of the K138$^{TEV\text{-}His}$ site from this construct to produce HB-EncK71$^{TEV}$ maintained this higher level of expression and cell density ($OD_{600}$ of 5.6), which was also similar to the EncK138$^{His}$ control.

Figure 23B:
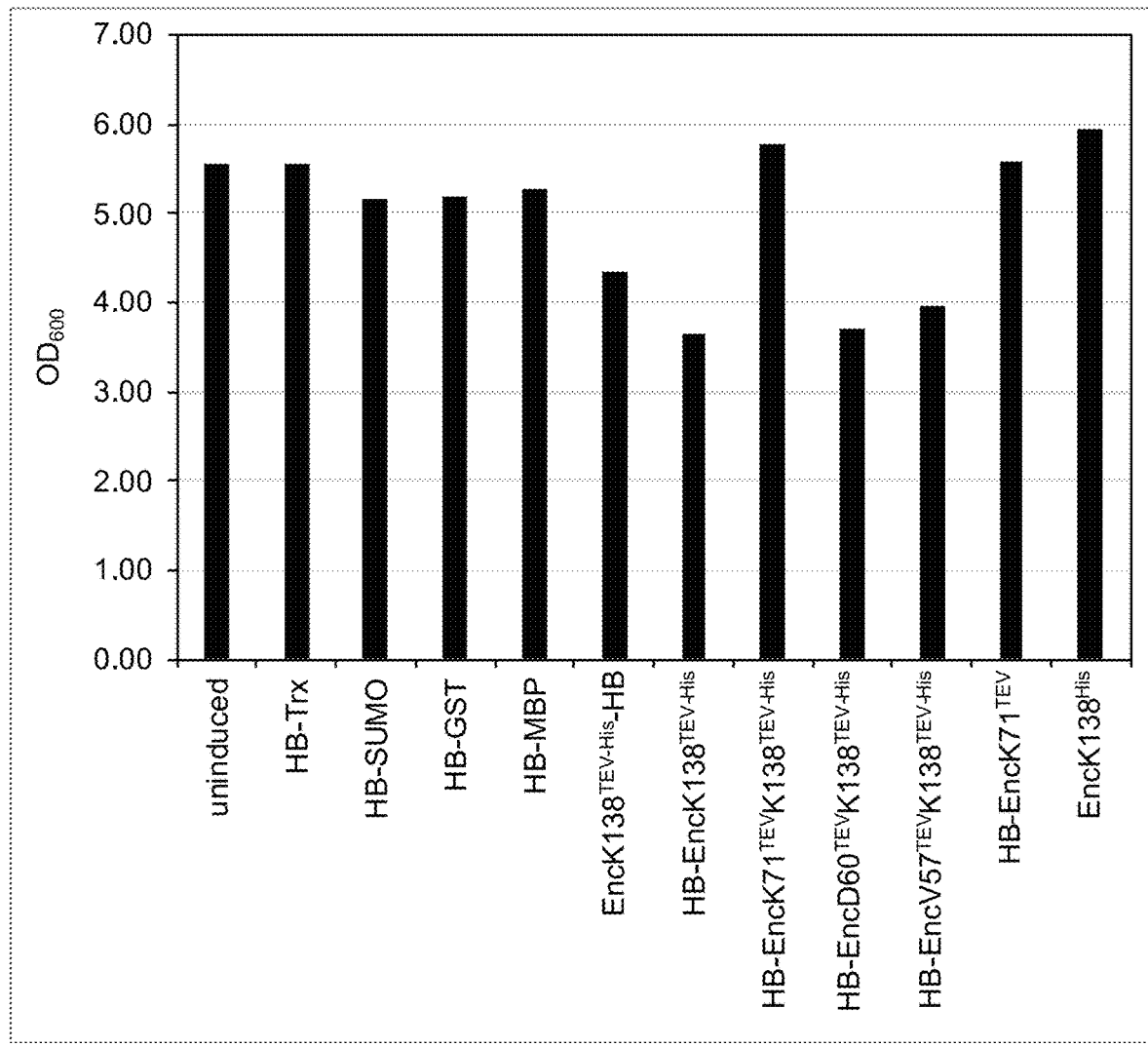
FIG. 23B shows a chart illustrating the final OD$_{600}$ of the C43(DE3) *E. coli* culture after overnight induction at 18° C.

Expression of N-terminal HB-fusions to the following other common carrier proteins with C-terminal His-tags was also tested: Small ubiquitin-like modifier (SUMO), thioredoxin (Trx), glutathione S-transferase (GST), and maltose-binding protein (MBP) (FIG. 23B). These constructs had minimal expression in C43(DE3) cells. Only HB-SUMO could be detected by SDS-PAGE, while all other constructs were only detected by anti-His-tag Western blot.

Expression of HB-Trx, HB-GST, and HB-MBP were found to produce truncated products, demonstrating that they are sensitive to proteolysis in cell lysate. Given that the truncated products can be detected by anti-His-tag and are nearly full length (<5 kDa difference) indicates that proteolysis occurred on the N-terminus of the protein close to or within the HBCM2 sequence. Expression of HB-EncK71$^{TEV}$K138$^{TEV\text{-}His}$ also showed some truncated products by Western blot, but degradation was minimal compared to HB-Trx, HB-GST, and HB-MBP. All other HB-Enc fusions did not show truncated products. HB-EncK71$^{TEV}$ cannot be detected by anti-His-tag given its lack of a His-tag.

The above results indicate that HB-Enc fusions exhibit robust expression in *E. coli* C43(DE3) cells compared to other HB-carrier protein fusions In particular, the expression data herein described reveals that HB peptide requires fusion to Enc for robust expression in C43(DE3) cells

Example 19: Purification and TEV Protease Digestion of HB-Enc Fusions

Constructs HB-EncK138$^{TEV\text{-}His}$, HB-EncD60$^{TEV}$K138$^{TEV\text{-}His}$, HB-EncV57$^{TEV}$K138$^{TEV\text{-}His}$ were purified as follows. Cells from 50 mL of culture were harvested and resuspended in phosphate buffer (50 mM sodium phosphate pH 8.0, 500 mM NaCl) and 10 U/mL of DNaseI. Cells were lysed via a French Pressure cell at 14,000 psi and then centrifuged at 12,000 g, 4° C. for 25 min. The supernatant (soluble) was isolated and then heated at 85° C. for 15 min. The material was then centrifuged at 12,000 g, 4° C. for 10 min and the soluble fraction was collected. Constructs were further purified by addition of ammonium sulfate to 25% (w/v) followed by centrifugation at 12,000 g, 4° C. for 25 min to collect the insoluble pellet. Purified material was re-suspended in 25 mM sodium phosphate pH 7.5, 100 mM NaCl, and stored for analysis.

Construct HB-EncK71$^{TEV}$ was purified as follows. Cells from 50 mL of culture were harvested and resuspended in 60% B-PER II in phosphate buffer (50 mM sodium phosphate pH 8.0, 500 mM NaCl), supplemented with 0.1 mg/mL lysozyme and 10 U/mL DNase. Cell lysate was incubated at 4° C. for 1 h to lyse the cells. The supernatant (soluble) was isolated and then heated at 70° C. for 15 min. The material was then centrifuged at 12,000 g, 4° C. for 10 min and the soluble fraction was collected. The soluble fraction was dialyzed overnight at 4° C. into phosphate buffer to remove the B-PER. The material was further purified by addition of ammonium sulfate to 50% (w/v) followed by centrifugation at 12,000 g, 4° C. for 25 min to collect the insoluble pellet. Purified material was re-suspended in 25 mM sodium phosphate pH 7.5, 100 mM NaCl, and stored for analysis.

Construct HB-EncK71$^{TEV}$K138$^{TEV\text{-}His}$ was partially purified Ni-NTA chromatography. Cells from 50 mL of culture were harvested and resuspended in 60% B-PER II in phosphate buffer (25 mM sodium phosphate pH 7.5, 100 mM NaCl), supplemented with 0.1 mg/mL lysozyme and 10 U/mL DNase. Cell lysate was incubated at 4° C. for 1 h to lyse the cells. The supernatant (soluble) was isolated, added to 250 uL of Ni-NTA resin (Qiagen), and equilibrated with the resin at 4° C. for 45 min with rocking. The resin was then packed into a column and the flow through (FT) was collected. The resin was then washed with 5×1 mL fraction of 5 mM imidazole in phosphate buffer. Protein was eluted with 7×200 uL fractions of 250 mM imidazole in phosphate buffer (fractions E1-E7). Fractions E2-E7 were pooled for each sample, concentrated, dialyzed into 25 mM sodium phosphate pH 7.5, 100 mM NaCl, and stored for analysis.

B-PER II was found to at least partially prevent proteolysis of HB-EncK71$^{TEV}$ and HB-EncK71$^{TEV}$K138$^{TEV\text{-}His}$, whereas many different protease inhibitors including pepstatin, EDTA, PMSF and Roche protease inhibitor cocktail were not effective.

Figure 24:
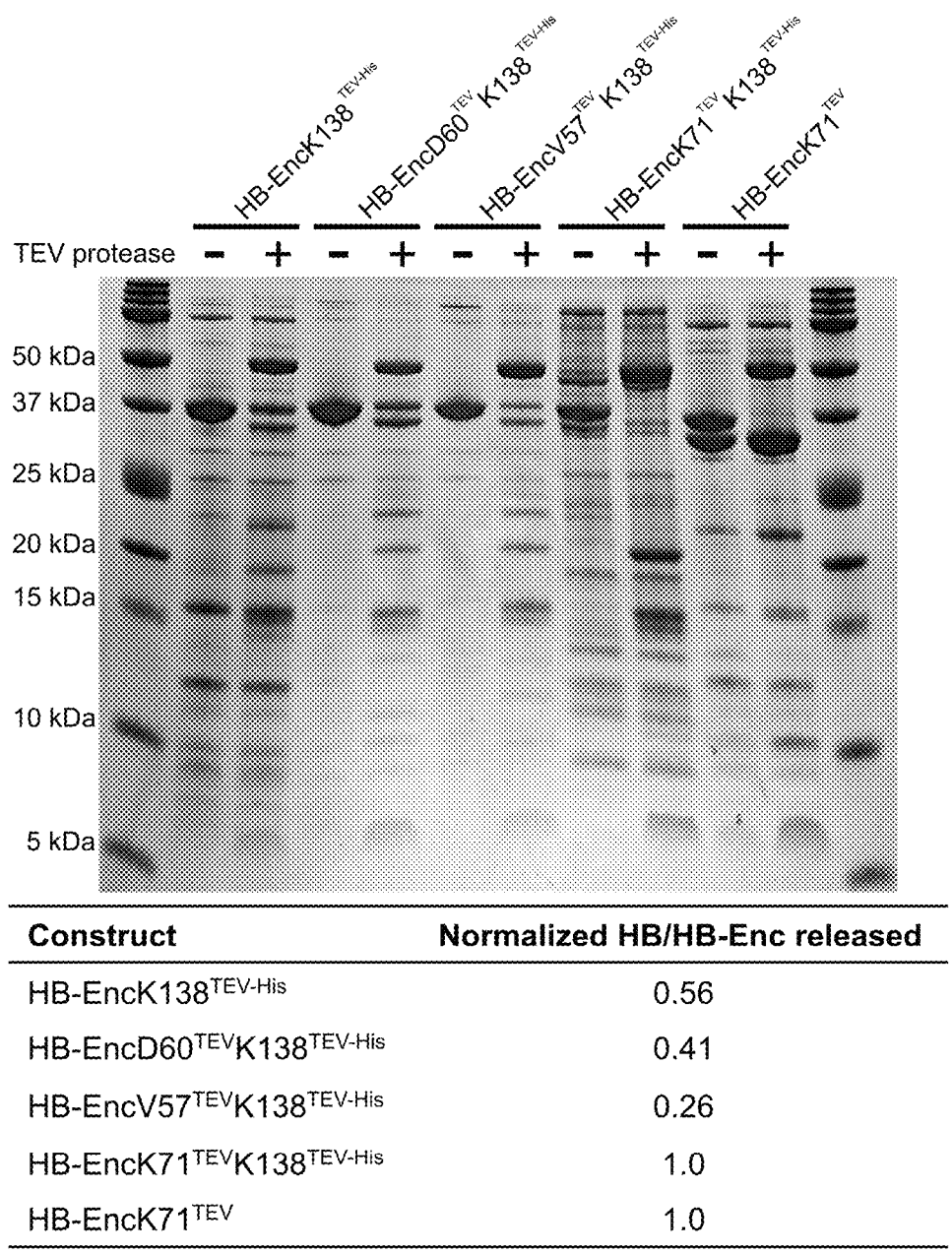
FIG. 24 shows an image of a gel including purified HB-Enc fusion proteins with or without TEV protease digestion at 4° C. overnight. Samples were resolved on a 16.5% Tris-Tricine gel and stained with Commassie blue. In the bottom portion a table shows the normalized ratio of HB released/HB-Enc fusion based on densitometry, assuming the HB/HB-Enc ratio for HB-EncK71$^{TEV}$K138$^{TEV-His}$ is 1.

All purified constructs were digested by addition of exogenous TEV protease, followed by overnight incubation at 4° C. Products were resolved on a 16.5% Tris-Tricine gel (Bio-Rad). All constructs were found to at least partially release HBCM2 peptide (FIG. 24). HB-EncK71$^{TEV}$K138$^{TEV\text{-}His}$ and HB-EncK71$^{TEV}$ released the most peptide with apparent complete digestion based on the sizes of the fragments observed after digestion. In contrast based on densitometry analysis, HB-EncK138$^{TEV\text{-}His}$ EncD60$^{TEV}$K138$^{TEV\text{-}His}$, and HB-EncV57$^{TEV}$K138$^{TEV\text{-}His}$ released fewer peptide per fusion protein. These constructs had a relative HB/HB-Enc ratio of 0.26 to 0.56, assuming that the HB/HB-EncK71$^{TEV}$K138$^{TEV\text{-}His}$ is 1.

Figure 25:
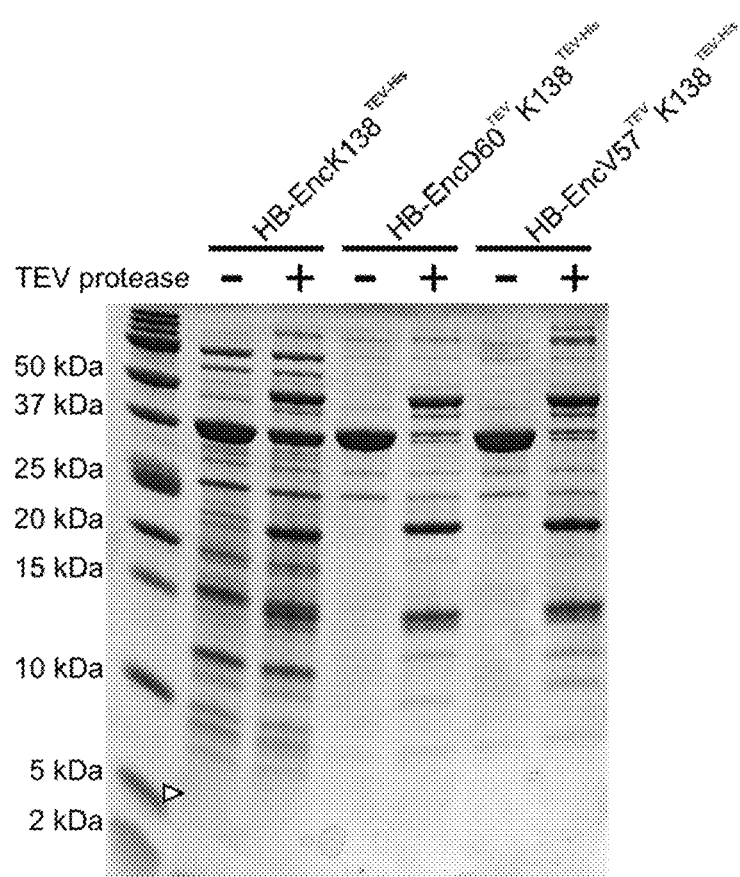
FIG. 25 shows an image of a gel including purified HB-Enc fusion proteins with a GT linker replacing the flexible G$_4$T linker between the HB peptide and the N-terminus of Enc. Fusions were digested with or without TEV protease at 4° C. overnight and samples were resolved on a 16.5% Tris-Tricine gel and stained with Commassie blue.

HB-EncK138$^{TEV\text{-}His}$, HB-EncD60$^{TEV}$K138$^{TEV\text{-}His}$, HB-EncV57$^{TEV}$K138$^{TEV\text{-}His}$ constructs with a GT linker between the TEV site and the N-terminus of Enc, instead of the flexible $G_4T$ linker, were also purified and tested for digestion for TEV protease digestion. However, the HB-EncK138$^{TEV\text{-}His}$, HB-EncD60$^{TEV}$K138$^{TEV\text{-}His}$, and HB-EncV57$^{TEV}$K138$^{TEV\text{-}His}$ with the shorter GT linker did not result in detectable release of HB peptide by SDS-PAGE (FIG. 25). These results suggest that the $G_4T$ linker is crucial to release of peptide for these constructs.

Figure 33A:
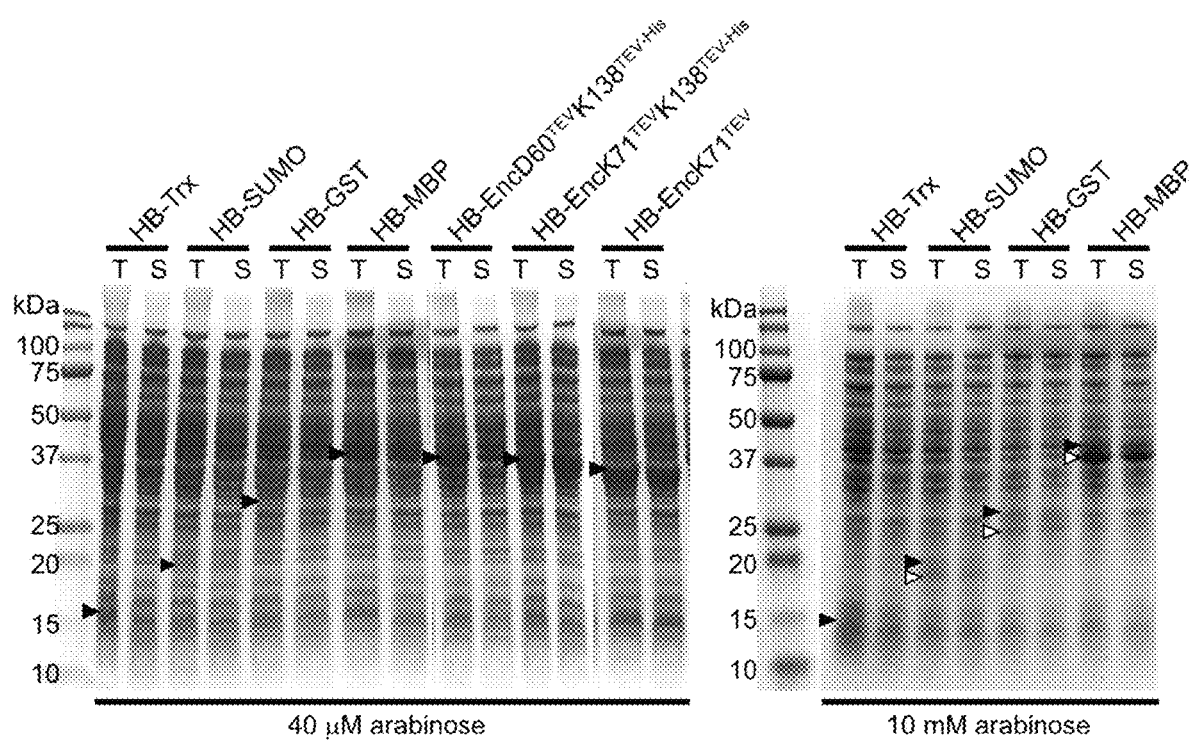
FIG. 33A shows expression of the HB fusion constructs in FIGS. 22A-B in TOP10 *E. coli* from a βBAD arabinose inducible promoter. Cells were induced with either 40 µM or 10 mM arabinose. Samples were resolved on an any-kDa SDS-PAGE gel and stained with Commassie blue. T denotes the total cell lysate, while S denotes the soluble fraction.
Figure 33B:
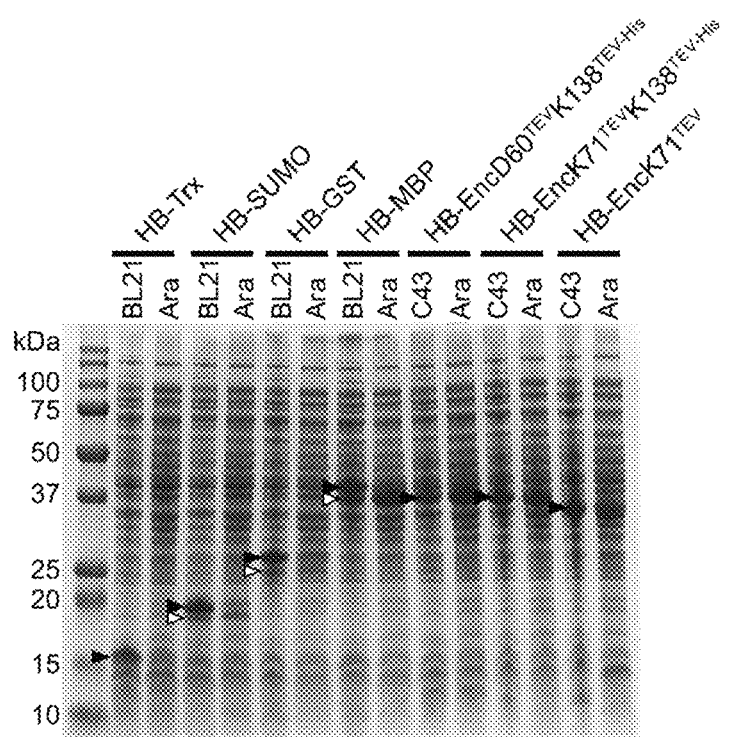
FIG. 33B shows comparison of full-length HB fusions expressed in either C43(DE3) cells (C43) or BL21(DE3) cells (BL21) versus HB fusions expressed in TOP10 cells from a βBAD promoter (Ara). In both FIGS. 33A and B, black arrows denote expected size of the expressed protein, while white arrows denote truncation products.

Example 20: Insertion of TEV Protease Site at Position K71 Disrupts Cage Formation which Enables Highly Efficient Release of Peptide by TEV Protease K71$^{TEV}$ containing constructs as well as its susceptibility to proteolysis, all of the HB-Enc constructs were analyzed by size-exclusion chromatography (SEC) and native PAGE to test for cage formation (FIGS. 33A and 33B). SEC analysis revealed that HB-EncK138$^{TEV\text{-}His}$, HB-EncD60$^{TEV}$K138$^{TEV\text{-}His}$, HB-EncV57$^{TEV}$K138$^{TEV\text{-}His}$, and the control EncK138$^{His}$ constructs primarily contain a high molecular weight (MW) species that migrated close to void volume, indicative of cages. In contrast, the majority of HB-EncK71$^{TEV}$K138$^{TEV-His}$ migrated as lower MW species. HB-EncK71$^{TEV}$ appeared to contain some high MW species, but primarily consisted of the lower MW species. These results were confirmed by Native PAGE which can also be used to test for cage formation. Protein is resolved by native PAGE on an any-kDa gel (Bio-Rad) in the absence of SDS in the running and loading buffers.

Figure 26:
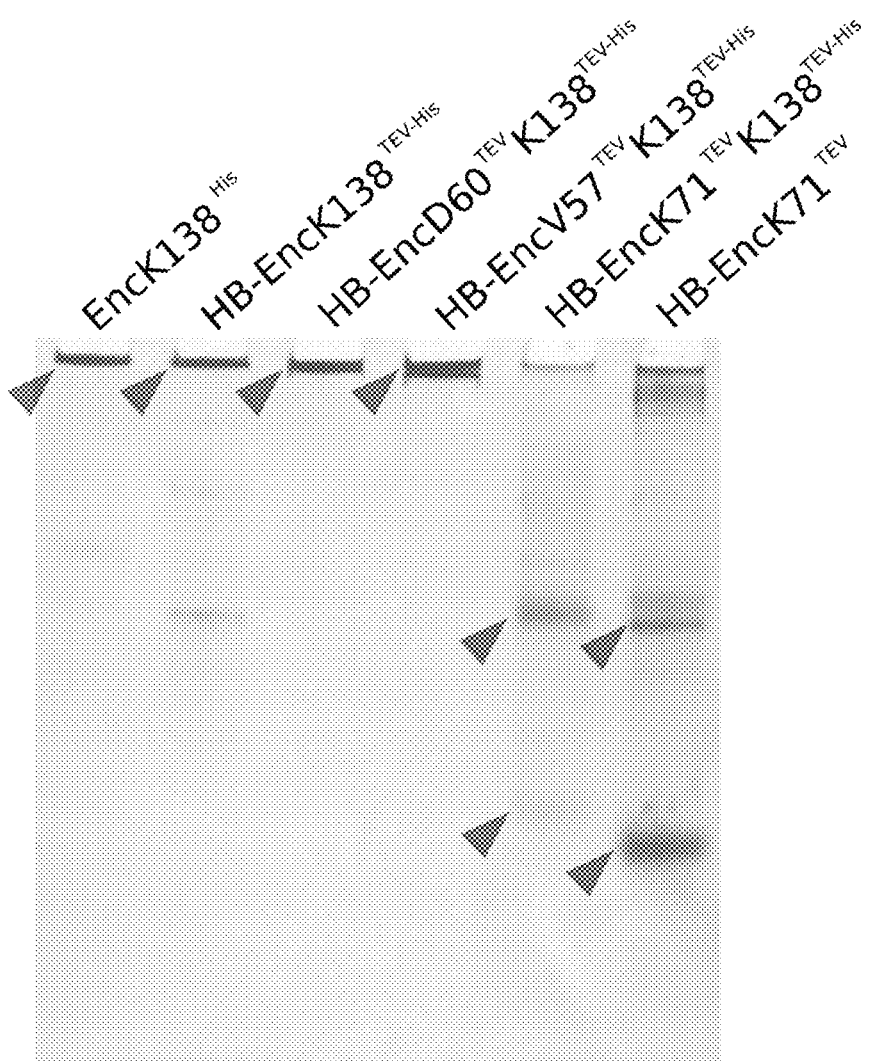
FIG. 26 shows an image illustrating the results of a Native PAGE analysis of the HB-Enc constructs. Samples were resolved on an any-kDa Native PAGE gel and stained with Coomassie blue. Arrows denote the majority species. High molecular weight (MW) species are located at the top of the gel in the well area. Low MW species enter the gel and migrate lower into the gel.

All purified HB-Enc constructs (with G$_4$T linker) were analyzed by native PAGE (FIG. 26). Native PAGE analysis revealed that HB-EncK138$^{TEV-His}$, HB-EncD60$^{TEV}$K138$^{TEV-His}$, HB-EncV57$^{TEV}$K138$^{TEV-His}$, and the control EncK138$^{His}$ constructs primarily contain a high molecular weight (MW) species that did not enter the gel, which is indicative of cages. In contrast, the majority of HB-EncK71$^{TEV}$K138$^{TEV-His}$ migrated as lower MW species that entered the gel. HB-EncK71$^{TEV}$ appeared to contain some high MW species, but primarily consisted of the lower MW species.

Figure 27:
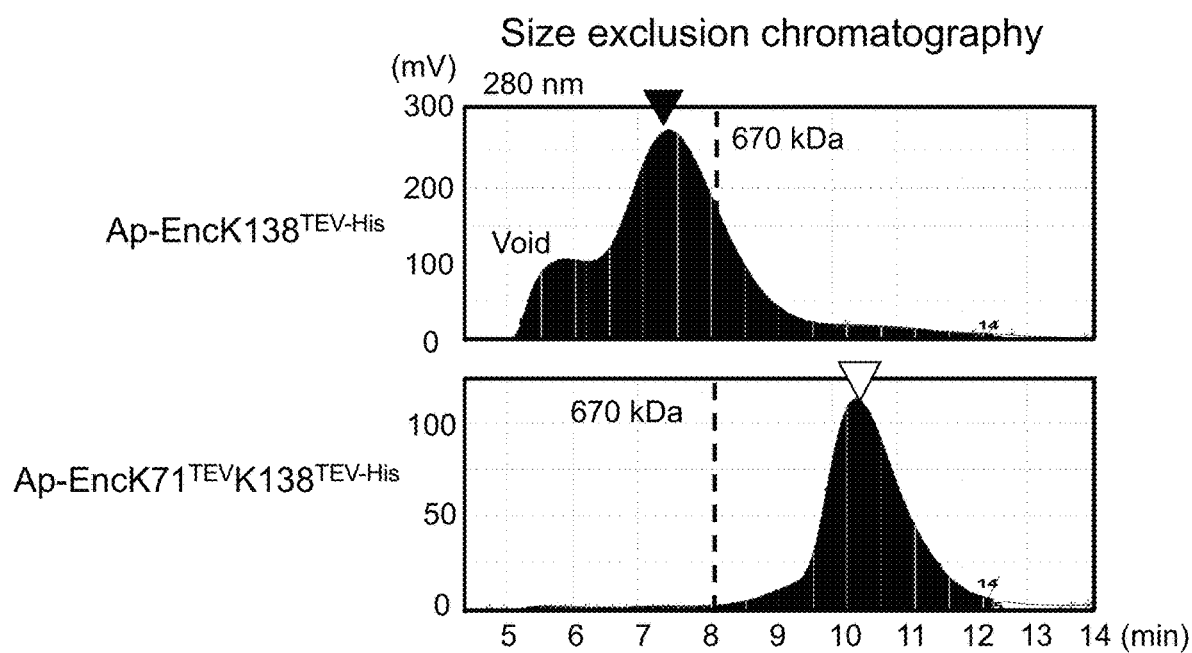
FIG. 27 shows charts illustrating size exclusion chromatography traces of absorbance at 280 nm for a cage-forming construct (Ap-EncK138$^{TEV-His}$) and a non-cage forming construct (Ap-EncK71$^{TEV}$K138$^{TEV-His}$). Dashed line denotes the retention time of a 670 kDa standard. The void volume is labeled. Cage-forming, high MW species is denoted by a black arrow, while the non-cage-forming, low MW species is denoted by a white arrow.

The high and low MW species can be isolated by size exclusion chromatography (SEC) on a SHIMADZU FPLC with a Superose 6 increase 3.2/300 column. Typically, 50 µL of a 1 mg/mL protein solution was loaded onto the column. Protein was eluted with 50 mM NaH$_2$PO$_4$, pH 8.0, 200 mM NaCl at a flow rate was 0.2 mL/min for 20 min. Species migrating at a retention time of 7-8 min were collected as the high MW species. Species migrating at a retention time of 10-11 min were collected as the low MW species. Example SEC traces for Ap-EncK138$^{TEV-His}$ and Ap-EncK71$^{TEV}$K138$^{TEV-His}$ can be found in FIG. 27.

Species can be analyzed by transmission electron microscopy (TEM). Purified material, 10 µL at a concentration of ~0.1-0.25 mg/mL, was spotted on a Cu grid coated with carbon type B-formvar for 3 min. Material was wicked away using filter paper. Grid was washed once with 10 µL of water for 1 min, then wicked away. Grid was then stained with 2% uranyl acetate in water for 3 min. Stain was wicked away and grid was washed an additional two more times with 10 µL of water for 1 min each wash. Grids were dried at room temperature for at least 1 h prior to TEM. Grids were imaged on a FEI Titan TEM at 80 kV.

Figure 28:
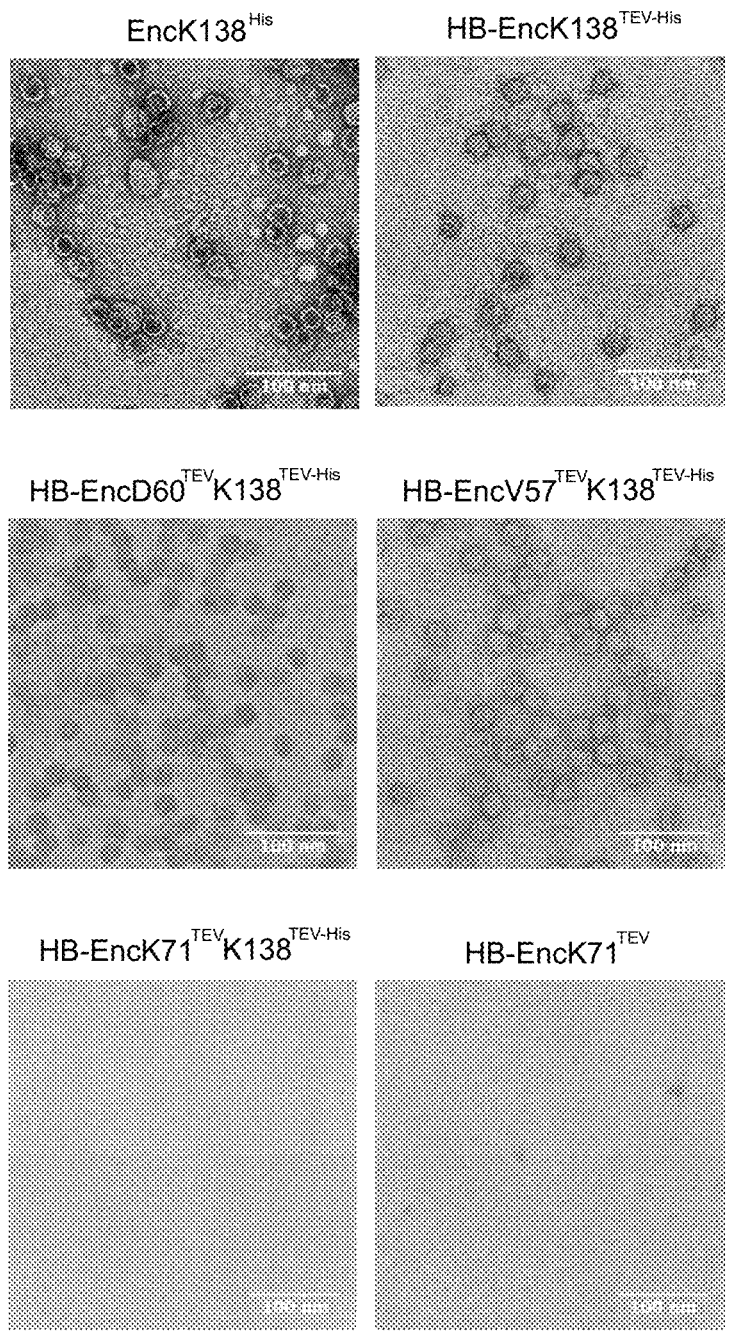
FIG. 28 shows TEM images of cage-forming (EncK138$^{His}$, HB-EncK138$^{TEV-His}$, HB-EncD60$^{TEV}$K138$^{TEV-His}$, HB-EncV57$^{TEV}$K138$^{TEV-His}$) and non-cage forming (HB-EncK71$^{TEV}$K138$^{TEV-His}$, HB-EncK71$^{TEV}$) HB-Enc constructs. Scale bar is 100 nm.

Isolation of the high and low MW HB-Enc constructs after SEC followed by transmission electron microscopy (TEM) analysis revealed that the high MW species indeed were comprised of encapsulin cages, while no cages were observed for the low MW species (FIG. 28). All observed cages were ~25 nm in diameter, with no significant difference observed among the different HB-Enc constructs.

Figure 29:
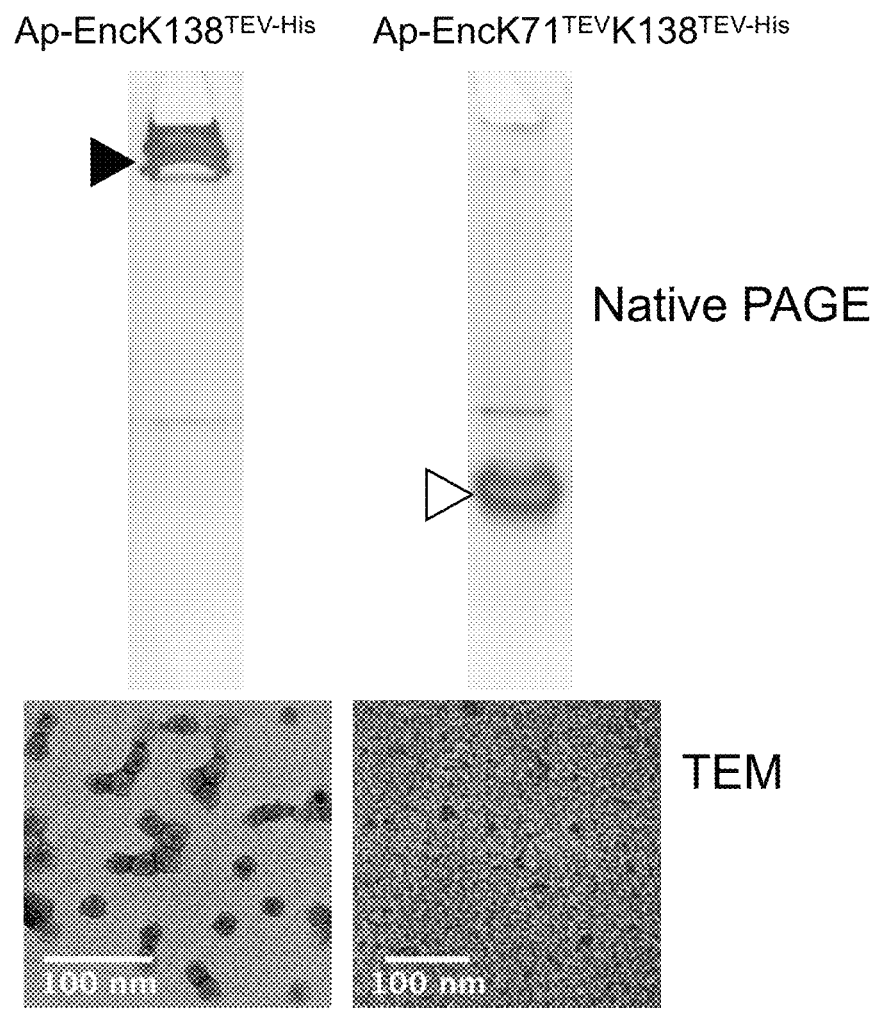
FIG. 29 shows an image illustrating Native PAGE analysis and TEM images of Ap-Enc fusions: Ap-EncK138$^{TEV-His}$ and Ap-EncK71$^{TEV}$K138$^{TEV-His}$. Black and white arrows denote high and low MW species, respectively. Scale bar on TEM images is 100 nm.

Similar results for Native PAGE and TEM analyses were obtained for Ap-Enc fusions (FIG. 29).

Example 21: Cage Forming HB-Enc Constructs are Resistant to Proteolysis in Cell Lysate To test for proteolysis in cell lysate, cells expressing the HB-Enc constructs from 25 mL of culture were harvested and resuspended in phosphate buffer (50 mM sodium phosphate pH 8.0, 500 mM NaCl) and 10 U/mL of DNaseI. Cells were lysed via a French Pressure cell at 14,000 psi and then centrifuged at 12,000 g, 4° C. for 25 min. The supernatant (soluble) fraction was collected and incubated at 4° C. overnight. Samples for SDS-PAGE analysis were collected immediately after lysis and after overnight incubation.

As controls, samples after BPER-II lysis were also prepared. Samples were resolved on an any-kDa SDS-PAGE gel (Bio-Rad) and stained with Coomassie blue. For Western blot analysis, samples were resolved on an any-kDa and blotted to a PVDF membrane using a Transblot Turbo System (Bio-Rad) at 2.5 A for 7 min. Samples were probed using a mouse anti-His-tag primary antibody and a rabbit anti-Mouse-HRP conjugated secondary antibody (both from Bio-Rad). HRP was detected on the membrane using chemiluminescence.

Figure 30:
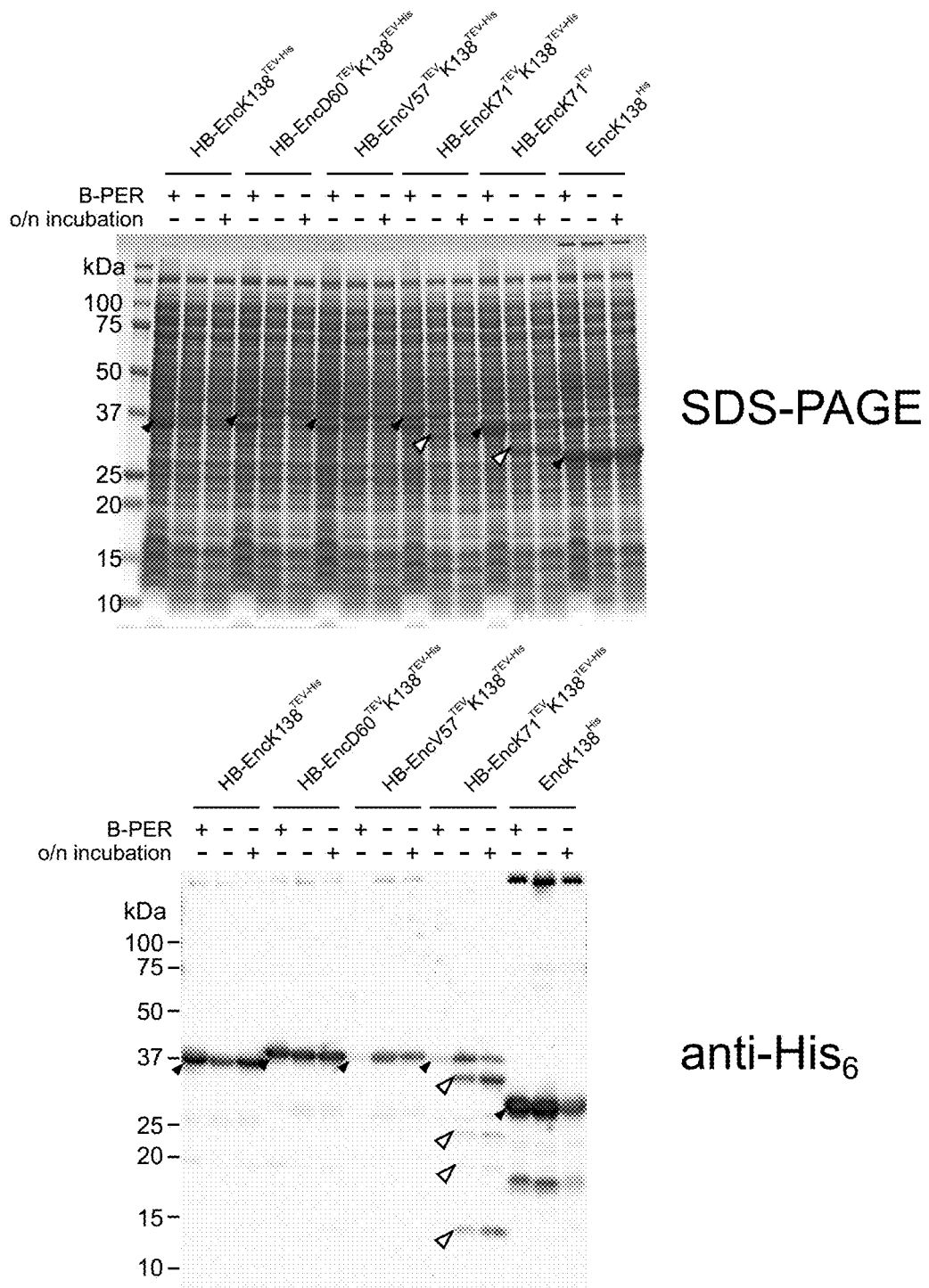
FIG. 30 shows results of experiments illustrating protease sensitivity of exemplary HB-Enc constructs in cell lysate. C43(DE3) *E. coli* expressing the constructs were either 1) lysed in the presence of BPER-II and lysozyme; 2) lysed in the absence of BPER-II by French pressure lysis; or 3) lysed in the absence of BPER-II by French pressure lysis and then incubated at 4° C. overnight. Samples were resolved on an any-kDa SDS-PAGE gel and stained with Commassie blue (top) or blotted to a PVDF membrane and probed with mouse anti-His$_6$ primary antibody and rabbit anti-mouse HRP conjugated secondary antibody (bottom). Black arrows denote size of full-length fusions. White arrows denote sizes of proteolysis products.

All three cage-forming constructs (HB-EncK138$^{TEV-His}$, HB-EncD60$^{TEV}$K138$^{TEV-His}$, and HB-EncV57$^{TEV}$K138$^{TEV-His}$) were resistant to proteolysis (FIG. 30). Full length product was observed even after overnight incubation with minimal degradation products. In contrast, non-cage forming HB-EncK71$^{TEV}$K138$^{TEV-His}$ and HB-EncK71$^{TEV}$ were both significantly degraded immediately after French press lysis and completely proteolyzed after overnight incubation. Given the detection of degradation products by anti-His-tag, proteolysis appears to primarily occur at the N-terminus of the HB-Enc fusion, degrading the HB peptide.

These results show that cage-forming HB-Enc constructs are capable of protecting the HB peptide from proteolysis, which has also been observed in other protein compartment systems [62]. In contrast, the non-cage forming, K71$^{TEV}$ containing HB-Enc constructs are susceptible to proteolysis, which very likely accounts for their ability to be completely digested by TEV protease. Interestingly, these constructs are able to be highly over-expressed in C43(DE3) E. coli compared to other HB-carrier protein fusions, suggesting that the K71$^{TEV}$ containing Enc constructs still enable HB expression, perhaps by partial occlusion of the peptide to prevent it from carrying out its toxic mode of action.

Example 22: Released HB-TEV Peptide has Anti-Bacterial Activity Against E. coli, while Ap-TEV Peptide is Inactive The anti-bacterial activity of HB-EncK71$^{TEV}$K138$^{TEV-His}$ and TEV protease-digested HB-EncK71$^{TEV}$K138$^{TEV-His}$ were tested for growth inhibition activity against BL21 (DE3) E. coli cells Growth inhibition activity can be tested against E. coli BL21(DE3) cells. Overnight cultures of cells were diluted to 200 µL of an initial OD$_{600}$ of 0.05-0.1 in LB medium. Diluted cultures were grown at 37° C., 1000 rpm in a PHMP-4 Microplate Shaker (Grant Instruments, Cambridge, England). Protein was added to the culture at an OD$_{600}$ of 0.1-0.2. Growth measured by OD$_{600}$ was monitored over time and were conducted in triplicate. TEV-digested material contained HB-Enc fusion protein (0.5 mg/mL) that was incubated with TEV protease (0.5 U/mL) overnight for 17 h at 4° C.

Figure 31:
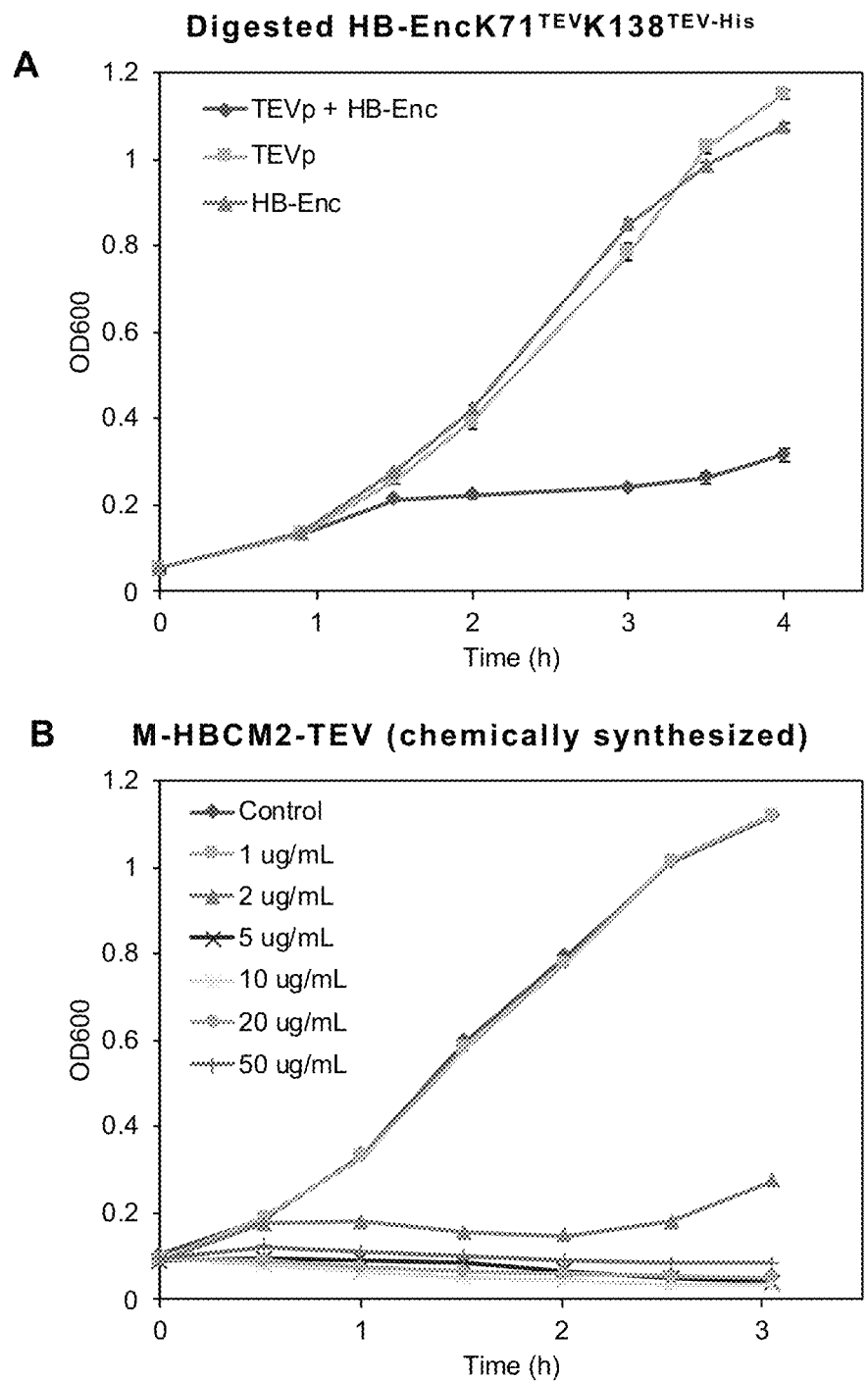
FIG. 31 Panel A shows anti-bacterial growth inhibition assays against *E. coli* BL21(DE3) for TEV-digested HB-EncK71$^{TEV}$K138$^{TEV}$ and negative controls of undigested HB-EncK71$^{TEV}$K138$^{TEV}$ alone and TEV protease alone. Only TEV-digested HB-EncK71$^{TEV}$K138$^{TEV}$ has activity.
Figure 32:
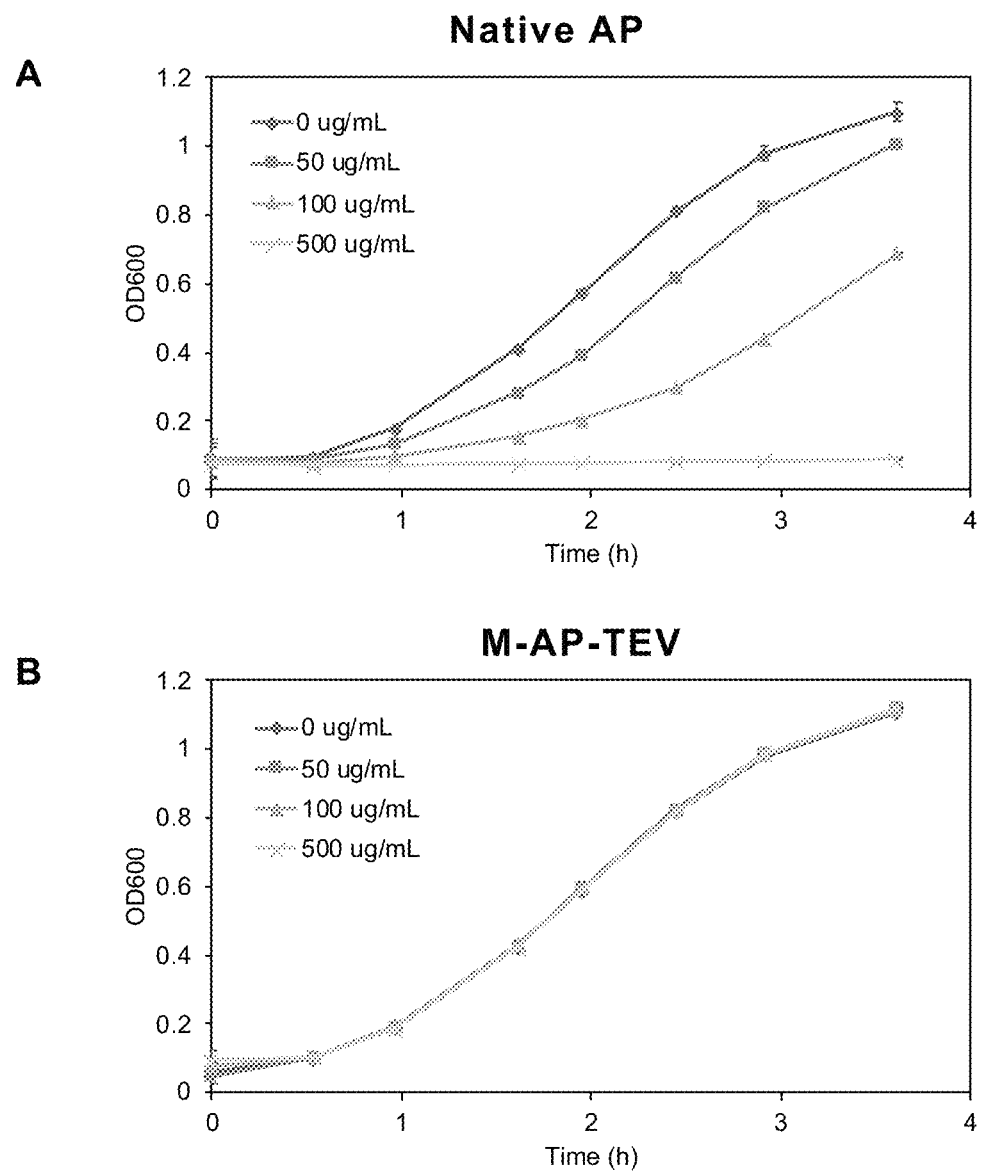
FIG. 32 shows charts illustrating the results of anti-bacterial growth inhibition assays against *E. coli* BL21 (DE3) for various concentrations of chemically synthesized native AP peptide (FIG. 32 Panel A) and M-AP-TEV peptide (FIG. 32 Panel B). Data shows M-AP-TEV peptide is not active compared to native AP peptide.

The results are shown in FIG. 31, panel A. The HB-EncK71$^{TEV}$K138$^{TEV-His}$ fusion protein did not inhibit the growth of E. coli at a concentration of 40 µg/mL. However, TEV protease-digested EncK71$^{TEV}$K138$^{TEV-His}$ showed significant bacteriostatic activity (theoretical HB peptide released was 4 µg/mL). A control with the addition of TEV protease alone also showed no growth inhibition, confirming that the inhibitory activity was due to released HB peptide.

Growth inhibition assays of chemically synthesized M-HB-TEV peptide (M-HBCM2-TEV, the peptide product that is released by digestion) showed significant anti-bacterial activity at 2 µg/mL (FIG. 31, panel B), consistent with the reported MIC [63], suggesting that the N-terminal Met residue and the residual C-terminal TEV site did not significantly affect activity.

Growth inhibition assays of chemically synthesized native Ap peptide and M-Ap-TEV peptide only showed significant anti-bacterial activity for the native Ap peptide starting at 100 µg/mL. The M-Ap-TEV peptide as inactive against BL21(DE3) *E. coli*. Thus, the Ap-Enc system serves as a model/case study for a non-active peptide.

Example 23: Expression of HB-Enc Constructs in TOP10 *E. coli* Cells from an Arabinose Inducible System All HB-Enc constructs as well as HB-Trx, HB-SUMO, HB-GST, and HB-MBP were cloned under a βBAD promoter for expression in TOP10 *E. coli*. Expression in TOP10 cells under 40 µM (low) or 10 mM (high) arabinose induction was tested. Overnight cultures of cells were diluted to 200 µL of an initial $OD_{600}$ of 0.1 in LB medium. Diluted cultures were grown at 37° C., 1000 rpm in a PHMP-4 Microplate Shaker (Grant Instruments, Cambridge, England). Arabinose inducer was added to the indicated concentrations once cultures reached an $OD_{600}$ of 0.2. After 4-5 h induction, cells were harvested and lysed as described in [00254] and tested for expression by SDS-PAGE analysis and anti-$His_6$ Western blot.

HB-Trx, HB-SUMO, and HB-GST had little to no detectable expression by SDS-PAGE analysis in TOP10 *E. coli* cells under an arabinose-inducible βBAD promoter (FIG. 33A). A partial HB-MBP was expressed under high arabinose induction (10 mM) but was truncated without the HB peptide at the N-terminus (FIG. 33B). In contrast, HB-EncD60$^{TEV}$K138$^{TEV-His}$, HB-EncK71$^{TEV}$K138$^{TEV-His}$, and HB-EncK71$^{TEV}$ could all be well expressed in the system under low arabinose induction (40 µM) conditions. Some truncation of the K71$^{TEV}$ containing constructs was observed in the expression gel, but it was not as significant as truncation of HB-MBP.

Figure 33C:
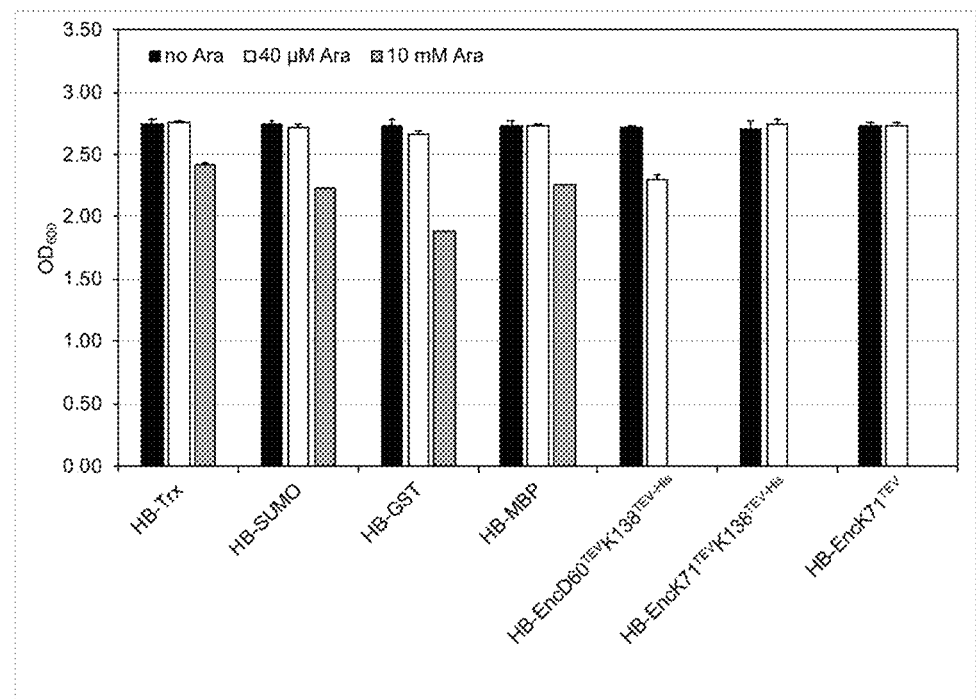
FIG. 33C shows the final OD$_{600}$ of the TOP10 *E. coli* cultures after 4-5 h induction at 37° C.

Despite low expression of HB-Trx, HB-SUMO, and HB-GST and truncated expression of HB-MBP under 10 mM arabinose induction, cells expressing these constructs reached a significantly lower $OD_{600}$ after induction (1.9-2.4) compared to cells significantly over-expressing HB-EncK71$^{TEV}$K138$^{TEV-His}$ and HB-EncK71$^{TEV}$ constructs at 40 µM arabinose ($OD_{600}$ 2.7) (FIG. 33C). These results suggest that the HB-Trx/SUMO/GST/MBP constructs may be conferring some toxicity to the expression cells, whereas the K71$^{TEV}$ containing HB-Enc constructs confer limited toxicity even when highly over-expressed. Expression of HB-EncD60$^{TEV}$K138$^{TEV-His}$ consistently results in lower cell density ($OD_{600}$ 2.3) compared to expression of the K71$^{TEV}$ containing HB-Enc fusions, likely associated with some insoluble cage expression.

Overall, these results are similar to the C43(DE3)/T7 induction system, where fusion of HB to the encapsulin constructs enabled its expression and prevented its proteolysis during expression.

Example 24: Expression of Protease-Sensitive HB-Trx, HB-SUMO, HB-GST, and HB-MBP Constructs in BL21(DE3) *E. coli* Cells from a T7 IPTG Inducible System HB-Trx, HB-SUMO, HB-GST, and HB-MBP were expressed in BL21(DE3) from a T7 IPTG inducible promoter using the same method as for C43(DE3) cells described in Example 12. Protease sensitivity of the constructs in lysate were tested as described in Example 21.

Figure 34:
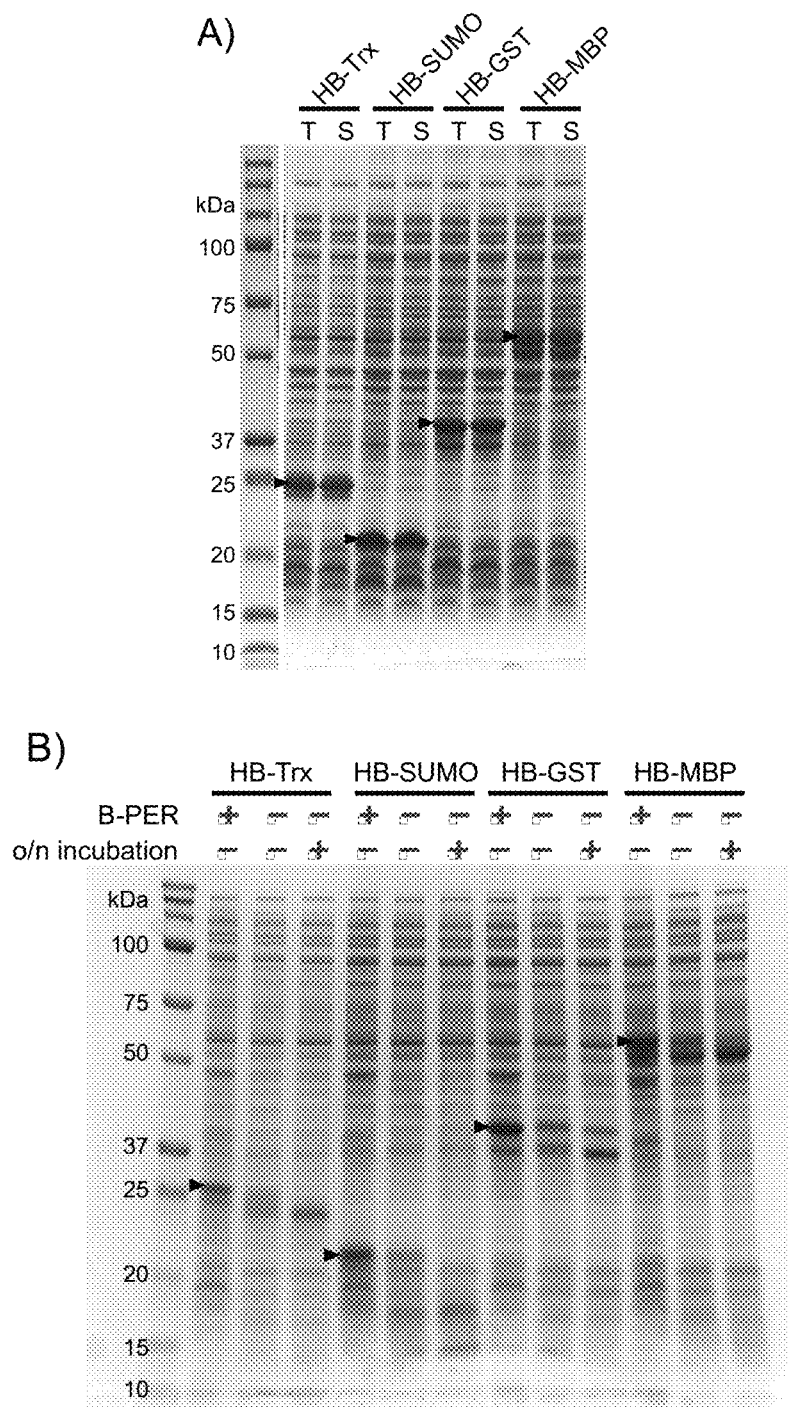
FIG. 34 shows results of experiments directed to illustrate expression and protease sensitivity of exemplary constructs HB-Trx, HB-SUMO, HB-GST, and HB-MBP.

HB-Trx, HB-SUMO, HB-GST, and HB-MBP were found to be significantly over-expressed in BL21(DE3) *E. coli* (FIG. 34A).

Despite significant over-expression of these constructs, they are all highly susceptible to proteolysis after cell lysis (FIG. 34B). Immediately following lysis in the presence of B-PER-II, significant proteolysis of HB-GST and HB-MBP were observed by SDS-PAGE, contrasting with the HB-Enc constructs which did not exhibit significant proteolysis in the presence of B-PER (FIG. 30). Following French press lysis in the absence of B-PER, all other HB carrier protein fusions were subjected to rapid proteolysis with complete disappearance of full-length protein after overnight incubation at 4° C.

It is possible that expression of non-Enc HB carrier protein fusions in BL21(DE3) cells is due to rapid protein synthesis relative to the rate of proteolysis in this strain, in contrast to C43(DE3) or TOP10 cells, where protein synthesis is possibly slower than proteolysis.

The data in all three expression systems (C43(DE3)/T7, BL21(DE3)/T7, TOP10/βBAD) demonstrate that fusions of HB to other common carrier proteins are highly susceptible to proteolysis. The non-cage forming HB-Enc fusions are also susceptible to proteolysis, but their expression is robust in all three expression systems, suggesting that 1) they are not as susceptible to proteolysis as the other fusions; and 2) the K71$^{TEV}$ containing Enc proteins may be providing some additional occlusion of the HB peptide to allow its expression. The cage-forming HB-Enc fusions fully protect the HB peptide from proteolysis, but their over-expression is not as robust because they appear to confer some toxicity to the expression strain upon over-expression.

Thus, there appears to be a trade-off between high over-expression and peptide release (non-cage forming HB-Enc) versus protection from proteolysis (cage forming HB-Enc).

Example 25: Enc Constructs Comprising M-Ap

Ap was fused to the various engineered Enc examined in this study as well as typical carrier proteins SUMO, Trx, GST, and MBP and expression of the fusions from a T7 promoter in *E. coli* C43(DE3) cells was tested (FIG. 36). Fusions of Ap to the N-terminus of the various engineered Enc proteins were over-expressed in C43(DE3) cells, as well as Ap-SUMO, Ap-GST, and Ap-MBP. However, Ap-Trx and a C-terminal EncK138$^{TEV-His}$-Ap fusion were not well expressed and could not be detected by SDS-PAGE. These data suggest that Enc works comparably to SUMO, GST, and MBP as a carrier protein for non-toxic Ap, but it must be fused to the N-terminus of Enc to enable Ap expression.

Interestingly, Ni-NTA purification of Ap-EncK71$^{TEV}$K138$^{TEV-His}$ was achieved with high affinity binding of the protein to the resin (FIG. 37). In contrast, Ap-EncK138$^{TEV-His}$, Ap-EncD60$^{TEV}$K138$^{TEV-His}$ and Ap-EncV57$^{TEV}$K138$^{TEV-His}$ did not bind well to the Ni-NTA resin and thus, needed to be purified using an alternative method of heat precipitation followed by ammonium sulfate precipitation. Characterization of the purified fusions by SEC, native PAGE, and TEM showed similar results to the HB-Enc fusions, where K71$^{TEV}$ containing Ap-Enc constructs did not form protein cages, whereas Ap-Enc without the K71$^{TEV}$ insertion were able to form cages (Fig S8).

Example 26: Isolation of M-Ap-TEV Peptide Following TEV Protease Cleavage

In addition to HBCM2 peptide, engineered Enc constructs were provided including the proline-rich, unstructured AMP, apidaecin Ia (Ap) [64].

The Ap peptide was initially tested as a model antimicrobial peptide with intercellular toxic activity; proline-rich AMPs are generally bacteriostatic by inhibition of the ribosome [65]. However, we later discovered that Ap with a residual C-terminal cleaved TEV site (Ap-TEV) was found to lack bacteriostatic activity, unlike native Ap, suggesting that the residual TEV site interferes with Ap activity. We proceeded to test whether fusion of Enc to Ap helps its expression as a case study for a non-toxic peptide.

In particular the engineered Enc construct Ap-EncK71$^{TEV}$K138$^{TEV\text{-}His}$ wherein 1) a TEV protease site followed by a GGT linker was placed between the C-terminus of Ap and the N-terminus of Enc; 2) a TEV protease site is inserted following residue K71 in Enc with GG-linkers on both the N- and C-termini of the insertion; and 3) a TEV protease site followed by a hexa-histidine tag is inserted following residue K138 in Enc with Gs-linkers on both the N- and C-termini of the insertion.

The engineered Enc construct Ap-EncK71$^{TEV}$K138$^{TEV\text{-}His}$ was tested for expression in C43(DE3) cells.

In particular, purified Ap-EncK71$^{TEV}$K138$^{TEV\text{-}His}$ was digested with TEV protease as described in Example 14. Following overnight digestion at 4° C., digested material was filtered through a centrifugal filter with 10 kDa molecular weight cutoff (Vivaspin, Satorius). Peptide was recovered in the filtrate. Material in the filter (<500 µL) was diluted an additional two times to 5 mL using phosphate buffer (25 mM sodium phosphate pH 7.5, 100 mM NaCl) and centrifuged to collect additional filtrate. All filtrate was pooled and lyophilized. Final purified material was analyzed by SDS-PAGE and quantified by absorbance at 280 nm.

Figure 35:
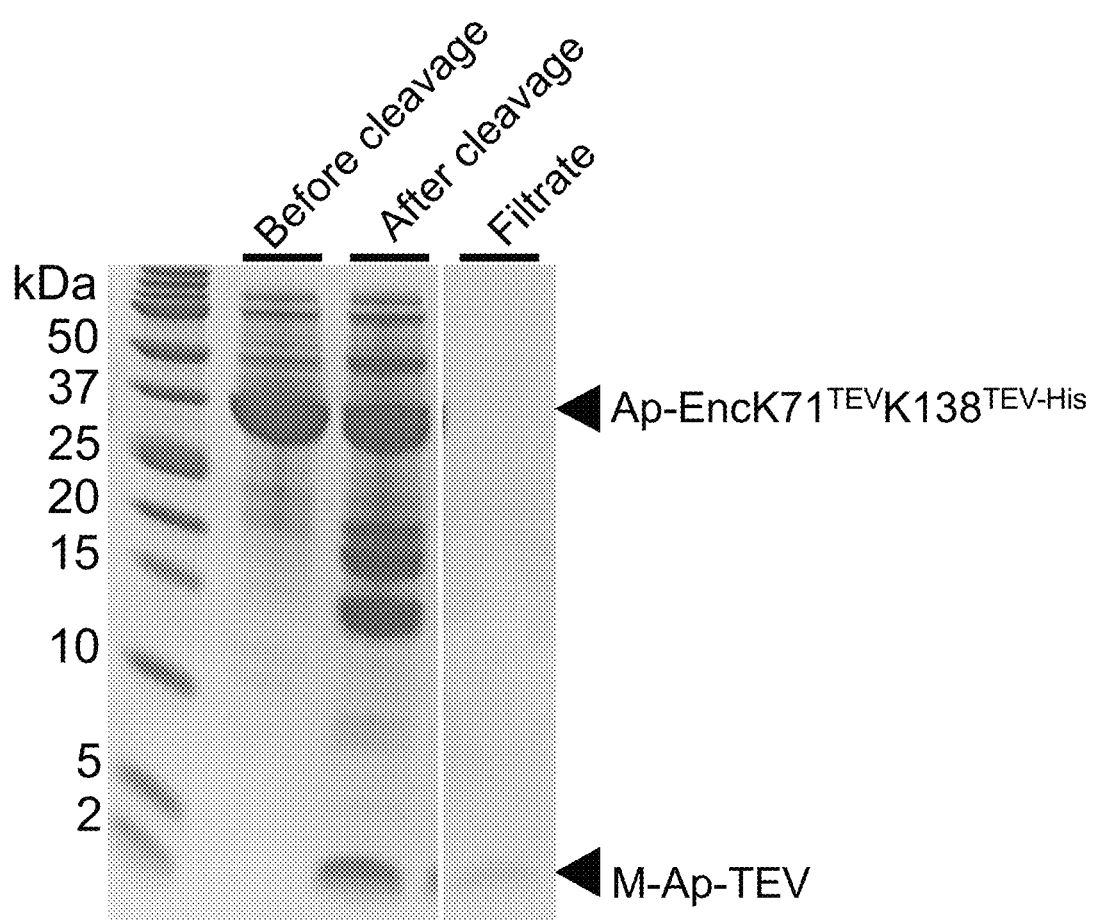
FIG. 35 shows an image of a gel illustrating isolation of M-Ap-TEV peptide following TEV protease cleavage of Ap-EncK71$^{TEV}$K138$^{TEV-His}$. Samples were collected before and after cleavage of Ap-EncK71$^{TEV}$K138$^{TEV-His}$ and peptide was collected in the filtrate after centrifugation on a 10 kDa molecular weight cutoff centrifugal filter. Samples were resolved on a 16.5% Tris-Tricine SDS-PAGE gel and stained with Commassie blue.

Ultimately, an overall yield of 3.5 mg/L culture of Ap-TEV peptide was obtained from 43 mg/L of Ap-EncK71$^{TEV}$K138$^{TEV\text{-}His}$ fusion protein (FIG. 35). These data collectively show that Enc can aid expression and purification of a non-toxic peptide.

Example 27: Prophetic Example of Engineered Constructs Designed to Allow Post Isolation Digestion of the Residual Protease Cleavage Site Attached to the C-Terminus of the Target Proteins In an example target protein (abbreviated TP) where a residual protease cleavage site on the C-terminus of TP interferes with the activity of TP, the following methods may be conducted to remove the majority of the residual site, leaving only a proline residue at the C-terminus of TP. Removal of residual site may possibly restore the activity/function of the TP.

First, a fused TP-Enc construct will need to be redesigned such that a proline residue is inserted between the C-terminus of TP and the N-terminus of the adjacent protease cleavage site. The new TP-Enc construct can then be over-expressed in C43(DE3) E. coli cells as described in Example 12, purified as described in Example 19, and digested with an appropriate protease as described in Example 14 and 19.

Following digestion, the released TP can be isolated by size exclusion chromatography or a centrifugal filter with an appropriate molecular weight cutoff. Alternatively, released TP can is isolated using ion exchange chromatography or reverse-phase (e.g., C18) chromatography, if appropriate.

Purified released TP can then be digested with commercially available carboxypeptidase A and/or B, according to manufacturer's instructions. Following carboxypeptidase digestion, TP with a residual proline at its C-terminus can be re-isolated using the same methods as in [00379].

Example 28: Isolation and Detection of Microcompartments from Bacteria

Cages from bacteria can be isolated by re-suspending cells in buffer and lysing the suspended cells. For example, cells can be re-suspended in a buffer such as 50 mM NaH$_2$PO$_4$, pH 8.0 with 200 mM NaCl and lysed by French pressure cell at 14,000 psi. Following removal of insoluble material by centrifugation at 12,000 g, 4° C. for 15 min, the supernatant is heated at 70-85° C. for 10 min. Only encapsulin cages will remain soluble under these conditions and insoluble material can again be removed by centrifugation. Ammonium sulfate precipitation at 25 or 50% can be performed to further purify the material, followed by size exclusion chromatography (SEC). SEC can be done using SHIMADZU FPLC with a Superose 6 increase 3.2/300 column (GE biosciences). One to 5 mg of sample is loaded, and protein is eluted with 50 mM NaH$_2$PO$_4$, pH 8.0, 200 mM NaCl at a flow rate of 0.2 mL/min for 20 min. Protein cages should elute as a high molecular weight species near the void volume, between 7 and 8 min.

Protein cages collected after SEC can be detected using transmission electron microscopy. For example, protein can be spotted on a copper TEM grid coated with carbon type B-formvar and stained using 2% uranyl nitrate, using standard methods. Grids can be examined on a transmission electron microscope (e.g., FEI Titan) at 80 kV. Hexagonal species of ~25 nm diameter is indicative of cage formation.

Observation of (1) a high molecular species by SEC and (2) hexagonal cage features by TEM confirms cage formation.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2138-US-ST25.txt is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Nichols, R. J., et al., *Encapsulins: molecular biology of the shell*. Crit Rev Biochem Mol Biol, 2017. 52: p. 1-12.
2. Sutter, M., et al., *Structural basis of enzyme encapsulation into a bacterial nanocompartment*. Nature Structural & Molecular Biology, 2008. 15(9): p. 939-947.
3. Eddy, S. R., *Where did the BLOSUM62 alignment score matrix come from?* Nature Biotechnology, 2004. 22(8): p. 1035-1036.
4. Altschul SF, M. T., Schäffer A A, Zhang J, Zhang Z, Miller W, Lipman DJ., *Gapped BLAST and PSI-BLAST: a new generation of protein database search programs*. Nucleic Acids Res., 1997. 25(17): p. 14.
5. Smith TF, W. M., *Identification of common molecular subsequences*. J Mol Biol, 1981. 147(1): p. 3.
6. WR, P., *Searching protein sequence libraries: comparison of the sensitivity and selectivity of the Smith-Waterman and FASTA algorithms*. Genomics, 1991. 11(3): p. 16.
7. Pearson WR, L. D., *Improved tools for biological sequence comparison*. Proc Natl Acad Sci USA, 1988. 85(8): p. 5.
8. Johnson LS, E. S., Portugaly E, *Hidden Markov model speed heuristic and iterative HMM search procedure*. BMC Bioinformatics, 2010. 11(431): p. 8.
9. Schechter, I. and A. Berger, *On the size of the active site in proteases. I. Papain*. Biochem Biophys Res Commun., 1967. 27(2): p. 157-162.
10. Schechter, I. and A. Berger, *On the active site of proteases. 3. Mapping the active site of papain; specific peptide inhibitors of papain*. Biochem Biophys Res Commun., 1968 32(5): p. 898-902.
11. Doherty, A. J., B. A. Connolly, and A. F. Worrall, *Overproduction of the toxic protein, bovine pancreatic DNaseI, in Escherichia coli using a tightly controlled T7-promoter-based vector*. Gene, 1993. 136(1): p. 337-340.
12. Dong, H., L. Nilsson, and C. G. Kurland, *Gratuitous overexpression of genes in Escherichia coli leads to growth inhibition and ribosome destruction*. Journal of bacteriology, 1995. 177(6): p. 1497-1504.
13. Chung, B. C., et al., *Crystal structure of MraY, an essential membrane enzyme for bacterial cell wall synthesis*. Science, 2013. 341(6149): p. 1012-1016.
14. Nguyen, L. T., E. F. Haney, and H. J. Vogel, *The expanding scope of antimicrobial peptide structures and their modes of action*. Trends in biotechnology, 2011. 29(9): p. 464-472.
15. Durand, S., et al., *Activation of RegB endoribonuclease by S1 ribosomal protein requires an 11 nt conserved sequence*. Nucleic Acids Res, 2006. 34(22): p. 6549-60.
16. Gaspar, D., A. S. Veiga, and M. A. Castanho, *From antimicrobial to anticancer peptides. A review*. Frontiers in Microbiology, 2013. 4: p. 294.
17. Hoskin, D. W. and A. Ramamoorthy, *Studies on anticancer activities of antimicrobial peptides*. Biochimica et Biophysica Acta (BBA)-Biomembranes, 2008. 1778(2): p. 357-375.
18. Scott, M. G., H. Yan, and R. E. Hancock, *Biological properties of structurally related alpha-helical cationic antimicrobial peptides*. Infect Immun, 1999. 67(4): p. 2005-9.
19. Zhang, L., et al., *Antimicrobial peptide therapeutics for cystic fibrosis*. Antimicrob Agents Chemother, 2005. 49(7): p. 2921-7.
20. Wolfe, M. S., *Intramembrane-cleaving proteases*. Journal of Biological Chemistry, 2009. 284(21): p. 13969-13973.
21. Schmelcher, M., D. M. Donovan, and M. J. Loessner, *Bacteriophage endolysins as novel antimicrobials*. Future microbiology, 2012. 7(10): p. 1147-1171.
22. Wang, G. S., X. Li, and Z. Wang, *APD3: the antimicrobial peptide database as a tool for research and education*. Nucleic Acids Res, 2016. 44(D1): p. D1087-D1093.
23. Marr, A. K., W. J. Gooderham, and R. E. W. Hancock, *Antibacterial peptides for therapeutic use: obstacles and realistic outlook*. Current Opinion in Pharmacology, 2006. 6(5): p. 468-472.

24. Menzella, H. G., *Comparison of two codon optimization strategies to enhance recombinant protein production in Escherichia coli*. Microbial cell factories, 2011. 10(1): p. 1.
25. Boman, H. G., B. Agerberth, and A. Boman, *Mechanisms of action on Escherichia coli of cecropin P1 and PR-39, two antibacterial peptides from pig intestine*. Infect Immun, 1993. 61(7): p. 2978-84.
26. Li, W. F., G. X. Ma, and X. X. Zhou, *Apidaecin-type peptides: biodiversity, structure function relationships and mode of action*. Peptides, 2006. 27(9): p. 2350-9.
27. Krom, R. J., et al., *Engineered Phagemids for Nonlytic, Targeted Antibacterial Therapies*. Nano Lett, 2015. 15(7): p. 4808-13.
28. Parachin, N. S., et al., *Expression systems for heterologous production of antimicrobial peptides*. Peptides, 2012. 38(2): p. 446-56.
29. Worsdorfer, B., K. J. Woycechowsky, and D. Hilvert, *Directed Evolution of a Protein Container*. Science, 2011. 331(6017): p. 589-592.
30. Yeates, T. O., C. S. Crowley, and S. Tanaka, *Bacterial microcompartment organelles: protein shell structure and evolution*. Annu Rev Biophys, 2010. 39: p. 185-205.
31. LaVallie, E. R., et al., *Enzymatic and chemical cleavage of fusion proteins*. Curr Protoc Mol Biol, 2001. Chapter 16: p. Unit 16 4B.
32. Sinha, S., et al., *The PduM Protein Is a Structural Component of the Microcompartments Involved in Coenzyme B-12-Dependent 1,2-Propanediol Degradation by Salmonella enterica*. Journal of Bacteriology, 2012. 194(8): p. 1912-1918.
33. Saeidi, N., et al., *Engineering microbes to sense and eradicate Pseudomonas aeruginosa, a human pathogen*. Mol Syst Biol, 2011. 7: p. 521.
34. Hwang, I. Y., et al., *Reprogramming Microbes to Be Pathogen-Seeking Killers*. ACS Synth Biol, 2014. 3(4): p. 228-237.
35. Zhang, G., S. Brokx, and J. H. Weiner, *Extracellular accumulation of recombinant proteins fused to the carrier protein YebF in Escherichia coli*. Nat Biotechnol, 2006. 24(1): p. 100-4.
36. Rutherford, S. T. and B. L. Bassler, *Bacterial quorum sensing: its role in virulence and possibilities for its control*. Cold Spring Harb Perspect Med, 2012. 2(11).
37. Gupta, S., E. E. Bram, and R. Weiss, *Genetically programmable pathogen sense and destroy*. ACS Synth Biol, 2013. 2(12): p. 715-23.
38. Davis, J. H., A. J. Rubin, and R. T. Sauer, *Design, construction and characterization of a set of insulated bacterial promoters*. Nucleic Acids Res, 2011. 39(3): p. 1131-41
39. Rhodius, V. A., et al., *Design of orthogonal genetic switches based on a crosstalk map of sigmas, anti-sigmas, and promoters*. Mol Syst Biol, 2013. 9: p. 702.
40. Shaner, N.C., P. A. Steinbach, and R. Y. Tsien, *A guide to choosing fluorescent proteins*. Nat Methods, 2005. 2(12): p. 905-9.
41. McGinness, K. E., T. A. Baker, and R. T. Sauer, *Engineering controllable protein degradation*. Mol Cell, 2006. 22(5): p. 701-7.
42. Salis, H. M., E. A. Mirsky, and C. A. Voigt, *Automated design of synthetic ribosome binding sites to control protein expression*. Nat Biotechnol, 2009. 27(10): p. 946-50.
43. Purnick, P. E. and R. Weiss, *The second wave of synthetic biology: from modules to systems*. Nat Rev Mol Cell Biol, 2009. 10(6): p. 410-22.
44. Darkoh, C., et al., *Toxin Synthesis by Clostridium difficile Is Regulated through Quorum Signaling*. Mbio, 2015. 6(2).
45. Volzing, K., et al., *Antimicrobial peptides targeting Gram-negative pathogens, produced and delivered by lactic acid bacteria*. ACS Synth Biol, 2013. 2(11): p. 643-50.
46. Bermudez-Humaran, L. G., et al., *Lactococci and lactobacilli as mucosal delivery vectors for therapeutic proteins and DNA vaccines*. Microbial Cell Factories, 2011. 10.
47. Fujitani, S., et al., *Pneumonia Due to Pseudomonas aeruginosa Part I: Epidemiology, Clinical Diagnosis, and Source*. Chest, 2011. 139(4): p. 909-919.
48. Harrison, J. J., et al., *Microtiter susceptibility testing of microbes growing on peg lids: a miniaturized biofilm model for high-throughput screening*. Nat Protoc, 2010. 5(7): p. 1236-54.
49. Merritt, J. H., D. E. Kadouri, and G. A. O'Toole, *Growing and analyzing static biofilms*. Curr Protoc Microbiol, 2005. Chapter 1: p. Unit 1B 1.
50. Batoni, G., G. Maisetta, and S. Esin, *Antimicrobial peptides and their interaction with biofilms of medically relevant bacteria*. Biochim Biophys Acta, 2016. 1858(5): p. 1044-60.
51. Whitchurch, C. B., et al., *Extracellular DNA required for bacterial biofilm formation*. Science, 2002. 295(5559): p. 1487.
52. Wong, T. Y., L. A. Preston, and N. L. Schiller, *ALGINATE LYASE: review of major sources and enzyme characteristics, structure-function analysis, biological roles, and applications*. Annu Rev Microbiol, 2000. 54: p. 289-340.
53. van de Loosdrecht, A. A., et al., *A tetrazolium-based colorimetric MTT assay to quantitate human monocyte mediated cytotoxicity against leukemic cells from cell lines and patients with acute myeloid leukemia*. J Immunol Methods, 1994. 174(1-2): p. 311-20.
54. Mamat, U., et al., *Detoxifying Escherichia coli for endotoxin free production of recombinant proteins*. Microbial Cell Factories, 2015. 14: p. 57.
55. Moon, H., et al., *Developing genetically engineered encapsulin protein cage nanoparticles as a targeted delivery nanoplatform*. Biomacromolecules, 2014. 15(10): p. 3794-3801.
56. Sutter, M., et al., *Structural basis of enzyme encapsulation into a bacterial nanocompartment*. Nat Struct Mol Biol, 2008. 15(9): p. 939-947.
57. Cassidy-Amstutz, C., et al., *Identification of a minimal peptide tag for in vivo and in vitro loading of encapsulin*. Biochemistry, 2016. 55(24): p. 3461-3468.
58. Yung, M. C., et al., *Re-directing bacterial microcompartment systems to enhance recombinant expression of lysis protein E from bacteriophage ΦX174 in Escherichia coli*. Microb Cell Fact, 2017. 16(1): p. 71.
59. Sargent, F., et al., *A synthetic system for expression of components of a bacterial microcompartment*. Microbiology-Sgm, 2013. 159: p. 2427-2436.
60. Lee, M. J., et al., *Employing bacterial microcompartment technology to engineer a shell-free enzyme-aggregate for enhanced 1,2-propanediol production in Escherichia coli*. Metabolic Engineering, 2016. 36: p. 48-56.
61. Fan, C. G., et al., *Short N-terminal sequences package proteins into bacterial microcompartments*. Proceedings of the National Academy of Sciences of the United States of America, 2010. 107(16): p. 7509-7514.

62. Lau, Y. H., et al., *Prokaryotic nanocompartments form synthetic organelles in a eukaryote*. bioRxiv, 2018.
63. Zhang, L., et al., *Antimicrobial peptide therapeutics for cystic fibrosis*. Antimicrobial Agents and Chemotherapy, 2005. 49(7): p. 2921-2927.
64. Li, W. F., G. X. Ma, and X. X. Zhou, *Apidaecin-type peptides: biodiversity, structure function relationships and mode of action*. Peptides, 2006. 27(9): p. 2350-2359.
65. Krizsan, A., et al., *Short Proline-Rich Antimicrobial Peptides Inhibit Either the Bacterial 70S Ribosome or the Assembly of its Large 50S Subunit*. Chembiochem, 2015. 16(16): p. 2304-2308.

The invention claimed is:

1. An engineered microcompartment protein, comprising an encapsulin protein having sequence SEQ ID NO: 1 or a sequence with at least 22% sequence identity or at least 40% sequence similarity to SEQ ID NO:1, and comprising a P-Domain (Peripheral Domain), an E-Loop (Elongated Loop) and an A-Domain (Axial Domain), wherein the P-Domain comprises a first fragment of the P-domain having an N-terminus and a C-terminus and comprising residues configured to form, in a folded encapsulin protein, a secondary structure comprising in a direction N-terminus to C-terminus a 4 to 26 residues alpha helix α1, linked to an optional first non-structured region having 0 to 22 residues, linked to a 4 to 11 residues alpha helix α2, linked to a 3 to 9 residues beta strand β1, linked to a 3 to 13 residues second non-structured region, a second fragment of the P-Domain having an N-terminus and a C-terminus and comprising residues configured to form, in a folded encapsulin protein, a secondary structure comprising a direction N-terminus to C-terminus a 9 to 15 residues beta strand β4, linked to a 6 to 15 residues alpha helix α3, linked to an optional first non-structured region having 0 to 10 residues, a 18 to 29 residues alpha helix α4, and a 9 to 21 residues second non-structured region, and a third fragment of the P-domain having an N-terminus and a C-terminus and comprising residues configured to form, in a folded microcompartment protein, a secondary structure comprising in a direction N-terminus to C-terminus a 4 to 10 residues beta strand β9, linked to a 3 to 16 residues first non-structured region, linked to a 7 to 13 residues beta strand β10, linked to a 1 to 15 residues second non-structured region, linked to a 10 to 19 residues beta strand β11;

the E-Loop has an N-terminus and a C-terminus and comprises residues configured to form in a folded encapsulin protein, a secondary structure comprising in a direction N-terminus to C-terminus a 8 to 16 residues beta strand β2, linked to a 2 to 24 residues first non-structured region, linked to a 7 to 15 residues beta strand β3, linked to an optional second non-structured region having 0 to 6 residues; and the A-Domain of the encapsulin protein has an N-terminus and a C-terminus and comprises residues configured to form in a folded encapsulin protein, a secondary structure comprising in a direction N-terminus to C-terminus an optional beta strand β5 having 0 to 8 residues, linked to a 1 to 15 residues first non-structured region, linked to a 16 to 23 residues alpha helix α5, linked to a 3 to 11 residues second non-structured region, linked to a 3 to 11 residues beta strand β6, linked to a 9 to 16 residues alpha helix α6, linked to a 1 to 24 third non-structured region, linked to an optional alpha helix α7 having 0 to 16 residues, linked to an optional fourth non-structured region having 0 to 8 residues, linked to a 1 to 10 residues beta strand β7, linked to a 1 to 12 residues fifth non-structured region, linked to a 3 to 10 residues beta strand β8, linked to a 2 to 12 residues sixth non-structured region;

and wherein the P-domain, A-domain and E-loop are arranged together in a configuration comprising, in a direction N-terminus to C-terminus, the first fragment of the P-domain linked to the E-loop linked to the second fragment of the P-domain linked to the A-domain linked to the third fragment of the P-domain;

the engineered microcompartment protein further comprising, a target protein having an N-terminus, a C-terminus inserted at the N-terminus of the first fragment of the P-domain of the encapsulin protein alone or in combination with a tag and/or a linker;

at least one first protease cleavage site inserted between the C-terminus of the target protein and the N-terminus of the first fragment of the P-Domain of the encapsulin protein, alone or in combination with a tag and/or a linker; and at least one second protease cleavage site inserted at an insertion site at the C terminus of the E-loop of the encapsulin protein, and/or within 1 to 17 amino acids adjacent to the C-terminal amino acid of the E-loop of the encapsulin protein and/or within 2-14 amino acids adjacent to the N-terminal amino acid of the A-domain of the encapsulin protein, alone or in combination with a tag and/or a linker to enable digestion of the encapsulin and release of the target protein.

2. The engineered microcompartment protein of claim 1, wherein the target protein comprises at least one non-native antimicrobial peptide.

3. The engineered microcompartment protein of claim 2, wherein the at least one non-native antimicrobial peptide is selected from Apidaecin 1a, HBCM-2, cecropins, magainins, melittin, protegrins, and nisins.

4. The engineered microcompartment protein of claim 1, wherein the target protein has a sequence up to 80 amino acids in length.

5. The engineered microcompartment protein of claim 1, wherein the at least one second protease cleavage site is inserted within 1 to 17 amino acids adjacent to the C-terminal amino acid of the E-loop of the encapsulin protein and within the first non-structured region of the E-loop to provide a cage-forming engineered microcompartment protein.

6. The engineered microcompartment protein of claim 5, wherein the at least one second protease cleavage site is inserted at positions 57 and/or 66 of SEQ ID NO: 1.

7. The engineered microcompartment protein of claim 6, wherein the E-loop has sequence YAAHPLGEVEVLSDE-NEVVKWGLRKSLP (SEQ ID NO: 59), YTVVPEGRLK-KIEDNPGNVCTGMYQVKP (SEQ ID NO: 60), YAAVNT-GELRPIDDTPEDVDMKLRQVQP (SEQ ID NO: 61), YAAVNTGRRTALEDKAEGASIFQRQVLP (SEQ ID NO: 62), or FSALGTGHVSRVAADTPGVEALQRHVVR (SEQ ID NO: 63).

8. The engineered microcompartment protein of claim 1, wherein the at least one second protease cleavage site is inserted within 1 to 17 amino acids adjacent to the C-terminal amino acid of the E-loop of the encapsulin protein and in the first non-structured region of the E-loop, and/or within 2-14 amino acids adjacent to the N-terminal amino acid of the A-domain of the encapsulin protein and in the β5 beta strand of the A-domain, and/or within 2-14 amino acids adjacent to the N-terminal amino acid of the A-domain of the encapsulin protein and in the alpha helix α5 of the A-Domain to provide a cage forming engineered microcompartment protein.

9. The engineered microcompartment protein of claim 8, wherein the at least one second protease cleavage site is inserted at any one of positions 132 and 144 of SEQ ID NO: 1.

10. The engineered microcompartment protein of claim 8, wherein the A-Domain has sequence LLSFEERKIECGST-PKDLLEAIVRALSIFSKDGIEGPYTLVINTDRWINFL-KEEAGHYPLEKRV EECLRGGKIITTPRIEDALVVSER (SEQ ID NO: 64), LREGTSNPKLALPSSASDY-PAAIAAALNQLRLAGVNGPYAVVLGAGVYTAL-SGGDDEGYP VFRHIESLIDGKIVWAPAIEGGFVLSTR (SEQ ID NO: 65) LLTEDGIVKFPISNWSEGENPFK-DISIGLAKFIENG IVGRKALVVSPNLFVQLQRIQPGT-GTT EYDRINKLLDGNIFSTPVLKDDKAVLVCSE (SEQ ID NO: 66), ILNAEGAQKLQISDWGQGENPYTDI-VKAINMIREKGIVGRFVLCLSQSLYFDLQRIQQGTGM TEAQRISSMIGNLYNVPVIKGKKAALICAE (SEQ ID NO: 67), or LLTVKGSSKIKKSDWSQGENSFA-DITAGVAQLAKTGYLGRYALVVSPDLFLDLQR-LQPNTG LLEIDRIKKLIGDNVYMTSVMGPGKAVLV-CAE (SEQ ID NO: 68).

11. The engineered microcompartment protein of claim 1, wherein the target protein is a protease sensitive target protein.

12. The engineered microcompartment protein of claim 1, wherein the at least one second protease cleavage site is inserted within 1 to 17 amino acids adjacent to the C-terminal amino acid of the E-loop of the encapsulin protein and within the beta-strand β3 of the E-loop to provide a non-cage-forming engineered microcompartment protein.

13. The engineered microcompartment protein of claim 12, wherein the encapsulin protein has SEQ ID NO: 47 and the at least one second protease cleavage site is inserted at position 71 of SEQ ID NO: 47.

14. The engineered microcompartment protein of claim 1, wherein the target protein is a protease sensitive target protein and the engineered microcompartment protein further comprises a proline between the N-terminus of the first at least one protease cleavage site and the C terminus of the target protein.

15. The engineered microcompartment protein of claim 1, wherein the at least one second protease cleavage site is inserted at any one of positions 57, 60, 71 and 139 of SEQ ID NO: 1.

16. The engineered microcompartment protein of claim 1, wherein the at least one encapsulin protein has a sequence of SEQ ID NO: 47.

17. The engineered microcompartment protein of claim 1, wherein the at least one encapsulin protein is from the PF04454 protein family.

18. The engineered microcompartment protein of claim 1, wherein the at least one first protease cleavage site and/or the at least one second protease cleavage site are selected from ENLYFQ\S(orG) (SEQ ID NO: 70) (TEV protease recognition), LEVLFQ/GP (SEQ ID NO: 13) (HRV 3C protease recognition), LVPR/GS (SEQ ID NO: 17) (thrombin recognition), DDDDK/ (SEQ ID NO: 14) (enterokinase recognition), and IEGR/ (SEQ ID NO: 15) (Factor Xa recognition).

19. The engineered microcompartment protein of claim 1, wherein the target protein is fused to the N-terminus of the first segment of the P-domain of the encapsulin protein in combination with a linker and/or a tag.

20. The engineered microcompartment protein of claim 1, wherein the at least one first protease cleavage site is fused to the target protein and the N-terminus of the first fragment of the P-Domain of the encapsulin protein together with a linker and/or a tag.

21. The engineered microcompartment protein of claim 1, wherein the at least one second protease cleavage site is fused to the C-terminus of the E-loop and/or to the N-terminus of the A-domain of the encapsulin protein together with a linker and/or a tag.

22. The engineered microcompartment protein of claim 1, wherein the tag is selected from His-Tag, Strep-Tag, FLAG-Tag, Avi-Tag, E-Tag, HA-Tag, Myc-Tag, and TC-Tag.

23. An engineered microcompartment comprising at least one engineered microcompartment protein of claim 1.

24. A method to produce in a bacterial cell a protein non-native to the bacterial cell, the method comprising
introducing into the bacterial cell at least one first polynucleotide encoding at least one engineered microcompartment protein of claim 1 in which the target protein is the protein non-native to the bacterial cell;
wherein the at least one first polynucleotide is operatively linked to one or more first regulatory elements leading to the expression of the at least one engineered microcompartment protein in the bacterial cell; and
wherein the introducing is performed to obtain expression in the bacterial cell of the at least one engineered microcompartment protein to obtain the protein non-native to the bacterial cell within at least one engineered microcompartment formed by the at least one engineered microcompartment protein.

25. The method of claim 24, wherein the at least one second protease cleavage site of the at least one engineered microcompartment protein is inserted within 1 to 17 amino acids adjacent to the C-terminal amino acid of the E-loop of the encapsulin protein and within the first non-structured region of the E-loop to provide a cage forming engineered microcompartment protein.

26. The method of claim 24, wherein the at least one second protease cleavage site the at least one engineered microcompartment protein is inserted within 1 to 17 amino acids adjacent to the C-terminal amino acid of the E-loop of the encapsulin protein and within the beta-strand β3 of the E-loop to provide a non-cage forming engineered microcompartment protein.

27. The method of claim 24, wherein the protein non-native to the bacterial cell is a toxic non-native protein capable of causing a cell damage.

28. The method of claim 24, wherein the protein non-native to the bacterial cell is a non-native protein capable of being degraded within the bacterial cell.

29. A system to produce, in bacterial cell, a protein non-native to the bacterial cell, the system comprising
at least one first polynucleotide encoding at least one engineered microcompartment protein of claim 1, wherein the target protein is the protein non-native to the bacterial cell, the at least one engineered microcompartment protein operatively linked to one or more first regulatory elements configured to enable the expression of the at least one engineered microcompartment protein in one or more bacterial cell, the at least one engineered microcompartment protein capable of assembling with one or more same and/or different engineered microcompartment proteins to form at least one microcompartment within the one or more bacterial cell,
the system further comprising at least one of:
the one or more bacterial cells capable of expressing the at least one first polynucleotide to provide an expressed engineered microcompartment protein;
at least one second polynucleotide encoding for at least one protease, the at least one second polynucleotide operably linked to one or more second regulatory elements leading to the expression of the at least one protease capable of targeting the protease cleavage sites of the engineered microcompartment protein to release the non-native protein from the engineered microcompartment protein in the bacterial cell to obtain the non-native protein; and
at least one protease capable of targeting the protease cleavage site of the engineered microcompartment protein to release the protein non-native to the bacterial cell from the engineered microcompartment protein in the bacterial cell.

30. A vector comprising at least one polynucleotide encoding for an engineered microcompartment protein of claim 1, alone or in combination with regulatory elements in accordance with the disclosure.

31. A bacterial cell comprising at least one engineered microcompartment of claim 23.

* * * * *

SEQUENCE LISTING

<160> NUMBER OF SEQ ID NOS: 145

<210> SEQ ID NO 1
<211> LENGTH: 253
<212> TYPE: PRT
<213> ORGANISM: Artificial Sequence
<220> FEATURE:
<223> OTHER INFORMATION: synthetic polypeptide

<400> SEQUENCE: 1

```
Met Asp Asn Leu Lys Arg Glu Leu Ala Pro Leu Thr Glu Glu Ala Trp
1               5                   10                  15

Ala Glu Ile Asp Glu Glu Ala Arg Glu Thr Ala Lys Arg His Leu Ala
                20                  25                  30

Gly Arg Arg Val Val Asp Val Glu Gly Pro Leu Gly Trp Gly Tyr Ser
            35                  40                  45

Ala Val Pro Leu Gly Arg Leu Glu Glu Ile Glu Gly Pro Ala Glu Gly
        50                  55                  60

Val Gln Ala Gly Val Arg Gln Val Leu Pro Leu Pro Glu Leu Arg Val
65                  70                  75                  80

Pro Phe Thr Leu Ser Arg Arg Asp Leu Asp Ala Val Glu Arg Gly Ala
                85                  90                  95

Lys Asp Leu Asp Leu Ser Pro Val Ala Glu Ala Arg Leu Leu Ala
                100                 105                 110

Arg Ala Glu Asp Arg Leu Ile Phe Asn Gly Tyr Ala Glu Ala Gly Ile
            115                 120                 125

Glu Gly Leu Leu Asn Ala Ser Gly Asn Leu Lys Leu Pro Leu Ser Ala
        130                 135                 140

Asp Pro Gly Asp Ile Pro Asp Ala Ile Ala Glu Ala Leu Thr Lys Leu
145                 150                 155                 160

Arg Glu Ala Gly Val Glu Gly Pro Tyr Ala Leu Val Leu Ser Pro Asp
                165                 170                 175

Leu Tyr Thr Ala Leu Phe Arg Val Tyr Asp Gly Thr Gly Tyr Pro Glu
            180                 185                 190

Ile Glu His Ile Lys Glu Leu Val Asp Gly Val Ile Trp Ala Pro
        195                 200                 205

Ala Leu Asp Gly Gly Ala Val Leu Val Ser Thr Arg Gly Gly Asp Phe
    210                 215                 220

Asp Leu Thr Leu Gly Gln Asp Leu Ser Ile Gly Tyr Leu Ser His Asp
225                 230                 235                 240

Ala Asp Asn Val Glu Leu Phe Leu Thr Glu Ser Phe Thr
                245                 250
```

<210> SEQ ID NO 2
<211> LENGTH: 253
<212> TYPE: PRT
<213> ORGANISM: Artificial Sequence
<220> FEATURE:
<223> OTHER INFORMATION: Synthetic polypeptide -continued

```
<400> SEQUENCE: 2

Met Asp Asn Leu Lys Arg Glu Leu Ala Pro Leu Thr Glu Glu Ala Trp
1               5                   10                  15

Ala Glu Ile Asp Glu Glu Ala Arg Glu Thr Ala Lys Arg His Leu Ala
            20                  25                  30

Gly Arg Arg Val Val Asp Val Glu Gly Pro Leu Gly Trp Gly Tyr Ser
        35                  40                  45

Ala Val Pro Leu Gly Arg Leu Glu Glu Ile Glu Gly Pro Ala Glu Gly
    50                  55                  60

Val Gln Ala Gly Val Arg Gln Val Leu Pro Leu Pro Glu Leu Arg Val
65                  70                  75                  80

Pro Phe Thr Leu Ser Arg Arg Asp Leu Asp Ala Val Glu Arg Gly Ala
                85                  90                  95

Lys Asp Leu Asp Leu Ser Pro Val Ala Glu Ala Ala Arg Lys Leu Ala
            100                 105                 110

Arg Ala Glu Asp Arg Leu Ile Phe Asn Gly Tyr Ala Glu Ala Gly Ile
        115                 120                 125

Glu Gly Leu Leu Asn Ala Ser Gly Asn Leu Lys Leu Pro Leu Ser Ala
130                 135                 140

Asp Pro Gly Asp Ile Pro Asp Ala Ile Ala Glu Ala Leu Thr Lys Leu
145                 150                 155                 160

Arg Glu Ala Gly Val Glu Gly Pro Tyr Ala Leu Val Leu Ser Pro Asp
                165                 170                 175

Leu Tyr Thr Ala Leu Phe Arg Val Tyr Asp Gly Thr Gly Tyr Pro Glu
            180                 185                 190

Ile Glu His Ile Lys Glu Leu Val Asp Gly Val Ile Trp Ala Pro
        195                 200                 205

Ala Leu Asp Gly Gly Ala Val Leu Val Ser Thr Arg Gly Gly Asp Phe
    210                 215                 220

Asp Leu Thr Leu Gly Gln Asp Leu Ser Ile Gly Tyr Leu Ser His Asp
225                 230                 235                 240

Ala Asp Asn Val Glu Leu Phe Leu Thr Glu Ser Phe Thr
                245                 250

<210> SEQ ID NO 3
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 3

Asp Asn Leu Lys Arg Glu Leu Ala Pro Leu Thr Glu Glu Ala Trp Ala
1               5                   10                  15

Glu Ile Asp Glu Glu Ala Arg Glu Thr Ala Lys Arg His Leu Ala Gly
            20                  25                  30

Arg Arg Val Val Asp Val Glu Gly Pro Leu Gly Trp Gly
        35                  40                  45

<210> SEQ ID NO 4
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 4
```

Tyr Ser Ala Val Pro Leu Gly Arg Leu Glu Ile Glu Gly Pro Ala
1               5                   10                  15

Glu Gly Val Gln Ala Gly Val Arg Gln Val Leu Pro
            20                  25

<210> SEQ ID NO 5
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 5

Leu Pro Glu Leu Arg Val Pro Phe Thr Leu Ser Arg Arg Asp Leu Asp
1               5                   10                  15

Ala Val Glu Arg Gly Ala Lys Asp Leu Asp Leu Ser Pro Val Ala Glu
            20                  25                  30

Ala Ala Arg Lys Leu Ala Arg Ala Glu Asp Arg Leu Ile Phe Asn Gly
        35                  40                  45

Tyr Ala Glu Ala Gly Ile Glu Gly
    50                  55

<210> SEQ ID NO 6
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 6

Leu Leu Asn Ala Ser Gly Asn Leu Lys Leu Pro Leu Ser Ala Asp Pro
1               5                   10                  15

Gly Asp Ile Pro Asp Ala Ile Ala Glu Ala Leu Thr Lys Leu Arg Glu
            20                  25                  30

Ala Gly Val Glu Gly Pro Tyr Ala Leu Val Leu Ser Pro Asp Leu Tyr
        35                  40                  45

Thr Ala Leu Phe Arg Val Tyr Asp Gly Thr Gly Tyr Pro Glu Ile Glu
    50                  55                  60

His Ile Lys Glu Leu Val Asp Gly Val Ile Trp Ala Pro Ala Leu
65                  70                  75                  80

Asp Gly Gly Ala Val Leu Val Ser Thr Arg
                85                  90

<210> SEQ ID NO 7
<211> LENGTH: 33
<212> TYPE: PRT
<213> ORGANISM: T. maritima

<400> SEQUENCE: 7

Gly Gly Asp Phe Asp Leu Thr Leu Gly Gln Asp Leu Ser Ile Gly Tyr
1               5                   10                  15

Leu Ser His Asp Ala Asp Asn Val Glu Leu Phe Leu Thr Glu Ser Phe
            20                  25                  30

Thr

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide

```
<220> FEATURE:
<221> NAME/KEY: misc_feature
<223> OTHER INFORMATION: wherein X1=D or N
<220> FEATURE:
<221> NAME/KEY: misc_feature
<223> OTHER INFORMATION: X can be any amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 8

Ala Xaa Leu Xaa Xaa
1               5

<210> SEQ ID NO 9
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 9

Lys Trp Lys Ser Phe Ile Lys Lys Leu Thr Lys Ala Ala Lys Lys Val
1               5                  10                  15

Val Thr Thr Ala Lys Lys Pro Leu Ile Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 10

Lys Trp Lys Lys Phe Ile Lys Ser Leu Thr Lys Ser Ala Ala Lys Thr
1               5                  10                  15

Val Val Lys Thr Ala Lys Lys Pro Leu Ile Val
            20                  25

<210> SEQ ID NO 11
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 11

Arg Arg Arg Pro Arg Pro Pro Tyr Leu Pro Arg Pro Arg Pro Pro Pro
1               5                  10                  15

Phe Phe Pro Pro Arg Leu Pro Pro Arg Ile Pro Pro Gly Phe Pro Pro
            20                  25                  30

Arg Phe Pro Pro Arg Phe Pro
            35

<210> SEQ ID NO 12
<211> LENGTH: 18
<212> TYPE: PRT
<213> ORGANISM: Artificial Sequence
<220> FEATURE:
<223> OTHER INFORMATION: Synthetic polypeptide
```

<400> SEQUENCE: 12

Gly Asn Asn Arg Pro Val Tyr Ile Pro Gln Pro Arg Pro Pro His Pro
1               5                   10                  15

Arg Ile

<210> SEQ ID NO 13
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 13

Leu Glu Val Leu Phe Gln Gly Pro Gly Pro
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 14

Asp Asp Asp Asp Lys
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 15

Ile Glu Gly Arg
1

<210> SEQ ID NO 16
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 16

Glu Asn Leu Tyr Phe Gln Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

Leu Val Pro Arg Gly Ser
1               5

<210> SEQ ID NO 18
<211> LENGTH: 320
<212> TYPE: PRT
<213> ORGANISM: Artificial Sequence
<220> FEATURE:
<223> OTHER INFORMATION: Synthetic polypeptide

<400> SEQUENCE: 18

```
Met Gly Asn Asn Arg Pro Val Tyr Ile Pro Gln Pro Arg Pro His
1               5                   10                  15

Pro Arg Ile Glu Asn Leu Tyr Phe Gln Gly Gly Thr Ser Glu Phe Leu
            20                  25                  30

Lys Arg Ser Phe Ala Pro Leu Thr Glu Lys Gln Trp Gln Glu Ile Asp
        35                  40                  45

Asn Arg Ala Arg Glu Ile Phe Lys Thr Gln Leu Tyr Gly Arg Lys Phe
    50                  55                  60

Val Asp Val Glu Gly Pro Tyr Gly Trp Glu Tyr Ala Ala His Pro Leu
65                  70                  75                  80

Gly Glu Val Gly Val Leu Ser Asp Glu Asn Glu Val Val Lys Trp Gly
                85                  90                  95

Leu Arg Lys Ser Leu Pro Leu Ile Glu Leu Arg Ala Thr Phe Thr Leu
            100                 105                 110

Asp Leu Trp Glu Leu Asp Asn Leu Glu Arg Gly Lys Pro Asn Val Asp
        115                 120                 125

Leu Ser Ser Leu Glu Glu Thr Val Arg Lys Val Ala Glu Phe Glu Asp
    130                 135                 140

Glu Val Ile Phe Arg Gly Cys Glu Lys Ser Gly Val Lys Gly Leu Leu
145                 150                 155                 160

Ser Phe Glu Glu Arg Lys Gly Gly Gly Gly Glu Asn Leu Tyr Phe
                165                 170                 175

Gln Gly His His His His His Gly Gly Gly Gly Ile Glu Cys
            180                 185                 190

Gly Ser Thr Pro Lys Asp Leu Leu Glu Ala Ile Val Arg Ala Leu Ser
            195                 200                 205

Ile Phe Ser Lys Asp Gly Ile Glu Gly Pro Tyr Thr Leu Val Ile Asn
        210                 215                 220

Thr Asp Arg Trp Ile Asn Phe Leu Lys Glu Glu Ala Gly His Tyr Pro
225                 230                 235                 240

Leu Glu Lys Arg Val Glu Glu Cys Leu Arg Gly Gly Lys Ile Ile Thr
                245                 250                 255

Thr Pro Arg Ile Glu Asp Ala Leu Val Val Ser Glu Arg Gly Gly Asp
            260                 265                 270

Phe Lys Leu Ile Leu Gly Gln Asp Leu Ser Ile Gly Tyr Glu Asp Arg
        275                 280                 285

Glu Lys Asp Ala Val Arg Leu Phe Ile Thr Glu Thr Phe Thr Phe Gln
    290                 295                 300

Val Val Asn Pro Glu Ala Leu Ile Leu Leu Lys Phe Ser Gly Gly Ser
305                 310                 315                 320
```

<210> SEQ ID NO 19
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 19

```
Gly Asn Asn Arg Pro Val Tyr Ile Pro Gln Pro Arg Pro His Pro
1               5                   10                  15

Arg Ile Glu Asn Leu Tyr Phe Gln
            20
```

```
<210> SEQ ID NO 20
<211> LENGTH: 37
<212> TYPE: PRT
<213> ORGANISM: Artificial Sequence
<220> FEATURE:
<223> OTHER INFORMATION: Synthetic polypeptide

<400> SEQUENCE: 20

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 21
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 21

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

<210> SEQ ID NO 22
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 22

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 23
<211> LENGTH: 315
<212> TYPE: PRT
<213> ORGANISM: Artificial Sequence
<220> FEATURE:
<223> OTHER INFORMATION: Synthetic polypeptide

<400> SEQUENCE: 23

Met Gly Asn Asn Arg Pro Val Tyr Ile Pro Gln Pro Arg Pro Pro His
1               5                   10                  15

Pro Arg Ile Glu Asn Leu Tyr Phe Gln Gly Gly Thr Ser Pro Asp Phe
            20                  25                  30

Leu Gly His Ala Glu Asn Pro Leu Arg Glu Glu Trp Ala Arg Leu
        35                  40                  45

Asn Glu Thr Val Ile Gln Val Ala Arg Arg Ser Leu Val Gly Arg Arg
    50                  55                  60

Ile Leu Asp Ile Tyr Gly Pro Leu Gly Ala Gly Val Gln Thr Val Pro
65                  70                  75                  80
```

Tyr Asp Glu Phe Gln Gly Val Ser Pro Gly Ala Val Asp Ile Val Gly
            85                  90                  95

Glu Gln Glu Thr Ala Met Val Phe Thr Asp Ala Arg Lys Phe Lys Thr
        100                 105                 110

Ile Pro Ile Ile Tyr Lys Asp Phe Leu Leu His Trp Arg Asp Ile Glu
        115                 120                 125

Ala Ala Arg Thr His Asn Met Pro Leu Asp Val Ser Ala Ala Ala Gly
        130                 135                 140

Ala Ala Ala Leu Cys Ala Gln Gln Glu Asp Glu Leu Ile Phe Tyr Gly
145                 150                 155                 160

Asp Ala Arg Leu Gly Tyr Glu Gly Leu Met Thr Ala Asn Gly Arg Leu
                165                 170                 175

Thr Val Pro Leu Gly Asp Trp Thr Ser Pro Gly Gly Phe Gln Ala
                180                 185                 190

Ile Val Glu Ala Thr Arg Lys Leu Asn Glu Gln Gly His Phe Gly Pro
                195                 200                 205

Tyr Ala Val Val Leu Ser Pro Arg Leu Tyr Ser Gln Leu His Arg Ile
        210                 215                 220

Tyr Glu Lys Thr Gly Val Leu Glu Ile Glu Thr Ile Arg Gln Leu Ala
225                 230                 235                 240

Ser Asp Gly Val Tyr Gln Ser Asn Arg Leu Arg Gly Glu Ser Gly Val
                245                 250                 255

Val Val Ser Thr Gly Arg Glu Asn Met Asp Leu Ala Val Ser Met Asp
                260                 265                 270

Met Val Ala Ala Tyr Leu Gly Ala Ser Arg Met Asn His Pro Phe Arg
                275                 280                 285

Val Leu Glu Ala Leu Leu Leu Arg Ile Lys His Pro Asp Ala Ile Cys
        290                 295                 300

Thr Leu Glu Gly Ala Gly Ala Thr Glu Arg Arg
305                 310                 315

<210> SEQ ID NO 24
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 24

Gly Leu Asn Asp Ile Phe Glu Ala Gln Lys Ile Glu Trp His Glu
1               5                   10                  15

<210> SEQ ID NO 25
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 25

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 26
<211> LENGTH: 6
<212> TYPE: PRT
<213> ORGANISM: Artificial Sequence

```
<220> FEATURE:
<223> OTHER INFORMATION: Synthetic polypeptide

<400> SEQUENCE: 26

Glu Glu Glu Glu Glu Glu
1               5

<210> SEQ ID NO 27
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 27

Gly Ala Pro Val Pro Tyr Pro Asp Pro Leu Glu Pro Arg
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 28

Asp Tyr Lys Asp Asp Asp Asp Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 29

Tyr Pro Tyr Asp Val Pro Asp Tyr Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 30

His His His His His His
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 31

Glu Gln Lys Leu Ile Ser Glu Glu Asp Leu
1               5                   10

<210> SEQ ID NO 32
<211> LENGTH: 18
<212> TYPE: PRT
<213> ORGANISM: Artificial Sequence
<220> FEATURE:
```

<223> OTHER INFORMATION: Synthetic polypeptide

<400> SEQUENCE: 32

Thr Lys Glu Asn Pro Arg Ser Asn Gln Glu Ser Tyr Asp Asp Asn
1               5                   10                  15

Glu Ser

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 33

Lys Glu Thr Ala Ala Ala Lys Phe Glu Arg Gln His Met Asp Ser
1               5                   10                  15

<210> SEQ ID NO 34
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 34

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
                20                  25                  30

Gln Gly Gln Arg Glu Pro
        35

<210> SEQ ID NO 35
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 35

Ser Leu Ala Glu Leu Leu Asn Ala Gly Leu Gly Gly Ser
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 36

Thr Gln Asp Pro Ser Arg Val Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 37

Trp Ser His Pro Gln Phe Glu Lys
1               5

```
<210> SEQ ID NO 38
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 38

Cys Cys Pro Gly Cys Cys
1               5

<210> SEQ ID NO 39
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 39

Gly Lys Pro Ile Pro Asn Pro Leu Leu Gly Leu Asp Ser Thr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 40

Tyr Thr Asp Ile Glu Met Asn Arg Leu Gly Lys
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 41

Asp Leu Tyr Asp Asp Asp Asp Lys
1               5

<210> SEQ ID NO 42
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 42

Thr Asp Lys Asp Met Thr Ile Thr Phe Thr Asn Lys Lys Asp Ala Glu
1               5                   10                  15

<210> SEQ ID NO 43
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 43

Ala His Ile Val Met Val Asp Ala Tyr Lys Pro Thr Lys
1               5                   10
```

<210> SEQ ID NO 44
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 44

Lys Leu Gly Asp Ile Glu Phe Ile Lys Val Asn Lys
1               5                   10

<210> SEQ ID NO 45
<211> LENGTH: 264
<212> TYPE: PRT
<213> ORGANISM: T. maritima

<400> SEQUENCE: 45

Glu Phe Leu Lys Arg Ser Phe Ala Pro Leu Thr Glu Lys Gln Trp Gln
1               5                   10                  15

Glu Ile Asp Asn Arg Ala Arg Glu Ile Phe Lys Thr Gln Leu Tyr Gly
                20                  25                  30

Arg Lys Phe Val Asp Val Glu Gly Pro Tyr Gly Trp Glu Tyr Ala Ala
            35                  40                  45

His Pro Leu Gly Glu Val Glu Val Leu Ser Asp Glu Asn Glu Val Val
        50                  55                  60

Lys Trp Gly Leu Arg Lys Ser Leu Pro Leu Ile Glu Leu Arg Ala Thr
65                  70                  75                  80

Phe Thr Leu Asp Leu Trp Glu Leu Asp Asn Leu Glu Arg Gly Lys Pro
                85                  90                  95

Asn Val Asp Leu Ser Ser Leu Glu Glu Thr Val Arg Lys Val Ala Glu
            100                 105                 110

Phe Glu Asp Glu Val Ile Phe Arg Gly Cys Glu Lys Ser Gly Val Lys
        115                 120                 125

Gly Leu Leu Ser Phe Glu Glu Arg Lys Ile Glu Cys Gly Ser Thr Pro
    130                 135                 140

Lys Asp Leu Leu Glu Ala Ile Val Arg Ala Leu Ser Ile Phe Ser Lys
145                 150                 155                 160

Asp Gly Ile Glu Gly Pro Tyr Thr Leu Val Ile Asn Thr Asp Arg Trp
                165                 170                 175

Ile Asn Phe Leu Lys Glu Glu Ala Gly His Tyr Pro Leu Glu Lys Arg
            180                 185                 190

Val Glu Glu Cys Leu Arg Gly Gly Lys Ile Ile Thr Thr Pro Arg Ile
        195                 200                 205

Glu Asp Ala Leu Val Val Ser Glu Arg Gly Gly Asp Phe Lys Leu Ile
    210                 215                 220

Leu Gly Gln Asp Leu Ser Ile Gly Tyr Glu Asp Arg Glu Lys Asp Ala
225                 230                 235                 240

Val Arg Leu Phe Ile Thr Glu Thr Phe Thr Phe Gln Val Val Asn Pro
                245                 250                 255

Glu Ala Leu Ile Leu Leu Lys Phe
            260

<210> SEQ ID NO 46
<211> LENGTH: 277
<212> TYPE: PRT
<213> ORGANISM: M. xanthus

<400> SEQUENCE: 46

Asp Phe Leu Gly His Ala Glu Asn Pro Leu Arg Glu Glu Trp Ala
1               5                   10                  15

Arg Leu Asn Glu Thr Val Ile Gln Val Ala Arg Arg Ser Leu Val Gly
            20                  25                  30

Arg Arg Ile Leu Asp Ile Tyr Gly Pro Leu Gly Ala Gly Val Gln Thr
                35                  40                  45

Val Pro Tyr Asp Glu Phe Gln Gly Val Ser Pro Gly Ala Val Asp Ile
    50                  55                  60

Val Gly Glu Gln Glu Thr Ala Met Val Phe Thr Asp Ala Arg Lys Phe
65                  70                  75                  80

Lys Thr Ile Pro Ile Ile Tyr Lys Asp Phe Leu Leu His Trp Arg Asp
                85                  90                  95

Ile Glu Ala Ala Arg Thr His Asn Met Pro Leu Asp Val Ser Ala Ala
                100                 105                 110

Ala Gly Ala Ala Ala Leu Cys Ala Gln Gln Glu Asp Glu Leu Ile Phe
            115                 120                 125

Tyr Gly Asp Ala Arg Leu Gly Tyr Glu Gly Leu Met Thr Ala Asn Gly
    130                 135                 140

Arg Leu Thr Val Pro Leu Gly Asp Trp Thr Ser Pro Gly Gly Phe
145                 150                 155                 160

Gln Ala Ile Val Glu Ala Thr Arg Lys Leu Asn Glu Gln Gly His Phe
                165                 170                 175

Gly Pro Tyr Ala Val Val Leu Ser Pro Arg Leu Tyr Ser Gln Leu His
            180                 185                 190

Arg Ile Tyr Glu Lys Thr Gly Val Leu Glu Ile Glu Thr Ile Arg Gln
                195                 200                 205

Leu Ala Ser Asp Gly Val Tyr Gln Ser Asn Arg Leu Arg Gly Glu Ser
    210                 215                 220

Gly Val Val Ser Thr Gly Arg Glu Asn Met Asp Leu Ala Val Ser
225                 230                 235                 240

Met Asp Met Val Ala Ala Tyr Leu Gly Ala Ser Arg Met Asn His Pro
                245                 250                 255

Phe Arg Val Leu Glu Ala Leu Leu Arg Ile Lys His Pro Asp Ala
            260                 265                 270

Ile Cys Thr Leu Glu
        275

<210> SEQ ID NO 47
<211> LENGTH: 269
<212> TYPE: PRT
<213> ORGANISM: T. maritima

<400> SEQUENCE: 47

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
                20                  25                  30

Gly Arg Lys Phe Val Asp Val Glu Gly Pro Tyr Gly Trp Glu Tyr Ala
            35                  40                  45

Ala His Pro Leu Gly Glu Val Glu Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys

Pro Asn Val Asp Leu Ser Ser Leu Glu Glu Thr Val Arg Lys Val Ala
            85                  90                  95             100

Glu Phe Glu Asp Glu Val Ile Phe Arg Gly Cys Glu Lys Ser Gly Val
            115                 120                 125

Lys Gly Leu Leu Ser Phe Glu Arg Lys Ile Glu Cys Gly Ser Thr
            130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
            165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
            210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
            245                 250                 255

Pro Glu Ala Leu Ile Leu Leu Lys Phe Ser Gly Gly Ser
            260                 265

<210> SEQ ID NO 48
<211> LENGTH: 286
<212> TYPE: PRT
<213> ORGANISM: Artificial Sequence
<220> FEATURE:
<223> OTHER INFORMATION: Synthetic polypeptide

<400> SEQUENCE: 48

Met Ser Glu Phe Leu Lys Arg Ser Phe Ala Pro Leu Thr Glu Lys Gln
1               5                   10                  15

Trp Gln Glu Ile Asp Asn Arg Ala Arg Glu Ile Phe Lys Thr Gln Leu
            20                  25                  30

Tyr Gly Arg Lys Phe Val Asp Val Glu Gly Pro Tyr Gly Trp Glu Tyr
            35                  40                  45

Ala Ala His Pro Leu Gly Glu Val Val Leu Ser Asp Glu Asn Glu
            50                  55                  60

Val Val Lys Trp Gly Leu Arg Lys Ser Leu Pro Leu Ile Glu Leu Arg
65                  70                  75                  80

Ala Thr Phe Thr Leu Asp Leu Trp Glu Leu Asp Asn Leu Glu Arg Gly
            85                  90                  95

Lys Pro Asn Val Asp Leu Ser Ser Leu Glu Glu Thr Val Arg Lys Val
            100                 105                 110

Ala Glu Phe Glu Asp Glu Val Ile Phe Arg Gly Cys Glu Lys Ser Gly
            115                 120                 125

Val Lys Gly Leu Leu Ser Phe Glu Arg Lys Gly Gly Gly Gly
            130                 135                 140

His His His His His Gly Gly Gly Gly Ile Glu Cys Gly Ser
145                 150                 155                 160

Thr Pro Lys Asp Leu Leu Glu Ala Ile Val Arg Ala Leu Ser Ile Phe
            165                 170                 175

Ser Lys Asp Gly Ile Glu Gly Pro Tyr Thr Leu Val Ile Asn Thr Asp

```
                 180                 185                 190
Arg Trp Ile Asn Phe Leu Lys Glu Glu Ala Gly His Tyr Pro Leu Glu
            195                 200                 205

Lys Arg Val Glu Glu Cys Leu Arg Gly Gly Lys Ile Thr Thr Pro
        210                 215                 220

Arg Ile Glu Asp Ala Leu Val Val Ser Glu Arg Gly Asp Phe Lys
225                 230                 235                 240

Leu Ile Leu Gly Gln Asp Leu Ser Ile Gly Tyr Glu Asp Arg Glu Lys
            245                 250                 255

Asp Ala Val Arg Leu Phe Ile Thr Glu Thr Phe Thr Phe Gln Val Val
        260                 265                 270

Asn Pro Glu Ala Leu Ile Leu Leu Lys Phe Ser Gly Ser
            275                 280                 285

<210> SEQ ID NO 49
<211> LENGTH: 331
<212> TYPE: PRT
<213> ORGANISM: Artificial Sequence
<220> FEATURE:
<223> OTHER INFORMATION: Synthetic polypeptide

<400> SEQUENCE: 49

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Gly Gly Thr Ser Glu Phe Leu Lys Arg Ser Phe Ala
        35                  40                  45

Pro Leu Thr Glu Lys Gln Trp Gln Glu Ile Asp Asn Arg Ala Arg Glu
    50                  55                  60

Ile Phe Lys Thr Gln Leu Tyr Gly Arg Lys Phe Val Asp Val Glu Gly
65                  70                  75                  80

Pro Tyr Gly Trp Glu Tyr Ala Ala His Pro Leu Gly Glu Val Glu Val
                85                  90                  95

Leu Ser Asp Glu Asn Glu Val Val Lys Trp Gly Leu Arg Lys Ser Leu
            100                 105                 110

Pro Leu Ile Glu Leu Arg Ala Thr Phe Thr Leu Asp Leu Trp Glu Leu
        115                 120                 125

Asp Asn Leu Glu Arg Gly Lys Pro Asn Val Asp Leu Ser Ser Leu Glu
    130                 135                 140

Glu Thr Val Arg Lys Val Ala Glu Phe Glu Asp Glu Val Ile Phe Arg
145                 150                 155                 160

Gly Cys Glu Lys Ser Gly Val Lys Gly Leu Leu Ser Phe Glu Glu Arg
                165                 170                 175

Lys Gly Gly Gly Gly Glu Asn Leu Tyr Phe Gln Gly His His His
            180                 185                 190

His His His Gly Gly Gly Gly Ile Glu Cys Gly Ser Thr Pro Lys
        195                 200                 205

Asp Leu Leu Glu Ala Ile Val Arg Ala Leu Ser Ile Phe Ser Lys Asp
    210                 215                 220

Gly Ile Glu Gly Pro Tyr Thr Leu Val Ile Asn Thr Asp Arg Trp Ile
225                 230                 235                 240

Asn Phe Leu Lys Glu Glu Ala Gly His Tyr Pro Leu Glu Lys Arg Val
                245                 250                 255

Glu Glu Cys Leu Arg Gly Gly Lys Ile Ile Thr Thr Pro Arg Ile Glu
```

```
                    260                 265                 270

Asp Ala Leu Val Val Ser Glu Arg Gly Gly Asp Phe Lys Leu Ile Leu
            275                 280                 285

Gly Gln Asp Leu Ser Ile Gly Tyr Glu Asp Arg Glu Lys Asp Ala Val
        290                 295                 300

Arg Leu Phe Ile Thr Glu Thr Phe Thr Phe Gln Val Val Asn Pro Glu
305                 310                 315                 320

Ala Leu Ile Leu Leu Lys Phe Ser Gly Gly Ser
                325                 330

<210> SEQ ID NO 50
<211> LENGTH: 342
<212> TYPE: PRT
<213> ORGANISM: Artificial Sequence
<220> FEATURE:
<223> OTHER INFORMATION: Synthetic polypeptide

<400> SEQUENCE: 50

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Gly Gly Thr Ser Glu Phe Leu Lys Arg Ser Phe Ala
        35                  40                  45

Pro Leu Thr Glu Lys Gln Trp Gln Glu Ile Asp Asn Arg Ala Arg Glu
    50                  55                  60

Ile Phe Lys Thr Gln Leu Tyr Gly Arg Lys Phe Val Asp Val Glu Gly
65                  70                  75                  80

Pro Tyr Gly Trp Glu Tyr Ala Ala His Pro Leu Gly Glu Val Glu Val
                85                  90                  95

Leu Ser Asp Glu Asn Glu Val Val Lys Trp Gly Leu Arg Lys Gly Gly
            100                 105                 110

Glu Asn Leu Tyr Phe Gln Gly Gly Gly Ser Leu Pro Leu Ile Glu Leu
        115                 120                 125

Arg Ala Thr Phe Thr Leu Asp Leu Trp Glu Leu Asp Asn Leu Glu Arg
    130                 135                 140

Gly Lys Pro Asn Val Asp Leu Ser Ser Leu Glu Glu Thr Val Arg Lys
145                 150                 155                 160

Val Ala Glu Phe Glu Asp Glu Val Ile Phe Arg Gly Cys Glu Lys Ser
                165                 170                 175

Gly Val Lys Gly Leu Leu Ser Phe Glu Glu Arg Lys Gly Gly Gly Gly
            180                 185                 190

Gly Glu Asn Leu Tyr Phe Gln Gly His His His His His Gly Gly
        195                 200                 205

Gly Gly Gly Ile Glu Cys Gly Ser Thr Pro Lys Asp Leu Leu Glu Ala
    210                 215                 220

Ile Val Arg Ala Leu Ser Ile Phe Ser Lys Asp Gly Ile Glu Gly Pro
225                 230                 235                 240

Tyr Thr Leu Val Ile Asn Thr Asp Arg Trp Ile Asn Phe Leu Lys Glu
                245                 250                 255

Glu Ala Gly His Tyr Pro Leu Glu Lys Arg Val Glu Glu Cys Leu Arg
            260                 265                 270

Gly Gly Lys Ile Ile Thr Thr Pro Arg Ile Glu Asp Ala Leu Val Val
        275                 280                 285

Ser Glu Arg Gly Gly Asp Phe Lys Leu Ile Leu Gly Gln Asp Leu Ser
```

```
            290                 295                 300
Ile Gly Tyr Glu Asp Arg Glu Lys Asp Ala Val Arg Leu Phe Ile Thr
305                 310                 315                 320

Glu Thr Phe Thr Phe Gln Val Val Asn Pro Glu Ala Leu Ile Leu Leu
                325                 330                 335

Lys Phe Ser Gly Gly Ser
            340

<210> SEQ ID NO 51
<211> LENGTH: 342
<212> TYPE: PRT
<213> ORGANISM: Artificial Sequence
<220> FEATURE:
<223> OTHER INFORMATION: Synthetic polypeptide

<400> SEQUENCE: 51

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Gly Gly Thr Ser Glu Phe Leu Lys Arg Ser Phe Ala
        35                  40                  45

Pro Leu Thr Glu Lys Gln Trp Gln Glu Ile Asp Asn Arg Ala Arg Glu
50                  55                  60

Ile Phe Lys Thr Gln Leu Tyr Gly Arg Lys Phe Val Asp Val Glu Gly
65                  70                  75                  80

Pro Tyr Gly Trp Glu Tyr Ala Ala His Pro Leu Gly Glu Val Glu Val
                85                  90                  95

Leu Ser Asp Gly Gly Glu Asn Leu Tyr Phe Gln Gly Gly Gly Glu Asn
            100                 105                 110

Glu Val Val Lys Trp Gly Leu Arg Lys Ser Leu Pro Leu Ile Glu Leu
        115                 120                 125

Arg Ala Thr Phe Thr Leu Asp Leu Trp Glu Leu Asp Asn Leu Glu Arg
    130                 135                 140

Gly Lys Pro Asn Val Asp Leu Ser Ser Leu Glu Glu Thr Val Arg Lys
145                 150                 155                 160

Val Ala Glu Phe Glu Asp Glu Val Ile Phe Arg Gly Cys Glu Lys Ser
                165                 170                 175

Gly Val Lys Gly Leu Leu Ser Phe Glu Glu Arg Lys Gly Gly Gly Gly
            180                 185                 190

Gly Glu Asn Leu Tyr Phe Gln Gly His His His His His Gly Gly
        195                 200                 205

Gly Gly Gly Ile Glu Cys Gly Ser Thr Pro Lys Asp Leu Leu Glu Ala
    210                 215                 220

Ile Val Arg Ala Leu Ser Ile Phe Ser Lys Asp Gly Ile Glu Gly Pro
225                 230                 235                 240

Tyr Thr Leu Val Ile Asn Thr Asp Arg Trp Ile Asn Phe Leu Lys Glu
                245                 250                 255

Glu Ala Gly His Tyr Pro Leu Glu Lys Arg Val Glu Glu Cys Leu Arg
            260                 265                 270

Gly Gly Lys Ile Ile Thr Thr Pro Arg Ile Glu Asp Ala Leu Val Val
        275                 280                 285

Ser Glu Arg Gly Gly Asp Phe Lys Leu Ile Leu Gly Gln Asp Leu Ser
    290                 295                 300

Ile Gly Tyr Glu Asp Arg Glu Lys Asp Ala Val Arg Leu Phe Ile Thr
```

Glu Thr Phe Thr Phe Gln Val Val Asn Pro Glu Ala Leu Ile Leu Leu
305                 310                 315                 320

Lys Phe Ser Gly Gly Ser
            325

<210> SEQ ID NO 52
<211> LENGTH: 342
<212> TYPE: PRT
<213> ORGANISM: Artificial Sequence
<220> FEATURE:
<223> OTHER INFORMATION: Synthetic polypeptide

<400> SEQUENCE: 52

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
                20                  25                  30

Gln Gly Gly Gly Gly Thr Ser Glu Phe Leu Lys Arg Ser Phe Ala
            35                  40                  45

Pro Leu Thr Glu Lys Gln Trp Gln Glu Ile Asp Asn Arg Ala Arg Glu
50                  55                  60

Ile Phe Lys Thr Gln Leu Tyr Gly Arg Lys Phe Val Asp Val Glu Gly
65                  70                  75                  80

Pro Tyr Gly Trp Glu Tyr Ala Ala His Pro Leu Gly Glu Val Glu Val
                85                  90                  95

Gly Gly Glu Asn Leu Tyr Phe Gln Gly Gly Gly Leu Ser Asp Glu Asn
            100                 105                 110

Glu Val Val Lys Trp Gly Leu Arg Lys Ser Leu Pro Leu Ile Glu Leu
            115                 120                 125

Arg Ala Thr Phe Thr Leu Asp Leu Trp Glu Leu Asp Asn Leu Glu Arg
            130                 135                 140

Gly Lys Pro Asn Val Asp Leu Ser Ser Leu Glu Glu Thr Val Arg Lys
145                 150                 155                 160

Val Ala Glu Phe Glu Asp Glu Val Ile Phe Arg Gly Cys Glu Lys Ser
                165                 170                 175

Gly Val Lys Gly Leu Leu Ser Phe Glu Glu Arg Lys Gly Gly Gly Gly
            180                 185                 190

Gly Glu Asn Leu Tyr Phe Gln Gly His His His His His Gly Gly
            195                 200                 205

Gly Gly Gly Ile Glu Cys Gly Ser Thr Pro Lys Asp Leu Leu Glu Ala
            210                 215                 220

Ile Val Arg Ala Leu Ser Ile Phe Ser Lys Asp Gly Ile Glu Gly Pro
225                 230                 235                 240

Tyr Thr Leu Val Ile Asn Thr Asp Arg Trp Ile Asn Phe Leu Lys Glu
                245                 250                 255

Glu Ala Gly His Tyr Pro Leu Gly Lys Arg Val Glu Glu Cys Leu Arg
            260                 265                 270

Gly Gly Lys Ile Ile Thr Thr Pro Arg Ile Glu Asp Ala Leu Val Val
            275                 280                 285

Ser Glu Arg Gly Gly Asp Phe Lys Leu Ile Leu Gly Gln Asp Leu Ser
            290                 295                 300

Ile Gly Tyr Glu Asp Arg Glu Lys Asp Ala Val Arg Leu Phe Ile Thr
305                 310                 315                 320

Glu Thr Phe Thr Phe Gln Val Val Asn Pro Glu Ala Leu Ile Leu Leu

<210> SEQ ID NO 53
<211> LENGTH: 319
<212> TYPE: PRT
<213> ORGANISM: Artificial Sequence
<220> FEATURE:
<223> OTHER INFORMATION: Synthetic polypeptide

<400> SEQUENCE: 53

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Gly Gly Thr Ser Glu Phe Leu Lys Arg Ser Phe Ala
        35                  40                  45

Pro Leu Thr Glu Lys Gln Trp Gln Glu Ile Asp Asn Arg Ala Arg Glu
    50                  55                  60

Ile Phe Lys Thr Gln Leu Tyr Gly Arg Lys Phe Val Asp Val Glu Gly
65                  70                  75                  80

Pro Tyr Gly Trp Glu Tyr Ala Ala His Pro Leu Gly Glu Val Glu Val
                85                  90                  95

Leu Ser Asp Glu Asn Glu Val Val Lys Trp Gly Leu Arg Lys Gly Gly
            100                 105                 110

Glu Asn Leu Tyr Phe Gln Gly Gly Gly Ser Leu Pro Leu Ile Glu Leu
        115                 120                 125

Arg Ala Thr Phe Thr Leu Asp Leu Trp Glu Leu Asp Asn Leu Glu Arg
    130                 135                 140

Gly Lys Pro Asn Val Asp Leu Ser Ser Leu Glu Glu Thr Val Arg Lys
145                 150                 155                 160

Val Ala Glu Phe Glu Asp Glu Val Ile Phe Arg Gly Cys Glu Lys Ser
                165                 170                 175

Gly Val Lys Gly Leu Leu Ser Phe Glu Glu Arg Lys Ile Glu Cys Gly
            180                 185                 190

Ser Thr Pro Lys Asp Leu Leu Glu Ala Ile Val Arg Ala Leu Ser Ile
        195                 200                 205

Phe Ser Lys Asp Gly Ile Glu Gly Pro Tyr Thr Leu Val Ile Asn Thr
    210                 215                 220

Asp Arg Trp Ile Asn Phe Leu Lys Glu Glu Ala Gly His Tyr Pro Leu
225                 230                 235                 240

Glu Lys Arg Val Glu Glu Cys Leu Arg Gly Gly Lys Ile Ile Thr Thr
                245                 250                 255

Pro Arg Ile Glu Asp Ala Leu Val Val Ser Glu Arg Gly Gly Asp Phe
            260                 265                 270

Lys Leu Ile Leu Gly Gln Asp Leu Ser Ile Gly Tyr Glu Asp Arg Glu
        275                 280                 285

Lys Asp Ala Val Arg Leu Phe Ile Thr Glu Thr Phe Thr Phe Gln Val
    290                 295                 300

Val Asn Pro Glu Ala Leu Ile Leu Leu Lys Phe Ser Gly Gly Ser
305                 310                 315

<210> SEQ ID NO 54
<211> LENGTH: 325
<212> TYPE: PRT

<213> ORGANISM: Artificial Sequence
<220> FEATURE:
<223> OTHER INFORMATION: Synthetic polypeptide

<400> SEQUENCE: 54

| | | | | | | | | | | | | | | |
|---|---|---|---|---|---|---|---|---|---|---|---|---|---|---|
| Met | Glu | Phe | Leu | Lys | Arg | Ser | Phe | Ala | Pro | Leu | Thr | Glu | Lys | Gln | Trp |
| 1 | | | | 5 | | | | | 10 | | | | | 15 | |
| Gln | Glu | Ile | Asp | Asn | Arg | Ala | Arg | Glu | Ile | Phe | Lys | Thr | Gln | Leu | Tyr |
| | | | 20 | | | | | 25 | | | | | 30 | | |
| Gly | Arg | Lys | Phe | Val | Asp | Val | Glu | Gly | Pro | Tyr | Gly | Trp | Glu | Tyr | Ala |
| | | 35 | | | | | 40 | | | | | 45 | | | |
| Ala | His | Pro | Leu | Gly | Glu | Val | Glu | Val | Leu | Ser | Asp | Glu | Asn | Glu | Val |
| | 50 | | | | | 55 | | | | | 60 | | | | |
| Val | Lys | Trp | Gly | Leu | Arg | Lys | Ser | Leu | Pro | Leu | Ile | Glu | Leu | Arg | Ala |
| 65 | | | | | 70 | | | | | 75 | | | | | 80 |
| Thr | Phe | Thr | Leu | Asp | Leu | Trp | Glu | Leu | Asp | Asn | Leu | Glu | Arg | Gly | Lys |
| | | | | 85 | | | | | 90 | | | | | 95 | |
| Pro | Asn | Val | Asp | Leu | Ser | Ser | Leu | Glu | Glu | Thr | Val | Arg | Lys | Val | Ala |
| | | | 100 | | | | | 105 | | | | | 110 | | |
| Glu | Phe | Glu | Asp | Glu | Val | Ile | Phe | Arg | Gly | Cys | Glu | Lys | Ser | Gly | Val |
| | | 115 | | | | | 120 | | | | | 125 | | | |
| Lys | Gly | Leu | Leu | Ser | Phe | Glu | Glu | Arg | Lys | Gly | Gly | Gly | Gly | Gly | Glu |
| | 130 | | | | | 135 | | | | | 140 | | | | |
| Asn | Leu | Tyr | Phe | Gln | Gly | His | His | His | His | His | Gly | Gly | Gly | Gly | Gly |
| 145 | | | | | 150 | | | | | 155 | | | | | 160 |
| Gly | Ile | Glu | Cys | Gly | Ser | Thr | Pro | Lys | Asp | Leu | Leu | Glu | Ala | Ile | Val |
| | | | | 165 | | | | | 170 | | | | | 175 | |
| Arg | Ala | Leu | Ser | Ile | Phe | Ser | Lys | Asp | Gly | Ile | Glu | Gly | Pro | Tyr | Thr |
| | | | 180 | | | | | 185 | | | | | 190 | | |
| Leu | Val | Ile | Asn | Thr | Asp | Arg | Trp | Ile | Asn | Phe | Leu | Lys | Glu | Glu | Ala |
| | | | | 195 | | | | | 200 | | | | | 205 | |
| Gly | His | Tyr | Pro | Leu | Glu | Lys | Arg | Val | Glu | Glu | Cys | Leu | Arg | Gly | Gly |
| | 210 | | | | | 215 | | | | | 220 | | | | |
| Lys | Ile | Ile | Thr | Thr | Pro | Arg | Ile | Glu | Asp | Ala | Leu | Val | Val | Ser | Glu |
| 225 | | | | | 230 | | | | | 235 | | | | | 240 |
| Arg | Gly | Gly | Asp | Phe | Lys | Leu | Ile | Leu | Gly | Gln | Asp | Leu | Ser | Ile | Gly |
| | | | | 245 | | | | | 250 | | | | | 255 | |
| Tyr | Glu | Asp | Arg | Glu | Lys | Asp | Ala | Val | Arg | Leu | Phe | Ile | Thr | Glu | Thr |
| | | | 260 | | | | | 265 | | | | | 270 | | |
| Phe | Thr | Phe | Gln | Val | Val | Asn | Pro | Glu | Ala | Leu | Ile | Leu | Leu | Lys | Phe |
| | | 275 | | | | | 280 | | | | | 285 | | | |
| Ser | Gly | Gly | Ser | Glu | Asn | Leu | Tyr | Phe | Gln | Gly | Lys | Trp | Lys | Ser | Phe |
| | 290 | | | | | 295 | | | | | 300 | | | | |
| Ile | Lys | Lys | Leu | Thr | Lys | Ala | Ala | Lys | Lys | Val | Val | Thr | Thr | Ala | Lys |
| 305 | | | | | 310 | | | | | 315 | | | | | 320 |
| Lys | Pro | Leu | Ile | Val | | | | | | | | | | | |
| | | | | 325 | | | | | | | | | | | |

<210> SEQ ID NO 55
<211> LENGTH: 157
<212> TYPE: PRT
<213> ORGANISM: Artificial Sequence
<220> FEATURE:
<223> OTHER INFORMATION: Synthetic polypeptide

<400> SEQUENCE: 55

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Thr Met Ser Asp Lys Ile Ile His Leu Thr Asp Asp Ser
            35                  40                  45

Phe Asp Thr Asp Val Leu Lys Ala Asp Gly Ala Ile Leu Val Asp Phe
50                  55                  60

Trp Ala Glu Trp Cys Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95

Ile Asp Gln Asn Pro Gly Thr Ala Pro Lys Tyr Gly Ile Arg Gly Ile
                100                 105                 110

Pro Thr Leu Leu Leu Phe Lys Asn Gly Glu Val Ala Ala Thr Lys Val
            115                 120                 125

Gly Ala Leu Ser Lys Gly Gln Leu Lys Glu Phe Leu Asp Ala Asn Leu
            130                 135                 140

Ala Gly Ser Gly Ser Gly Thr His His His His His His
145                 150                 155

<210> SEQ ID NO 56
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 56

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Thr Met Ser Asp Ser Glu Val Asn Gln Glu Ala Lys Pro
            35                  40                  45

Glu Val Lys Pro Glu Val Lys Pro Glu Thr His Ile Asn Leu Lys Val
50                  55                  60

Ser Asp Gly Ser Ser Glu Ile Phe Phe Lys Ile Lys Lys Thr Thr Pro
65                  70                  75                  80

Leu Arg Arg Leu Met Glu Ala Phe Ala Lys Arg Gln Gly Lys Glu Met
                85                  90                  95

Asp Ser Leu Arg Phe Leu Tyr Asp Gly Ile Arg Ile Gln Ala Asp Gln
                100                 105                 110

Thr Pro Glu Asp Leu Asp Met Glu Asp Asn Asp Ile Ile Glu Ala His
            115                 120                 125

Arg Glu Gln Ile Gly Gly Gly Ser Leu Glu His His His His His His
            130                 135                 140

<210> SEQ ID NO 57
<211> LENGTH: 264
<212> TYPE: PRT
<213> ORGANISM: Artificial Sequence
<220> FEATURE:
<223> OTHER INFORMATION: Synthetic polypeptide

<400> SEQUENCE: 57

Met Lys Trp Lys Ser Phe Ile Lys Lys Leu Thr Lys Ala Ala Lys Lys
1               5                   10                  15

```
Val Val Thr Thr Ala Lys Lys Pro Leu Ile Val Glu Asn Leu Tyr Phe
            20                  25                  30

Gln Gly Gly Thr Met Ser Pro Ile Leu Gly Tyr Trp Lys Ile Lys Gly
        35                  40                  45

Leu Val Gln Pro Thr Arg Leu Leu Leu Glu Tyr Leu Glu Glu Lys Tyr
 50                  55                  60

Glu Glu His Leu Tyr Glu Arg Asp Gly Asp Lys Trp Arg Asn Lys
65                  70                  75                  80

Lys Phe Glu Leu Gly Leu Glu Phe Pro Asn Leu Pro Tyr Tyr Ile Asp
                85                  90                  95

Gly Asp Val Lys Leu Thr Gln Ser Met Ala Ile Ile Arg Tyr Ile Ala
            100                 105                 110

Asp Lys His Asn Met Leu Gly Gly Cys Pro Lys Glu Arg Ala Glu Ile
        115                 120                 125

Ser Met Leu Glu Gly Ala Val Leu Asp Ile Arg Tyr Gly Val Ser Arg
130                 135                 140

Ile Ala Tyr Ser Lys Asp Phe Glu Thr Leu Lys Val Asp Phe Leu Ser
145                 150                 155                 160

Lys Leu Pro Glu Met Leu Lys Met Phe Glu Asp Arg Leu Cys His Lys
                165                 170                 175

Thr Tyr Leu Asn Gly Asp His Val Thr His Pro Asp Phe Met Leu Tyr
            180                 185                 190

Asp Ala Leu Asp Val Val Leu Tyr Met Asp Pro Met Cys Leu Asp Ala
        195                 200                 205

Phe Pro Lys Leu Val Cys Phe Lys Lys Arg Ile Glu Ala Ile Pro Gln
210                 215                 220

Ile Asp Lys Tyr Leu Lys Ser Ser Lys Tyr Ile Ala Trp Pro Leu Gln
225                 230                 235                 240

Gly Trp Gln Ala Thr Phe Gly Gly Gly Asp His Pro Pro Lys Gly Ser
                245                 250                 255

Leu Glu His His His His His His
            260

<210> SEQ ID NO 58
<211> LENGTH: 413
<212> TYPE: PRT
<213> ORGANISM: Artificial Sequence
<220> FEATURE:
<223> OTHER INFORMATION: Synthetic polypeptide

<400> SEQUENCE: 58

Met Lys Trp Lys Ser Phe Ile Lys Lys Leu Thr Lys Ala Ala Lys Lys
1               5                   10                  15

Val Val Thr Thr Ala Lys Lys Pro Leu Ile Val Glu Asn Leu Tyr Phe
            20                  25                  30

Gln Gly Gly Thr Met Lys Ile Glu Gly Lys Leu Val Ile Trp Ile
        35                  40                  45

Asn Gly Asp Lys Gly Tyr Asn Gly Leu Ala Glu Val Gly Lys Lys Phe
 50                  55                  60

Glu Lys Asp Thr Gly Ile Lys Val Thr Val Glu His Pro Asp Lys Leu
65                  70                  75                  80

Glu Glu Lys Phe Pro Gln Val Ala Ala Thr Gly Asp Gly Pro Asp Ile
                85                  90                  95

Ile Phe Trp Ala His Asp Arg Phe Gly Gly Tyr Ala Gln Ser Gly Leu
            100                 105                 110
```

-continued

Leu Ala Glu Ile Thr Pro Asp Lys Ala Phe Gln Asp Lys Leu Tyr Pro
            115                 120                 125

Phe Thr Trp Asp Ala Val Arg Tyr Asn Gly Lys Leu Ile Ala Tyr Pro
        130                 135                 140

Ile Ala Val Glu Ala Leu Ser Leu Ile Tyr Asn Lys Asp Leu Leu Pro
145                 150                 155                 160

Asn Pro Pro Lys Thr Trp Glu Ile Pro Ala Leu Asp Lys Glu Leu
                165                 170                 175

Lys Ala Lys Gly Lys Ser Ala Leu Met Phe Asn Leu Gln Glu Pro Tyr
                180                 185                 190

Phe Thr Trp Pro Leu Ile Ala Ala Asp Gly Gly Tyr Ala Phe Lys Tyr
                195                 200                 205

Glu Asn Gly Lys Tyr Asp Ile Lys Asp Val Gly Val Asp Asn Ala Gly
        210                 215                 220

Ala Lys Ala Gly Leu Thr Phe Leu Val Asp Leu Ile Lys Asn Lys His
225                 230                 235                 240

Met Asn Ala Asp Thr Asp Tyr Ser Ile Ala Glu Ala Ala Phe Asn Lys
                245                 250                 255

Gly Glu Thr Ala Met Thr Ile Asn Gly Pro Trp Ala Trp Ser Asn Ile
        260                 265                 270

Asp Thr Ser Lys Val Asn Tyr Gly Val Thr Val Leu Pro Thr Phe Lys
                275                 280                 285

Gly Gln Pro Ser Lys Pro Phe Val Gly Val Leu Ser Ala Gly Ile Asn
        290                 295                 300

Ala Ala Ser Pro Asn Lys Glu Leu Ala Lys Glu Phe Leu Glu Asn Tyr
305                 310                 315                 320

Leu Leu Thr Asp Glu Gly Leu Glu Ala Val Asn Lys Asp Lys Pro Leu
                325                 330                 335

Gly Ala Val Ala Leu Lys Ser Tyr Glu Glu Glu Leu Val Lys Asp Pro
                340                 345                 350

Arg Ile Ala Ala Thr Met Glu Asn Ala Gln Lys Gly Glu Ile Met Pro
            355                 360                 365

Asn Ile Pro Gln Met Ser Ala Phe Trp Tyr Ala Val Arg Thr Ala Val
        370                 375                 380

Ile Asn Ala Ala Ser Gly Arg Gln Thr Val Asp Glu Ala Leu Lys Asp
385                 390                 395                 400

Ala Gln Thr Gly Ser Leu Glu His His His His His
                405                 410

<210> SEQ ID NO 59
<211> LENGTH: 28
<212> TYPE: PRT
<213> ORGANISM: T. maritima

<400> SEQUENCE: 59

Tyr Ala Ala His Pro Leu Gly Glu Val Glu Val Leu Ser Asp Glu Asn
1               5                   10                  15

Glu Val Val Lys Trp Gly Leu Arg Lys Ser Leu Pro
                20                  25

<210> SEQ ID NO 60
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 60

Tyr Thr Val Val Pro Glu Gly Arg Leu Lys Lys Ile Glu Asp Asn Pro
1               5                   10                  15

Gly Asn Val Cys Thr Gly Met Tyr Gln Val Lys Pro
            20                  25

<210> SEQ ID NO 61
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 61

Tyr Ala Ala Val Asn Thr Gly Glu Leu Arg Pro Ile Asp Asp Thr Pro
1               5                   10                  15

Glu Asp Val Asp Met Lys Leu Arg Gln Val Gln Pro
            20                  25

<210> SEQ ID NO 62
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 62

Tyr Ala Ala Val Asn Thr Gly Arg Arg Thr Ala Leu Glu Asp Lys Ala
1               5                   10                  15

Glu Gly Ala Ser Ile Phe Gln Arg Gln Val Leu Pro
            20                  25

<210> SEQ ID NO 63
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 63

Phe Ser Ala Leu Gly Thr Gly His Val Ser Arg Val Ala Ala Asp Thr
1               5                   10                  15

Pro Gly Val Glu Ala Leu Gln Arg His Val Val Arg
            20                  25

<210> SEQ ID NO 64
<211> LENGTH: 88
<212> TYPE: PRT
<213> ORGANISM: T. maritima

<400> SEQUENCE: 64

Leu Leu Ser Phe Glu Glu Arg Lys Ile Glu Cys Gly Ser Thr Pro Lys
1               5                   10                  15

Asp Leu Leu Glu Ala Ile Val Arg Ala Leu Ser Ile Phe Ser Lys Asp
            20                  25                  30

Gly Ile Glu Gly Pro Tyr Thr Leu Val Ile Asn Thr Asp Arg Trp Ile
        35                  40                  45

Asn Phe Leu Lys Glu Glu Ala Gly His Tyr Pro Leu Glu Lys Arg Val
    50                  55                  60

Glu Glu Cys Leu Arg Gly Gly Lys Ile Ile Thr Thr Pro Arg Ile Glu
65                  70                  75                  80

Asp Ala Leu Val Val Ser Glu Arg
                85

<210> SEQ ID NO 65
<211> LENGTH: 88
<212> TYPE: PRT
<213> ORGANISM: Gluconacetobacter diazotrophicus

<400> SEQUENCE: 65

Leu Arg Glu Gly Thr Ser Asn Pro Lys Leu Ala Leu Pro Ser Ser Ala
1               5                   10                  15

Ser Asp Tyr Pro Ala Ala Ile Ala Ala Ala Leu Asn Gln Leu Arg Leu
            20                  25                  30

Ala Gly Val Asn Gly Pro Tyr Ala Val Val Leu Gly Ala Gly Val Tyr
        35                  40                  45

Thr Ala Leu Ser Gly Gly Asp Asp Glu Gly Tyr Pro Val Phe Arg His
    50                  55                  60

Ile Glu Ser Leu Ile Asp Gly Lys Ile Val Trp Ala Pro Ala Ile Glu
65                  70                  75                  80

Gly Gly Phe Val Leu Ser Thr Arg
                85

<210> SEQ ID NO 66
<211> LENGTH: 93
<212> TYPE: PRT
<213> ORGANISM: Hungateiclostridium thermocellum

<400> SEQUENCE: 66

Leu Leu Thr Glu Asp Gly Ile Val Lys Phe Pro Ile Ser Asn Trp Ser
1               5                   10                  15

Glu Gly Glu Asn Pro Phe Lys Asp Ile Ser Ile Gly Leu Ala Lys Phe
            20                  25                  30

Ile Glu Asn Gly Ile Val Gly Arg Lys Ala Leu Val Val Ser Pro Asn
        35                  40                  45

Leu Phe Val Gln Leu Gln Arg Ile Gln Pro Gly Thr Gly Thr Thr Glu
    50                  55                  60

Tyr Asp Arg Ile Asn Lys Leu Leu Asp Gly Asn Ile Phe Ser Thr Pro
65                  70                  75                  80

Val Leu Lys Asp Asp Lys Ala Val Leu Val Cys Ser Glu
                85                  90

<210> SEQ ID NO 67
<211> LENGTH: 92
<212> TYPE: PRT
<213> ORGANISM: Brachyspira hyodysenteriae

<400> SEQUENCE: 67

Ile Leu Asn Ala Glu Gly Ala Gln Lys Leu Gln Ile Ser Asp Trp Gly
1               5                   10                  15

Gln Gly Glu Asn Pro Tyr Thr Asp Ile Val Lys Ala Ile Asn Met Ile
            20                  25                  30

Arg Glu Lys Gly Ile Val Gly Arg Phe Val Leu Cys Leu Ser Gln Ser
        35                  40                  45

Leu Tyr Phe Asp Leu Gln Arg Ile Gln Gln Gly Thr Gly Met Thr Glu
    50                  55                  60

Ala Gln Arg Ile Ser Ser Met Ile Gly Asn Leu Tyr Asn Val Pro Val
65                  70                  75                  80

```
Ile Lys Gly Lys Lys Ala Ala Leu Ile Cys Ala Glu
                85                  90
```

<210> SEQ ID NO 68
<211> LENGTH: 93
<212> TYPE: PRT
<213> ORGANISM: Eggerthella

<400> SEQUENCE: 68

```
Leu Leu Thr Val Lys Gly Ser Ser Lys Ile Lys Ser Asp Trp Ser
1               5                   10                  15

Gln Gly Glu Asn Ser Phe Ala Asp Ile Thr Ala Gly Val Ala Gln Leu
                20                  25                  30

Ala Lys Thr Gly Tyr Leu Gly Arg Tyr Ala Leu Val Val Ser Pro Asp
            35                  40                  45

Leu Phe Leu Asp Leu Gln Arg Leu Gln Pro Asn Thr Gly Leu Leu Glu
        50                  55                  60

Ile Asp Arg Ile Lys Lys Leu Ile Gly Asp Asn Val Tyr Met Thr Ser
65                  70                  75                  80

Val Met Gly Pro Gly Lys Ala Val Leu Val Cys Ala Glu
                85                  90
```

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 69

```
Glu Asn Leu Tyr Phe Gln Gly
1               5
```

<210> SEQ ID NO 70
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: wherein X = S or G
<220> FEATURE:
<221> NAME/KEY: misc_feature
<222> LOCATION: (7)..(7)
<223> OTHER INFORMATION: Xaa can be any naturally occurring amino acid

<400> SEQUENCE: 70

```
Glu Asn Leu Tyr Phe Gln Xaa
1               5
```

<210> SEQ ID NO 71
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 71

```
Asp Asp Asp Asp Lys
1               5
```

<210> SEQ ID NO 72
<211> LENGTH: 7
<212> TYPE: PRT

```
<213> ORGANISM: Artificial Sequence
<220> FEATURE:
<223> OTHER INFORMATION: Synthetic polypeptide

<400> SEQUENCE: 72

Glu Asn Leu Tyr Phe Gln Gly
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 73

Leu Glu Val Leu Phe Gln Gly Pro
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 74

Leu Val Pro Arg Gly Ser
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 75

Gly Gly Gly Gly Ser
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 76

Gly Ser Gly Ser Gly
1               5

<210> SEQ ID NO 77
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 77

Gly Gly Gly Gly
1

<210> SEQ ID NO 78
<211> LENGTH: 3
<212> TYPE: PRT
<213> ORGANISM: Artificial Sequence
```

```
<220> FEATURE:
<223> OTHER INFORMATION: Synthetic polypeptide

<400> SEQUENCE: 78

Gly Gly Gly
1

<210> SEQ ID NO 79
<211> LENGTH: 2
<212> TYPE: PRT
<213> ORGANISM: Artificial Sequence
<220> FEATURE:
<223> OTHER INFORMATION: Synthetic polypeptide

<400> SEQUENCE: 79

Gly Gly
1

<210> SEQ ID NO 80
<211> LENGTH: 2
<212> TYPE: PRT
<213> ORGANISM: Artificial Sequence
<220> FEATURE:
<223> OTHER INFORMATION: Synthetic polypeptide

<400> SEQUENCE: 80

Gly Ser
1

<210> SEQ ID NO 81
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 81

Gly Ser Gly Ser
1

<210> SEQ ID NO 82
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 82

Gly Gly Gly Ser
1

<210> SEQ ID NO 83
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 83

Gly Gly Ser
1

<210> SEQ ID NO 84
<211> LENGTH: 3
<212> TYPE: PRT
<213> ORGANISM: Artificial Sequence
<220> FEATURE:
```

<223> OTHER INFORMATION: Synthetic polypeptide

<400> SEQUENCE: 84

Gly Thr Ser
1

<210> SEQ ID NO 85
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 85

Gly Gly Gly Gly Thr
1               5

<210> SEQ ID NO 86
<211> LENGTH: 265
<212> TYPE: PRT
<213> ORGANISM: Stigmatella aurantiaca DW4/3?1

<400> SEQUENCE: 86

Pro Asp Phe Leu Gly His Ala Glu Asn Pro Leu Arg Glu Glu Glu Trp
1               5                   10                  15

Ala Arg Leu Asn Glu Thr Val Ile Gln Val Ala Arg Arg Ser Leu Val
            20                  25                  30

Gly Arg Arg Ile Leu Asp Ile Tyr Gly Pro Leu Gly Ala Gly Val Gln
        35                  40                  45

Ser Val Pro His Asp Glu Tyr Gln Gly Val Ser Ser Gly Ala Ile Asp
    50                  55                  60

Ile Val Gly Glu Gln Glu Thr Ala Thr Val Phe Thr Asp Val Arg Lys
65                  70                  75                  80

Phe Lys Thr Ile Pro Ile Ile Tyr Lys Asp Phe Leu Leu His Trp Arg
                85                  90                  95

Asp Ile Glu Ala Ala Arg Ile His Asn Met Pro Leu Asp Val Ser Ala
            100                 105                 110

Ala Ala Gly Ala Ala Ala Leu Cys Ala Gln Gln Glu Asp Glu Leu Ile
        115                 120                 125

Phe Tyr Gly Asp Pro Lys Leu Gly His Glu Gly Leu Met Thr Ala Thr
    130                 135                 140

Asp Arg Leu Thr Val Pro Leu Gly Asp Trp Ala Thr Pro Gly Ala Gly
145                 150                 155                 160

Tyr Val Ala Ile Val Glu Ala Thr Arg Lys Leu Asn Glu His Gly His
                165                 170                 175

Tyr Gly Pro Tyr Ala Val Val Leu Ser Pro Arg Leu Tyr Ser Leu Leu
            180                 185                 190

His Arg Ile Phe Glu Lys Thr Gly Val Leu Glu Ile Glu Thr Ile Arg
        195                 200                 205

Gln Leu Ala Ser Asp Gly Val Phe Gln Ser Asn Arg Leu Arg Gly Asp
    210                 215                 220

Ser Gly Val Val Val Ser Thr Gly Arg Glu Asn Met Asp Leu Thr Val
225                 230                 235                 240

Ala Met Asp Met Val Thr Ala Tyr Leu Gly Ala Ser Arg Met Asn His
                245                 250                 255

Pro Phe Arg Val Leu Glu Ala Leu Ile
            260                 265

```
<210> SEQ ID NO 87
<211> LENGTH: 258
<212> TYPE: PRT
<213> ORGANISM: Rhodospirillum rubrum ATCC 11170

<400> SEQUENCE: 87

Met Asn Asp Leu Met Arg Asp Leu Ala Pro Ile Ser Ala Lys Ala Trp
1               5                   10                  15

Ala Glu Ile Glu Thr Glu Ala Arg Gly Thr Leu Thr Val Thr Leu Ala
            20                  25                  30

Ala Arg Lys Val Val Asp Phe Lys Gly Pro Leu Gly Trp Asp Ala Ser
        35                  40                  45

Ser Val Ser Leu Gly Arg Thr Glu Ala Leu Ala Glu Glu Pro Lys Ala
    50                  55                  60

Ala Gly Ser Ala Ala Val Val Thr Val Arg Lys Arg Ala Val Gln Pro
65                  70                  75                  80

Leu Ile Glu Leu Cys Val Pro Phe Thr Leu Lys Arg Ala Glu Leu Glu
                85                  90                  95

Ala Ile Ala Arg Gly Ala Ser Asp Ala Asp Leu Asp Pro Val Ile Glu
            100                 105                 110

Ala Ala Arg Ala Ile Ala Ile Ala Glu Asp Arg Ala Val Phe His Gly
        115                 120                 125

Phe Ala Ala Gly Gly Ile Thr Gly Ile Gly Glu Ala Ser Ala Glu His
    130                 135                 140

Ala Leu Asp Leu Pro Ala Asp Leu Ala Asp Phe Pro Gly Val Leu Val
145                 150                 155                 160

Arg Ala Leu Ala Val Leu Arg Asp Arg Gly Val Asp Gly Pro Tyr Ala
                165                 170                 175

Leu Val Leu Gly Arg Thr Val Tyr Gln Gln Leu Met Glu Thr Thr Thr
            180                 185                 190

Pro Gly Gly Tyr Pro Val Leu Gln His Val Arg Arg Leu Phe Glu Gly
        195                 200                 205

Pro Leu Ile Trp Ala Pro Gly Val Asp Gly Ala Met Leu Ile Ser Gln
    210                 215                 220

Arg Gly Gly Asp Phe Glu Leu Thr Val Gly Arg Asp Phe Ser Ile Gly
225                 230                 235                 240

Tyr His Asp His Asp Ala Gln Ser Val His Leu Tyr Leu Gln Glu Ser
                245                 250                 255

Met Thr

<210> SEQ ID NO 88
<211> LENGTH: 253
<212> TYPE: PRT
<213> ORGANISM: Frankia alni ACN14a

<400> SEQUENCE: 88

Met Asn His Leu Leu Arg Gly His Ala Pro Leu Thr Asp Ala Ala Trp
1               5                   10                  15

Lys Ala Val Asp Asp Glu Ala Lys Ala Arg Leu Thr Thr Asn Leu Ala
            20                  25                  30

Ala Arg Lys Val Val Asp Phe Ala Gly Pro His Gly Trp Glu Tyr Ser
        35                  40                  45

Ala Thr Ala Leu Gly Arg Val Ala Ala Leu Ser Ala Pro Pro Ala Ala
    50                  55                  60

Gly Val Gln Ala Arg Val Arg Gln Val Gln Pro Val Ile Glu Leu Arg
```

```
                65                  70                  75                  80
Val Gly Phe Thr Leu Asp Arg Ala Glu Leu Ala Asp Ala Asp Arg Gly
                    85                  90                  95

Ala Asp Asp Leu Asp Leu Ala Pro Leu Glu Glu Ala Val Arg Arg Ile
                100                 105                 110

Ala Val Thr Glu Asn Ser Val Phe His Gly Tyr Gln Glu Ala Gly
                115                 120                 125

Leu Val Gly Ile Thr Gln Ala Ser Ser His Pro Gln Leu Thr Leu Glu
                130                 135                 140

Ala Gly Thr Asp Thr Tyr Pro Arg Thr Val Ala Lys Ala Val Ala Leu
145                 150                 155                 160

Leu Arg Arg Ala Gly Ile Ala Gly Pro Tyr Ala Leu Ala Leu Glu Pro
                165                 170                 175

Asp Ser Tyr Thr Ala Val Ile Glu Thr Ala Glu His Gly Gly Tyr Leu
                180                 185                 190

Leu Leu Thr His Leu Gln His Ile Leu Asp Gly Pro Val Val Gln Ala
                195                 200                 205

Pro Gly Val Thr Gly Ala Val Val Leu Ser Leu Arg Gly Gly Asp Phe
                210                 215                 220

Val Leu Glu Ser Gly Gln Asp Leu Ser Ile Gly Tyr Ala Ser His Thr
225                 230                 235                 240

Ala Asp Thr Val Asp Leu Tyr Leu Glu Glu Ser Phe Thr
                245                 250

<210> SEQ ID NO 89
<211> LENGTH: 251
<212> TYPE: PRT
<213> ORGANISM: Rhodococcus jostii RHA1

<400> SEQUENCE: 89

Ser Ser Asn Leu His Arg Asn Leu Ala Pro Val Thr Glu Val Ala Trp
1               5                   10                  15

Gln Gln Ile Gly Glu Glu Ala Ala Arg Thr Phe Lys Arg His Val Ala
                20                  25                  30

Gly Arg Arg Val Val Asp Val Ala Gly Pro Phe Gly Tyr Ser Tyr Ser
                35                  40                  45

Ala His Asn Leu Gly Arg Val Thr Pro Ile Lys Thr Ser Asp Ser Arg
                50                  55                  60

Ile Arg Ala Gln Gln Arg Gln Val Asn Pro Leu Val Glu Leu Arg Phe
65                  70                  75                  80

Pro Phe Thr Leu Ser Arg Ala Glu Val Asp Val Ala Arg Gly Ser
                85                  90                  95

Leu Asp Ser Asp Trp Gln Pro Val Lys Asp Ala Ala Lys Ala Val Ala
                100                 105                 110

Phe Ala Glu Asp Gln Ser Ile Phe Gln Gly Phe Asp Glu Ala Gly Ile
                115                 120                 125

Arg Gly Leu Gly Pro Ser Ser Asp Asn Pro Val Leu Ser Leu Pro Glu
                130                 135                 140

Asp Pro Leu Leu Ile Pro Asp Ala Val Ala Ser Ala Leu Ser Ala Leu
145                 150                 155                 160

Arg Leu Ala Gly Val Glu Gly Pro Tyr Ser Val Val Leu Asp Ala Asp
                165                 170                 175

Ala Tyr Thr Ala Val Ser Glu Thr Arg Asp Glu Gly His Pro Val Phe
                180                 185                 190
```

```
His His Leu Arg Asp Leu Val Ala Gly Asp Ile Ile Trp Ala Pro Ala
            195                 200                 205

Ile Ser Gly Gly Tyr Val Leu Ser Thr Arg Gly Asp Asn Gln Leu
    210                 215                 220

Thr Leu Gly Thr Asp Leu Ser Ile Gly Tyr Asp Ser His Thr Ala Thr
225                 230                 235                 240

Asp Val Thr Leu Tyr Leu Glu Glu Thr Phe Thr
                245                 250

<210> SEQ ID NO 90
<211> LENGTH: 252
<212> TYPE: PRT
<213> ORGANISM: Nocardia farcinica

<400> SEQUENCE: 90

Met Asn Asn Leu His Arg Glu Leu Ala Pro Ile Thr Ser Glu Ala Trp
1               5                  10                  15

Ala Ala Ile Glu Glu Glu Ala Gly Arg Thr Phe Lys Arg His Ile Ala
            20                  25                  30

Gly Arg Arg Val Val Asp Val Ala Gly Pro His Gly Val Asp Phe Ser
        35                  40                  45

Ala Val Gly Leu Gly Arg Thr Thr Gly Ile Ala Ala Pro Asp Glu Gly
    50                  55                  60

Val Gln Ala Arg Gln Arg Val Val Ala Pro Leu Val Glu Leu Arg Val
65                  70                  75                  80

Pro Phe Thr Leu Ser Arg Glu Glu Leu Asp Asn Val Glu Arg Gly Ala
                85                  90                  95

Lys Asp Thr Asp Leu Asp Ala Val Lys Glu Ala Ala Arg Arg Ile Ala
            100                 105                 110

Phe Ala Glu Asp Arg Ala Ile Phe Glu Gly Tyr Pro Ala Ala Gly Ile
        115                 120                 125

Thr Gly Ile Arg Ala Ala Gly Ser Asn Ala Pro Ile Thr Val Pro Asp
    130                 135                 140

Asp Ala Arg Leu Val Pro Glu Ala Ile Thr Gln Ala Leu Thr Ala Leu
145                 150                 155                 160

Arg Leu Ala Gly Val Asp Gly Pro Tyr Ser Val Leu Leu Ser Ala Glu
                165                 170                 175

Leu Tyr Thr Glu Val Ser Glu Thr Ser Asp His Gly Tyr Pro Ile Arg
            180                 185                 190

Thr His Ile Glu Arg Leu Ile Pro Asp Gly Glu Ile Ile Trp Ala Pro
        195                 200                 205

Ala Ile Asp Gly Ala Phe Val Leu Thr Thr Arg Gly Gly Asp Tyr Glu
    210                 215                 220

Leu Thr Leu Gly Gln Asp Val Ser Ile Gly Tyr Leu Ser His Asp Ala
225                 230                 235                 240

Asp Thr Val Arg Leu Tyr Phe Gln Gln Thr Met Gln
                245                 250

<210> SEQ ID NO 91
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(9)
<223> OTHER INFORMATION: X1, X2, X3, X4, X5, X6, X7, X8, X9 are any
``` amino acid forming N-terminal of the 1st fragment P-domain in an
engineered microcompartment protein

<400> SEQUENCE: 91

Xaa Xaa Xaa Xaa Xaa Xaa Xaa Xaa Xaa
1               5

<210> SEQ ID NO 92
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(9)
<223> OTHER INFORMATION: X1, X2, X3, X4, X5, X6, X7, X8, X9 are any
      amino acid forming the N-terminal of the 1st fragment P-domain in
      an engineered microcompartment protein
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (100)..(103)
<223> OTHER INFORMATION: X100, X101, X102, X103 are any amino acid
      forming an inserted target peptide

<400> SEQUENCE: 92

Xaa Xaa Xaa Xaa Xaa Xaa Xaa Xaa Xaa Xaa Xaa Xaa Xaa
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(14)
<223> OTHER INFORMATION: Xaa can be any naturally occurring amino acid
<220> FEATURE:
<221> NAME/KEY: misc_feature
<222> LOCATION: (65)..(78)
<223> OTHER INFORMATION: X65, X66, X67, X68, X69, X70, X71, X72, X73,
      X74, X75, X76, X77, X78 are any amino acid forming the C-terminal
      of an E-loop in an engineered microcompartment protein

<400> SEQUENCE: 93

Xaa Xaa Xaa Xaa Xaa Xaa Xaa Xaa Xaa Xaa Xaa Xaa Xaa Xaa
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(14)
<223> OTHER INFORMATION: Xaa can be any naturally occurring amino acid
<220> FEATURE:
<221> NAME/KEY: misc_feature
<222> LOCATION: (131)..(144)
<223> OTHER INFORMATION: X131, X132, X133, X134, X135, X136, X137, X138,
      X139, X140, X141, X142, X143, X144 are any amino acid forming the
      N-terminal of an A-Domain in an engineered microcompartment
      protein

<400> SEQUENCE: 94

Xaa Xaa Xaa Xaa Xaa Xaa Xaa Xaa Xaa Xaa Xaa Xaa
1               5                   10

<210> SEQ ID NO 95
<211> LENGTH: 252
<212> TYPE: PRT
<213> ORGANISM: Wolinella succinogenes

<400> SEQUENCE: 95

Met Asp Ile Leu Arg Arg Glu Asn Ala Gln Phe Pro Ala Ser Ile Trp
1               5                   10                  15

Ser Ala Ile Glu Lys Glu Ala Gly Leu Val Phe Gly Lys His Leu Thr
                20                  25                  30

Gly Arg Lys Val Val Asp Phe Lys Gly Gly Leu Gly Ile Gly Phe Ser
            35                  40                  45

Ser Leu Pro Thr Gly Arg Val Ile Ser Ser Lys Glu Lys Leu Gly Glu
        50                  55                  60

Ala Ser Val Gly Val Arg Met Asn Thr Pro Val Ile Glu Leu Lys Ile
65                  70                  75                  80

Pro Phe Ser Phe Pro Glu Ser Glu Val Glu Ala Ile Leu Arg Glu Ala
                85                  90                  95

Asn Ala Phe Asp Ile Ser Ser Ile Glu Lys Ala Ala Lys Lys Val Cys
                100                 105                 110

Val Ala Glu Asn Glu Leu Val Phe Tyr Gly Leu Lys Lys Glu Gly Ile
            115                 120                 125

Glu Gly Leu Ile Pro Ser Ile Pro His Lys Pro Ile Lys Ala Lys Gly
    130                 135                 140

Asp Glu Ile Leu Pro Ala Val Ala Gly Ile Lys Glu Leu Val Asn
145                 150                 155                 160

Ser Glu Ile Glu Gly Pro Tyr Ala Leu Leu Ile Gln Pro Gln Tyr Phe
                165                 170                 175

Gly Lys Leu Phe Gly Val Ala Gly Asn Ser Gly Tyr Pro Leu Thr Leu
            180                 185                 190

Lys Leu Ala Glu Leu Leu Gln Gly Asn Asn Ile Ile Val Ala Pro Ala
        195                 200                 205

Leu Lys Ser Gly Ala Leu Leu Val Ser Leu Arg Gly Gly Asp Tyr Glu
    210                 215                 220

Leu Tyr Ser Gly Met Asp Ile Gly Val Gly Tyr Ser Glu Lys Lys Ser
225                 230                 235                 240

Thr Asn His Glu Leu Phe Phe Phe Glu Thr Leu Thr
                245                 250

<210> SEQ ID NO 96
<211> LENGTH: 234
<212> TYPE: PRT
<213> ORGANISM: Saccharolobus solfataricus

<400> SEQUENCE: 96

Glu Thr Lys Asp Phe Pro Leu Ile Pro Thr Ser Ser Lys Glu Ile Ser
1               5                   10                  15

Lys Asp His Ile Val Ser Trp Ile Thr Glu Gly Ile Val Ser Ser Arg
                20                  25                  30

Ile Met Arg Asn Ile Gly Asn Thr Ile Lys Tyr Glu Phe Thr Thr Ile
            35                  40                  45

Pro Leu Ser Glu Ile Lys Glu Asp Ser Gly Asp Ile Ile Gln Ser Lys
        50                  55                  60

```
Ser Ala Ser Leu Tyr Glu Val Pro Leu Ile Asn Ser Gln Val Lys Phe
 65                  70                  75                  80

Tyr Leu Gly Gln Lys Ser Asp Ser Arg Arg Thr Ala Val Leu Ala Gly
                 85                  90                  95

Lys Ser Phe Ala Lys Met Glu Asn Tyr Leu Leu Lys Asn His Pro
            100                 105                 110

Leu Ser Pro Leu Lys Ile Gly Leu Lys Ile Thr Gly Ser Asp Trp Asn
            115                 120                 125

Val Ala Gly Asn Ile Leu Leu Asp Val Leu Arg Ala Tyr Glu Asn Leu
130                 135                 140

Thr Arg Glu Gly Phe Gly Lys Asp Val Tyr Ile Leu Met Ser Ser Leu
145                 150                 155                 160

Asn Tyr Ser Lys Thr Phe Arg Val Val Asp Arg Ser Gly Thr Tyr Glu
                165                 170                 175

Ile Glu Met Ile Lys Glu Ile Gly Asn Val Val Pro Thr Asp Ile Val
            180                 185                 190

Ser Asn Asp Glu Ile Tyr Val Ile Ser Lys Gln Gly Phe Asp Ile Leu
            195                 200                 205

Val Phe Ser Asp Leu Asn Val Glu Tyr Leu Ser Lys Glu Lys Asp Tyr
        210                 215                 220

Glu Val Tyr Leu Ile Thr Glu Gln Ile Ala
225                 230
```

<210> SEQ ID NO 97
<211> LENGTH: 265
<212> TYPE: PRT
<213> ORGANISM: Geobacillus kaustophilus

<400> SEQUENCE: 97

```
Met Asp Lys Thr Lys Leu Tyr Pro Glu Ala Pro Leu Thr Ser Ser Gln
  1               5                  10                  15

Trp Gly Glu Leu Asp Glu Leu Val Ile Glu Thr Ala Arg Arg Gln Leu
                 20                  25                  30

Val Gly Arg Arg Phe Ile Asp Leu Tyr Gly Pro Leu Gly Glu Gly Val
             35                  40                  45

Gln Ser Val Ala Asn Asp Ile Tyr Met Asn Pro Glu Gln Gly Asp Met
 50                  55                  60

Ser Phe His Gly Lys Glu Leu Ser Leu Ser Glu Pro Ala Arg Arg Val
 65                  70                  75                  80

His Leu Thr Ile Pro Leu Leu Tyr Lys Asp Phe Ile Leu Tyr Trp Arg
                 85                  90                  95

Asp Ile Glu Gln Ala Lys Gln Leu Gly Ser Pro Ile Asp Phe Ser Ala
            100                 105                 110

Ala Ala Asn Ala Ala Gln Gln Cys Ala Leu Leu Glu Asp Asp Leu Ile
            115                 120                 125

Phe Asn Gly Ser Thr Glu Phe Asp Val Pro Gly Ile Met Asn Val Lys
130                 135                 140

Gly Lys Ile Ala His Ile Arg Ser Asp Trp Met Lys Ser Gly Asn Ala
145                 150                 155                 160

Phe Thr Asp Val Val Glu Ala Arg Asn Lys Leu Leu Gln Leu Gly His
                165                 170                 175

Thr Gly Pro Tyr Ala Leu Val Leu Ser Pro Glu Leu Tyr Ala Leu Ile
            180                 185                 190

His Arg Val His Glu Gly Thr His Val Leu Glu Ile Glu His Ile Arg
```

```
            195                 200                 205
Glu Leu Met Thr Ala Gly Ile Tyr Gln Thr Pro Val Ile Lys Gly Lys
        210                 215                 220

Arg Gly Val Val Ile Asp Thr Gly Arg Gln Asn Ile Asp Leu Ala Val
225                 230                 235                 240

Ala Val Asp Val Gln Thr Ala Phe Leu Asp Thr Glu Asn Met Asn Tyr
                245                 250                 255

Leu Phe Arg Val Tyr Glu Ser Val Val
            260                 265

<210> SEQ ID NO 98
<211> LENGTH: 267
<212> TYPE: PRT
<213> ORGANISM: Aquifex aeolicus

<400> SEQUENCE: 98

Met Glu Phe Leu Gln Arg Asp Gln Ala Pro Leu Thr Ala Glu Glu Trp
1               5                   10                  15

Glu Gln Ile Asp Lys Thr Ala Tyr Glu Val Phe Lys Ser Thr Val Val
            20                  25                  30

Cys Arg Lys Phe Met Pro Val Val Gly Pro Phe Ala Gly His Gln
            35                  40                  45

Val Val Ser Tyr Asp Val Leu Tyr Gly Val Glu Pro Gly Val Cys Glu
50                  55                  60

Val Lys Pro Gly Gln Glu Tyr Lys Val Cys Glu Pro Val Arg Thr Gly
65                  70                  75                  80

Glu Arg Lys His Val Pro Val Pro Thr Leu Tyr Lys Asp Phe Val Ile
                85                  90                  95

Ser Trp Arg Asp Leu Glu His Trp Arg Gln Phe Asn Leu Pro Val Asp
            100                 105                 110

Thr Thr Gly Val Ala Ala Ala Ser Ser Leu Ala Val Ala Glu Asp
            115                 120                 125

Lys Leu Ile Leu Phe Gly Asn Gln Glu Met Gly Ile Glu Gly Phe Leu
130                 135                 140

Thr Ala Lys Gly Thr Leu Arg Glu Glu Leu Ser Asp Trp Glu Lys Val
145                 150                 155                 160

Gly Asn Ala Phe Gln Asp Val Val Lys Gly Ile Ser Arg Leu Val Glu
                165                 170                 175

Lys Gly Phe Tyr Thr Asn Tyr Tyr Leu Ile Val Asn Pro Lys Arg Tyr
            180                 185                 190

Phe Leu Leu Asn Arg Ile His Asp Asn Thr Gly Leu Leu Glu Leu Glu
            195                 200                 205

Gln Ile Lys Lys Val Val Lys Glu Val Tyr Gln Thr Pro Ile Ile Pro
        210                 215                 220

Glu Asp Ile Val Leu Leu Val Ser Ala Ser Pro Ala Asn Phe Asp Leu
225                 230                 235                 240

Ala Ile Ala Leu Asp Val Asn Val Ala Phe Val Glu Thr Ser Asn Met
                245                 250                 255

Asn His Thr Phe Arg Val Met Glu Met Val Val
            260                 265

<210> SEQ ID NO 99
<211> LENGTH: 259
<212> TYPE: PRT
<213> ORGANISM: Anaeromyxobacter dehalogenans 2CP?C
```

<400> SEQUENCE: 99

Met Ser Trp Gln Asp Arg Asp Gly Ala Pro Phe Gly Gln Gln Val Trp
1               5                   10                  15

Asp Arg Ile Asp Glu Ala Ile Glu Ala Ala Ala Glu Ala Arg Ala
            20                  25                  30

Gly Arg Arg Leu Leu Arg Val Ile Gly Pro Leu Gly Phe Glu Ala Arg
            35                  40                  45

Ala Gly Val Ala Asp Asp Ala Pro Ala Gly Glu Asp Glu Pro Glu
    50                  55                  60

Ala Gly Asp Glu Thr His Val His Val Pro Ser Val Arg Ala Leu Pro
65                  70                  75                  80

Val Leu His Arg Thr Phe Arg Leu Gly Ala Arg Ala Val Glu Ala Leu
                85                  90                  95

Glu Arg Arg Gly Glu Pro Leu Thr Leu Thr Glu Ala Ala Glu Ala Ala
            100                 105                 110

Arg Arg Ile Ala Arg Ala Glu Asp Arg Leu Leu Phe Glu Gly His Ala
            115                 120                 125

Gly Ala Gly Val Arg Gly Leu Leu Glu His Pro Gly Leu Val Glu Val
    130                 135                 140

Pro Ala Gly Asp Trp Ala Asp Pro Gly Arg Ala Gly Asp Ala Leu Leu
145                 150                 155                 160

Ala Ala Leu Thr Ala Leu Asp Asp Ala Gly Arg His Gly Pro Tyr Ala
                165                 170                 175

Ala Ala Val Ser Pro Ala Arg Phe Tyr Gln Leu Phe Arg Pro Phe Ala
            180                 185                 190

Gly Thr Ala Leu Thr Pro Tyr Gln Gln Leu Leu Pro Ala Phe Glu Gly
            195                 200                 205

Gly Ile Val Lys Ala Pro Gly Leu Arg Asp Gly Ala Val Val Val Val
            210                 215                 220

Arg Ser Ala Ser Gly Pro Gln Ala Val Val Gly Gln Glu Leu Thr Ala
225                 230                 235                 240

Ala Tyr Asp Gly Arg Glu Gly Ile Phe His Leu Val Ser Leu Ala Glu
                245                 250                 255

Ser Val Thr

<210> SEQ ID NO 100
<211> LENGTH: 251
<212> TYPE: PRT
<213> ORGANISM: Gluconacetobacter diazotrophicus

<400> SEQUENCE: 100

Met Asn Asn Leu His Arg Glu Leu Ala Pro Ile Ser Glu Ala Ala Trp
1               5                   10                  15

Ala Gln Ile Glu Glu Glu Ala Ser Arg Thr Leu Lys Arg Tyr Leu Ala
            20                  25                  30

Ala Arg Arg Val Val Asp Val Pro Glu Ala Lys Gly Phe Gly Phe Ser
            35                  40                  45

Ala Val Gly Thr Gly His Val Glu Arg Ile Asp Ala Pro Gly Ser Asp
    50                  55                  60

Ile Arg Ala Val Arg Arg Asn Val Leu Pro Leu Val Glu Leu Arg Val
65                  70                  75                  80

Pro Phe Thr Leu Ala Arg Asp Ala Ile Asp Asp Val Glu Arg Gly Ala
                85                  90                  95

Gly Asp Ser Asp Trp Gln Pro Leu Lys Asp Ala Ala Lys Lys Ile Ala

Phe Ala Glu Asp Arg Ala Val Phe Asp Gly Tyr Ala Ala Ala Gly Ile
            100                 105                 110

Leu Gly Leu Arg Glu Gly Thr Ser Asn Pro Lys Leu Ala Leu Pro Ser
        115                 120                 125

Ser Ala Ser Asp Tyr Pro Ala Ala Ile Ala Ala Leu Asn Gln Leu
145                 150                 155                 160

Arg Leu Ala Gly Val Asn Gly Pro Tyr Ala Val Val Leu Gly Ala Gly
                165                 170                 175

Val Tyr Thr Ala Leu Ser Gly Gly Asp Asp Glu Gly Tyr Pro Val Phe
                180                 185                 190

Arg His Ile Glu Ser Leu Ile Asp Gly Lys Ile Val Trp Ala Pro Ala
                195                 200                 205

Ile Glu Gly Gly Phe Val Leu Ser Thr Arg Gly Gly Asp Phe Glu Leu
210                 215                 220

Asp Ile Gly Gln Asp Phe Ser Ile Gly Tyr Ser Ser His Ser Ala Asp
225                 230                 235                 240

Ser Val Glu Leu Tyr Leu Gln Glu Ser Phe Thr
                245                 250

<210> SEQ ID NO 101
<211> LENGTH: 251
<212> TYPE: PRT
<213> ORGANISM: Methylorubrum extorquens

<400> SEQUENCE: 101

Met Asn Asn Leu His Arg Glu Leu Ala Pro Ile Ser Asp Ala Ala Trp
1               5                   10                  15

Ala Gln Ile Glu Asp Glu Ala Ser Arg Thr Leu Lys Arg Tyr Leu Ala
            20                  25                  30

Ala Arg Arg Val Val Asp Val Val Gly Pro Lys Gly Pro Gly Tyr Ala
        35                  40                  45

Ala Ala Gly Thr Gly His Thr Arg Pro Ile Glu Ala Pro Gly Glu Gly
    50                  55                  60

Ile Arg Ser Leu Leu Arg Glu Ala Gln Pro Leu Val Glu Leu Arg Val
65                  70                  75                  80

Pro Phe Thr Leu Thr Arg Gln Ala Ile Asp Asp Val Glu Arg Gly Ser
                85                  90                  95

Glu Asp Ser Asp Trp Gln Pro Leu Lys Asp Ala Ala Arg Met Leu Ala
            100                 105                 110

Phe Ala Glu Asp Arg Ala Val Phe Glu Gly Tyr Ala Ala Ala Gly Ile
        115                 120                 125

Gly Gly Ile Gly Lys Gly Ser Ser Asn Ala Ala Val Pro Leu Pro Ala
    130                 135                 140

Thr Leu Asp Asp Tyr Pro Glu Ala Val Ala Arg Ala Leu Asn Asp Leu
145                 150                 155                 160

Lys Leu Ala Gly Cys Asn Gly Pro Tyr Val Leu Val Leu Gly Gly Asp
                165                 170                 175

Val Tyr Arg Ala Ala Ser Gly Gly Asn Glu Glu Gly Tyr Pro Ile Phe
                180                 185                 190

His His Leu Glu Arg Ile Val Asp Gly Gly Val Ile Trp Ala Pro Ala
                195                 200                 205

Ile Ala Gly Gly Phe Val Leu Thr Thr Arg Gly Gly Asp Phe Glu Leu
210                 215                 220

Asp Ile Gly Gln Asp Ile Ser Ile Gly Tyr Leu Ser His Ser Ala Thr
225                 230                 235                 240

Thr Val Glu Leu Tyr Leu Gln Glu Ser Phe Thr
                245                 250

<210> SEQ ID NO 102
<211> LENGTH: 250
<212> TYPE: PRT
<213> ORGANISM: Alkaliphilus metalliredigens

<400> SEQUENCE: 102

Met Asp Ile Leu Lys Arg Asp Met Ala Pro Leu Thr Glu Ser Val Trp
1               5                   10                  15

Glu Glu Ile Asp Gln Arg Ala Ala Glu Val Leu Lys Thr His Leu Ser
                20                  25                  30

Ala Arg Arg Val Val Asn Ile Val Gly Pro Lys Gly Trp Asp Tyr Thr
            35                  40                  45

Val Val Pro Glu Gly Arg Leu Lys Lys Ile Glu Asp Asn Pro Gly Asn
50                  55                  60

Val Cys Thr Gly Met Tyr Gln Val Lys Pro Leu Val Glu Ala Arg Ile
65                  70                  75                  80

Ser Phe Lys Leu Asp Arg Trp Glu Met Asp Asn Leu Ile Arg Gly Ala
                85                  90                  95

Lys Asp Ile Lys Leu Asp Ala Leu Glu Glu Ala Ala Glu Lys Met Ala
            100                 105                 110

Ile Phe Glu Glu Asn Met Leu Tyr Asn Gly Tyr Lys Pro Gly Asp Ile
        115                 120                 125

Glu Gly Leu Ile Glu Ala Ser Ser His Lys Leu Ser Gln Phe Gly Asn
130                 135                 140

Asn Gly Glu Glu Ile Met Glu Asn Leu Ala Gln Gly Met Ile Leu Leu
145                 150                 155                 160

Lys Glu Ala Tyr Val Asp Gln Pro Val Thr Leu Val Val Gly Ile Asp
                165                 170                 175

Ala Trp Lys Arg Ile Asn Arg Glu Met Gln Gly His Pro Leu Ile Asn
            180                 185                 190

Arg Ile Gln Glu Leu Thr Gly Ser Lys Val Ile Tyr Ser Pro Val Val
        195                 200                 205

Glu Gly Ala Leu Leu Leu Pro Tyr Asp His Gly Asp Leu Glu Leu Thr
210                 215                 220

Ile Gly Arg Asp Phe Ser Ile Gly Tyr Glu Tyr His Asp Ala Lys Thr
225                 230                 235                 240

Val Gln Leu Phe Ile Thr Glu Ser Leu Thr
                245                 250

<210> SEQ ID NO 103
<211> LENGTH: 251
<212> TYPE: PRT
<213> ORGANISM: Desulfovibrio

<400> SEQUENCE: 103

Met Asp Ile Leu Lys Arg Asp Leu Ala Pro Val Thr Ala Ala Ala Trp
1               5                   10                  15

Gln Ala Val Asp Ser Arg Ala Arg Gln Thr Leu Thr Thr Met Leu Ser
                20                  25                  30

Gly Arg Arg Val Val Asp Val Ala Gly Pro Leu Gly Trp Glu Tyr Ala
            35                  40                  45

Ala Val Pro Leu Gly Arg Ile Glu Tyr Ala Lys Thr Gln Ser Val Ser
    50                  55                  60

Gly Ile Thr Tyr Gly Leu His Gln Val Lys Pro Leu Val Glu Val Lys
65                  70                  75                  80

Val Pro Phe Thr Leu Asp Ile Ala Glu Ile Asp Asn Ala Ala Arg Gly
                85                  90                  95

Gly Lys Asp Ile Asp Leu Ala Ala Leu Asp Glu Ala Ala Glu Lys Leu
            100                 105                 110

Ala Arg Phe Glu Glu Ala Leu Tyr His Gly Phe Ala Pro Ala Gly
        115                 120                 125

Ile Lys Gly Leu Ser Glu Val Ser Ser Gln Thr Arg Leu Gln Val Ser
130                 135                 140

Ser Asn Pro Glu Asp Ile Ala Glu Lys Val Ser Lys Ala Leu Thr Ala
145                 150                 155                 160

Leu Arg Lys Thr Ser Val Glu Gly Pro Tyr Ala Leu Val Val Gly Pro
                165                 170                 175

Glu Leu Trp Val Ala Leu Ser Gly His Val Arg Gly Tyr Pro Leu Ser
            180                 185                 190

Gln Tyr Leu Glu Thr Met Leu Gly Gly Gln Val Ile Val Ser Pro Phe
        195                 200                 205

Ile Glu Glu Ala Tyr Leu Leu Ser Thr Arg Gly Gly Asp Leu Glu Met
210                 215                 220

Thr Leu Gly Gly Asp Ile Ala Ile Gly Tyr Ala Ser His Asp Thr Glu
225                 230                 235                 240

Lys Val Ala Leu Phe Phe Leu Glu Ser Phe Thr
                245                 250

<210> SEQ ID NO 104
<211> LENGTH: 251
<212> TYPE: PRT
<213> ORGANISM: Haliangium ochraceum

<400> SEQUENCE: 104

Met Asp Leu Leu Lys Arg His Leu Ala Pro Ile Val Pro Asp Ala Trp
1               5                   10                  15

Ser Ala Ile Asp Glu Glu Ala Lys Glu Ile Phe Gln Gly His Leu Ala
                20                  25                  30

Gly Arg Lys Leu Val Asp Phe Arg Gly Pro Phe Trp Glu Tyr Ala
            35                  40                  45

Ala Val Asn Thr Gly Glu Leu Arg Pro Ile Asp Asp Thr Pro Glu Asp
    50                  55                  60

Val Asp Met Lys Leu Arg Gln Val Gln Pro Leu Ala Glu Val Arg Val
65                  70                  75                  80

Pro Phe Thr Leu Asp Val Thr Glu Leu Asp Ser Val Ala Arg Gly Ala
                85                  90                  95

Thr Asn Pro Asp Leu Asp Asp Val Ala Arg Ala Ala Glu Arg Met Val
            100                 105                 110

Glu Ala Glu Asp Ser Ala Ile Phe His Gly Trp Ala Gln Ala Gly Ile
        115                 120                 125

Lys Gly Ile Val Asp Ser Thr Pro His Glu Ala Leu Ala Val Ala Ser
130                 135                 140

Val Ser Asp Phe Pro Arg Ala Val Leu Ser Ala Ala Asp Thr Leu Arg
145                 150                 155                 160

Lys Ala Gly Val Thr Gly Pro Tyr Ala Leu Val Leu Gly Pro Lys Ala
                165                 170                 175

Tyr Asp Asp Leu Phe Ala Ala Thr Gln Asp Gly Tyr Pro Val Ala Lys
            180                 185                 190

Gln Val Gln Arg Leu Val Val Asp Gly Pro Leu Val Arg Ala Asn Ala
        195                 200                 205

Leu Ala Gly Ala Leu Val Met Ser Met Arg Gly Gly Asp Tyr Glu Leu
210                 215                 220

Thr Val Gly Gln Asp Leu Ser Ile Gly Tyr Ala Phe His Asp Arg Ser
225                 230                 235                 240

Lys Val Glu Leu Phe Val Ala Glu Ser Phe Thr
                245                 250

<210> SEQ ID NO 105
<211> LENGTH: 252
<212> TYPE: PRT
<213> ORGANISM: Sorangium cellulosum

<400> SEQUENCE: 105

Met Asp Leu Leu Lys Arg Glu Leu Ala Pro Ile Leu Pro Ala Ala Trp
1               5                   10                  15

Asp Leu Ile Asp His Glu Ala Thr Arg Val Leu Lys Leu His Leu Ala
            20                  25                  30

Gly Arg Lys Val Val Asp Phe Arg Gly Pro Phe Gly Trp Glu Val Ala
        35                  40                  45

Ala Val Asn Thr Gly Arg Leu Arg Ala Ile Glu Arg Lys Glu Gly Pro
    50                  55                  60

Ala Val Ser Ala Gly Val Arg Leu Val Arg Pro Leu Val Glu Phe Arg
65                  70                  75                  80

Ala Pro Ile Arg Leu Glu Leu Ala Glu Leu Asp Ala Val Gly Arg Gly
                85                  90                  95

Ala Gln Glu Pro Asn Ile Glu Asp Val Val Arg Ala Ala Glu His Ala
            100                 105                 110

Ala Arg Phe Glu Asp Gly Ala Ile Phe Asn Gly Leu Ala Ala Ala Gly
        115                 120                 125

Ile Glu Gly Ile Leu Glu Val Ala Pro His Lys Pro Val Val Ile Pro
130                 135                 140

Ala Pro Glu Ala Trp Pro Arg Ala Val Ala Glu Ala Arg Glu Val Leu
145                 150                 155                 160

Arg Ala Ala Gly Val Asp Gly Pro Tyr Ala Leu Ala Leu Gly Pro Lys
                165                 170                 175

Ala Tyr Asp Glu Leu Ala Ala Ala Glu Asp Gly Tyr Pro Leu Arg
            180                 185                 190

Lys His Ile Glu Gly Gln Leu Ile Asp Gly Pro Ile Val Trp Ala Pro
        195                 200                 205

Ala Leu Glu Gly Gly Val Leu Leu Ser Thr Arg Gly Asp Phe Glu
    210                 215                 220

Leu Thr Val Gly Glu Asp Leu Ser Ile Gly Tyr Asp Gly His Asp Arg
225                 230                 235                 240

Gln Val Val Glu Leu Phe Leu Thr Glu Ser Phe Thr
                245                 250

<210> SEQ ID NO 106
<211> LENGTH: 257
<212> TYPE: PRT
<213> ORGANISM: Hungateiclostridium thermocellum

<400> SEQUENCE: 106

Met Asp Phe Leu Ser Arg Glu Gly Ser Pro Ile Ser Ala Glu Leu Trp
1               5                   10                  15

Glu Lys Ile Asp Glu Ala Val Val Ser Ala Ala Lys Lys Ile Leu Thr
            20                  25                  30

Gly Arg Arg Phe Ile Ser Ile Tyr Gly Pro Leu Gly Ala Gly Ile Gln
            35                  40                  45

Ala Ile Asn Val Asp Asn Ile Ser Glu Leu Asp Glu Thr Glu Glu Asn
50                  55                  60

Ile Ser Val Ile Arg Gly Arg Thr Tyr Arg His Ile Pro Leu Ile Asn
65                  70                  75                  80

Glu Asp Phe Ser Leu Leu Trp Arg Asp Leu Glu Phe Ser Glu Gln Met
            85                  90                  95

Gly Leu Pro Val Asp Leu Ser Ser Ala Ser Arg Ala Ala Thr Gln Cys
            100                 105                 110

Ala Leu Arg Glu Asp Lys Leu Ile Phe Tyr Gly Asn Asp Glu Leu Gly
            115                 120                 125

Tyr Lys Gly Leu Leu Thr Glu Asp Gly Ile Val Lys Phe Pro Ile Ser
    130                 135                 140

Asn Trp Ser Glu Gly Asn Pro Phe Lys Asp Ile Ser Ile Gly Leu
145                 150                 155                 160

Ala Lys Phe Ile Glu Asn Gly Ile Val Gly Arg Lys Ala Leu Val Val
            165                 170                 175

Ser Pro Asn Leu Phe Val Gln Leu Gln Arg Ile Gln Pro Gly Thr Gly
            180                 185                 190

Thr Thr Glu Tyr Asp Arg Ile Asn Lys Leu Leu Asp Gly Asn Ile Phe
            195                 200                 205

Ser Thr Pro Val Leu Lys Asp Asp Lys Ala Val Leu Val Cys Ser Glu
            210                 215                 220

Pro Gln Asn Ile Asp Leu Val Ile Gly Gln Asp Met Ile Thr Ser Tyr
225                 230                 235                 240

Leu Glu Thr Lys Asn Leu Asn His Tyr Phe Arg Ile Met Glu Thr Ile
            245                 250                 255

Leu

<210> SEQ ID NO 107
<211> LENGTH: 251
<212> TYPE: PRT
<213> ORGANISM: Natranaerobius thermophilus

<400> SEQUENCE: 107

Met Asn Leu Phe Lys Glu Gln Leu Ala Pro Leu Thr Asn Ala Ala Trp
1               5                   10                  15

Asn Glu Ile Asn Asp Arg Ala Ala Gln Val Ile Lys Ser Asn Leu Ser
            20                  25                  30

Thr Arg Lys Val Phe Lys Ile Asn Gly Pro Lys Gly Leu Asp Tyr Pro
            35                  40                  45

Ala Val Ser Glu Gly Arg Leu Ser Glu Ile Phe His Gly His Gln Gln
50                  55                  60

Gly Glu Val Lys Ala Gly Leu His Gln Val Lys Pro Leu Met Glu Thr
65                  70                  75                  80

Arg Ile Thr Phe Lys Leu Asp Arg Trp Glu Leu Asp Asn Ile Glu Arg
            85                  90                  95

Gly Ala Gln Asp Ile Asp Leu Glu Pro Leu Glu Asp Ala Ala Arg Lys
            100                 105                 110

```
Ile Ala Leu Phe Glu Glu Asn Ala Ile Tyr Asn Gly His Asn Asp Gly
            115                 120                 125

Gln Ile Pro Gly Leu Lys Thr Val Leu Thr Gln Asp Leu Pro Leu Gly
        130                 135                 140

Asn Thr Gly Ser Glu Ile Met Glu Ser Ile Thr Arg Gly Ile Ile Thr
145                 150                 155                 160

Leu Arg Lys Ala Tyr Ile Ser Gln Asn Met Thr Leu Ile Val Gly Glu
                165                 170                 175

Glu Ala Trp Arg Lys Ile Asn Lys Glu Met Ser Gly Glu Pro Leu Ile
            180                 185                 190

Glu Arg Ile His Glu Leu Thr Gly Ser Lys Val Val Ile Ser Pro Ile
        195                 200                 205

Val Asp Gly Ala Tyr Leu Val Pro Tyr Asp His Asp Asp Leu Glu Leu
210                 215                 220

Thr Ile Gly Leu Asp Phe Ser Ile Gly Tyr Glu His His Asp Glu His
225                 230                 235                 240

His Val Gln Leu Phe Ile Thr Glu Ser Phe Thr
                245                 250

<210> SEQ ID NO 108
<211> LENGTH: 249
<212> TYPE: PRT
<213> ORGANISM: Halothermothrix orenii

<400> SEQUENCE: 108

Met Val Asn Leu Lys Arg Ser Leu Ala Pro Ile Thr Pro Asp Ala Trp
1               5                   10                  15

Glu Phe Ile Asp Lys Glu Ala Arg Arg Val Leu Lys Leu Lys Leu Ser
            20                  25                  30

Ala Arg Lys Ala Val Asp Phe Val Gly Pro Lys Gly Ile Lys Tyr Ala
        35                  40                  45

Ala Val Asn Thr Gly Arg Arg Thr Ala Leu Glu Asp Lys Ala Glu Gly
    50                  55                  60

Ala Ser Ile Phe Gln Arg Gln Val Leu Pro Leu Val Glu Val Glu Ile
65                  70                  75                  80

Pro Phe Arg Leu His Leu Glu Glu Leu Glu Ala Phe Val Arg Gly Ala
                85                  90                  95

Glu Asp Val Asn Ile Asp Asn Leu Leu Glu Ser Ala Asn Glu Leu Ala
            100                 105                 110

Arg Ile Glu Asn Lys Ala Ile Phe Phe Gly Met Asp Ser Ala Gly Ile
        115                 120                 125

Ser Gly Leu Val Asn Ser Ser Gly Gln Thr Leu Asp Thr Pro Ala Thr
    130                 135                 140

Gly Leu Ile Ser Ser Val Ala Glu Gly Ile Asn Asn Leu Val Lys Ala
145                 150                 155                 160

Gly Val Asn Gly Pro Tyr Thr Leu Leu Leu Gly Pro Glu Leu Tyr His
                165                 170                 175

Ser Leu Tyr Thr Arg Asn Asp Arg Gly Tyr Pro Leu Glu Lys Arg Ile
            180                 185                 190

Ser Asp Ile Ile Gly Gly Asp Ile Leu Phe Thr Pro Asp Leu Glu Gly
        195                 200                 205

Tyr Gly Leu Leu Leu Ser Lys Arg Gly Gly Asp Phe Glu Leu Ile Val
    210                 215                 220

Gly Gln Asp Ile Ala Ile Gly Phe Ser Gly Gln Phe Gly Asp Glu Leu
```

```
225                 230                 235                 240

Glu Phe Phe Leu Leu Glu Ser Phe Thr
                        245

<210> SEQ ID NO 109
<211> LENGTH: 251
<212> TYPE: PRT
<213> ORGANISM: Petrotoga mobilis

<400> SEQUENCE: 109

Met Asp Phe Leu Lys Arg Glu Leu Ala Pro Ile Thr Glu Glu Ala Trp
1               5                   10                  15

Glu Glu Leu Asp Glu Arg Ala Lys Glu Ile Phe Lys Asn Lys Leu Lys
            20                  25                  30

Ile Arg Pro Ile Ile Asp Val Glu Gly Pro Tyr Gly Trp Asp Tyr Ser
        35                  40                  45

Ser Tyr Asn Leu Gly Thr Asn Glu Leu Ile Glu Asn Pro Arg Asp Gly
    50                  55                  60

Leu Gly Trp Gly Ile Arg Gln Val Leu Pro Ile Val Glu Ile Arg Asn
65                  70                  75                  80

Pro Phe Val Leu Lys Gln Trp Glu Leu Asp Asn Ile Glu Arg Gly Leu
                85                  90                  95

Lys Thr Pro Asp Leu Glu Gly Leu Glu Thr Ala Ala Lys Gln Leu Ala
            100                 105                 110

Ser Phe Glu Asn Lys Leu Ile Leu Lys Gly Ile Glu Lys Ala Asn Ile
        115                 120                 125

Ile Gly Leu Gln Thr Leu Ala Lys Gln Asn Ser Val Glu Ser Ser Lys
    130                 135                 140

Glu Ser Leu Lys Asp Phe Val Lys Ser Leu Phe Glu Val Lys Lys Arg
145                 150                 155                 160

Phe Met Glu Gln Gly Ile Glu Gly Pro Tyr Thr Leu Val Ile Asn Lys
                165                 170                 175

Glu Leu Trp Gln Asp Leu Phe Thr Met Asn Leu Ser Tyr Pro Leu Asp
            180                 185                 190

Leu Val Val Lys Glu Ile Ile Asp Ala Lys Val Lys Pro Met His Glu
        195                 200                 205

Val Asp Glu Ser Phe Val Val Ser Asn Arg Gly Gly Asp Phe Lys Leu
    210                 215                 220

Ile Leu Gly Gln Asp Ile Ser Leu Gly Tyr Glu Ser Lys Phe Asp Glu
225                 230                 235                 240

Gln Leu Lys Phe Phe Phe Thr Glu Ser Leu Thr
                245                 250

<210> SEQ ID NO 110
<211> LENGTH: 265
<212> TYPE: PRT
<213> ORGANISM: Sulfurihydrogenibium sp. YO3AOP1

<400> SEQUENCE: 110

Met Glu Phe Leu Lys Arg Asn Glu Ala Pro Leu Ser Glu Ser Asp Trp
1               5                   10                  15

Glu Lys Ile Asp Lys Val Val Glu Thr Ala Lys Arg Val Leu Val
            20                  25                  30

Gly Arg Arg Phe Ile Glu Ile Ser Gly Pro Tyr Asp Pro Ser Val Gln
        35                  40                  45

Phe Val Pro Tyr Asp Tyr Ile Glu Asp Gly Asn Ser Gly Ala Cys Gly
```

```
                    50                  55                  60
Leu Phe Gly Glu Val Asp Cys Gly Val Lys Val Lys Glu Arg Lys
 65                  70                  75                  80

Ile Leu Pro Leu Pro Ile Ile Tyr Lys Asp Phe Lys Ile His Trp Arg
                     85                  90                  95

Asp Val Glu Ser Ser Lys Lys Phe Asn Ile Pro Ile Asp Phe Ser Val
                100                 105                 110

Ala Ala Ala Ala Ala Ser Gln Val Ala Ile Ala Glu Asp Arg Leu Ile
                115                 120                 125

Phe His Gly Asp Ile Glu Thr Gly Phe Pro Gly Leu Leu Asn Val Glu
                130                 135                 140

Gly Lys Asn Ser Ile Ser Ile Ser Asp Trp Asn Gln Thr Gly Glu Ala
145                 150                 155                 160

Phe Lys Asp Ile Leu Asn Ala Ile Val Lys Leu Asn Glu Asn Gly Phe
                165                 170                 175

Tyr Asn Asn Phe Ala Leu Val Leu Asn Pro Gln Asp Tyr Ala Met Leu
                180                 185                 190

Asn Arg Leu Tyr Gly Asn Ser Gly Ile Leu Glu Ile Asp Gln Ile Lys
                195                 200                 205

Lys Leu Phe Asp Val Gly Val Phe Thr Thr Pro Val Ile Pro Gln Phe
210                 215                 220

Thr Ala Val Val Val Ser Thr Gly Ile Glu Asn Leu Asp Leu Phe Ile
225                 230                 235                 240

Ser Gln Asp Met Ile Thr Ser Tyr Leu Asn Tyr Asp Asn Met Asp His
                245                 250                 255

Tyr Phe Arg Val Phe Glu Ile Leu Ala
                260                 265

<210> SEQ ID NO 111
<211> LENGTH: 252
<212> TYPE: PRT
<213> ORGANISM: Kocuria

<400> SEQUENCE: 111

Met Asn Asn Leu His Arg Asp Leu Ala Pro Ile Ser Ser Ala Ala Trp
 1               5                  10                  15

Ala Asp Met Gly Asp Glu Ala Arg Arg Thr Phe Ala Ala Arg Ala Ala
                20                  25                  30

Ala Arg Arg Thr Val Asp Met Pro Glu Pro Ala Gly Ala Glu Phe Ser
                35                  40                  45

Ala Leu Gly Thr Gly His Val Ser Arg Val Ala Ala Asp Thr Pro Gly
                50                  55                  60

Val Glu Ala Leu Gln Arg His Val Val Arg Val Glu Leu Arg Ala
 65                  70                  75                  80

Pro Phe Thr Leu Lys Arg Ser Asp Ile Asp Asp Val Glu Arg Gly Ala
                85                  90                  95

Ala Asp Pro Asp Trp Gln Pro Val Lys Asp Ala Val Ala Leu Ala
                100                 105                 110

Ser Ala Glu Asp Arg Thr Val Phe Tyr Gly Ser Asp Ser Ala Gly Ile
                115                 120                 125

Gln Gly Ile Ala Pro Ala Ser Asp Asn Glu Arg Leu Ser Leu Pro Gln
                130                 135                 140

Asp Val Arg Glu Phe Pro Asn Ala Val Ala Lys Ala Lys Thr Glu Leu
145                 150                 155                 160
```

```
Arg Leu Ala Gly Val Ala Gly Pro Tyr Asn Leu Leu Pro Ala Glu
                165                 170                 175

Leu Tyr Thr Glu Val Thr Glu Thr Thr Asp His Gly Tyr Pro Val His
            180                 185                 190

Glu His Val Ser Arg Ile Leu Gly Glu Gly Ser Ile Ile Trp Ala Pro
        195                 200                 205

Ala Leu Asp Asp Ala Leu Leu Val Ser Ala Arg Gly Gly Asp Tyr Glu
210                 215                 220

Leu His Leu Gly Gln Asp Ala Ala Ile Gly Tyr Thr Ser His Thr Ala
225                 230                 235                 240

Glu Thr Val Glu Leu Tyr Leu Arg Glu Thr Leu Thr
                245                 250
```

<210> SEQ ID NO 112
<211> LENGTH: 265
<212> TYPE: PRT
<213> ORGANISM: Hydrogenobaculum

<400> SEQUENCE: 112

```
Met Asn Phe Leu His Arg Glu Glu Ser Pro Leu Thr Ala Gln Glu Trp
1               5                   10                  15

Gln Thr Ile Asp Asn Ile Val Val Asn Thr Ala Arg Asn His Leu Val
            20                  25                  30

Gly Arg Arg Phe Ile Glu Leu Thr Gln Ala Leu Asp Pro Ala Ile Gln
        35                  40                  45

Ser Val Ala Tyr Asp Thr Ile Pro Ser Leu Asp Asn Gly Ala Cys Gly
    50                  55                  60

Leu Phe Gly Glu Lys Glu Cys Gly Ile Ala Lys Ile Lys Ser Arg Lys
65                  70                  75                  80

Phe Leu Pro Ile Pro Gln Ile Tyr Lys Asp Phe Lys Ile His Trp Arg
                85                  90                  95

Asp Ile Glu Thr Ser Arg Lys Leu Asn Ile Pro Leu Asp Val Ser Val
            100                 105                 110

Val Ala Leu Ala Thr Arg Glu Val Ala Leu Ala Glu Asp Arg Phe Ile
        115                 120                 125

Phe His Gly Asp Ser Glu Ile Gly Tyr Pro Gly Leu Leu Asn Val Glu
130                 135                 140

Gly Arg Ser Ile Ile Lys Asn Lys Asn Phe Asp Glu Glu Gly Gly Ile
145                 150                 155                 160

Phe Lys Thr Ala Leu Ala Cys Val Glu Thr Leu Val Glu Lys Gly Phe
                165                 170                 175

Ser Lys Asn Leu Ala Tyr Ile Leu Asn Pro Lys Asp Tyr Thr Lys Ala
            180                 185                 190

Phe Arg Ile Tyr Gly Asn Ser Gly Val Leu Glu Ile Thr His Ile Lys
        195                 200                 205

Glu Leu Phe Asp Val Gly Val Phe Thr Ser His Ala Val Asp Glu Gly
210                 215                 220

Lys Thr Ile Ala Val Ala Thr Gly Val Glu Asn Met Asp Ile Phe Leu
225                 230                 235                 240

Val Gln Asp Met Ile Ser Ala Phe Ile Asp Tyr Glu Asn Met Asp Tyr
                245                 250                 255

Tyr Phe Arg Val Phe Glu Ile Leu Ala
            260                 265
```

<210> SEQ ID NO 113

```
<211> LENGTH: 256
<212> TYPE: PRT
<213> ORGANISM: Brachyspira hyodysenteriae

<400> SEQUENCE: 113

Met Asp Tyr Leu Ala Arg Glu Ser Ser Pro Phe Glu Ser Phe Trp
1               5                   10                  15

Gln Asn Ile Asp Lys Val Val Glu Thr Ala Ser Arg Thr Leu Ile
            20                  25                  30

Gly Arg Arg Phe Leu Ser Ile Tyr Gly Pro Leu Gly Ala Gly Ala Ile
        35                  40                  45

Ser Val Gln Tyr Asp Lys Ser Asp Arg Glu Glu Val Phe Glu Asp Gly
    50                  55                  60

Phe Val Lys Thr Ser Gly Arg Lys Ser Val Glu Leu Pro Gln Ile Tyr
65                  70                  75                  80

Gln Asp Phe Thr Leu Leu Trp Arg Asp Leu Glu Asn Asn Ile Ser Asn
                85                  90                  95

Lys Leu Pro Leu Asp Leu Ser Ile Val Ser Gln Ala Ala Gln Thr Leu
            100                 105                 110

Ala Asn Lys Glu Asp Asn Leu Ile Phe Asn Gly Asn Asp Phe Leu Glu
        115                 120                 125

Leu Lys Gly Ile Leu Asn Ala Glu Gly Ala Gln Lys Leu Gln Ile Ser
    130                 135                 140

Asp Trp Gly Gln Gly Glu Asn Pro Tyr Thr Asp Ile Val Lys Ala Ile
145                 150                 155                 160

Asn Met Ile Arg Glu Lys Gly Ile Val Gly Arg Phe Val Leu Cys Leu
                165                 170                 175

Ser Gln Ser Leu Tyr Phe Asp Leu Gln Arg Ile Gln Gln Gly Thr Gly
            180                 185                 190

Met Thr Glu Ala Gln Arg Ile Ser Ser Met Ile Gly Asn Leu Tyr Asn
        195                 200                 205

Val Pro Val Ile Lys Gly Lys Lys Ala Ala Leu Ile Cys Ala Glu Pro
    210                 215                 220

Gln Tyr Met Asp Leu Ala Val Gly Ile Asp Met Ser Thr Ala Tyr Leu
225                 230                 235                 240

Glu Gln Lys Asp Leu Asn His Ser Phe Arg Ile Met Glu Thr Ile Ile
                245                 250                 255

<210> SEQ ID NO 114
<211> LENGTH: 251
<212> TYPE: PRT
<213> ORGANISM: Denitrovibrio acetiphilus

<400> SEQUENCE: 114

Met Asn Leu Leu Arg Lys Asp Phe Ala Pro Ile Gly Ser Ala Ala Trp
1               5                   10                  15

Asp Glu Ile Asn Thr Ile Ala Lys Glu Thr Leu Lys Ala Asn Leu Ser
            20                  25                  30

Ala Arg Arg Phe Ala Asp Val Glu Gly Pro Tyr Gly Ile Asn Phe Ala
        35                  40                  45

Ala Val Asn Leu Gly Arg Leu Lys Ile Ser Asp Asn Lys Ser Pro Lys
    50                  55                  60

Asp Val Val Tyr Gly Val Asn Thr Val Leu Pro Leu Val Glu Ala Arg
65                  70                  75                  80

Ile Asn Phe Ser Leu Asp Ile Trp Glu Leu Asp Asn Ile Asp Arg Gly
                85                  90                  95
```

```
Ala Lys Asp Ile Ala Leu Asp Asp Leu Ala Glu Ala Ala Arg Lys Met
            100                 105                 110

Ala Asp Phe Glu Glu Asn Ala Val Tyr Asn Gly Phe Lys Asp Ser Gly
            115                 120                 125

Ile Val Gly Leu Asn Gln Val Ala Ala Lys Asn Arg Ile Asn Met Thr
            130                 135                 140

Leu Asp Lys Asp Asn Leu Val Asp Ala Ile Ser Glu Ala Gln Gly Arg
145                 150                 155                 160

Met Arg Lys Glu Gly Ile Ala Ser Gly Ala Asn Leu Val Val Asn Pro
                165                 170                 175

Ala Leu Trp Gln Phe Leu Ala His Val Val Pro Gly Gly Thr Leu Gly
            180                 185                 190

Asp Thr Val Arg Arg Gln Ile Lys Gly Asp Ile Ile Tyr Ser Glu Thr
            195                 200                 205

Val Asp Gly Ala Leu Leu Val Ala Asp Arg Glu Gly Asp Val Glu Leu
            210                 215                 220

Thr Thr Gly Gln Asp Phe Ala Ile Gly Tyr His Ser His Asp Ala Ser
225                 230                 235                 240

Lys Val Asn Leu Phe Leu Thr Glu Ser Phe Thr
                245                 250

<210> SEQ ID NO 115
<211> LENGTH: 249
<212> TYPE: PRT
<213> ORGANISM: Thermanaerovibrio acidaminovorans

<400> SEQUENCE: 115

Met Asp Val Leu Lys Arg Gly Phe Ala Pro Ile Ser Gln Glu Ala Trp
1               5                   10                  15

Gly Val Leu Asp Gln Gln Ala Arg Val Ile Leu Arg Glu Asn Leu Ser
            20                  25                  30

Ala Arg Arg Phe Val Asp Val Glu Gly Pro Lys Gly Trp Asp Phe Pro
        35                  40                  45

Gly Phe Gly Thr Gly Arg Leu Val Leu Pro Glu Gly Gln Gln Lys Gly
    50                  55                  60

Ala Val Arg Phe Gly Val Arg Gln Phe Gln Pro Met Ile Glu Thr Arg
65                  70                  75                  80

Val Ser Phe Glu Ile Ser Ile Trp Asp Leu Asp Asp Ile Ser Arg Gly
                85                  90                  95

Ala Val Asp Val Asp Leu Ser Ser Leu Glu Asp Ala Ala Arg Lys Met
            100                 105                 110

Ala Glu Phe Glu Glu Arg Ala Ile Tyr His Gly Leu Asp Glu Gly Cys
            115                 120                 125

Ile Glu Gly Ile Val Lys Ser Ala Gly Tyr Thr Ala Glu Leu Ser Val
            130                 135                 140

Ser Lys Ser Lys Asp Met Ile Met Gly Ile Ala Lys Gly Val Arg Thr
145                 150                 155                 160

Met Gly Ala Ser Val Glu Gly Pro Phe Ala Leu Val Gly Gly Asp Lys
                165                 170                 175

Leu Phe Ala Ala Ile Asp Gly Phe Ser Glu Pro Tyr Pro Met Arg Lys
            180                 185                 190

Asn Leu Ala Glu Leu Val Asp Lys Val Ile Tyr Ala Pro Ala Leu Asp
            195                 200                 205

Gly Ala Leu Leu Val Ser Leu Ala Gly Gly His Leu Gln Leu Thr Leu
```

```
                210                 215                 220
Gly Gln Asp Met Ser Leu Gly Tyr Glu Ala His Asp Ser Thr Thr Val
225                 230                 235                 240

Arg Leu Phe Phe Thr Glu Thr Phe Ala
                245

<210> SEQ ID NO 116
<211> LENGTH: 257
<212> TYPE: PRT
<213> ORGANISM: Eggerthella

<400> SEQUENCE: 116

Met Asp Tyr Leu Ala Arg Glu Ser Ala Asp Leu Ser Asp Gly Leu Trp
1               5                   10                  15

Asn Arg Ile Asp Glu Thr Val Ile Gly Thr Ala Arg Ala Gln Leu Thr
            20                  25                  30

Cys Arg Arg Phe Leu Lys Val Phe Gly Pro Leu Gly Ala Gly Val Thr
        35                  40                  45

Thr Val Ala Val Asp Gly Val Asn Lys Glu Glu Val Leu Glu Asp Gly
    50                  55                  60

Ile Gly Arg Ile Val Gly Arg Thr Gln Leu Glu Leu Pro Leu Phe Tyr
65                  70                  75                  80

Glu Asp Phe Thr Leu Leu Ser Arg Asp Met Glu Tyr Ala Ala Gln Thr
                85                  90                  95

Gly Tyr Pro Leu Asp Leu Ser Val Ala Ile Ala Ala Lys Lys Ala
            100                 105                 110

Ser Arg Arg Glu Asp Asp Leu Ile Leu Asn Gly Ser Lys Ala Leu Gly
        115                 120                 125

Thr Asp Gly Leu Leu Thr Val Lys Gly Ser Ser Lys Ile Lys Lys Ser
    130                 135                 140

Asp Trp Ser Gln Gly Glu Asn Ser Phe Ala Asp Ile Thr Ala Gly Val
145                 150                 155                 160

Ala Gln Leu Ala Lys Thr Gly Tyr Leu Gly Arg Tyr Ala Leu Val Val
                165                 170                 175

Ser Pro Asp Leu Phe Leu Asp Leu Gln Arg Leu Gln Pro Asn Thr Gly
            180                 185                 190

Leu Leu Glu Ile Asp Arg Ile Lys Lys Leu Ile Gly Asp Asn Val Tyr
        195                 200                 205

Met Thr Ser Val Met Gly Pro Gly Lys Ala Val Leu Val Cys Ala Glu
    210                 215                 220

Pro Glu Tyr Leu Asp Leu Ala Ile Gly Leu Asp Leu Ser Val Gly Tyr
225                 230                 235                 240

Leu Glu Leu Ala Asp Phe Asn His Thr Phe Arg Ile Met Glu Thr Ala
                245                 250                 255

Ala

<210> SEQ ID NO 117
<211> LENGTH: 246
<212> TYPE: PRT
<213> ORGANISM: Pseudothermotoga

<400> SEQUENCE: 117

Ala Asn Lys Tyr Leu Met Gln Glu Asp Ala Pro Phe Asp Pro Lys Leu
1               5                   10                  15

Trp Gln Leu Phe Asn Glu Thr Met Thr Asp Ile Ala Lys Ala Gln Leu
            20                  25                  30
```

```
Val Gly Arg Arg Ile Leu Ser Val Lys Gly Pro Phe Gly Leu Gly Leu
            35                  40                  45

Lys Gln Ile Ser Ile Thr Asp Val Gln Ile Glu Pro Gly Val Phe Ser
 50                  55                  60

Asn Lys Thr Leu Pro Leu Phe Tyr Ile His Lys Thr Phe Asn Ile Ser
 65                  70                  75                  80

Lys Arg Asp Ile Ala Ser Tyr Glu Arg Glu Gly Val Thr Leu Asp Leu
                    85                  90                  95

Lys Asn Leu Ile Thr Ala Val Arg Glu Cys Ala Thr Ile Glu Asp Arg
                100                 105                 110

Leu Ile Phe Glu Gly Ile Asn Ser His Gly Leu Val Ser Ala Pro Gly
            115                 120                 125

Thr Ile Ser Met Glu Leu Ser Asp Trp Lys Asn Val Gly Gln Ala Ala
130                 135                 140

Ser Asp Val Ile Glu Ala Val Thr Lys Leu Asp Glu Ala Gly Phe His
145                 150                 155                 160

Gly Pro Tyr Leu Leu Ala Leu Ser Pro Asp Arg Tyr Asn Leu Leu Phe
                165                 170                 175

Arg Arg Tyr Glu Ser Gly Asn Gln Thr Glu Tyr Glu His Leu Ser Met
            180                 185                 190

Ile Ile Lys Gly Ile Tyr Lys Ala Pro Val Leu Lys Asn Ser Gly Val
        195                 200                 205

Leu Met Ser Asp Ser Glu Ala Tyr Ala Ser Ile Ile Leu Gly Gln Asp
    210                 215                 220

Leu Ser Ile Gly Phe Ile Gly Pro Ala Glu Glu Arg Phe Glu Phe Ser
225                 230                 235                 240

Ile Ser Glu Ser Leu Ala
                245

<210> SEQ ID NO 118
<211> LENGTH: 254
<212> TYPE: PRT
<213> ORGANISM: Anaeromyxobacter sp. Fw109?5

<400> SEQUENCE: 118

Thr Thr Trp Leu Asp Arg Glu Gly Ala Pro Phe Ala Gln Glu Val Trp
1               5                  10                  15

Asp Arg Ile Asp Ala Val Ala Arg Ser Ala Ala Asp Glu Val Arg Ala
                20                  25                  30

Gly Arg Arg Leu Leu Glu Val Val Gly Pro Leu Gly Phe Gly Ala Arg
            35                  40                  45

Ala Gly Val Ala Glu Asp Leu Pro Leu Gly Glu Glu Pro Glu Gly Ala
 50                  55                  60

His Val His Val Pro Arg Val Arg Pro Leu Pro Val Ile His Arg Thr
 65                  70                  75                  80

Phe Ala Leu Gly Ala Arg Ala Leu Glu Ala Asp Ala Ala Cys Gly Glu
                    85                  90                  95

Pro Leu Val Leu Ser Glu Ala Ser Glu Ala Ala Arg Gln Ile Ala Arg
                100                 105                 110

Ala Glu Asp Arg Ile Val Phe Glu Gly Leu Pro Arg Ala Gly Val Ser
            115                 120                 125

Gly Leu Leu Gly His Glu Gly Ala Val Glu Leu Pro Ala Gly Asp Trp
130                 135                 140

Ser Asp Pro Ala Arg Val Ala Asp Asp Leu Leu Gly Ala Leu Ala Lys
```

```
            145                 150                 155                 160
Leu Asp Glu Ala Gly Arg His Gly Pro Tyr Ala Leu Ala Val Ser Pro
                    165                 170                 175

Gly Arg Phe Tyr Gln Leu Leu Arg Pro Tyr Pro Gly Thr Ala Leu Thr
                    180                 185                 190

Pro His Gln Gln Leu Gln Pro Ala Phe Ala Gly Gly Ile Val Lys Ala
                    195                 200                 205

Pro Ala Ile Gln Asp Gly Ala Val Ile Val Met Arg Thr Pro Ser Gly
                    210                 215                 220

Pro Arg Ile Leu Val Gly Gln Glu Leu Ala Ala Ala Tyr Asp Gly Arg
225                 230                 235                 240

Glu Gly Ile Phe His Gln Ile Ser Leu Val Glu Ser Val Thr
                    245                 250

<210> SEQ ID NO 119
<211> LENGTH: 265
<212> TYPE: PRT
<213> ORGANISM: Myxococcus xanthus DK 1622

<400> SEQUENCE: 119

Pro Asp Phe Leu Gly His Ala Glu Asn Pro Leu Arg Glu Glu Glu Trp
1               5                   10                  15

Ala Arg Leu Asn Glu Thr Val Ile Gln Val Ala Arg Arg Ser Leu Val
                20                  25                  30

Gly Arg Arg Ile Leu Asp Ile Tyr Gly Pro Leu Gly Ala Gly Val Gln
            35                  40                  45

Thr Val Pro Tyr Asp Glu Phe Gln Gly Val Ser Pro Gly Ala Val Asp
        50                  55                  60

Ile Val Gly Glu Gln Glu Thr Ala Met Val Phe Thr Asp Ala Arg Lys
65                  70                  75                  80

Phe Lys Thr Ile Pro Ile Ile Tyr Lys Asp Phe Leu Leu His Trp Arg
                85                  90                  95

Asp Ile Glu Ala Ala Arg Thr His Asn Met Pro Leu Asp Val Ser Ala
                100                 105                 110

Ala Ala Gly Ala Ala Ala Leu Cys Ala Gln Gln Glu Asp Glu Leu Ile
            115                 120                 125

Phe Tyr Gly Asp Ala Arg Leu Gly Tyr Glu Gly Leu Met Thr Ala Asn
        130                 135                 140

Gly Arg Leu Thr Val Pro Leu Gly Asp Trp Thr Ser Pro Gly Gly Gly
145                 150                 155                 160

Phe Gln Ala Ile Val Glu Ala Thr Arg Lys Leu Asn Glu Gln Gly His
                165                 170                 175

Phe Gly Pro Tyr Ala Val Val Leu Ser Pro Arg Leu Tyr Ser Gln Leu
                180                 185                 190

His Arg Ile Tyr Glu Lys Thr Gly Val Leu Glu Ile Glu Thr Ile Arg
            195                 200                 205

Gln Leu Ala Ser Asp Gly Val Tyr Gln Ser Asn Arg Leu Arg Gly Glu
        210                 215                 220

Ser Gly Val Val Val Ser Thr Gly Arg Glu Asn Met Asp Leu Ala Val
225                 230                 235                 240

Ser Met Asp Met Val Ala Ala Tyr Leu Gly Ala Ser Arg Met Asn His
                245                 250                 255

Pro Phe Arg Val Leu Glu Ala Leu Leu
                260                 265
```

<210> SEQ ID NO 120
<211> LENGTH: 248
<212> TYPE: PRT
<213> ORGANISM: Methanoregula boonei

<400> SEQUENCE: 120

Ala Asn Val Tyr Leu Gly Arg Asp Glu Ala Pro Ile Gly Ala Glu Ser
1               5                   10                  15

Trp Lys Leu Ile Asp Asp Val Ala Val Gln Ala Ala Lys Gly Gln Leu
            20                  25                  30

Ala Gly Arg Arg Leu Leu Ala Ile Glu Gly Pro Tyr Gly Phe Gly Leu
        35                  40                  45

Lys Ala Ile Pro Leu Gly Asp Tyr Ala Leu Glu Asp Gly Ile Ser Ala
    50                  55                  60

Ser Val Ser Leu Pro Leu Ser Leu Ile Arg Thr Glu Phe Ser Leu Gly
65                  70                  75                  80

Lys Arg Asp Leu Ala Ala Tyr Glu Arg Asp His Leu Ile Leu Asp Thr
                85                  90                  95

Ala Pro Val Ala Cys Ala Ala Met Asp Ala Ala Lys Glu Asp Arg
            100                 105                 110

Ile Ile Phe Asn Gly Leu Ala Gly Thr Pro Gly Leu Leu Asn Ala Glu
        115                 120                 125

Gly Ala Gly Ser Leu Thr Leu Ser Lys Trp Asp Lys Val Gly Ala Ala
    130                 135                 140

Ala Asp Gln Ile Ile Asp Ala Val Thr Lys Leu Asp Ala Ala Gly Phe
145                 150                 155                 160

His Gly Pro Tyr Ser Leu Ala Leu Ala Pro Ala Gln Tyr Asn Leu Leu
                165                 170                 175

Leu Arg Arg Tyr Pro Gln Gly Asp Gly Thr Glu Leu Asp His Val Ser
            180                 185                 190

Ser Ile Val Gly Asp Gly Val Ile Lys Ala Pro Val Leu Lys Lys Gly
        195                 200                 205

Gly Val Leu Val Ala Ser Gly Ser Gln Tyr Ala Ser Val Ala Leu Gly
    210                 215                 220

Gln Asp Leu Ala Val Gly Tyr Asn Gly Pro Val Gly Asp Leu Leu Glu
225                 230                 235                 240

Phe Gln Ile Tyr Glu Ser Leu Ala
                245

<210> SEQ ID NO 121
<211> LENGTH: 248
<212> TYPE: PRT
<213> ORGANISM: Methanosphaerula palustris

<400> SEQUENCE: 121

Gly Glu Ser Tyr Leu Gly Arg Ser Asp Ala Pro Ile Thr Ala Glu Thr
1               5                   10                  15

Trp Thr Ile Ile Asp Thr Thr Met Val Glu Ala Ala Lys Ser Met Leu
            20                  25                  30

Thr Gly Arg Arg Leu Leu His Leu Glu Gly Pro Tyr Gly Leu Gly Leu
        35                  40                  45

Lys Ala Ile Pro Leu Gln Asp Ser Val Ser Glu Gly Asn Leu Ile Arg
    50                  55                  60

Ser Gly Phe Ala Pro Val Asp Leu Ile Gln Thr Ser Phe Ser Leu Ser
65                  70                  75                  80

```
Lys Arg Asp Leu Ala Ala Tyr Glu Arg Asp Gly Met Leu Pro Asn Thr
                85                  90                  95

Ser Ala Val Ala Val Ala Ala Ile Glu Ala Ala Arg Gln Glu Asp Ala
            100                 105                 110

Val Ile Phe Thr Gly Thr Asp Gln Val Lys Gly Leu Met Asn Thr Gly
        115                 120                 125

Gly Ser Gln Ser Val Lys Leu Ala Ser Trp Glu Lys Ile Gly Ala Ala
    130                 135                 140

Ala Asp Asp Leu Ile Lys Ala Val Thr Ala Leu Asp Leu Ala Gly Phe
145                 150                 155                 160

His Gly Pro Tyr Ala Leu Ala Leu Ser Pro Ala Arg Tyr Asn Leu Leu
                165                 170                 175

Phe Arg Arg Tyr Pro Gln Gly Ser Thr Thr Glu Leu Glu His Leu Gln
                180                 185                 190

Gln Met Ile Thr Asp Gly Ile Phe Lys Ala Pro Val Leu Lys Asp Gly
            195                 200                 205

Gly Val Leu Ile Ala Thr Gly Gln Gln Tyr Ala Ala Ile Val Leu Gly
        210                 215                 220

Gln Asp Met Thr Ile Gly Phe Thr Gly Pro Ser Lys Glu Ser Leu Asp
225                 230                 235                 240

Phe Thr Ile Ser Glu Ser Leu Ala
                245

<210> SEQ ID NO 122
<211> LENGTH: 265
<212> TYPE: PRT
<213> ORGANISM: Brevibacillus

<400> SEQUENCE: 122

Met Asp Lys Leu Arg Lys Tyr Pro Asp Ser Pro Leu Thr Thr Glu Glu
1               5                   10                  15

Trp Asn Gln Leu Asp Ala Thr Val Val Asp Met Ala Arg Arg Gln Leu
            20                  25                  30

Val Gly Arg Arg Phe Ile Asp Ile Tyr Gly Pro Leu Gly Glu Gly Ile
        35                  40                  45

Gln Thr Ile Thr Asn Asp Val Tyr Glu Glu Ser Arg Phe Gly Gly Leu
    50                  55                  60

Ser Leu Arg Gly Glu Ser Leu Glu Met Thr Gln Pro Ser Arg Arg Val
65              70                  75                  80

Ser Met Thr Ile Pro Ile Leu Tyr Lys Asp Phe Met Leu Tyr Trp Arg
                85                  90                  95

Asp Val Ala Gln Ala Arg Thr Leu Gly Met Pro Leu Asp Met Ser Ala
            100                 105                 110

Ala Ala Asn Ala Ala Ala Gly Gly Ala Leu Met Glu Asp Asp Leu Ile
        115                 120                 125

Phe Asn Gly Ala Ala Glu Phe Asp Leu Pro Gly Leu Met Asn Val Lys
    130                 135                 140

Gly Arg Leu Thr His Leu Lys Ser Asp Trp Met Glu Ser Gly Asn Ala
145                 150                 155                 160

Phe Ala Asp Ile Val Glu Ala Arg Asn Lys Leu Leu Lys Met Gly His
                165                 170                 175

Ser Gly Pro Tyr Ala Leu Val Val Ser Pro Glu Leu Tyr Ser Leu Leu
            180                 185                 190

His Arg Val His Lys Gly Thr Asn Val Leu Glu Ile Glu His Val Arg
        195                 200                 205
```

Asn Leu Val Thr Asp Gly Val Phe Gln Ser Pro Thr Ile Lys Gly Arg
    210                 215                 220

Ser Gly Val Leu Val Ala Thr Gly Arg His Asn Leu Asp Leu Ala Ile
225                 230                 235                 240

Ala Glu Asp Phe Asp Ser Ala Phe Leu Gly Asp Glu Gln Met Asn Ser
            245                 250                 255

Leu Phe Arg Val Tyr Glu Cys Val Val
            260                 265

<210> SEQ ID NO 123
<211> LENGTH: 251
<212> TYPE: PRT
<213> ORGANISM: Mycobacterium

<400> SEQUENCE: 123

Met Asn Asn Leu Tyr Arg Asp Leu Ala Pro Val Thr Glu Ala Ala Trp
1               5                   10                  15

Ala Glu Ile Glu Leu Glu Ala Thr Arg Thr Phe Lys Arg His Ile Ala
            20                  25                  30

Gly Arg Arg Val Val Asp Val Ser Asp Pro Gly Gly Pro Val Thr Ala
        35                  40                  45

Ala Val Ser Thr Gly Arg Leu Ile Asp Val Lys Ala Pro Thr Asp Gly
    50                  55                  60

Val Ile Ala His Leu Arg Ala Ser Lys Pro Leu Val Arg Leu Arg Val
65                  70                  75                  80

Pro Phe Thr Leu Ser Arg Asn Glu Ile Asp Asp Val Glu Arg Gly Ser
                85                  90                  95

Gln Asp Ser Asp Trp Asp Pro Val Lys Ala Ala Lys Gln Leu Ala
            100                 105                 110

Phe Val Glu Asp Arg Thr Ile Phe Glu Gly Tyr Gly Ala Ala Ser Ile
            115                 120                 125

Glu Gly Ile Arg Ser Ser Ser Asn Pro Pro Leu Thr Leu Pro Glu
    130                 135                 140

Asp Pro Arg Glu Ile Pro Asp Val Ile Thr Gln Ala Leu Ser Glu Leu
145                 150                 155                 160

Arg Leu Ala Gly Val Asp Gly Pro Tyr Ser Val Leu Leu Ala Ala Asp
                165                 170                 175

Val Tyr Thr Lys Val Ser Glu Thr Thr Glu His Gly Tyr Pro Ile Arg
            180                 185                 190

Glu His Leu Asn Arg Leu Val Asp Gly Asp Ile Ile Trp Ala Pro Ala
        195                 200                 205

Ile Asp Gly Ala Phe Val Leu Thr Thr Arg Gly Gly Asp Phe Asp Leu
    210                 215                 220

Gln Leu Gly Thr Asp Val Ala Ile Gly Tyr Thr Ser His Asp Ala Asp
225                 230                 235                 240

Thr Val Gln Leu Tyr Leu Gln Glu Thr Leu Thr
                245                 250

<210> SEQ ID NO 124
<211> LENGTH: 251
<212> TYPE: PRT
<213> ORGANISM: Tsukamurella paurometabola

<400> SEQUENCE: 124

Met Asn Asn Leu Tyr Arg Asp Leu Ala Pro Val Thr Ser Ala Ala Trp
1               5                   10                  15

-continued

Ser Glu Ile Glu Thr Glu Ala Thr Arg Thr Phe Lys Arg Asn Ile Ala
                20                  25                  30

Gly Arg Arg Val Val Asp Leu Gly Asp Pro Leu Gly Pro Thr Ala Ser
            35                  40                  45

Ala Val Gly Thr Gly His Leu Leu Glu Val Gly Gly Pro Ala Glu Gly
 50                  55                  60

Val Gln Ala His Leu Arg Asp Ser Arg Pro Leu Val Arg Leu Arg Val
65                  70                  75                  80

Pro Phe Thr Leu Ser Arg Lys Ala Ile Asp Ser Val Glu Arg Gly Ala
                85                  90                  95

Gln Asp Ala Asp Trp Asp Pro Val Lys Asp Ala Ala Arg Ser Leu Ala
            100                 105                 110

Tyr Ala Glu Asp Arg Ala Ile Phe Glu Gly Tyr Pro Asp Ala Ser Ile
        115                 120                 125

Pro Gly Ile Arg Thr Thr Ala Ala Gly Ser Asp Leu Lys Leu Pro Asp
    130                 135                 140

Asp Pro Arg Asp Ile Pro Asp Val Val Ser Gln Ala Leu Ser Asp Leu
145                 150                 155                 160

Arg Leu Ala Gly Val Asp Gly Pro Tyr Ser Val Leu Leu Ser Ala Asp
                165                 170                 175

Val Tyr Thr Arg Val Ser Glu Thr Ser Asp His Gly Tyr Pro Val Arg
            180                 185                 190

Glu His Leu Asn Arg Leu Val Asp Gly Asp Ile Ile Trp Ala Pro Ala
        195                 200                 205

Ile Asp Gly Ala Phe Val Leu Thr Thr Arg Gly Gly Asp Phe Asp Leu
    210                 215                 220

Arg Leu Gly Thr Asp Val Glu Ile Gly Tyr Leu Ser His Thr Ala Asp
225                 230                 235                 240

Thr Val Asp Leu Tyr Leu Gln Glu Thr Phe Thr
                245                 250

<210> SEQ ID NO 125
<211> LENGTH: 251
<212> TYPE: PRT
<213> ORGANISM: Rhodococcus

<400> SEQUENCE: 125

Met Thr Asn Leu His Arg Asp Leu Ala Pro Ile Ser Ala Ala Ala Trp
1               5                   10                  15

Ala Glu Ile Glu Glu Glu Ala Ser Arg Thr Phe Lys Arg His Val Ala
                20                  25                  30

Gly Arg Arg Val Val Asp Val Glu Gly Pro Ser Gly Asp Asp Leu Ala
            35                  40                  45

Ala Ile Pro Leu Gly His Gln Val Pro Ile Asn Pro Leu Ala Asp Gly
 50                  55                  60

Val Ile Ala His Ala Arg Gln Ser Gln Pro Val Ile Glu Leu Arg Val
65                  70                  75                  80

Pro Phe Thr Val Ser Arg Gln Ala Ile Asp Asp Val Glu Arg Gly Ala
                85                  90                  95

Lys Asp Ser Asp Trp Gln Pro Val Lys Asp Ala Ala Lys Gln Ile Ala
            100                 105                 110

Phe Ala Glu Asp Arg Ala Ile Phe Glu Gly Tyr Pro Ala Ala Ser Ile
        115                 120                 125

Thr Gly Val Arg Ala Ser Gly Ser Asn Pro Glu Leu Lys Leu Pro Ile

```
                130             135             140
Asp Ala Lys Asp Tyr Pro Glu Ala Ile Ser Gln Ala Ile Thr Ser Leu
145                 150                 155                 160

Arg Leu Ala Gly Val Asn Gly Pro Tyr Ser Leu Leu Asn Ala Asp
                165                 170                 175

Ala Phe Thr Ala Ile Asn Glu Thr Ser Asp His Gly Tyr Pro Ile Arg
                180                 185                 190

Glu His Leu Arg Arg Val Leu Asp Gly Glu Ile Ile Trp Ala Pro Ala
                195                 200                 205

Ile Asp Gly Ala Phe Leu Leu Ser Thr Arg Gly Gly Asp Tyr Glu Leu
                210                 215                 220

His Leu Gly Gln Asp Leu Ser Ile Gly Tyr Leu Ser His Asp Ala Asn
225                 230                 235                 240

Ser Val Glu Leu Tyr Phe Gln Glu Ser Met Thr
                245                 250

<210> SEQ ID NO 126
<211> LENGTH: 251
<212> TYPE: PRT
<213> ORGANISM: Streptomyces griseus

<400> SEQUENCE: 126

Met Asn Asn Leu His Arg Glu Leu Ala Pro Val Thr Pro Ser Ala Trp
1               5                   10                  15

Glu Glu Ile Glu Glu Ala Arg Arg Thr Phe Arg Arg His Val Ala
                20                  25                  30

Gly Arg Arg Val Val Asp Val Ser Asp Pro Ala Gly Pro Thr Leu Ala
                35                  40                  45

Ala Val Gly Asp Gly His Leu Thr Asp Ile Asp Pro Pro Thr Pro Asp
50                  55                  60

Val Ala Ala Arg Ala Arg Thr Ser Thr Pro Val Ile Glu Trp Arg Val
65                  70                  75                  80

Pro Phe Thr Val Thr Arg Gln Ala Val Asp Asp Val Glu Arg Gly Ser
                85                  90                  95

Ala Asp Ser Asp Trp Gln Pro Val Lys Asp Ala Ala Arg Thr Cys Ala
                100                 105                 110

Phe Ala Glu Asp Met Ala Ile Ile Asp Gly Tyr Gly Ala Ala Gly Ile
                115                 120                 125

Thr Gly Leu Arg Asp Gly Ser Ser His Asp Pro Leu Pro Leu Pro Ala
                130                 135                 140

Asp Ala Arg Asp Tyr Pro Val Ala Val Ser Gln Ala Val Thr Arg Leu
145                 150                 155                 160

Arg Leu Ala Gly Val Asp Gly Pro Tyr Arg Leu Leu Leu Gly Ala Asp
                165                 170                 175

Ala Phe Thr Glu Ala Ala Glu Thr Ser Asp His Gly Tyr Pro Val Lys
                180                 185                 190

Thr His Leu Ser Arg Leu Val Asp Glu Ile Leu Trp Ala Pro Ala
                195                 200                 205

Val Lys Gly Gly Val Leu Leu Ser Thr Arg Gly Gly Asp Phe Glu Leu
                210                 215                 220

Cys Leu Gly Gln Asp Leu Ser Ile Gly Tyr Ala Asp His Asp Ala Thr
225                 230                 235                 240

Ser Val His Leu Tyr Phe Gln Gln Ala Phe Thr
                245                 250
```

<210> SEQ ID NO 127
<211> LENGTH: 251
<212> TYPE: PRT
<213> ORGANISM: Paraburkholderia phymatum

<400> SEQUENCE: 127

```
Met Asn Asn Leu His Arg Glu Leu Ala Pro Ile Ser Ser Glu Ala Trp
1               5                   10                  15

Ser Gln Ile Glu Glu Val Ala Arg Thr Phe Lys Arg Ser Val Ala
            20                  25                  30

Gly Arg Arg Val Val Asp Val Lys Gly Pro Gly Gly Val Asp Leu Ser
            35                  40                  45

Gly Val Gly Thr Gly His Gln Ser Thr Ile Ala Ala Pro His His Gly
    50                  55                  60

Val Ile Ala Lys Leu Ser Glu Val Lys Ala Leu Val Gln Leu Thr Val
65                  70                  75                  80

Pro Phe Glu Leu Ser Arg Asp Ala Ile Asp Ala Val Glu Arg Gly Ala
                85                  90                  95

Asn Asp Ser Asp Trp Gln Ala Ala Lys Asp Ala Ala Lys Glu Leu Ala
            100                 105                 110

Tyr Ala Glu Asp Arg Ala Ile Phe Asp Gly Tyr Lys Ala Ala Gly Ile
        115                 120                 125

Val Gly Ile Arg Glu Gly Ser Ser Asn Thr Ser Leu Ala Leu Pro Ala
    130                 135                 140

Asp Val Ala Asp Tyr Pro Asn Ala Ile Gly Gly Ala Leu Gln Gln Leu
145                 150                 155                 160

Arg Leu Ala Gly Val Asp Gly Pro Tyr Ser Val Leu Leu Gly Ala Asp
                165                 170                 175

Ala Tyr Thr Ala Leu Gly Glu Ala Ser Asp Gln Gly Tyr Pro Val Ile
            180                 185                 190

Glu His Ile Lys Arg Ile Val Asn Gly Glu Ile Ile Trp Ala Pro Ala
        195                 200                 205

Leu Glu Gly Gly Ser Val Leu Ser Met Arg Gly Gly Asp Tyr Glu Leu
    210                 215                 220

His Leu Gly Gln Asp Val Ser Ile Gly Tyr Gln Ser His Thr Asp Ser
225                 230                 235                 240

Thr Val Arg Leu Tyr Leu Arg Glu Thr Leu Thr
                245                 250
```

<210> SEQ ID NO 128
<211> LENGTH: 251
<212> TYPE: PRT
<213> ORGANISM: Methylocella silvestris

<400> SEQUENCE: 128

```
Met Asn Asn Leu His Arg Glu Leu Ala Pro Ile Ser Asp Ala Ala Trp
1               5                   10                  15

Ala Gln Ile Glu Glu Thr Thr Arg Thr Leu Lys Arg Tyr Leu Ala
            20                  25                  30

Gly Arg Arg Val Val Asp Met Pro Gln Thr Gly Gly Val Ala Leu Ser
            35                  40                  45

Ala Val Gly Thr Gly His Leu Leu Ser Ile Ala Ala Pro Ala Glu Gly
    50                  55                  60

Val Leu Ala Arg Gln Arg Glu Val Lys Pro Leu Val Glu Leu Arg Val
65                  70                  75                  80
```

```
Pro Phe Glu Leu Ser Arg Ala Ala Ile Asp Val Glu Arg Gly Ala
                85                  90                  95

Asp Asp Ser Asp Trp Gln Pro Ala Lys Asp Ala Ala Lys Thr Ile Ala
            100                 105                 110

Phe Ala Glu Asp Arg Ala Ile Phe Asp Gly Tyr Ala Asp Ala Ala Ile
            115                 120                 125

Thr Gly Val Arg Gln Gly Thr Ser Asn Pro Ile Met Thr Leu Pro Ala
            130                 135                 140

Asp Val Arg Asp Tyr Pro Asp Ala Ile Ala His Ala Leu Ser Gln Leu
145                 150                 155                 160

Arg Leu Val Gly Val Asn Gly Pro Tyr Ala Val Leu Phe Gly Ala Glu
                165                 170                 175

Ala Tyr Thr Ala Leu Ala Glu Thr Ser Asp His Gly Phe Pro Val Leu
            180                 185                 190

Glu His Val Lys Arg Leu Val Glu Asp Gln Ile Phe Trp Ala Pro Ala
            195                 200                 205

Ile Ala Gly Ala Phe Val Leu Thr Thr Arg Gly Gly Asp Phe Glu Leu
210                 215                 220

Thr Leu Gly Gln Asp Val Ser Ile Gly Tyr Leu Ser His Thr Ala Glu
225                 230                 235                 240

Thr Val Gln Leu Tyr Leu Gln Glu Ser Phe Thr
                245                 250

<210> SEQ ID NO 129
<211> LENGTH: 251
<212> TYPE: PRT
<213> ORGANISM: Paracoccus denitrificans

<400> SEQUENCE: 129

Met Asp Asn Leu His Arg Lys Leu Ala Pro Ile Ser Asp Ala Ala Trp
1               5                   10                  15

Ala Gln Ile Glu Asp Glu Ala Arg Thr Leu Lys Arg Tyr Leu Gly
            20                  25                  30

Ala Arg Arg Val Val Asp Val His Gly Pro Glu Gly Phe Gly Leu Ser
            35                  40                  45

Ala Val Gly Thr Gly His Leu Arg Pro Ala Thr Ala Leu Ala Glu Gly
        50                  55                  60

Val Glu Ser His Arg Arg Glu Val Asn Pro Leu Leu Glu Leu Arg Val
65                  70                  75                  80

Pro Phe Thr Leu Thr Arg Ala Ala Ile Asp Asp Val Ala Arg Gly Ser
                85                  90                  95

Asn Asp Ser Asp Trp Gln Pro Leu Lys Asp Ala Ala Arg Lys Ile Ala
            100                 105                 110

Leu Ala Glu Asp Arg Leu Val Phe Leu Gly His Gly Asp Ala Gly Ile
            115                 120                 125

Arg Gly Ile Leu Pro Glu Thr Ser Asn Pro Ile Val Ala Leu Pro Ala
            130                 135                 140

Asn Val Ala Asp Tyr Pro Glu Ala Val Ala Ser Ala Val Ser Glu Leu
145                 150                 155                 160

Arg Leu Ala Gly Val Asn Gly Pro Tyr Ala Leu Ile Leu Gly Thr Thr
                165                 170                 175

Ala Phe Thr Ala Ala Asn Gly Gly Ala Glu Asp Gly Tyr Pro Val Leu
            180                 185                 190

Lys His Leu Glu Arg Leu Val Asp Val Pro Val Val Trp Ser Gln Ala
            195                 200                 205
```

```
Leu Glu Gly Gly Ala Val Val Thr Thr Arg Gly Gly Asp Phe Asp Leu
    210                 215                 220

Trp Leu Gly Gln Asp Ile Ser Ile Gly Tyr Leu Ser His Asp Ala Ala
225                 230                 235                 240

Ser Val Thr Leu Tyr Leu Gln Glu Ser Leu Thr
                245                 250

<210> SEQ ID NO 130
<211> LENGTH: 251
<212> TYPE: PRT
<213> ORGANISM: Agrobacterium

<400> SEQUENCE: 130

Met Asn Asn Leu His Arg Gln Leu Ala Pro Ile Ser Asp Ser Ala Trp
1               5                   10                  15

Ala Gln Ile Glu Glu Ala Ser Arg Thr Leu Lys Arg His Leu Ala
            20                  25                  30

Ala Arg Arg Val Val Asp Val Gln Asp Pro Gly Gly Val Glu Leu Ser
            35                  40                  45

Ala Val Gly Thr Gly His Leu Lys Pro Ile Pro Gly Pro Gly Asp Gly
        50                  55                  60

Val Gln Thr Ala Leu Arg Glu Val Lys Thr Leu Val Glu Leu Arg Val
65                  70                  75                  80

Pro Phe Lys Leu Thr Arg Gln Ala Ile Asp Asp Val Glu Arg Gly Ala
                85                  90                  95

Glu Asp Ser Asp Trp Ser Pro Val Lys Asp Ala Ala Arg Lys Ile Ala
            100                 105                 110

Phe Ala Glu Asp Arg Ser Val Phe Asp Gly Tyr Ala Ala Ala Gly Ile
        115                 120                 125

Gln Gly Ile Arg Glu Gly Ser Ser Asn Pro Ile Leu Pro Leu Pro Ser
    130                 135                 140

Asn Val Arg Gly Tyr Pro Asp Ala Ile Ala Lys Ala Val Ser Gln Leu
145                 150                 155                 160

Arg Leu Ala Gly Val Asn Gly Pro Tyr Ala Leu Val Leu Gly Thr Glu
                165                 170                 175

Ala Tyr Thr Ala Ala Ser Gly Gly Ser Asp Asp Gly Tyr Pro Val Phe
            180                 185                 190

His His Ile Glu Arg Val Val Asp Gly Ile Ile Trp Ala Pro Ala
        195                 200                 205

Ile Glu Gly Gly Phe Val Leu Thr Thr Arg Gly Gly Asp Phe Glu Leu
    210                 215                 220

Asp Ile Gly Gln Asp Ile Ser Ile Gly Tyr Leu Ser His Ser Ser Thr
225                 230                 235                 240

Val Val Glu Leu Tyr Leu Gln Glu Thr Phe Thr
                245                 250

<210> SEQ ID NO 131
<211> LENGTH: 253
<212> TYPE: PRT
<213> ORGANISM: Frankia

<400> SEQUENCE: 131

Met Asn His Leu Leu Arg Gly His Ala Pro Leu Ser Glu Glu Ala Trp
1               5                   10                  15

Lys Ala Val Asp Glu Glu Ala Arg Ser Arg Leu Thr Thr Asn Leu Ala
            20                  25                  30
```

Ala Arg Lys Leu Ile Asp Phe Ala Gly Pro His Gly Trp Ala Tyr Ser
            35                  40                  45

Ala Thr Pro Ile Gly Arg Val Thr Ala Leu Gln Ala Pro Pro Gly Glu
        50                  55                  60

Gly Val Arg Ala Arg Leu Arg Arg Val Leu Pro Val Met Glu Leu Arg
65                  70                  75                  80

Ala Ala Phe Ser Ile Asp Arg Gly Leu Asp Ala Ile Asp Arg Gly
            85                  90                  95

Ala Asp Asp Ile Asp Leu Ser Ala Leu Glu Glu Ala Ala Arg Arg Val
                100                 105                 110

Ala Thr Thr Glu Asn Ser Val Val Phe His Gly Tyr Ala Glu Ala Gly
            115                 120                 125

Ile Ile Gly Ile Thr Glu Ala Ser Ser His Pro Val Leu Glu Leu Gly
        130                 135                 140

Ala Asp Thr Asp Ser Tyr Pro Arg Thr Val Lys Ala Val Ala Leu
145                 150                 155                 160

Leu Arg Arg Ala Gly Ile Gly Gly Pro Tyr Gly Leu Ala Ile Asp Pro
                165                 170                 175

Asp Gly Tyr Thr Ala Ile Leu Glu Ala Thr Glu His Gly Gly Tyr Leu
            180                 185                 190

Leu Leu Asn His Leu Lys Gln Ile Leu Asp Gly Pro Val Val Arg Ala
        195                 200                 205

Pro Gly Val Arg Gly Ala Val Val Leu Ser Gln Arg Gly Gly Asp Phe
    210                 215                 220

Ile Leu Glu Ser Gly Gln Asp Leu Ser Val Gly Tyr Ser Ser His Thr
225                 230                 235                 240

Ala Glu Glu Val Glu Leu Tyr Leu Glu Gln Ser Phe Ser
            245                 250

<210> SEQ ID NO 132
<211> LENGTH: 253
<212> TYPE: PRT
<213> ORGANISM: Artificial Sequence
<220> FEATURE:
<223> OTHER INFORMATION: Synthetic polypeptide

<400> SEQUENCE: 132

Met Asp Asn Leu Lys Arg Glu Leu Ala Pro Leu Thr Glu Glu Ala Trp
1               5                   10                  15

Ala Glu Ile Asp Glu Glu Ala Arg Glu Thr Ala Lys Arg His Leu Ala
            20                  25                  30

Gly Arg Arg Val Val Asp Val Glu Gly Pro Leu Gly Trp Gly Tyr Ser
        35                  40                  45

Ala Val Pro Leu Gly Arg Leu Glu Glu Ile Glu Gly Pro Ala Glu Gly
    50                  55                  60

Val Gln Ala Gly Val Arg Gln Val Leu Pro Leu Pro Glu Leu Arg Val
65                  70                  75                  80

Pro Phe Thr Leu Ser Arg Arg Asp Leu Asp Ala Val Glu Arg Gly Ala
            85                  90                  95

Lys Asp Leu Asp Leu Ser Pro Val Ala Glu Ala Ala Arg Lys Leu Ala
                100                 105                 110

Arg Ala Glu Asp Arg Leu Ile Phe Asn Gly Tyr Ala Glu Ala Gly Ile
            115                 120                 125

Glu Gly Leu Leu Asn Ala Ser Gly Asn Leu Lys Leu Pro Leu Ser Ala
        130                 135                 140

Asp Pro Gly Asp Ile Pro Asp Ala Ile Ala Glu Ala Leu Thr Lys Leu
145                 150                 155                 160

Arg Glu Ala Gly Val Glu Gly Pro Tyr Ala Leu Val Leu Ser Pro Asp
                165                 170                 175

Leu Tyr Thr Ala Leu Phe Arg Val Tyr Asp Gly Thr Gly Tyr Pro Glu
            180                 185                 190

Ile Glu His Ile Lys Glu Leu Val Asp Gly Val Ile Trp Ala Pro
            195                 200                 205

Ala Leu Asp Gly Gly Ala Val Leu Val Ser Thr Arg Gly Gly Asp Phe
        210                 215                 220

Asp Leu Thr Leu Gly Gln Asp Leu Ser Ile Gly Tyr Leu Ser His Asp
225                 230                 235                 240

Ala Asp Asn Val Glu Leu Phe Leu Thr Glu Ser Phe Thr
                245                 250

<210> SEQ ID NO 133
<211> LENGTH: 269
<212> TYPE: PRT
<213> ORGANISM: T. maritima

<400> SEQUENCE: 133

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe Ser Gly Gly Ser
            260                 265

-continued

```
                260                 265

<210> SEQ ID NO 134
<211> LENGTH: 315
<212> TYPE: PRT
<213> ORGANISM: Artificial Sequence
<220> FEATURE:
<223> OTHER INFORMATION: Synthetic polypeptide

<400> SEQUENCE: 134

Met Gly Asn Asn Arg Pro Val Tyr Ile Pro Gln Pro Arg Pro Pro His
1               5                   10                  15

Pro Arg Ile Glu Asn Leu Tyr Phe Gln Gly Gly Thr Ser Pro Asp Phe
            20                  25                  30

Leu Gly His Ala Glu Asn Pro Leu Arg Glu Glu Trp Ala Arg Leu
        35                  40                  45

Asn Glu Thr Val Ile Gln Val Ala Arg Arg Ser Leu Val Gly Arg Arg
 50                  55                  60

Ile Leu Asp Ile Tyr Gly Pro Leu Gly Ala Gly Val Gln Thr Val Pro
65                  70                  75                  80

Tyr Asp Glu Phe Gln Gly Val Ser Pro Gly Ala Val Asp Ile Val Gly
                85                  90                  95

Glu Gln Glu Thr Ala Met Val Phe Thr Asp Ala Arg Lys Phe Lys Thr
            100                 105                 110

Ile Pro Ile Ile Tyr Lys Asp Phe Leu Leu His Trp Arg Asp Ile Glu
        115                 120                 125

Ala Ala Arg Thr His Asn Met Pro Leu Asp Val Ser Ala Ala Ala Gly
    130                 135                 140

Ala Ala Ala Leu Cys Ala Gln Gln Glu Asp Glu Leu Ile Phe Tyr Gly
145                 150                 155                 160

Asp Ala Arg Leu Gly Tyr Glu Gly Leu Met Thr Ala Asn Gly Arg Leu
                165                 170                 175

Thr Val Pro Leu Gly Asp Trp Thr Ser Pro Gly Gly Gly Phe Gln Ala
            180                 185                 190

Ile Val Glu Ala Thr Arg Lys Leu Asn Glu Gln Gly His Phe Gly Pro
        195                 200                 205

Tyr Ala Val Val Leu Ser Pro Arg Leu Tyr Ser Gln Leu His Arg Ile
    210                 215                 220

Tyr Glu Lys Thr Gly Val Leu Glu Ile Glu Thr Ile Arg Gln Leu Ala
225                 230                 235                 240

Ser Asp Gly Val Tyr Gln Ser Asn Arg Leu Arg Gly Glu Ser Gly Val
                245                 250                 255

Val Val Ser Thr Gly Arg Glu Asn Met Asp Leu Ala Val Ser Met Asp
            260                 265                 270

Met Val Ala Ala Tyr Leu Gly Ala Ser Arg Met Asn His Pro Phe Arg
        275                 280                 285

Val Leu Glu Ala Leu Leu Leu Arg Ile Lys His Pro Asp Ala Ile Cys
    290                 295                 300

Thr Leu Glu Gly Ala Gly Ala Thr Glu Arg Arg
305                 310                 315

<210> SEQ ID NO 135
<211> LENGTH: 320
<212> TYPE: PRT
<213> ORGANISM: Artificial Sequence
<220> FEATURE:
<223> OTHER INFORMATION: Synthetic polypeptide
```

<400> SEQUENCE: 135

Met Gly Asn Asn Arg Pro Val Tyr Ile Pro Gln Pro Arg Pro Pro His
1               5                   10                  15

Pro Arg Ile Glu Asn Leu Tyr Phe Gln Gly Gly Thr Ser Glu Phe Leu
            20                  25                  30

Lys Arg Ser Phe Ala Pro Leu Thr Glu Lys Gln Trp Gln Glu Ile Asp
        35                  40                  45

Asn Arg Ala Arg Glu Ile Phe Lys Thr Gln Leu Tyr Gly Arg Lys Phe
    50                  55                  60

Val Asp Val Glu Gly Pro Tyr Gly Trp Glu Tyr Ala Ala His Pro Leu
65                  70                  75                  80

Gly Glu Val Gly Val Leu Ser Asp Glu Asn Glu Val Val Lys Trp Gly
                85                  90                  95

Leu Arg Lys Ser Leu Pro Leu Ile Glu Leu Arg Ala Thr Phe Thr Leu
            100                 105                 110

Asp Leu Trp Glu Leu Asp Asn Leu Glu Arg Gly Lys Pro Asn Val Asp
        115                 120                 125

Leu Ser Ser Leu Glu Glu Thr Val Arg Lys Val Ala Glu Phe Glu Asp
    130                 135                 140

Glu Val Ile Phe Arg Gly Cys Glu Lys Ser Gly Val Lys Gly Leu Leu
145                 150                 155                 160

Ser Phe Glu Glu Arg Lys Gly Gly Gly Gly Glu Asn Leu Tyr Phe
                165                 170                 175

Gln Gly His His His His His Gly Gly Gly Gly Ile Glu Cys
            180                 185                 190

Gly Ser Thr Pro Lys Asp Leu Leu Glu Ala Ile Val Arg Ala Leu Ser
            195                 200                 205

Ile Phe Ser Lys Asp Gly Ile Glu Gly Pro Tyr Thr Leu Val Ile Asn
        210                 215                 220

Thr Asp Arg Trp Ile Asn Phe Leu Lys Glu Glu Ala Gly His Tyr Pro
225                 230                 235                 240

Leu Glu Lys Arg Val Glu Glu Cys Leu Arg Gly Gly Lys Ile Ile Thr
            245                 250                 255

Thr Pro Arg Ile Glu Asp Ala Leu Val Val Ser Glu Arg Gly Gly Asp
            260                 265                 270

Phe Lys Leu Ile Leu Gly Gln Asp Leu Ser Ile Gly Tyr Glu Asp Arg
        275                 280                 285

Glu Lys Asp Ala Val Arg Leu Phe Ile Thr Glu Thr Phe Thr Phe Gln
    290                 295                 300

Val Val Asn Pro Glu Ala Leu Ile Leu Leu Lys Phe Ser Gly Gly Ser
305                 310                 315                 320

<210> SEQ ID NO 136
<211> LENGTH: 331
<212> TYPE: PRT
<213> ORGANISM: Artificial Sequence
<220> FEATURE:
<223> OTHER INFORMATION: Synthetic polypeptide

<400> SEQUENCE: 136

Met Gly Asn Asn Arg Pro Val Tyr Ile Pro Gln Pro Arg Pro Pro His
1               5                   10                  15

Pro Arg Ile Glu Asn Leu Tyr Phe Gln Gly Gly Thr Ser Glu Phe Leu
            20                  25                  30

Lys Arg Ser Phe Ala Pro Leu Thr Glu Lys Gln Trp Gln Glu Ile Asp
            35                  40                  45

Asn Arg Ala Arg Glu Ile Phe Lys Thr Gln Leu Tyr Gly Arg Lys Phe
 50                  55                  60

Val Asp Val Glu Gly Pro Tyr Gly Trp Glu Tyr Ala Ala His Pro Leu
 65                  70                  75                  80

Gly Glu Val Glu Val Leu Ser Asp Glu Asn Glu Val Val Lys Trp Gly
                85                  90                  95

Leu Arg Lys Gly Gly Glu Asn Leu Tyr Phe Gln Gly Gly Ser Leu
                100                 105                 110

Pro Leu Ile Glu Leu Arg Ala Thr Phe Thr Leu Asp Leu Trp Glu Leu
                115                 120                 125

Asp Asn Leu Glu Arg Gly Lys Pro Asn Val Asp Leu Ser Ser Leu Glu
130                 135                 140

Glu Thr Val Arg Lys Val Ala Glu Phe Glu Asp Glu Val Ile Phe Arg
145                 150                 155                 160

Gly Cys Glu Lys Ser Gly Val Lys Gly Leu Leu Ser Phe Glu Glu Arg
                165                 170                 175

Lys Gly Gly Gly Gly Glu Asn Leu Tyr Phe Gln Gly His His His
                180                 185                 190

His His His Gly Gly Gly Gly Ile Glu Cys Gly Ser Thr Pro Lys
            195                 200                 205

Asp Leu Leu Glu Ala Ile Val Arg Ala Leu Ser Ile Phe Ser Lys Asp
                210                 215                 220

Gly Ile Glu Gly Pro Tyr Thr Leu Val Ile Asn Thr Asp Arg Trp Ile
225                 230                 235                 240

Asn Phe Leu Lys Glu Glu Ala Gly His Tyr Pro Leu Glu Lys Arg Val
                245                 250                 255

Glu Glu Cys Leu Arg Gly Gly Lys Ile Ile Thr Thr Pro Arg Ile Glu
                260                 265                 270

Asp Ala Leu Val Val Ser Glu Arg Gly Gly Asp Phe Lys Leu Ile Leu
                275                 280                 285

Gly Gln Asp Leu Ser Ile Gly Tyr Glu Asp Arg Glu Lys Asp Ala Val
                290                 295                 300

Arg Leu Phe Ile Thr Glu Thr Phe Thr Phe Gln Val Val Asn Pro Glu
305                 310                 315                 320

Ala Leu Ile Leu Leu Lys Phe Ser Gly Gly Ser
                325                 330

<210> SEQ ID NO 137
<211> LENGTH: 996
<212> TYPE: DNA
<213> ORGANISM: Artificial Sequence
<220> FEATURE:
<223> OTHER INFORMATION: Synthetic polynucleotide

<400> SEQUENCE: 137
atggggaaca accgtcccgt ctacatccca cagccgcgcc ctccacatcc ccgtattgaa    60
aacttgtatt tcaaggtgg tacctccgag tttctgaaac gcagcttcgc cccgctgacc    120
gagaagcagt ggcaggagat cgacaatcgc gcccgcgaga tcttcaagac acagctgtac    180
ggtcgcaagt tcgtggacgt ggaaggcccg tacggctggg aatatgccgc acaccctctg    240
ggtgaggtgg aggtgctgag cgacgagaac gaagtggtta agtggggtct gcgcaagggt    300
ggtgaaaacc tgtatttcca aggtggtggt agcctgccgt taatcgaact gcgcgcaacc    360

```
ttcaccctgg acctgtggga gctggacaac ctggagcgcg gcaagccgaa cgtggacctg    420
agtagcctgg aggaaaccgt gcgtaaggtg gccgagtttg aggacgaagt gattttccgc    480
ggctgcgaga gagcggcgt taagggtctg ctgagcttcg aagagcgcaa gggtgggga     540 ggcggtgaaa acttgtattt tcaaggtcat catcaccacc atcatggtgg aggggcggc    600 atcgagtgcg gcagcacccc gaaagatctg ctggaggcca tcgttcgcgc cctgagcatc    660
ttcagtaagg acggcatcga gggcccgtac accctggtga ttaacaccga ccgttggatc    720
aacttcctga agaagaggc gggtcactac ccgctggaaa aacgcgtgga agagtgtctg    780
cgcggcggca agatcatcac cacacctcgc atcgaagacg ccttagtggt tagcgagcgc    840
ggcggcgact ttaagctgat cctgggccag gacctgagca tcggctatga ggaccgtgaa    900
aaggacgccg tgcgtctgtt catcacagaa accttcacct tccaggtggt gaacccggaa    960
gccctgatcc tgctgaagtt cagcggtgga tcctaa                             996
```

<210> SEQ ID NO 138
<211> LENGTH: 331
<212> TYPE: PRT
<213> ORGANISM: Artificial Sequence
<220> FEATURE:
<223> OTHER INFORMATION: Synthetic polypeptide

<400> SEQUENCE: 138

```
Met Gly Asn Asn Arg Pro Val Tyr Ile Pro Gln Pro Arg Pro His
1               5                   10                  15

Pro Arg Ile Glu Asn Leu Tyr Phe Gln Gly Gly Thr Ser Glu Phe Leu
            20                  25                  30

Lys Arg Ser Phe Ala Pro Leu Thr Glu Lys Gln Trp Gln Glu Ile Asp
        35                  40                  45

Asn Arg Ala Arg Glu Ile Phe Lys Thr Gln Leu Tyr Gly Arg Lys Phe
    50                  55                  60

Val Asp Val Glu Gly Pro Tyr Gly Trp Glu Tyr Ala Ala His Pro Leu
65                  70                  75                  80

Gly Glu Val Glu Val Leu Ser Asp Gly Gly Glu Asn Leu Tyr Phe Gln
                85                  90                  95

Gly Gly Gly Glu Asn Glu Val Val Lys Trp Gly Leu Arg Lys Ser Leu
            100                 105                 110

Pro Leu Ile Glu Leu Arg Ala Thr Phe Thr Leu Asp Leu Trp Glu Leu
        115                 120                 125

Asp Asn Leu Glu Arg Gly Lys Pro Asn Val Asp Leu Ser Ser Leu Glu
130                 135                 140

Glu Thr Val Arg Lys Val Ala Glu Phe Glu Asp Glu Val Ile Phe Arg
145                 150                 155                 160

Gly Cys Glu Lys Ser Gly Val Lys Gly Leu Leu Ser Phe Glu Glu Arg
                165                 170                 175

Lys Gly Gly Gly Gly Glu Asn Leu Tyr Phe Gln Gly His His His
            180                 185                 190

His His His Gly Gly Gly Gly Ile Glu Cys Gly Ser Thr Pro Lys
        195                 200                 205

Asp Leu Leu Glu Ala Ile Val Arg Ala Leu Ser Ile Phe Ser Lys Asp
    210                 215                 220

Gly Ile Glu Gly Pro Tyr Thr Leu Val Ile Asn Thr Asp Arg Trp Ile
225                 230                 235                 240

Asn Phe Leu Lys Glu Glu Ala Gly His Tyr Pro Leu Glu Lys Arg Val
                245                 250                 255
```

```
Glu Glu Cys Leu Arg Gly Gly Lys Ile Ile Thr Thr Pro Arg Ile Glu
            260                 265                 270

Asp Ala Leu Val Val Ser Glu Arg Gly Gly Asp Phe Lys Leu Ile Leu
        275                 280                 285

Gly Gln Asp Leu Ser Ile Gly Tyr Glu Asp Arg Glu Lys Asp Ala Val
    290                 295                 300

Arg Leu Phe Ile Thr Glu Thr Phe Thr Phe Gln Val Val Asn Pro Glu
305                 310                 315                 320

Ala Leu Ile Leu Leu Lys Phe Ser Gly Gly Ser
                325                 330

<210> SEQ ID NO 139
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 139

Glu Ile Glu Gly Pro Ala Glu Gly Val
1               5

<210> SEQ ID NO 140
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 140

Gly Gly Glu Asn Leu Tyr Phe Gln Gly Gly Gly
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 141

Leu Asn Ala Ser Gly Asn Leu Lys Leu Pro Leu Ser Ala
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 142

Gln Ala Gly Val Arg Gln Val Leu Pro
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 143

Gly Gly Gly Gly Gly
```

<210> SEQ ID NO 144
<211> LENGTH: 253
<212> TYPE: PRT
<213> ORGANISM: Artificial Sequence
<220> FEATURE:
<223> OTHER INFORMATION: synthetic polypeptide

<400> SEQUENCE: 144

```
Met Asp Asn Leu Lys Arg Glu Leu Ala Pro Leu Thr Glu Glu Ala Trp
1               5                   10                  15

Ala Glu Ile Asp Glu Glu Ala Arg Glu Thr Ala Lys Arg His Leu Ala
            20                  25                  30

Gly Arg Arg Val Val Asp Val Glu Gly Pro Leu Gly Trp Gly Tyr Ser
        35                  40                  45

Ala Val Pro Leu Gly Arg Leu Glu Glu Ile Glu Gly Pro Ala Glu Gly
    50                  55                  60

Val Gln Ala Gly Val Arg Gln Val Leu Pro Leu Pro Glu Leu Arg Val
65                  70                  75                  80

Pro Phe Thr Leu Ser Arg Arg Asp Leu Asp Ala Val Glu Arg Gly Ala
                85                  90                  95

Lys Asp Leu Asp Leu Ser Pro Val Ala Glu Ala Arg Lys Leu Ala
            100                 105                 110

Arg Ala Glu Asp Arg Leu Ile Phe Asn Gly Tyr Ala Glu Ala Gly Ile
        115                 120                 125

Glu Gly Leu Leu Asn Ala Ser Gly Asn Leu Lys Leu Pro Leu Ser Ala
    130                 135                 140

Asp Pro Gly Asp Ile Pro Asp Ala Ile Ala Glu Ala Leu Thr Lys Leu
145                 150                 155                 160

Arg Glu Ala Gly Val Glu Gly Pro Tyr Ala Leu Val Leu Ser Pro Asp
                165                 170                 175

Leu Tyr Thr Ala Leu Phe Arg Val Tyr Asp Gly Thr Gly Tyr Pro Glu
            180                 185                 190

Ile Glu His Ile Lys Glu Leu Val Asp Gly Gly Val Ile Trp Ala Pro
        195                 200                 205

Ala Leu Asp Gly Gly Ala Val Leu Val Ser Thr Arg Gly Gly Asp Phe
    210                 215                 220

Asp Leu Thr Leu Gly Gln Asp Leu Ser Ile Gly Tyr Leu Ser His Asp
225                 230                 235                 240

Ala Asp Asn Val Glu Leu Phe Leu Thr Glu Ser Phe Thr
                245                 250
```

<210> SEQ ID NO 145
<211> LENGTH: 251
<212> TYPE: PRT
<213> ORGANISM: Artificial Sequence
<220> FEATURE:
<223> OTHER INFORMATION: synthetic polypeptide

<400> SEQUENCE: 145

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45
```

-continued

```
Ala His Pro Leu Gly Glu Val Glu Val Leu Ser Asp Glu Asn Glu Val
    50                  55                  60
Val Lys Trp Gly Leu Arg Lys Ser Leu Pro Leu Ile Glu Leu Arg Ala
 65                  70                  75                  80
Thr Phe Thr Leu Asp Leu Trp Glu Leu Asp Asn Leu Glu Arg Gly Lys
                 85                  90                  95
Pro Asn Val Asp Leu Ser Ser Leu Glu Glu Thr Val Arg Lys Val Ala
                100                 105                 110
Glu Phe Glu Asp Glu Val Ile Phe Arg Gly Cys Glu Lys Ser Gly Val
            115                 120                 125
Lys Gly Leu Leu Ser Phe Glu Glu Arg Lys Ile Glu Cys Gly Ser Thr
        130                 135                 140
Pro Lys Asp Leu Leu Glu Ala Ile Val Arg Ala Leu Ser Ile Phe Ser
145                 150                 155                 160
Lys Asp Gly Ile Glu Gly Pro Tyr Thr Leu Val Ile Asn Thr Asp Arg
                165                 170                 175
Trp Ile Asn Phe Leu Lys Glu Glu Ala Gly His Tyr Pro Leu Glu Lys
            180                 185                 190
Arg Val Glu Glu Cys Leu Arg Gly Gly Lys Ile Ile Thr Thr Pro Arg
            195                 200                 205
Ile Glu Asp Ala Leu Val Val Ser Glu Arg Gly Gly Asp Phe Lys Leu
        210                 215                 220
Ile Leu Gly Gln Asp Leu Ser Ile Gly Tyr Glu Asp Arg Glu Lys Asp
225                 230                 235                 240
Ala Val Arg Leu Phe Ile Thr Glu Thr Phe Thr
                245                 250
```